United States Patent [19]
Ohara et al.

[11] Patent Number: 5,955,481
[45] Date of Patent: Sep. 21, 1999

[54] PYRIDINE TYPE THIAZOLIDINES

[75] Inventors: Yoshio Ohara; Mikio Suzuki; Nobuhide Miyachi; Katsuhiro Kato; Keisuke Ohdoi; Tetsuya Kobayashi, all of Funabashi; Ken-ichi Shikada, Shiraoka-machi; Takeshi Naito, Shiraoka-machi; Takashi Yotsumoto, Shiraoka-machi, all of Japan

[73] Assignee: Nissan Chemical Industries, Ltd., Tokyo, Japan

[21] Appl. No.: 09/018,843

[22] Filed: Feb. 4, 1998

Related U.S. Application Data

[63] Continuation-in-part of application No. 08/704,774, Mar. 27, 1995, abandoned.

[30] Foreign Application Priority Data

Mar. 28, 1994 [JP] Japan ..................................... 6-057192
Nov. 29, 1994 [JP] Japan ..................................... 6-295177

[51] Int. Cl.[6] ...................... C07D 417/06; C07D 417/14; A61K 31/42; A61K 31/425
[52] U.S. Cl. ........................ 514/342; 514/340; 546/269.7; 546/271.4
[58] Field of Search ............................. 540/269.7, 271.4; 514/340, 342

[56] References Cited

PUBLICATIONS

Takeda Chemical, Chemical Abstracts, vol. 93, No. 17, Abstract No. 168,259 K, Oct. 27, 1980.

Sohda et al, Chemical & Pharmaceutical Bulletin, vol. 30, No. 10, pp. 3580–3600, Oct. 1980.

*Primary Examiner*—Zinna Northington Davis
*Attorney, Agent, or Firm*—Oblon, Spivak, McClelland, Maier & Neustadt, P.C.

[57] ABSTRACT

The present invention provides novel pyridine type thiazolidines and their salts, expressed by the following formula (I):

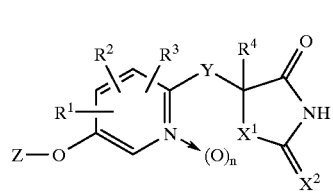

19 Claims, No Drawings

PYRIDINE TYPE THIAZOLIDINES

This application is a continuation in part of U.S. patent application Ser. No. 08/704,774 filed Mar. 27, 1995, now abandoned and incorporated entirely herein by reference.

TECHNICAL FIELD

The present invention relates to novel pyridine type thiazolidines having a hypoglycemic effect and an anti-glycation effect, which are useful in medical and veterinary fields, particularly useful for preventing or treating diabetes mellitus and diabetic complications.

BACKGROUND ART

Heretofore, various sulfonylurea derivatives and biguanide derivatives have been widely used as oral hypoglycemic agents for lowering blood sugar values. However, these agents had disadvantages of causing serious hypoglycemic coma and lactic acidosis revelation, and therefore every possible care must have been taken for practical use. "Chem. Pharm. Bull., vol. 30, p. 3563 (1982)", "J. Med. Chem., vol. 32, p. 421 (1989)", "J. Med. Chem., vol. 34, p. 318 (1991)", "J. Med. Chem., vol. 33, p. 1418 (1990)", Japanese Unexamined Patent Publication No. 64586/1980, and European Laid Open Patent Publications No. 177353, No. 283035, No. 283036, No. 332331, No. 332332 and No. 605228 disclose various thiazolidindiones which achieve a hypoglycemic effect, and these are particularly useful for treating Type II diabetes and are noted as agents for hardly causing such hypoglycemic symptoms as caused by the above-mentioned oral hypoglycemic agents. However, although these compounds have a function of effectively lowering a blood sugar value, but it is not proved that these compounds have effects for reducing or preventing various chronic symptoms caused by diabetes, such as diabetic nephropathy, diabetic cataract, diabetic retinopathy, diabetic neuropathy and the like.

On the other hand, non-enzymatic glycosylation of vital protein has been recently noted for causing various diseases accompanied by diabetes and arteriosclerosis. Generally, the reaction of reducing sugars with amino acids and proteins caused by heat treatment of foods or during storing foods is known as Maillard reaction. It was recognized in 1970's that the Maillard reaction is actually caused in a living body, and this reaction is recently called as glycation (see "J. Biol. Chem., vol. 252, p. 2998 (1977)"). Also, it has been proved that glycation is exacerbated in such chronic hyperglycemic state as in diabetes, and it is presumed that the glycation becomes a trigger for causing various diabetic complications (see "New Eng. J. Med., vol. 314, p. 403(1986)"). The process of glycation is not completely clear, but it is considered that various vital proteins are reacted with reducing sugars to non-enzymatically form Schiff base, and that this is crosslinked after causing Amadori rearrangement and is converted to fluorescent browning materials, i.e. AGE (advanced glycosylation end products). It was recognized in rat's diabetic cataract that glycation of crystallin of lens protein is exacerbated. Also, it is presumed that glycation of myelin protein causes diabetic neuropathy and that glycation of collagen and elastin present in connective tissue causes renal dysfunction-inducing thickening of renal glomerular basement membrane and atherosclerosis. Brownlee et al reported that the anti-glycation effect of aminoguanidine prevents formation of AGE protein on arterial walls of a rat suffering from diabetes, and the aminoguanidine becomes remarkable as an agent for preventing diseases including diabetes mellitus (see "Science, vol. 232, p. 1629 (1986)").

However, the above-mentioned function of aminoguanidine is not always sufficient, and an agent achieving an anti-glycation effect satisfactory for practical use has not been found yet.

On the other hand, aldose reductase (AR) is known to be an enzyme for reducing aldoses such as glucose and galactose to polyols such as sorbitol and galactitol in a living body. It is also known that accumulation of the polyols thus produced by the enzyme in organs induces or exacerbates various diabetic complications such as diabetic retinopathy, diabetic neuropathy and diabetic nephropathy, and therefore an inhibitor against this enzyme is useful as an agent for treating these diabetic complications.

Under these circumstances, the present inventors have synthesized various thiazolidines which are not disclosed in the above-mentioned literatures, and have studied their properties. As this result, the present inventors have found a compound having an anti-glycation effect and aldose-reductase inhibitory activities which were not exhibited by the above-mentioned known compounds. Thus, the present invention provides pyridine type thiazolidines capable of preventing or treating diabetes mellitus and diabetic complications.

DISCLOSURE OF THE INVENTION

The novel pyridine type thiazolidine derivatives of the present invention are pyridine type thiazolidines and their salts, expressed by the following formula (I).

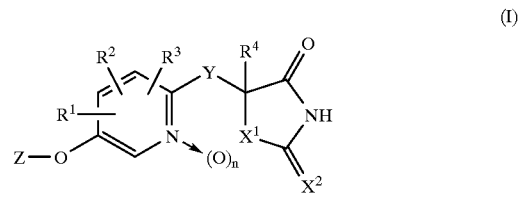

(wherein
$X^1$ is S or O;
$X^2$ is S, O or NH;
Y is $CR^6R^7$ (wherein $R^6$ is a hydrogen atom, a $C_1$–$C_7$ alkyl group or a $C_3$–$C_7$ cycloalkyl group, and $R^7$ is a hydrogen atom, a $C_1$–$C_7$ alkyl group or a $C_3$–$C_7$ cycloalkyl group or forms a bond together with $R^4$), or $SO_2$;
Z is a $C_1$–$C_{10}$ alkyl group, a $C_2$–$C_{10}$ alkenyl group, a $C_2$–$C_{10}$ alkynyl group, a $C_3$–$C_7$ cycloalkyl group, a $C_3$–$C_7$ cycloalkenyl group (each of said alkyl, alkenyl, alkynyl, cycloalkyl and cycloalkenyl groups may be substituted with at most 3 of hydroxyl, oxo, $C_1$–$C_7$ alkyl and $C_1$–$C_7$ alkoxy groups), a phenyl group, a biphenyl group, an α-naphthyl group, a β-naphthyl group, a benzyl group, a pyridyl group, a pyrimidinyl group, a pyridazinyl group, a furanyl group, a thienyl group, a pyrrolyl group, a pyrazolyl group, an imidazolyl group, a pyranyl group (each of said phenyl, biphenyl, α-naphthyl, β-naphthyl, benzyl, pyridyl, pyrimidinyl, pyridazinyl, furanyl, thienyl, pyrrolyl, pyrazolyl, imidazolyl and pyranyl groups may be substituted with at most 3 of hydroxyl, $C_1$–$C_7$ alkyl and $C_1$–$C_7$ alkoxy groups and a halogen atom), a substituted silyl group, a $C_1$–$C_{14}$ aliphatic acyl group, a $C_6$–$C_{10}$ aromatic acyl group or -A-B (wherein A is a divalent $C_1$–$C_6$ saturated or $C_2$–$C_6$ unsaturated hydrocarbon group which may be substituted with at most 3 of hydroxyl, oxo and $C_1$–$C_7$ alkyl groups, and B is $C_3$–$C_{10}$ cycloalkyl, $C_3$–$C_7$ cycloalkenyl, $C_6$–$C_{14}$ aromatic and $C_4$–$C_{12}$ heterocyclic aromatic groups, which may have at most 5 substituents in total (said heterocyclic aromatic group may contain at most 5 hetero atoms selected from the group consisting of an oxygen atom, a sulfur atom and a nitrogen atom as constituents for the heterocyclic ring), or a $C_4$–$C_6$ hetero-cycloaliphatic group (said hetero-cycloaliphatic group may contain at most 3 hetero atoms selected from the group consisting of an oxygen atom, a sulfur atom and a nitrogen atom as constituents for the heterocyclic ring));

each of $R^1$, $R^2$ and $R^3$ is independently a hydrogen atom, a $C_1$–$C_7$ alkyl group (which may be substituted with a hydroxyl group), a $C_3$–$C_7$ cycloalkyl group, a hydroxyl group or a halogen atom;

$R^4$ is a hydrogen atom or a $C_1$–$C_7$ alkyl group, or forms a bond together with $R^7$; and n is 0 or 1.)

Substituents of the compound having the formula (I) of the present invention are defined by illustrating examples, but the scope of the present invention should not be limited to these examples.

Each substituent in the formula (I) is concretely illustrated hereinafter.

Examples of a $C_1$–$C_{10}$ alkyl group include methyl, ethyl, n-propyl, i-propyl, n-butyl, i-butyl, s-butyl, t-butyl, 1-pentyl, 2-pentyl, 3-pentyl, i-pentyl, neopentyl, t-pentyl, 1-hexyl, 2-hexyl, 3-hexyl, 1-methyl-1-ethyl-n-pentyl, 1,1,2-trimethyl-n-propyl, 1,2,2-trimethyl-n-propyl, 3,3-dimethyl-n-butyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl, and the like.

Examples of a $C_1$–$C_7$ alkyl group include methyl, ethyl, n-propyl, i-propyl, n-butyl, i-butyl, s-butyl, t-butyl, 1-pentyl, 2-pentyl, 3-pentyl, i-pentyl, neopentyl, t-pentyl, 1-hexyl, 2-hexyl, 3-hexyl, 1-methyl-1-ethyl-n-pentyl, 1,1,2-trimethyl-n-propyl, 1,2,2,-trimethyl-n-propyl, 3,3-dimethyl-n-butyl, 1-heptyl, 2-heptyl, 1-ethyl-1,2-dimethyl-n-propyl, 1-ethyl-2,2-dimethyl-n-propyl, and the like.

Examples of a $C_1$–$C_3$ alkyl group include methyl, ethyl, n-propyl, i-propyl, and the like.

Examples of a $C_2$–$C_{10}$ alkenyl group include ethenyl, 1-methylvinyl, 1-propenyl, 1-methyl-1-propenyl, 1-methyl-2-propenyl, 2-methyl-2-propenyl, 1-ethyl-2-vinyl, 1,2-dimethyl-1-propenyl, 1,2-dimethyl-2-propenyl, 1-ethyl-1-propenyl, 1-ethyl-2-propenyl, 1-methyl-1-butenyl, 1-methyl-2-butenyl, 2-methyl-1-butenyl, 1-i-propylvinyl, 1-methyl-1-pentenyl, allyl, 1-butenyl, 2-butenyl, 3-butenyl, 1-pentenyl, 2-pentenyl, 3-pentenyl, 4-pentenyl, 2,4-pentadienyl, 1-hexenyl, 2-hexenyl, 3-hexenyl, 4-hexenyl, 5-hexenyl, 2,4-hexadienyl, 1-heptenyl, 1-octenyl, 1-nonenyl, 1-decenyl, and the like.

Examples of a $C_2$–$C_{10}$ alkynyl group include ethynyl, propargyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, and the like.

Examples of a $C_3$–$C_{10}$ cycloalkyl group include cyclopropyl, 1-methyl-c-propyl, 2-methyl-c-propyl, c-propylmethyl, 4-methyl-c-hexyl, cyclobutyl, cyclopentyl, cyclohexyl, cycloheptanyl, cyclooctanyl, cyclononanyl, cyclodecanyl, bicyclo[2.2.1heptyl, bicyclo[3.1.1]heptyl, bicyclo[2.2.2]octyl, 1-adamantyl, 2-adamantyl, and the like.

Examples of a $C_3$–$C_7$ cycloalkyl group include cyclopropyl, 1-methyl-c-propyl, 2-methyl-c-propyl, c-propylmethyl, 4-methyl-c-hexyl, cyclobutyl, cyclopentyl, cyclohexyl, cycloheptyl, and the like.

Examples of a $C_3$–$C_7$ cycloalkenyl group include 1-cyclohexenyl, 2-cyclohexenyl, 3-cyclohexenyl, cyclopentadienyl, 2-bicyclo[2.2.1]heptenyl, 2,5-bicyclo [2.2.1]heptadienyl, and the like.

Examples of a $C_1$–$C_7$ alkoxy group include methoxy, ethoxy, n-propoxy, i-propoxy, n-butoxy, i-butoxy, s-butoxy, t-butoxy, pentyloxy, hexyloxy, heptyloxy, and the like.

Examples of a substituted silyl group include trimethylsilyl, triethylsilyl, tri-n-propylsilyl, tri-i-propylsilyl, tri-n-butylsilyl, tri-i-butylsilyl, tri-n-hexylsilyl, dimethylethylsilyl, dimethyl-n-propylsilyl, dimethyl-n-butylsilyl, dimethyl-i-butylsilyl, dimethyl-tert-butylsilyl, dimethyl-n-pentylsilyl, dimethyl-n-octylsilyl, dimethylcyclohexylsilyl, dimethylhexylsilyl, dimethyl-2,3-dimethylpropylsilyl, dimethyl-2-(bicycloheptyl)silyl, dimethylbenzylsilyl, dimethylphenylsilyl, dimethyl-p-tolylsilyl, dimethylflophemesylsilyl, methyldiphenylsilyl, triphenylsilyl, diphenyl-t-butylsilyl, tribenzylsilyl, diphenylvinylsilyl, diphenyl-n-butylsilyl, phenylmethylvinylsilyl, and the like.

Examples of a $C_1$–$C_{14}$ aliphatic acyl group include formyl, acetyl, propionyl, butyryl, isobutyryl, valeryl, isovaleryl, pivaloyl, lauroyl, myristoyl, acryloyl, propioloyl, methacryloyl, crotonoyl, and the like.

Examples of a $C_6$–$C_{10}$ aromatic acyl group include benzoyl, 2-toluoyl, 3-toluoyl, 4-toluoyl, α-naphthoyl, β-naphthoyl, cinnamoyl, and the like.

Examples of a $C_6$–$C_{14}$ aromatic group include phenyl, α-naphthyl, β-naphthyl, 1-indenyl, 2-indenyl, 3-indenyl, 4-indenyl, 5-indenyl, 6-indenyl, 7-indenyl, 1-indanyl, 2-indanyl, 4-indanyl, 5-indanyl, 1-fluorenyl, 2-fluorenyl, 3-fluorenyl, 4-fluorenyl, 9-fluorenyl and the like.

Examples of a $C_4$–$C_{12}$ heterocyclic aromatic group include 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 3-furazanyl, 1-pyrazolyl, 3-pyrazolyl, 4-pyrazolyl, 3-oxopyrazol-1-yl, 3-oxopyrazol-2-yl, 3-oxopyrazol-3-yl, 3-oxopyrazol-4-yl, 4-oxopyrazol-3-yl, 1-imidazolyl, 2-imidazolyl, 4-imidazolyl, 2-oxoimidazol-1-yl, 2-oxoimidazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,2, 4-triazol-4-yl, 1,2,4(2H,4H)-triazol-3-on-2-yl, 1,2,4-(2H, 4H)-triazol-3-on-4-yl, 1,2,4(2H,4H)-triazol-3-on-5-yl, 1,2,4 (1H,2H)-triazol-3-on-1-yl, 1,2,4(1H,2H)-triazol-3-on-2-yl, 1,2,4(1H,2H)-triazol-3-on-5-yl, 1-tetrazolyl, 2-tetrazolyl, 5-tetrazolyl, 2-pyranyl, 3-pyranyl, 4-pyranyl, 2-pyridyl, 3-pyridyl, 4-pyridyl, 2-pyridon-1-yl, 2-pyridon-3-yl, 2-pyridon-4-yl, 2-pyridon-5-yl, 2-pyridon-6-yl, 4-pyridon-1-yl, 4-pyridon-2-yl, 4-pyridon-3-yl, 3-pyridazinyl, 4-pyridazinyl, 3(2H)-pyridazinon-2-yl, 3(2H)-pyridazinon-4-yl, 3(2H)-pyridazinon-5-yl, 3(2H)-pyridazinon-6-yl, 4(3H)-pyridazinon-1-yl, 4(1H)-pyridazinon-3-yl, 4(1H)-pyridazinon-1-yl, 4(1H)-pyridazinon-6-yl, 2-pyrimidinyl, 4-pyrimidinyl, 5-pyrimidinyl, 2(1H)-pyrimidinon-1-yl, 2(1H)-pyrimidinon-4-yl, 2(1H)-pyrimidinon-5-yl, 2(1H)-pyrimidinon-6-yl, 4(3H)-pyrimidinon-2-yl, 4(3H)-pyrimidinon-3-yl, 4(3H)-pyrimidinon-5-yl, 4(3H)-pyrimidinon-6-yl, 4(1H)-pyrimidinon-1-yl, 4(1H)-pyrimidinon-2-yl, 4(1H)-pyrimidinon-5-yl, 4(1H)- pyrimidinon-6-yl, 2-pyrazinyl, 2(1H)-pyrazin-1-yl, 2(1H)-pyrazin-3-yl, 2(1H)-pyrazin-5 -yl, 2(1H)-pyrazin-6-yl, 1,2,3-triazin-4-yl, 1,2,3-triazin-5-yl, 1,2,4-triazin-3-yl, 1,2,4-triazin-5-yl, 1,2,4-triazin-6-yl, 1,2,3,4-tetrazin-5-yl, 1,2,4,5-tetrazin-3-yl, 1-indolyl, 2-indolyl, 3-indolyl, 4-indolyl, 5-indolyl, 6-indolyl, 7-indolyl, 2-quinolyl, 3-quinolyl, 4-quinolyl, 5-quinolyl, 6-quinolyl, 7-quinolyl, 8-quinolyl, 2-quinolon-1-yl, 2-quinolon-3-yl, 2-quinolon-4-yl, 2-quinolon-5-yl, 2-quinolon-6-yl, 2-quinolon-7-yl, 2-quinolon-8-yl, 4-quinolon-1-yl, 4-quinolon-2-yl, 4-quinolon-3-yl, 4-quinolon-5-yl, 4-quinolon-6-yl, 4-quinolon-7-yl, 4-quinolon-8-yl, 2-benzofuranyl, 3-benzofuranyl, 4-benzofuranyl, 5-benzofuranyl, 6-benzofuranyl, 7-benzofuranyl, 2-benzothienyl, 3-benzothienyl, 4-benzothienyl, 5-benzothienyl, 6-benzothienyl, 7-benzothienyl, 1-isoquinolyl, 3-isoquinolyl, 4-isoquinolyl, 5-isoquinolyl, 6-isoquinolyl, 7-isoquinolyl, 8-isoquinolyl, 1-isoquinolon-2-yl, 1-isoquinolon-3-yl, 1-isoquinolon-4-yl, 1-isoquinolon-5-yl, 1-isoquinolon-6-yl, 1-isoquinolon-7-yl, 1-isoquinolon-8-yl, 3-isoquinolon-2-yl, 3-isoquinolon-4-yl, 3-isoquinolon-5-yl, 3-isoquinolon-6-yl, 3-isoquinolon-7-yl, 3-isoquinolon-8-yl, 2-benzoxazolyl, 4-benzoxazolyl, 5-benzoxazolyl, 6-benzoxazolyl, 7-benzoxazolyl, 2-benzothiazolyl, 4-benzothiazolyl, 5-benzothiazolyl, 6-benzothiazolyl, 7-benzothiazolyl, 1-benzopyrazolyl, 2-benzopyrazolyl, 3-benzopyrazolyl, 4-benzopyrazolyl, 5-benzopyrazolyl, 6-benzopyrazolyl, 7-benzopyrazolyl, 1 -benzimidazolyl, 2-benzimidazolyl, 4-benzimidazolyl, 5-benzimidazolyl, 1-benzotriazolyl, 4-benzotriazolyl, 5-benzotriazolyl, 2-benzopyranyl, 3-benzopyranyl, 4-benzopyranyl, 5-benzopyranyl, 6-benzopyranyl, 7-benzopyranyl, 8-benzopyranyl, 1-indolizinyl, 2-indolizinyl, 3-indolizinyl, 5-indolizinyl, 6-indolizinyl, 7-indolizinyl, 8-indolizinyl, 2-purinyl, 6-purinyl, 7-purinyl, 8-purinyl, 1-phthalazinyl, 5-phthalazinyl, 6-phthalazinyl, 1-oxophthalazin-2-yl, 1-oxophthalazin-4-yl, 1-oxophthalazin-5-yl, 1-oxophthalazin-6-yl, 1-oxophthalazin-7-yl, 1-oxophthalazin-8-yl, 2-naphthyridinyl, 3-naphthyridinyl, 4-naphthyridinyl, 2-quinoxalinyl, 5-quinoxalinyl, 6-quinoxalinyl, 2-quinazolinyl, 4-quinazolinyl, 5-quinazolinyl, 6-quinazolinyl, 7-quinazolinyl, 8-quinazolinyl, 3-cinnolinyl, 4-cinnolinyl, 5-cinnolinyl, 6-cinnolinyl, 7-cinnolinyl, 8-cinnolinyl, 1,4-benzodioxan-2-yl, 1,4-benzodioxan-5-yl, 1,4-benzodioxan-6-yl, 1,4-oxonaphthalen-2-yl, 1,4-oxonaphthalen-5-yl, 1,4-oxonaphthalen-6-yl, 2,3-dihydro-4-benzofuranyl, 2,3-dihydro-5-benzofuranyl, 2,3-dihydro-6-benzofuranyl, 2,3-dihydro-7-benzofuranyl, 1,4-benzothiazin-2-yl, 1,4-benzothiazin-3-yl, 1,4-benzothiazin-4-yl, 1,4-benzothiazin-5-yl, 1,4-benzothiazin-6-yl, 1,4-benzothiazin-7-yl, 1,4-benzothiazin-8-yl, 2-pteridinyl, 4-pteridinyl, 6-pteridinyl, 7-pteridinyl, pyrazolo[1,5-a]pyrimidin-2-yl, pyrazolo[1,5-a]pyrimidin-3-yl, pyrazolo[1,5-a]pyrimidin-5-yl, pyrazolo[1,5-a]pyrimidin-6-yl, pyrazolo[1,5-a]pyrimidin-7-yl, pyrazolo[5,1-c][1,2,4]triazin-3-yl, pyrazolo[5,1-c][1,2,4]triazin-4-yl, pyrazolo[5,1-c][1,2,4]triazin-7-yl, pyrazolo[5,1-c][1,2,4]triazin-8-yl, thiazolo[3,2-b]triazol-2-yl, thiazolo[3,2-b]triazol-5-yl, thiazolo[3,2-b]triazol-6-yl, benzopyrano[2,3-b]pyridin-2-yl, benzopyrano[2,3-b]pyridin-3-yl, benzopyrano[2,3-b]pyridin-4-yl, benzopyrano[2,3-b]pyridin-5-yl, benzopyrano[2,3-b]pyridin-6-yl, benzopyrano[2,3-b]pyridin-7-yl, benzopyrano[2,3-b]pyridin-8-yl, benzopyrano[2,3-b]pyridin-9-yl, 5H-benzopyrano[2,3-b]pyridin-5-on-2-yl, 5H-benzopyrano[2,3-b]pyridin-5-on-3-yl, 5H-benzopyrano[2,3-b]pyridin-5-on-4-yl, 5H-benzopyrano[2,3-b]pyridin-5-on-6-yl, 5H-benzopyrano[2,3-b]pyridin-5-on-7-yl, 5H-benzopyrano[2,3-b]pyridin-5-on-8-yl, 1-xanthenyl, 2-xanthenyl, 3-xanthenyl, 4-xanthenyl, 9-xanthenyl, 1-phenoxathiinyl, 2-phenoxathiinyl, 3-phenoxathiinyl, 4-phenoxathiinyl, 1-carbazolyl, 2-carbazolyl, 3-carbazolyl, 4-carbazolyl, 9-carbazolyl, 1-acridinyl, 2-acridinyl, 3-acridinyl, 4-acridinyl, 9-acridinyl, 1-phenazinyl, 2-phenazinyl, 3-phenazinyl, 4-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 1-thianthrenyl, 2-thianthrenyl, 3-thianthrenyl, 4-thianthrenyl, 6-thianthrenyl, 7-thianthrenyl, 8 -thianthrenyl, 9-thianthrenyl, and the like.

Examples of a $C_4$–$C_6$ heterocycloaliphatic group include 1-piperidyl, 2-piperidyl, 3-piperidyl, 4-piperidyl, 1-pyrrolidinyl, 2-pyrrolidinyl, 3-pyrrolidinyl, 1-imidazolidinyl, 2-imidazolidinyl, 4-imidazolidinyl, 1-pyrazolidinyl, 3-pyrazolidinyl, 4-pyrazolidinyl, 2-morpholinyl, 3-morpholinyl, 4-morpholinyl, 2-tetrahydrofuranyl, 3-tetrahydrofuranyl, and the like.

In the present specification, "n" means normal, "i" means iso, "s" means secondary, "t" means tertiary, "c" means cyclo, "Me" means methyl, "Et" means ethyl, "Pr" means propyl, "Bu" means butyl, "Pen" means pentyl, "Hex" means hexyl, "Ph" means phenyl, and "Hal" means halogen.

Among these compounds, there is a compound having an asymmetric carbon atom at the 5-position of thiazolidine ring. The compound having the above formula (I) includes all of these optical isomers and their mixtures.

Preferable Examples (1) to (10) of the compound of the formula (I) of the present invention are further illustrated hereinafter.

(1) A pyridine type thiazolidine compound of the formula (I) and its salt, wherein:

$X^2$ is S or O;

Y is $CR^6R^7$ (wherein $R^6$ is a hydrogen atom or a $C_1$–$C_3$ alkyl group and $R^7$ is a hydrogen atom or a $C_1$–$C_3$ alkyl group or forms a bond together with $R^4$);

Z is -A-B (wherein A is a divalent $C_1$–$C_6$ saturated or $C_2$–$C_6$ unsaturated hydrocarbon group which may be substituted with at most 3 hydroxy, oxo and $C_1$–$C_7$ alkyl groups, and B is $C_3$–$C_{10}$ cycloalkyl, $C_3$–$C_7$ cycloalkenyl, $C_6$–$C_{14}$ aromatic and $C_4$–$C_{12}$ heterocyclic aromatic groups, which may have at most 5 substituents in total (said heterocyclic aromatic group may contain at most 5 hetero atoms selected from the group consisting of an oxygen atom, a sulfur atom and a nitrogen atom as constituents for the heterocyclic ring), or a $C_4$–$C_6$ heterocycloaliphatic group (said heterocycloaliphatic group may contain at most 3 hetero atoms selected from the group consisting of an oxygen atom, a sulfur atom and a nitrogen atom as constituents for the heterocyclic ring)), among groups of B, said $C_3$–$C_{10}$ cycloalkyl group being cyclopropyl, cyclobutyl, cyclopentyl, cyclohexyl, cycloheptanyl, cyclooctanyl, cyclononanyl, cyclodecanyl, bicyclo[2.2.1]heptyl, bicyclo[3.1.1] heptyl, bicyclo[2.2.2]octyl, 1-adamantyl or 2-adamantyl, said $C_3$–$C_7$ cycloalkenyl group being 1-cyclohexenyl, 2-cyclohexenyl, 3-cyclohexenyl, cyclpentadienyl, 2-bicylo[2.2.1]heptenyl or 2,5-bicyclo [2.2.1]heptadienyl, said $C_6$–$C_{14}$ aromatic group being phenyl, α-naphthyl, β-naphthyl, 1-indenyl, 2-indenyl, 3-indenyl, 4-indenyl, 5-indenyl, 6-indenyl, 7-indenyl, 1-indanyl, 2-indanyl, 4-indanyl, 5-indanyl, 1-fluorenyl, 2-fluorenyl, 3 -fluorenyl, 4-fluorenyl or 9-fluorenyl, said $C_4$–$C_{12}$ heterocyclic aromatic group being 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 3-furazanyl, 1-pyrazolyl, 3-pyrazolyl, 4-pyrazolyl, 3-oxopyrazol-1-yl, 3-oxopyrazol-2-yl, 3-oxopyrazol-3-yl, 3-oxopyrazol-4-yl, 4-oxopyrazol-3-yl, 1-imidazolyl, 2-imidazolyl, 4-imidazolyl, 2-oxoimidazol-1-yl, 2-oxoimidazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, 1,2,4(2H,4H)-triazol-3-on-2-yl, 1,2,4-(2H,4H)-triazol-3-on-4-yl, 1,2,4(2H,4H)-triazol-3-on-5-yl, 1,2,4(1H,2H)-triazol-3-on-1-yl, 1,2,4(1H,2H)-triazol-3-on-2-yl, 1,2,4(1H,2H)-triazol-3-on-5-yl, 1-tetrazolyl, 2-tetrazolyl, 5-tetrazolyl, 2-pyranyl, 3-pyranyl, 4-pyranyl, 2-pyridyl, 3-pyridyl, 4-pyridyl, 2-pyridon-1-yl, 2-pyridon-3-yl, 2-pyridon-4-yl, 2-pyridon-5-yl, 2-pyridon-6-yl, 4-pyridon-1-yl, 4-pyridon-2-yl, 4-pyridon-3-yl, 3-pyridazinyl, 4-pyridazinyl, 3(2H)-pyridazinon-2-yl, 3(2H)-pyridazinon-4-yl, 3(2H)-pyridazinon-5-yl, 3(2H)-pyridazinon-6-yl, 4(1H)-pyridazinon-1-yl, 4(1H)-pyridazinon-3-yl, 4(1H)-pyridazinon-5-yl, 4(1H)-pyridazinon-6-yl, 2-pyrimidinyl, 4-pyrimidinyl, 5-pyrimidinyl, 2(1H)-pyrimidinon-1-yl, 2(1H)-pyrimidinon-4-yl, 2(1H)-pyrimidinon-5-yl, 2(1H)-pyrimidinon- 6-yl, 4(3H)-pyrimidinon-2-yl, 4(3H)-pyrimidinon-3-yl, 4(3H)-pyrimidinon-5-yl, 4(3H)-pyrimidinon-6-yl, 4(1H)-pyrimidinon-1-yl, 4(1H)-pyrimidinon-2-yl, 4(1H)-pyridiminon-5-yl, 4(1H)-pyrimidinon-6-yl, 2-pyrazinyl, 2(1H)-pyrazin-1-yl, 2(1H)-pyrazin-3-yl, 2(1H)-pyrazin-5-yl, 2(1H)-pyrazin-6-yl, 1,2,3-triazin-4-yl, 1,2,3-triazin-5-yl, 1,2,4-triazin-3-yl, 1,2,4-triazin-5-yl, 1,2,4-triazin-6-yl, 1,2,3,4-tetrazin-5-yl, 1,2,4,5-tetrazin-3-yl, 1-indolyl, 2-indolyl, 3-indolyl, 4-indolyl, 5-indolyl, 6-indolyl, 7-indolyl, 2-quinolyl, 3-quinolyl, 4-quinolyl, 5-quinolyl, 6-quinolyl, 7-quinolyl, 8-quinolyl, 2-quinolon-1-yl, 2-quinolon-3-yl, 2-quinolon-4-yl, 2-quinolon-5-yl, 2-quinolon-6-yl, 2-quinolon-7-yl, 2-quinolon-8-yl, 4-quinolon-1-yl, 4-quinolon-2-yl, 4-quinolon-3-yl, 4-quinolon-5-yl, 4-quinolon-6-yl, 4-quinolon-7-yl, 4-quinolon-8-yl, 2-benzofuranyl, 3-benzofuranyl, 4-benzofuranyl, 5-benzofuranyl, 6-benzofuranyl, 7-benzofuranyl, 2-benzothienyl, 3-benzothienyl, 4-benzothienyl, 5-benzothienyl, 6-benzothienyl, 7-benzothienyl, 1-isoquinolyl, 3-isoquinolyl, 4-isoquinolyl, 5-isoquinolyl, 6-isoquinolyl, 7-isoquinolyl, 8-isoquinolyl, 1-isoquinolon-2-yl, 1-isoquinolon-3-yl, 1-isoquinolon-4-yl, 1-isoquinolon-5-yl, 1-isoquinolon-6-yl, 1-isoquinolon-7-yl, 1-isoquinolon-8-yl, 3-isoquinolon-2-yl, 3-isoquinolon-4-yl, 3-isoquinolon-5-yl, 3-isoquinolon-6-yl, 3-isoquinolon-7-yl, 3-isoquinolon-8-yl, 2-benzoxazolyl, 4-benzoxazolyl, 5-benzoxazolyl, 6-benzoxazolyl, 7-benzoxazolyl, 2-benzothiazolyl, 4-benzothiazolyl, 5-benzothiazolyl, 6-benzothiazolyl, 7-benzothiazolyl, 1-benzopyrazolyl, 2-benzopyrazolyl, 3-benzopyrazolyl, 4-benzopyrazolyl, 5-benzopyrazolyl, 6-benzopyrazolyl, 7-benzopyrazolyl, 1-benzimidazolyl, 2-benzimidazolyl, 4-benzimidazolyl, 5-benzimidazolyl, 1-benzotriazolyl, 4-benzotriazolyl, 5-benzotriazolyl, 2-benzopyranyl, 3-benzopyranyl, 4-benzopyranyl, 5-benzopyranyl, 6-benzopyranyl, 7-benzopyranyl, 8-benzopyranyl, 1-indolizinyl, 2-indolizinyl, 3-indolizinyl, 5-indolizinyl, 6-indolizinyl, 7-indolizinyl, 8-indolizinyl, 2-purinyl, 6-purinyl, 7-purinyl, 8-purinyl, 1-phthalazinyl, 5-phthalazinyl, 6-phthalazinyl, 1-oxophthalazin-2-yl, 1-oxophthalazin-4-yl, 1-oxophthalazin-5-yl, 1-oxophthalazin-6-yl, 1-oxophthalazin-7-yl, 1-oxophthalazin-8-yl, 2-naphthyridinyl, 3-naphthyridinyl, 4-naphthyridinyl, 2-quinoxalinyl, 5-quinoxalinyl, 6-quinoxalinyl, 2-quinazolinyl, 4-quinazolinyl, 5-quinazolinyl, 6-quinazolinyl, 7-quinazolinyl, 8-quinazolinyl, 3-cinnolinyl, 4-cinnolinyl, 5-cinnolinyl, 6-cinnolinyl, 7-cinnolinyl, 8-cinnolinyl, 1,4-benzodioxan-2-yl, 1,4-benzodioxan-5-yl, 1,4-benzodioxan-6-yl, 1,4-oxonaphthalen-2-yl, 1,4-oxonaphthalen-5-yl, 1,4-oxonaphthalen-6-yl, 2,3-dihydro-4-benzofuranyl, 2,3-dihydro-5-benzofuranyl, 2,3-dihydro-6-benzofuranyl, 2,3 -dihydro-7-benzofuranyl, 1,4-benzothiazin-2-yl, 1,4-benzothiazin-3-yl, 1,4-benzothiazin-4-yl, 1,4-benzothiazin-5-yl, 1,4-benzothiazin-6-yl, 1,4-benzothiazin-7-yl, 1,4-benzothiazin-8-yl, 2-pteridinyl, 4-pteridinyl, 6-pteridinyl, 7-pteridinyl, pyrazolo[1,5-a]pyrimidin-2-yl, pyrazolo[1,5-a]pyrimidin-3-yl, pyrazolo[1,5-a]pyrimidin-5-yl, pyrazolo[1,5-a]pyrimidin-6-yl, pyrazolo[1,5-a]pyrimidin-7-yl, pyrazolo(5,1-c][1,2,4]triazin-3-yl, pyrazolo[5,1-c][1,2,4]triazin-4-yl, pyrazolo[5,1-c][1,2,4]triazin-7-yl, pyrazolo[5,1-c][1,2,4]triazin-8-yl, thiazolo[3,2-b]triazol-2-yl, thiazolo[3,2-b]triazol-5-yl, thiazolo[3,2-b]triazol-6-yl, benzopyrano[2,3-b]pyridin-2-yl, benzopyrano[2,3-b]pyridin-3-yl, benzopyrano[2,3-b]pyridin-4-yl, benzopyrano[2,3-b]pyridin-5-yl, benzopyrano[2,3-b]pyridin-6-yl, benzopyrano[2,3-b]pyridin-7-yl, benzopyrano[2,3-b]pyridin-8-yl, benzopyrano[2,3-b]pyridin-9-yl, 5H-benzopyrano[2,3-b]pyridin-5-on-2-yl, 5H-benzopyrano[2,3-b]pyridin-5-on-3-yl, 5H-benzopyrano[2,3-b]pyridin-5-on-4-yl, 5H-benzopyrano[2,3-b]pyridin-5-on-6-yl, 5H-benzopyrano[2,3-b]pyridin-5-on-7-yl, 5H-benzopyrano[2,3-b]pyridin-5-on-8-yl, 1-xanthenyl, 2-xanthenyl, 3-xanthenyl, 4-xanthenyl, 9-xanthenyl, 1-phenoxathiinyl, 2-phenoxathiinyl, 3-phenoxathiinyl, 4-phenoxathiinyl, 1-carbazolyl, 2-carbazolyl, 3-carbazolyl, 4-carbazolyl, 9-carbazolyl, 1-acridinyl, 2-acridinyl, 3-acridinyl, 4-acridinyl, 9-acridinyl, 1-phenazinyl, 2 -phenazinyl, 3-phenazinyl, 4-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 1-thianthrenyl, 2-thianthrenyl, 3-thianthrenyl, 4-thianthrenyl, 6-thianthrenyl, 7-thianthrenyl, 8-thianthrenyl, or 9-thianthrenyl, and said $C_4$–$C_6$ heterocycloaliphatic group being 1-piperidyl, 2-piperidyl, 3-piperidyl, 4-piperidyl, 1-pyrrolidinyl, 2-pyrrolidinyl, 3-pyrrolidinyl, 1-imidazolidinyl, 2-imidazolidinyl, 4-imidazolidinyl, 1-pyrazolidinyl, 3-pyrazolidinyl, 4-pyrazolidinyl, 2-morpholinyl, 3-morpholinyl, 4-morpholinyl, 2-tetrahydrofuranyl, or 3-tetrahydrofuranyl;

each of $R^1$, $R^2$ and $R^3$ is independently a hydrogen atom, a $C_1$–$C_3$ alkyl group (which may be substituted with a hydroxyl group), a hydroxyl group or a halogen atom;

$R^4$ is a hydrogen atom or a $C_1$–$C_3$ alkyl group, or forms a bond together with $R^7$; and n is 0.

(2) A pyridine type thiazolidine compound of the formula (I) and its salt, wherein:

each of $R^1$, $R^2$ and $R^3$ is independently a hydrogen atom, a methyl group, a hydroxy group or a chlorine atom; and
B is
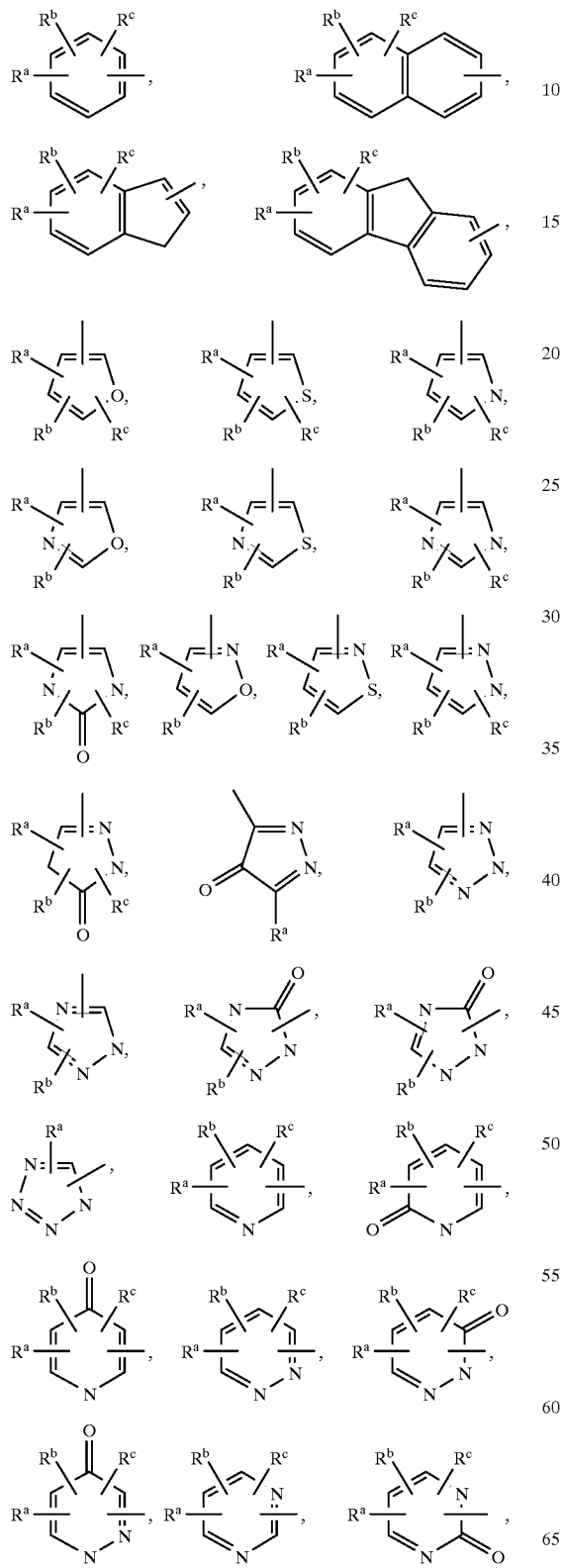
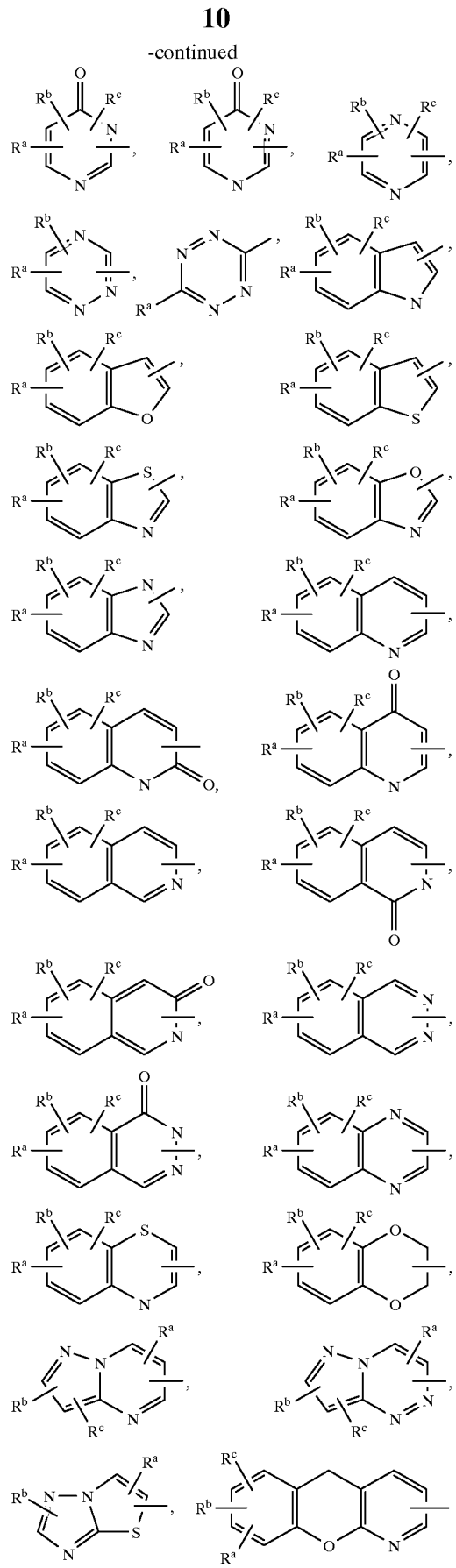

or 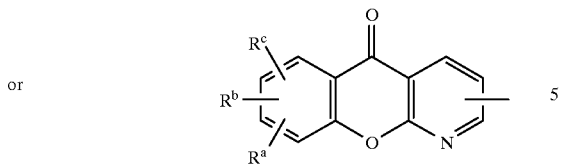

(wherein each $R^a$ and $R^b$ is independently a hydrogen atom, a $C_1$–$C_7$ alkyl group, a $C_3$–$C_7$ cycloalkyl group, a $C_3$–$C_7$ cycloalkenyl group (said alkyl, cycloalkyl and cycloalkenyl groups may be substituted with a hydroxyl group), a hydroxy group, a $C_1$–$C_7$ alkoxy group, a $C_1$–$C_7$ alkylthio group, a fluorine atom, a chlorine atom, a bromine atom, a trifluoromethyl group, a nitro group, an amino group, a methylamino group, a dimethylamino group, an acetamide group, a methanesulfonylamide group, a carboxyl group, a $C_1$–$C_3$ alkoxycarbonyl group, a nitrile group, a carbamoyl group, a sulfamoyl group, a phenoxy group, a benzyloxy group, a phenyl, α-naphthyl, β-naphthyl, furanyl, thienyl, imidazolyl, pyridyl or benzyl group (each of said phenyl, α-naphthyl, β-naphthyl, furanyl, thienyl, imidazolyl, pyridyl and benzyl groups may be substituted with at most 5 substituents selected from the group consisting of phenyl, methyl, ethyl, n-propyl, isopropyl, cyclopropyl, n-butyl, isobutyl, s-butyl, t-butyl, n-hexyl, cyclohexyl, methoxy, ethoxy, n-propoxy, isopropoxy, methylthio, ethylthio, n-propylthio, isopropylthio, hydroxy, fluorine, chlorine, bromine, nitro and dimethylamino groups), a 1-tetrazolyl group, a 3-tetrazolyl group, a 5-tetrazolyl group, a thiazolidindion-5-yl group or a thiazolidindion-5-yl methyl group, and $R^c$ is a hydrogen atom, a $C_1$–$C_7$ alkyl group, a $C_3$–$C_7$ cycloalkyl group or a hydroxymethyl group).

(3) A pyridine type thiazolidine compound of the formula (I) and its salt, wherein:

each of $R^1$, $R^2$, and $R^3$ is independently a hydrogen atom, a methyl group, a hydroxyl group or a chlorine atom; and B is

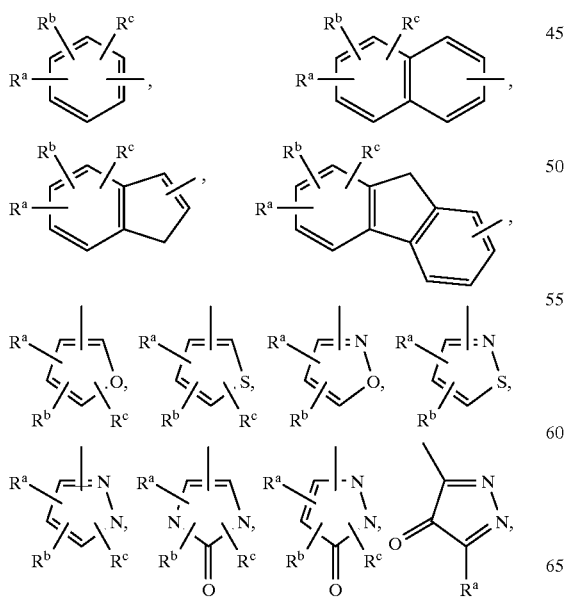

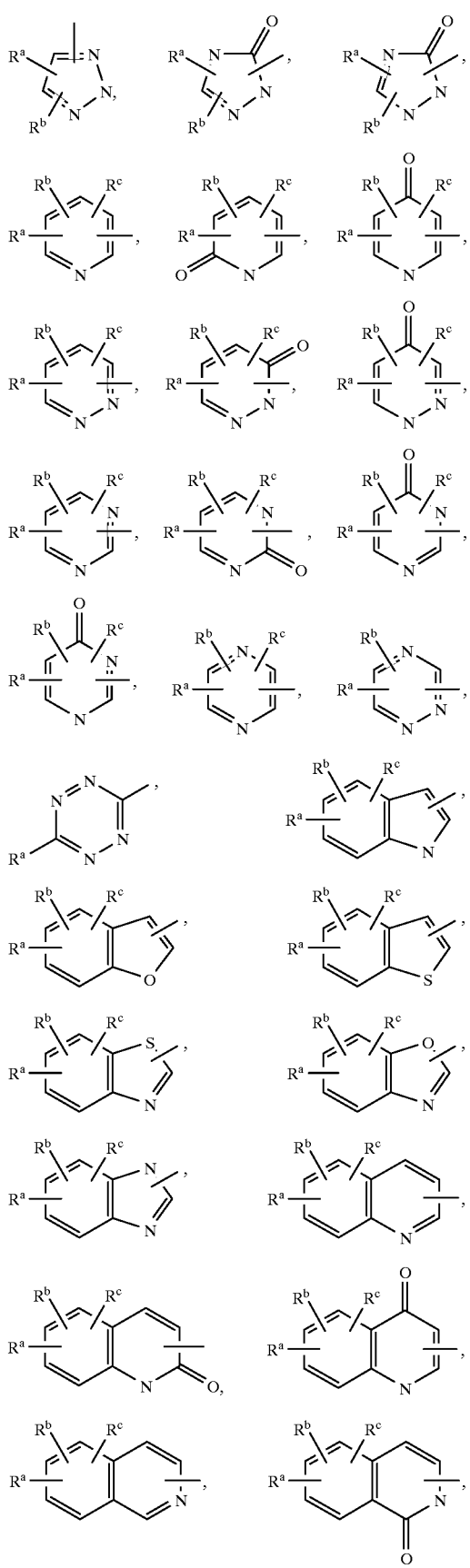

-continued

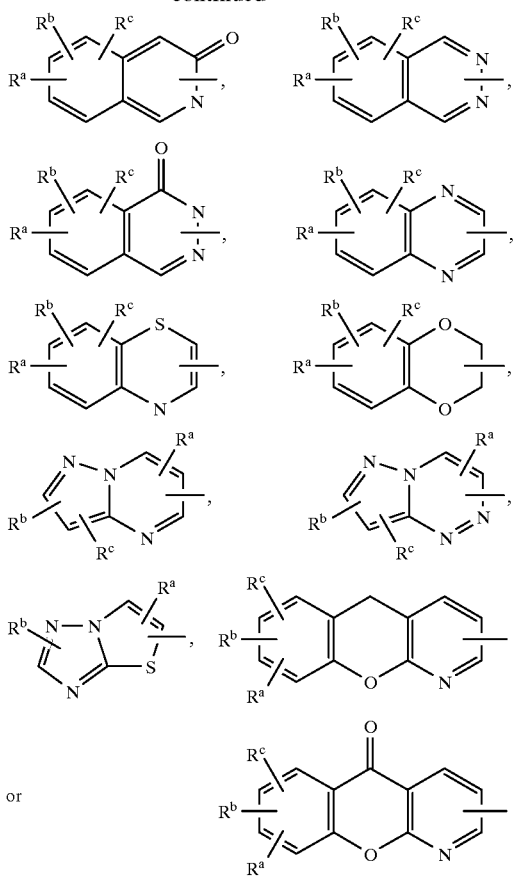

(wherein each of $R^a$ and $R^b$ is independently a hydrogen atom, a $C_1$–$C_7$ alkyl group, a $C_3$–$C_7$ cycloalkyl group, a $C_3$–$C_7$ cycloalkenyl group (said alkyl, cycloalkyl and cycloalkenyl group may be substituted with a hydroxy group), a hydroxy group, a $C_1$–$C_7$ alkoxy group, a $C_1$–$C_7$ alkylthio group, a fluorine atom, a chlorine atom, a bromine atom, a trifluoromethyl group, a nitro group, an amino group, a methylamino group, a dimethylamino group, an acetamide group, a methanesulfonylamide group, a carboxyl group, a $C_1$–$C_3$ alkoxycarbonyl group, a nitrile group, a carbamoyl group, a sulfamoyl group, a phenoxy group, a benzyloxy group, a phenyl, α-naphthyl, β-naphthyl, furanyl, thienyl, imidazolyl, pyridyl or benzyl group (said phenyl, α-naphthyl, β-naphthyl, furanyl, thienyl, imidazolyl, pyridyl and benzyl groups may be substituted with at most 5 substituents selected from the group consisting of phenyl, methyl, ethyl, n-propyl, isopropyl, cyclopropyl, n-butyl, isobutyl, s-butyl, t-butyl, n-hexyl, cyclohexyl, methoxy, ethoxy, n-propoxy, isopropoxy, methylthio, ethylthio, n-propylthio, isopropylthio, hydroxy, fluorine, chlorine, bromine, nitro and dimethylamino groups), a 1-tetrazolyl group, a 3-tetrazolyl group, a 5-tetrazolyl group, a thiazolidindion-5-yl group or a thiazolidindion-5-yl methyl group, and $R^c$ is a hydrogen atom, a $C_1$–$C_7$ alkyl group, a $C_3$–$C_7$ cycloalkyl group or a hydroxymethyl group).

(4) A pyridine type thiazolidine compound of the formula (I) and its salt, wherein:

$X^1$ is S:

$R^1$, $R^2$ and $R^3$ are a hydrogen atom;

Y is $CR^6R^7$ ($R^6$ is a hydrogen atom or a methyl group, and $R^7$ is a hydrogen atom or forms a bond together with $R^4$);

$R^4$ is a hydrogen atom or a methyl group, or forms a bond together with $R^7$; and A is a divalent $C_1$–$C_6$ saturated or $C_2$–$C_6$ unsaturated hydrocarbon group which may be substituted with at most 2 hydroxy, oxo and $C_1$–$C_7$ alkyl groups (provided that the first carbon atom bonded with the oxygen atom at the 5-position of the pyridine ring of the compound of the formula (I) is not substituted with a hydroxy group or an oxo group).

(5) A pyridine type thiazolidine compound of the formula (I) and its salt, wherein:

Y is —$CH_2$—; and $R^4$ is a hydrogen atom.

(6) A pyridine type thiazolidine compound of the formula (I) and its salt, wherein:

Y is $CHR^7$ ($R^7$ forms a bond together with $R^4$); and $R^4$ forms a bond together with $R^7$.

(7) A pyridine type thiazolidine compound of the formula (I) and its salt, wherein:

A is

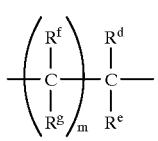

(wherein m is from 0 to 5, e ach of $R^d$ and $R^e$ is independently a hydrogen atom or a methyl group, and each of $R^f$ and $R^g$ is independently a hydrogen atom, a methyl group or a hydroxyl group, or $R^f$ and $R^g$ together form an oxo group, or adjacent $R^d$ and $R^f$ together form a double bond, or adjacent $R^d$, $R^f$, $R^e$ and $R^g$ together form a triple bond, or adjacent $R^f$'s together form a double bond when m is 2 to 5, or adjacent $R^f$ and $R^g$ together form a triple bond).

(8) A pyridine type thiazolidine compound of the formula (I) and its salt, wherein:

A is

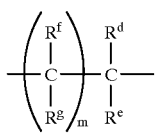

(wherein m is from 0 to 2, each of $R^d$ and $R^e$ is independently a hydrogen atom or a methyl group, and each of $R^f$ and $R^g$ is independently a hydrogen atom, a methyl group or a hydroxyl group, or $R^f$ and $R^g$ together form an oxo group, or adjacent $R^d$ and $R^f$ together form a double bond, or adjacent $R^d$, $R^f$, $R^e$ and $R^g$ together form a triple bond, or adjacent $R^f$'s together form a double bond when m is 2, or adjacent $R^f$ and $R^g$ together form a triple bond).

(9) A pyridine type thiazolidine compound of the formula (I) and its salt, wherein:

A is

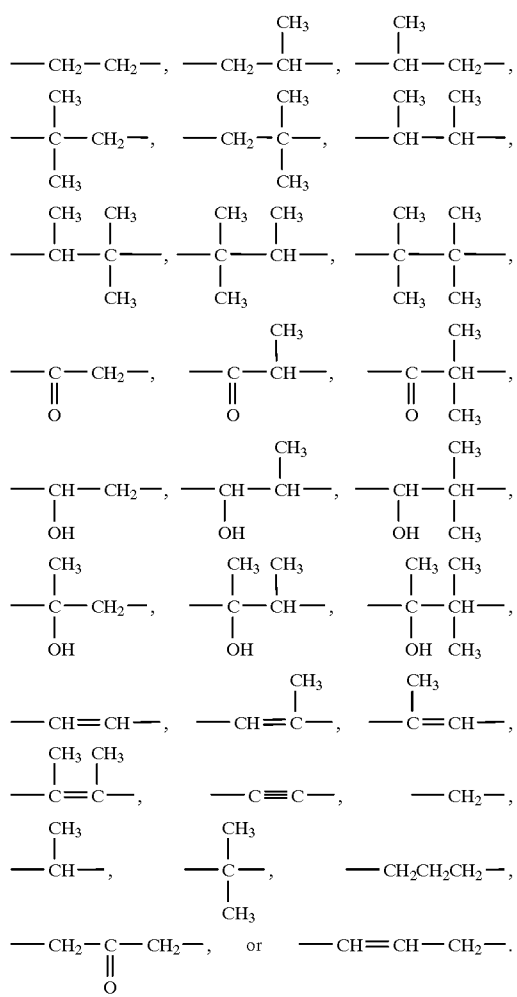

(10) A pyridine type thiazolidine compound of the formula (I) and its salt, wherein:

A is

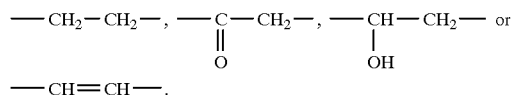

Since the compound having the above formula (I) of the present invention includes both acidic nitrogen on a thiazolidine ring and basic nitrogen on a pyridine ring in a molecule, it can form a pharmaceutically acceptable nontoxic salt with an appropriate base or acid if desired. The compound of the formula (I) can be used for the purpose of the present invention either in the free form or in the form of a pharmaceutically acceptable salt. Examples of the basic salt include an alkali metal salt (lithium salt, sodium salt, potassium salt and the like), an alkali earth metal salt (calcium salt, magnesium salt and the like), an aluminum salt, an ammonium salt which may be unsubstituted or substituted with a methyl, ethyl or benzyl group, an organic amine salt (methylamine salt, ethylamine salt, dimethylamine salt, diethylamine salt, trimethylamine salt, triethylamine salt, cyclohexylamine salt, ethylenediamine salt, bicyclohexylamine salt, ethanolamine salt, diethanolamine salt, triethanolamine salt, piperazine salt, dibenzylpiperidine salt, dehydroabietilamine salt, N,N'-bisdehydroabietilamine salt, benzathine(N,N'-dibenzylethylenediamine) salt, glucamine salt, meglumine(N-methylglucamine) salt, benetamine(N-benzylphenetylamine)salt, trometamine(2-amino-2-hydroxymethyl-1,3-propanediol)salt, choline salt, procaine salt), a basic amino acid salt (lysine salt, ornithine salt, arginine salt and the like), a pyridine salt, a collidine salt, a quinoline salt, and the like. Examples of an acid-addition salt include a mineral acid salt (hydrochloride, hydrobromide, sulfate, hydrogensulfate, nitrate, phosphate, hydrogenphosphate, dihydrogenphosphate and the like), an organic acid salt (formate, acetate, propionate, succinate, malonate, oxalate, maleate, fumarate, malate, citrate, tartrate, lactate, glutamate, asparate, picrate, carbonate and the like), a sulfonic acid salt (methanesulfonate, benzenesulfonate, toluenesulfonate and the like), and the like. Each of these salts can be prepared by a known method.

The compound having the formula (I), i.e. pyridine type thiazolidines, can be prepared by the following synthetic methods.

A reaction solvent used in the preparation is stable under the reaction conditions, and is preferably so inert as not to inhibit the reaction. Examples of the reaction solvent include water, alcohols (such as methanol, ethanol, propanol, butanol and octanol), cellosolves (such as methoxyethanol and ethoxyethanol), aprotic polar organic solvents (such as dimethylformamide, dimethylsulfoxide, dimethylacetamide, tetramethylurea, sulfolane and N,N-dimethylimidazolidinone), ethers (such as diethyl ether, diisopropyl ether, tetrahydrofuran and dioxane), aliphatic hydrocarbons (such as pentane, n-hexane, c-hexane, octane, decaline and petroleum ether), aromatic hydrocarbons (such as benzene, chlorobenzene, nitrobenzene, toluene, xylene and tetralin), halogenated hydrocarbons (such as chloroform, dichloromethane and dichloroethane), ketones (such as acetone, methyl ethyl ketone and methyl butyl ketone), lower aliphatic acid esters (such as methyl acetate, ethyl acetate and methyl propionate), alkoxy alkanes (such as dimethoxyethane and diethoxyethane), acetonitrile, and the like. These solvents are optionally selected depending on the reactivity of the aimed reaction, and are respectively used alone or in a mixture. In some cases, there are used as a non-aqueous solvent by using a dehydrating agent or a drying agent. The above-mentioned solvents are merely examples which can be used in the reaction of the present invention, and the present invention is not limited to these conditions.

Process 1

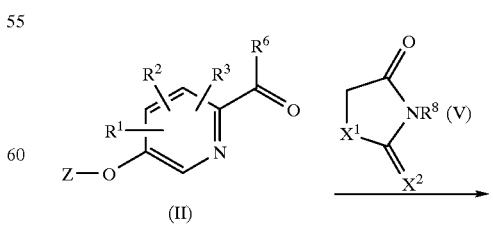

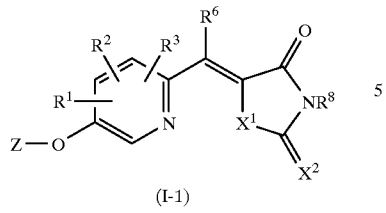

(I-1)

(wherein $R^1$, $R^2$, $R^3$, $R^6$, $X^1$, $X^2$ and Z are as defined above, and $R^8$ is a hydrogen atom or a protecting group of amide (such as Tr: trityl)).

A compound wherein $R^4$ and $R^7$ are bonded together in the formula (I), i.e. a compound of the formula (I-1), can be obtained by dehydration-condensation of a compound of the formula (II) and a compound of the formula (V). The compound of the formula (V) is a well known compound or can be synthesized by the method disclosed in "J. Prakt. Chem." (vol. 2, p. 253, 1909), "J. Prakt. Chem." (vol. 3, p. 45, 1919), "Chem. Ber." (vol. 118, p. 774, 1985), and German Laid Open Patent Publication No. DE-3045059. The compound of the formula (V) wherein $R^8$ is hydrogen, can be used in this reaction after protecting its basic amideproton with an appropriate substituent (such as TR: trityl) by a well known method.

This reaction is conducted usually in an appropriate organic solvent in the presence of base or acid. Examples of such a solvent include alcohols, cellosolves, aprotic polar organic solvents, ethers, aromatic hydrocarbons, halogenated hydrocarbons, alkoxyalkanes and acetonitrile.

Examples of the base and the acid include organic amines (such as dimethylamine, diethylamine, diisopropylamine, diisopropylethylamine, trimethylamine, triethylamine, piperidine, piperazine, pyrrolidine, morpholine, pyridine, methanolamine and ethanolamine), metal alkoxides (such as sodium methoxide, sodium ethoxide and lithium isopropoxide), inorganic alkali metal salts (such as potassium carbonate, sodium carbonate, sodium hydrogencarbonate, potassium hydrogencarbonate, sodium hydride, sodium acetate and potassium acetate), organic acids (such as acetic acid, trichloroacetic acid and trifluoroacetic acid), inorganic acids (such as phosphoric acid), and the like. These materials are selected appropriately depending on the reactivity of the aimed reaction.

This reaction can be accelerated by removing water formed during reaction out of the system by using an appropriate dehydrating agent such as molecular sieves and anhydrous sodium sulfate or by azeotropic distillation using Dean-Stark tube.

This reaction is conducted usually at a temperature ranging from 0° C. to a boiling point of a solvent used, preferably from 20° C. to 120° C., for from 0.5 to 30 hours.

Process 2

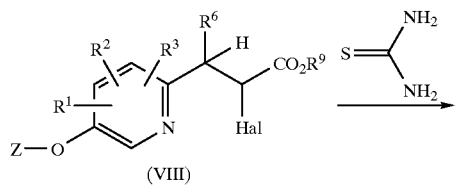

(VIII)

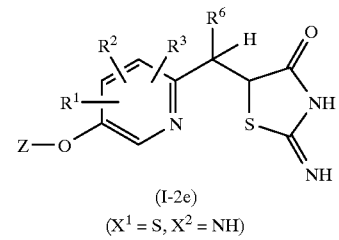

(I-2e)
($X^1$ = S, $X^2$ = NH)

(wherein $R^1$, $R^2$, $R^3$, $R^6$ and Z are as defined above, $R^9$ is $C_1$–$C_4$ alkyl such as methyl, ethyl, n-propyl, i-propyl, n-butyl and t-butyl, and Hal is a chlorine atom, a bromine atom or an iodine atom).

A compound of the formula (I) wherein $R^4$ and $R^7$ are hydrogen, $X^1$ is S and $X^2$ is NH, i.e. a compound of the formula (I-2e) ($R^4$, $R^7$=H, $X^1$=S, $X^2$=NH), can be obtained by reacting thiourea with a halocarboxylic acid ester of the formula (VIII).

This reaction is conducted usually in an appropriate organic solvent in the presence of base or acid. Examples of the solvent used include alcohols, cellosolves and aprotic polar organic solvents, and preferably sulfolane is used.

This reaction is conducted usually at a temperature ranging from 0° C. to a boiling point of a solvent used, preferably from 50° C. to 150° C., for 0.5 to 10 hours.

During the reaction, hydrogen halide is by-produced, but can be captured with an appropriate base to accelerate the reaction. Examples of the base thus used include organic amines (such as dimethylamine, diethylamine, diisopropylamine, diisopropylethylamine, trimethylamine, triethylamine, piperidine, piperazine, pyrrolidine, morpholine, pyridine, methanolamine and ethanolamine), inorganic alkali metal salts (such as sodium acetate and potassium acetate), and the like.

Process 3

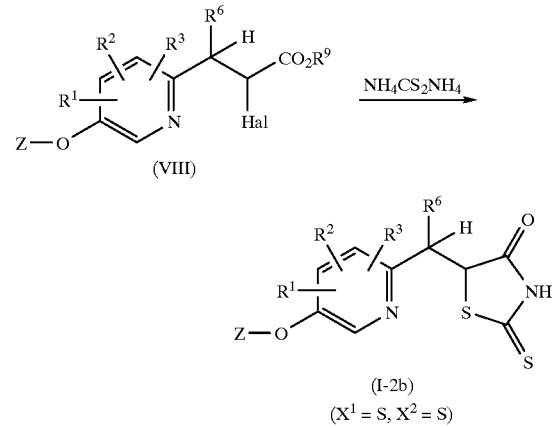

(I-2b)
($X^1$ = S, $X^2$ = S)

(wherein $R^1$, $R^2$, $R^3$, $R^6$, $R^9$, Z and Hal are as defined above).

A compound of the formula (I) wherein $R^4$ and $R^7$ are H, and $X^1$ and $X^2$ are S, i.e. a compound of the formula (I-2b) ($R^4$, $R^7$=H, $X^1$, $X^2$=S), can be obtained by reacting ammonium dithiocarbamate with a halocarboxylic acid ester of the formula (VIII).

This reaction is conducted usually in water or an appropriate organic solvent, or in a mixture thereof. Examples of the solvent thus used include alcohols, cellosolves and aprotic polar organic solvents.

This reaction is conducted usually at a temperature ranging from –10° C. to 50° C., preferably from 0° C. to 30° C., for 0.5 to 50 hours.

During this reaction, hydrogen halide is by-produced, but can be captured with an appropriate base to accelerate the reaction. Examples of the base thus used include organic amines (such as dimethylamine, diethylamine, diisopropylamine, diisopropylethylamine, trimethylamine, triethylamine, piperidine, piperazine, pyrrolidine, morpholine, pyridine, methanolamine and ethanolamine), inorganic alkali metal salts (such as potassium carbonate, sodium carbonate, sodium acetate and potassium acetate), and the like.

The addition product thus obtained is treated with an acid (such as hydrochloric acid) to obtain a compound of the formula (I-2b).

Process 4

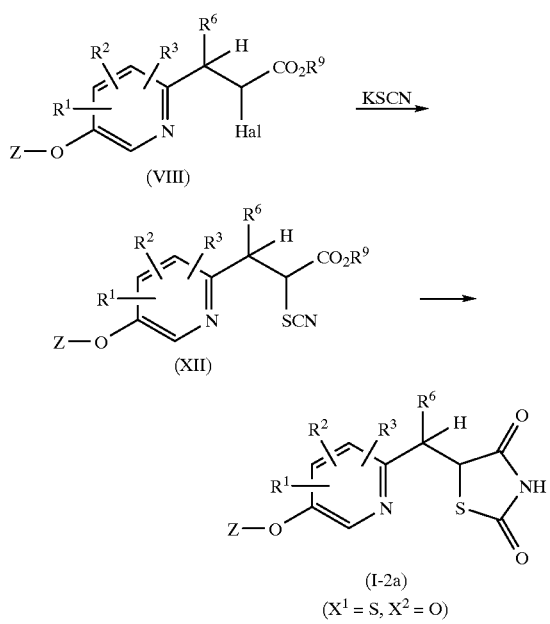

(wherein $R^1$, $R^2$, $R^3$, $R^6$, $R^9$, Z and Hal are as defined above).

A compound of the formula (I) wherein $R^4$ and $R^7$ are H, $X^1$ is S and $X^2$ is O, i.e. a compound of the formula (I-2a) ($R^4$, $R^7$=H, $X^1$=O, $X^2$=S), can be obtained by reacting an alkalithiocyanate (such as potassium thiocyanate or sodium thiocyanate) with a halocarboxylic acid ester of the formula (VIII) to prepare a compound of the formula (XII) and by treating the compound with an acid.

This reaction is conducted usually in an appropriate organic solvent. Examples of the solvent thus used include aprotic polar organic solvents.

This reaction is conducted usually at a temperature ranging from 50° C. to 150° C., preferably from 80° C. to 120° C., for 0.5 to 10 hours.

A compound of the formula (XII) is isolated, or it is further subjected to acid treatment in the reaction system without being isolated therefrom to obtain the aimed compound of the formula (I-2a). Examples of the acid thus used include hydrochloric acid, and the acid treatment is conducted in an alcohol or an aprotic polar organic solvent. This reaction is conducted at a temperature of from 50° C. to 150° C., preferably from 70° C. to 100° C., for 5 to 50 hours.

Process 5

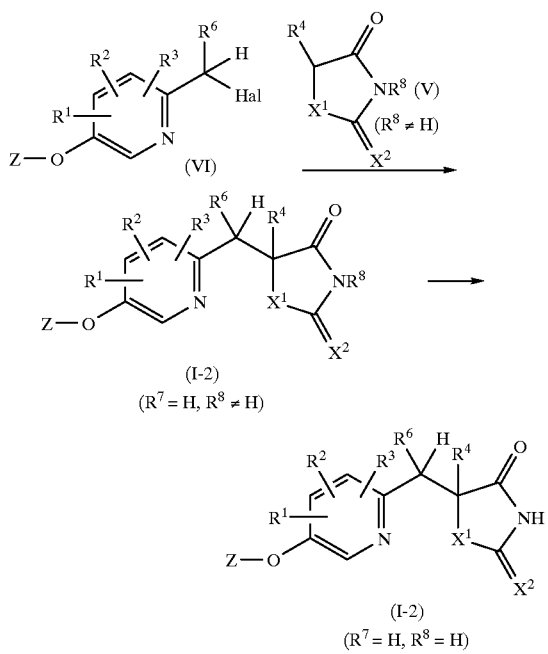

(wherein $R^1$, $R^2$ $R^3$, $R^4$, $R^6$, $R^8$, $X^1$, $X^2$, Z and Hal are as defined above).

A compound of the formula (I) wherein $R^7$ is hydrogen, i.e. a compound of the formula (I-2), can be obtained by reacting a compound of the formula (V) with a halopyridine of the formula (VI). The compound of the formula (V) used herein is a well known compound or can be synthesized by a method disclosed in "Ukr. Khim. Zr." (vol. 16, p. 545, 1950), "J. Med. Chem." (vol. 34, p. 1538, 1991), "J. Prakt. Chem." (vol. 2, 79, P. 253 (1909), "J. Prakt. Chem." (vol. 2, 99, P. 56 (1919) or Japanese Unexamined Patent Publication No. 216882/1984. The compound of the formula (V) wherein $R^8$ is hydrogen, is used in this reaction preferably after protecting its basic amide proton with an appropriate substituent (such as Tr: trityl) by a known method.

This reaction is conducted usually in an appropriate organic solvent in the presence of base. Examples of the solvent thus used include aprotic polar organic solvents, ethers and alkoxyalkanes. Examples of the base thus used include a strong base such as alkali metal amides (e.g. sodium amide and potassium amide). These materials are selected optionally depending on the reactivity of the aimed reaction.

Also, this reaction can be conducted in accordance with a method disclosed in "J. Amer. Chem. Soc." (vol. 87, p. 4588, 1965) or "J. Med. Chem." (vol. 34, p. 1538, 1991). In such a case, a compound of the formula (V) is reacted with magnesium methylcarbonate in an inert gas atmosphere such as nitrogen and in an aprotic polar organic solvent such as dimethylformamide to form a chelate compound, and the chelate compound thus formed is further reacted with a halopyridine of the formula (VI) to obtain a compound of the formula (I-2). This reaction is conducted usually at a temperature ranging from 20° C. to 150° C., preferably from 70° C. to 100° C. The reaction time varies depend ing on t he materials used, but the formation of the chelate compound takes from 0.5 to 2 hours and the reaction with the halopyridine takes from 0.5 to 5 hours.

In some cases, an amide group at the 3-position of thiazolidine of the compound of the formula (I-2) thus obtained may be deprotected by a well-known method. When $R^8$ is Tr (trityl), this method is conducted by using an organic acid such as trifluoroacetic acid and trichloroacetic acid or an inorganic acid such as hydrochloric acid and sulfuric acid. This reaction is conducted in the absence of a solvent or in the presence of a solvent such as ethers including tetrahydrofuran and dioxane and halogenated solvents including chloroform and dichloromethane, at a temperature ranging from 0° C. to 100° C., preferably from 10° C. to 50° C., for 0.1 to 5 hours.

Process 6

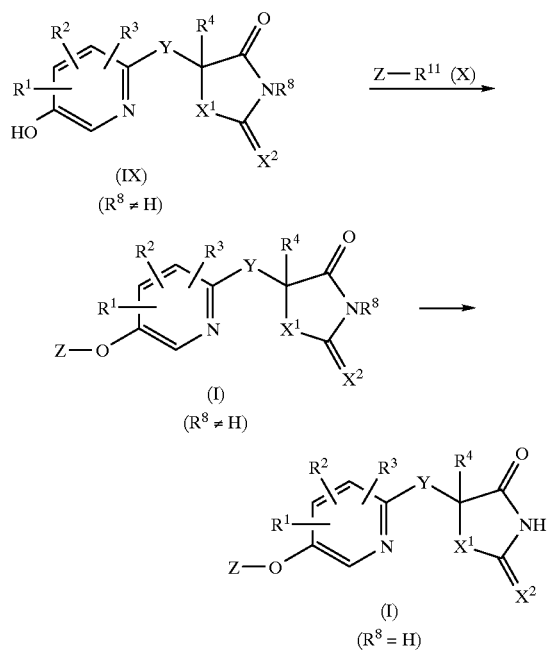

(wherein $R^1$, $R^2$, $R^3$, $R^4$, $R^8$, $X^1$ $X^2$, Y and Z are as defined above, and $R^{11}$ is an appropriate leaving group in nucleophilic substitution reaction, examples of which include a halogen such as chlorine, bromine and iodine, and an aromatic or aliphatic sulfonyloxy group such as p-toluenesulfonyloxy, benzenesulfonyloxy and methanesulfonyloxy).

Among compounds of formula (I), a compound wherein A is $COCH_2$ (m=1, $R^d$, $R^e$=H, $R^f$ and $R^g$ together represent oxo) can be obtained by using a compound of the formula (X) such as B—$COCH_2$—Hal (Z=B—$COCH_2$, $R^{11}$=Hal, B and Hal are substituents explained above). Such a compound is well known and is commercially available, or can be obtained by a well known method (for example, British Laid Open Patent Publication No. 1107677 discloses a compound wherein B is pyrrole, Japanese Unexamined Patent Publication No. 85372/1986 discloses a compound wherein B is oxazole or thiazole and U.S. Pat. No. 4,167,626 discloses a compound wherein B is triazole). Also, such a compound can be obtained by halogenating B—$COCH_3$ (for example, "Bull. Soc. Chim. Fr., p. 1760 (1973)" discloses a compound wherein B is furan, "Tetrahedron, 29(2), p. 413 (1973)" discloses a compound wherein B is thiophene, "J. Heterocyclic Chem., 27(5), p. 1209 (1990)" discloses a compound wherein B is pyrrole, "Bull. Soc. Chim. Fr., p. 540 (1988)", "Bull. Soc. Chim. Fr., p. 318 (1987)", "J. Heterocyclic Chem., 23(1), P. 275 (1986)", "Arch. Pharm., 316(7), p. 608 (1983)" and "Synlett., (7), p. 483 (1991)" disclose a compound wherein B is pyrazole, "J. Heterocyclic Chem., 17(8), p. 1723 (1980)" discloses a compound wherein B is imidazole, and "J. Chem. Soc. C(20), p. 2005 (1976)" and "Heterocycles, 26(3), p. 745 (1987)" disclose a compound wherein B is triazole) as a starting material by means of an appropriate well known halogenation method (e.g. a method disclosed in Japanese Unexamined Patent Publication No. 85372/1986). Also, such a compound can be obtained by subjecting B—$CO_2R'$ (R'=lower alkyl or substituted or unsubstituted benzyl) (for example, "Z. Chem., 9(1), p. 22 (1969)" and "Synth. Commun., 20(16), p. 2537 (1990)" disclose a compound wherein B is thiophene, "J. Org. Chem., 55(15), p. 4735 (1990)" and "Chem. Pharm. Bull., 17(3), p. 582 (1969)" disclose a compound wherein B is pyrrole, European Laid Open Patent Publication No. 506194 discloses a compound wherein B is imidazole, and "Chem. Ber., 117(3), p. 1194 (1984)" discloses a compound wherein B is pyrazole or triazole) as a starting material to an appropriate well known reduction-oxidation reaction (for example, reduction by diisobutyl aluminum hydride and then oxidation by manganese dioxide) to obtain B—CHO, and further by converting the product thus obtained to B—$COCH_2$-hal by an appropriate method (e.g. a method disclosed in "Tetrahedron Letters, p. 4661 (1972)").

A compound of the formula (I) can also be obtained by reacting a compound of the formula (X) with a hydroxy group at the 5-position of a compound of the formula (IX) by nucleophilic substitution reaction. The compound of the formula (IX) is preferably protected by substituting hydrogen of $R^8$ with an appropriate substituent (e.g. Tr: trityl).

This reaction is usually conducted in an appropriate organic solvent in the presence of base. Examples of the solvent used include aprotic polar organic solvents, ethers, aromatic hydrocarbons, hydrogenated hydrocarbons, alkoxyalkanes, acetonitrile, and the like.

Examples of the base thus used include organic amines (such as dimethylamine, diethylamine, diisopropylamine, diisopropylethylamine, trimethylamine, triethylamine, piperidine, piperazine, pyrrolidine, morpholine, pyridine, methanolamine and ethanolamine), metal alkoxides (such as sodium methoxide, sodium ethoxide, lithium isopropoxide and potassium t-butoxide), inorganic alkali metal salts (such as sodium hydroxide, potassium hydroxide, lithium hydroxide, potassium carbonate, sodium carbonate, sodium hydrogencarbonate, potassium hydrogencarbonate, sodium hydride, sodium acetate and potassium acetate), and alkali metal amides (such as sodium amide). These materials are selected appropriately depending on the reactivity of the aimed reaction.

This reaction is conducted usually at a temperature ranging from −20° C. to a boiling point of the solvent used, preferably from 20° C. to 150° C., for from 0.5 to 30 hours.

An amino group at the 3-position of thiazolidine of the compound of the formula (I) thus obtained may be deprotected by the method described in the above Process 5.

Process 7

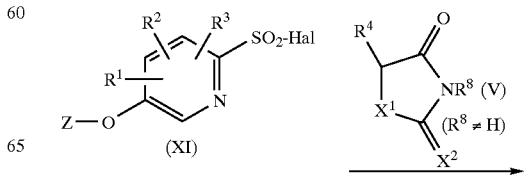

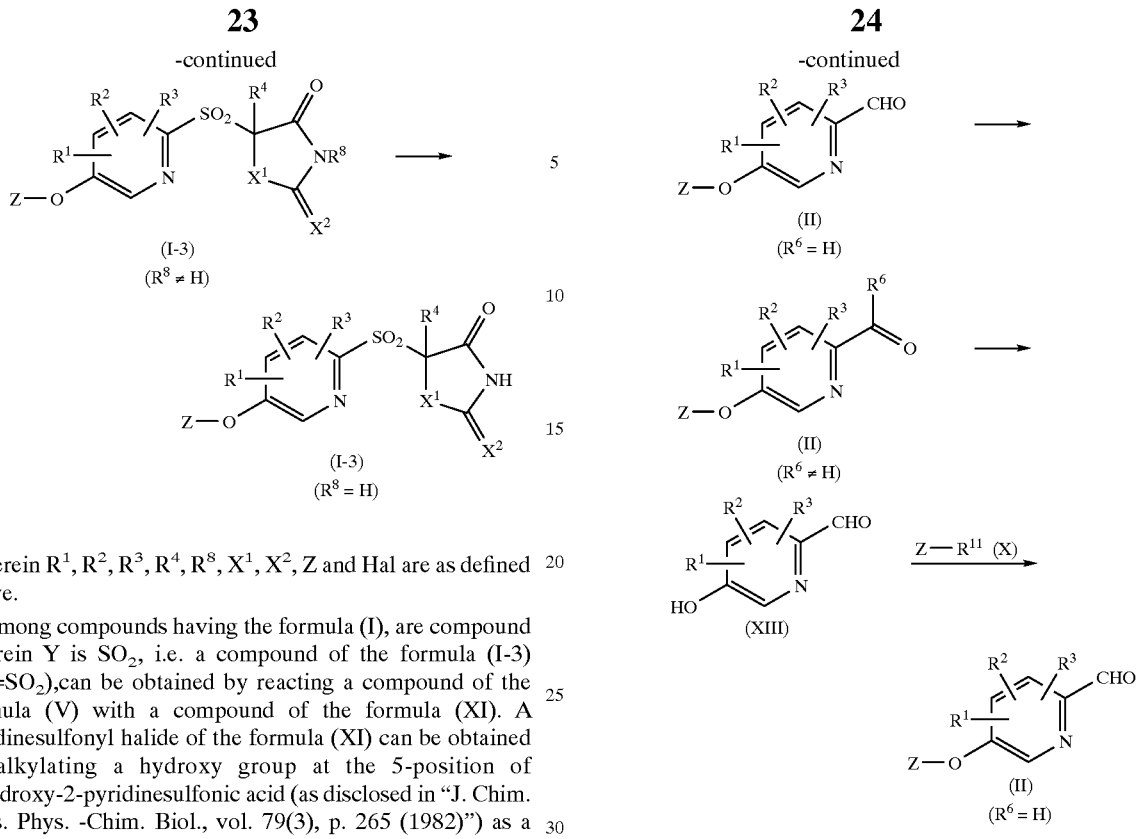

(wherein $R^1$, $R^2$, $R^3$, $R^4$, $R^8$, $X^1$, $X^2$, Z and Hal are as defined above).

Among compounds having the formula (I), are compound wherein Y is $SO_2$, i.e. a compound of the formula (I-3) (Y=$SO_2$), can be obtained by reacting a compound of the formula (V) with a compound of the formula (XI). A pyridinesulfonyl halide of the formula (XI) can be obtained by alkylating a hydroxy group at the 5-position of 5-hydroxy-2-pyridinesulfonic acid (as disclosed in "J. Chim. Phys. Phys. -Chim. Biol., vol. 79(3), p. 265 (1982)") as a starting material by means of an appropriate well known method, and further by halogenating the alkylated product with an appropriate halogenating agent (for example, $PCl_5$ as disclosed in "Org. Synth. Coll. vol. I, p. 84 (1941)" and "J. Amer. Chem. Soc., vol. 69, p. 1170 (1947)" and $SOCl_2$/DMF as disclosed in "Helv. Chim. Acta., vol. 42, p. 1653 (1959)").

This reaction is conducted usually under an inert gas atmosphere such as nitrogen gas in an appropriate organic solvent in the presence of a strong base. Examples of the solvent thus used include ethers, preferably tetrahydrofuran. Examples of the base thus used include alkali metal amides (such as LDA: lithium diisopropylamide), aliphatic or aromatic lithium compounds (such as n-butyl lithium, t-butyl lithium and phenyl lithium). These materials are selected appropriately depending on the reactivity of the aimed reaction.

This reaction is conducted usually at a temperature ranging from −100° C. to 50° C., preferably from −78° C. to 20° C., for from 0.1 to 10 hours.

An intermediate used in the synthesis of the compound of the present invention is prepared as illustrated hereinafter.

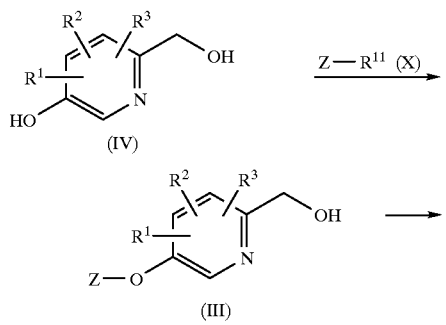

(wherein $R^1$ $R^2$, $R^3$, $R^6$, $R^{11}$, and Z are as defined above).

Among compounds having the formula (II), a compound wherein $R^6$ is hydrogen can be obtained by reacting a compound of the formula (X) with a hydroxy group at the 5-position of 5-hydroxypyridinemethanol of the formula (IV) by nucleophilic substitution reaction to produce a compound of the formula (III), and by oxidizing a hydroxymethyl group at the 2-position of the compound of the formula (III) thus prepared.

5-Hydroxypyridine methanols of the formula (IV) can be synthesized by such a method as disclosed in U.S. Pat. No. 4,202,901. In this method, 5-hydroxypyridine methanol can be obtained by oxidizing 5-hydroxy-2-picoline with an appropriate oxidizing agent (such as hydrogen peroxide in acetic acid) to form pyridine-N-oxide, transforming the pyridine-N-oxide into acyloxy methylpyridine by an appropriate organic acid anhydride (such as acetic anhydride), and hydrolyzing the acyloxy methylpyridine with an appropriate acid or base to form 5-hydroxypyridine methanol. Also, a methyl-substituted product can be obtained by such a method as disclosed in "J. Med. Chem., vol. 20(10), p. 1528 (1977)" and "J. Med. Chem., vol. 35(20), p. 3667 (1992)", a hydroxy-substituted product can be obtained by such a method as disclosed in "Bull. Chem. Sci. Jpn., vol. 52(1), p. 107 (1979)", and a bromo- or chloro-substituted product can be obtained by such a method as disclosed in U.S. Pat. No. 4,025,333 and "J. Med. Chem., vol. 17(2), p. 172 (1974)".

The step of preparing the compound of the formula (III) can be conducted under the same conditions as described with regard to the process 6.

The step of preparing the compound of the formula (II) can be conducted by using an appropriate oxidizing agent (such as manganese dioxide, PCC: pyridinium chlorochromate, PDC: pyridinium dichromate, DDQ: dichlorodicyanobenzoquinone, chloranil, Swern oxidation: oxalylchloride-dimethylsulfoxide-tertiary amine, and sulfur trioxide-pyridine complex).

Also, the compound of the formula (II) can be obtained by reacting a compound of the formula (X) with a hydroxy group at the 5-position of hydroxypyridine aldehyde of the formula (XIII) by nucleophilic substitution reaction. The hydroxypyridine aldehyde of the formula (XIII) can be prepared by such a method as disclosed in Japanese Unexamined Patent Publication No. 273659/1990, or by oxidizing a hydroxymethyl group of the compound of the formula (IV) with an appropriate well known oxidizing agent such as PCC (pyridinium chlorochromate). The step of preparing the compound of the formula (II) is conducted by reacting the material in an appropriate organic solvent or in the presence of base. Examples of the solvent thus used include aprotic polar organic solvents, ethers, aromatic hydrocarbons, halogenated hydrocarbons, alkoxyalkanes and acetonitrile, and among them, dimethylformamide (DMF) is preferably used. Examples of the base thus used include organic amines (such as dimethylamine, diethylamine, diisopropylamine, diisopropylethylamine, trimethylamine, triethylamine, piperidine, piperazine, pyrrolidine, morpholine, pyridine, methanolamine, ethanolamine, Acid Captor H: 3,4-dihydro-2H-pyrido[1,2-a]pyrimidin-2-one and Acid Captor 9M: 9-methyl-3,4-dihydro-2H-pyrido[1,2-a]pyrimidin-2-one), and inorganic alkali metal salts (such as sodium hydroxide, potassium hydroxide, lithium hydroxide, potassium carbonate, sodium carbonate, sodium hydrogencarbonate, potassium hydrogencarbonate, sodium hydride, sodium acetate and potassium acetate), and among them, diisopropyl ethylamine, Acid Captor 9M and sodium hydrogencarbonate are preferably used. These materials are selected appropriately depending on the reactivity of the aimed reaction. This reaction is conducted usually at a temperature ranging from −10° C. to 100° C., preferably from 0° C. to 50° C., for from 0.5 to 5 hours.

The compound of the formula (II) ($R^6$=H) obtained by the above-mentioned method, can be further modified into a compound of the formula (II) ($R^6 \neq$H) by alkylating a formyl group with an appropriate alkylating agent by means of a well known method.

This step can be conducted by a method using diazomethane as described in "Tetrahedron Letters, p. 955 (1963)" and "Chem. Ber. vol. 40, p 479 (1907)", a method using halogenated alkyl as described in "Synth. Commun., vol. 14(8), p. 743 (1984)" or a method using alkyl lithium as described in "J. Org. Chem., vol. 30, p. 226 (1965)".

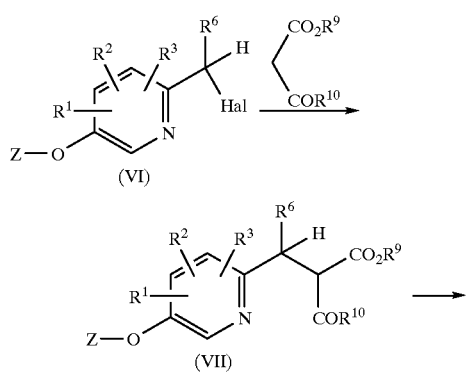

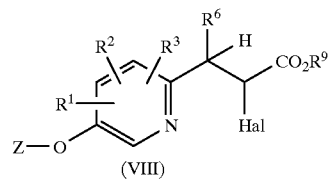

(wherein $R^1$, $R^2$, $R^3$, $R^6$, $R^9$, Z and Hal are as defined above, and $R^{10}$ represents $OR^9$ ($R^9$ is as defined above) or $C_1$–$C_3$ alkyl such as methyl, ethyl, n-propyl and i-propyl).

A halocarboxylic acid ester of the formula (VIII) can be obtained by reacting a halomethylpyridine with a malonic acid ester or a lower acylacetic acid ester by a known method to form a compound of the formula (VII), and by halogenating the compound thus formed.

A halomethylpyridine of the formula (VI) can be synthesized by such a method as described in "Bull. Pol. Acad. Sci. Chem., vol. 38, No. 1-12, p.17 (1990)". Thus, the halomethylpyridine of the formula (VI) can be obtained by halogenating acyloxy methylpyridine described in the synthesis of the compounds of the formula (III) or (IV), with an appropriate halogenating agent (such as thionyl halide, phosphorus oxyhalide, phosphorus trihalide, phosphorus pentahalide, hydrochloric acid and hydrobromic acid). Also, it can be obtained by halogenating a pyridine-N-oxide as a starting material with phosphorus oxyhalide, benzenesulfonyl halide or p-toluenesulfonyl halide by means of a method as described in U.S. Pat. No. 5,202,321, "J. Org. Chem., vol. 27, p. 3856 (1962)" or "J. Org. Chem., vol. 38, p. 927 (1973)".

Among the compounds having the formula (VII), a compound wherein $R^{10}$ is $C_1$–$C_3$ alkyl, can be obtained by reacting a halomethylpyridine of the formula (VI) with a lower acylacetic acid ester such as methyl acetoacetate and ethyl acetoacetate in the presence of an appropriate base (such as sodium hydroxide, potassium hydroxide, sodium methoxide, sodium ethoxide, sodium amide, potassium amide, diisopropyl amide, butyl lithium, metal sodium and potassium carbonate) in accordance with such a method as described in "J. Amer. Chem. Soc., vol. 64, p. 435 (1942)".

Among the compounds having the formula (VII), a compound wherein $R^{10}$ is $OR^9$, can be obtained by reacting a halomethylpyridine of the formula (VI) with a malonic acid ester such as diethyl malonate and di-t-butyl malonate in the presence of an appropriate base as mentioned above, in accordance with such a method as described in "J. Amer. Chem. Soc., vol. 74, p. 831 (1952)" and "Org. Synth. Coll. vol. 3, p. 705 (1955)".

The step of synthesizing a compound of the formula (VIII) can be conducted by using an appropriate halogenating agent (such as bromine and N-chlorosuccinimide) in the presence of an appropriate base (such as sodium hydroxide, sodium methoxide and potassium carbonate) in accordance with such a method as described in "J. Amer. Chem. Soc., vol. 71, p. 3107 (1949)" and "Tetrahedron Letters, vol. 28, p. 5505 (1987)".

Also, a compound of the formula (VIII) can be obtained by reacting a halomethylpyridine of the formula (VI) with a diazoacetic ester in the presence of a copper catalyst in accordance with such a method as described in "Zur. Russ. Fiz-Chim., vol. 21, p. 851 (1951)".

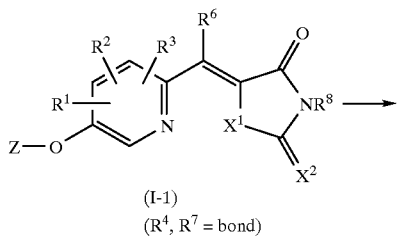

(I-1)
($R^4$, $R^7$ = bond)

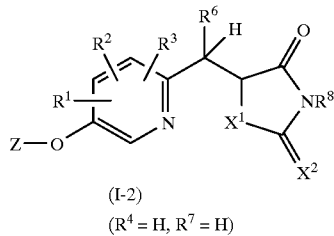

(I-2)
($R^4$ = H, $R^7$ = H)

(wherein $R^1$, $R^2$, $R^3$, $R^6$, $R^8$, $X^1$, $X^2$ and Z are as defined above).

A compound of the formula (I-1) (wherein $R^4$ and $R^7$ are bonded together) obtained by the above method can be modified into a compound of the formula (I-2) ($R^4$, $R^7$=H) by appropriately reducing a double bond between a pyridine ring and a thiazolidine ring (for example by catalytic hydrogenation in the presence of an appropriate catalyst, by using an appropriate metal-hydrogen complex compound, or by using magnesium or sodium amalgam in methanol).

The catalytic hydrogenation is conducted usually in alcohols, cellosolves, aprotic polar organic solvents, ethers, alkoxyalkanes, lower aliphatic acid esters or lower aliphatic acids, and particularly methanol, ethanol, methoxyethanol, dimethylformamide, tetrahydrofuran, dioxane, dimethoxyethane, ethyl acetate or acetic acid is preferably used alone or in a mixture. Examples of the catalyst used include palladium black, palladium carbon and platinum oxide. This reaction can proceed at normal temperature under normal pressure, but it is preferable to conduct the reaction at an elevated temperature under a increased pressure depending on the reactivity of the aimed reaction.

The reduction by a metal-hydrogen complex compound is conducted by using sodium borohydride, potassium borohydride, lithium borohydride, tetramethyl ammonium borohydride or zinc borohydride in an aprotic polar organic solvent at a temperature ranging from 0° C. to 150° C., preferably from 0° C. to 30° C. In this reduction, undesired side-reaction can be inhibited by using a Co reagent such as $CoCl_2$, $CoCl_3$ or $Co(OAc)_2$ in the presence of a ligand such as dimethyl glyoxime, 2,2'-bipyridyl or 1,10-phenanthroline (see WO93/13095).

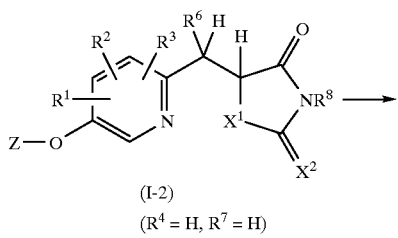

(I-2)
($R^4$ = H, $R^7$ = H)

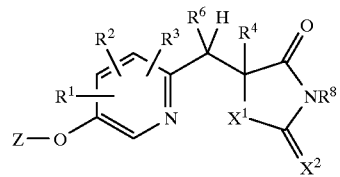

(I-2)
($R^4$ ≠ H, $R^7$ = H)

(wherein $R^1$, $R^2$, $R^3$, $R^4$, $R^6$, $R^8$, $X^1$, $X^2$ and Z are as defined above).

A compound of the formula (I-2) ($R^4$, $R^7$=H) can be modified into a compound of the formula (I-2) ($R^4$≠H, $R^7$=H) by alkylating hydrogen at the 5-position of thiazolidine with an appropriate alkylating agent (such as halogenated alkyl including methyl iodide or ethyl iodide, alkyl sulfate including dimethyl sulfate or diethyl sulfate, and aliphatic or aromatic sulfonic acid esters including methyl tosylate or methyl mesylate) in accordance with a well known method.

This reaction is conducted usually in an appropriate organic solvent in the presence of base. Examples of the solvent thus used include aprotic polar organic solvents, ethers, alkoxyalkanes and the like, and among them, tetrahydrofuran and dimethoxyethane are particularly preferable. Examples of the base include alkali metal amides (such as lithium diisopropylamide (LDA) and potassium amide) and aliphatic or aromatic lithium compounds (such as n-butyl lithium, t-butyl lithium and phenyl lithium). These materials selected appropriately depending on the reactivity of the aimed reaction.

This reaction is conducted usually at a temperature ranging from –20° C. to 100° C., preferably from –10° C. to 30° C., for from 0.1 to 10 hours.

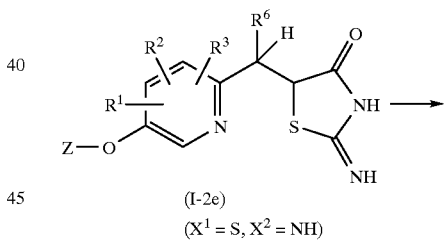

(I-2e)
($X^1$ = S, $X^2$ = NH)

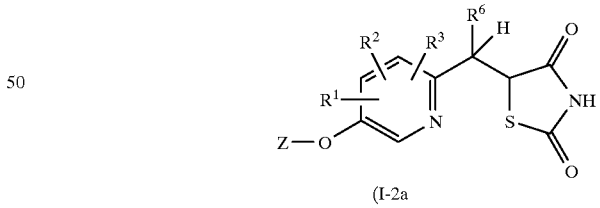

(I-2a)
($X^1$ = S, $X^2$ = O)

(wherein $R^1$, $R^2$, $R^3$, $R^6$ and Z are as defined above).

A compound of the formula (I-2e) ($X^1$=S, $X^2$=NH) can be modified into a compound of the formula (I-2a) ($X^1$=S, $X^2$=O) by hydrolyzing an imino group at the 2-position of the thiazolidine in accordance with a well known method.

This reaction is conducted usually in an appropriate organic solvent in the presence of water or acid. Examples of the solvent thus used include alcohols, cellosolves, aprotic polar organic solvents, ethers, alkoxyalkanes, and the like, and particularly methanol, ethanol, methoxyethanol, sulfolane, dioxane and dimethoxyethane are preferably used. Examples of the acid thus used include inorganic acids (such as hydrochloric acid, sulfuric acid and hydrobromic acid). These materials are selected appropriately depending on the reactivity of the aimed reaction.

This reaction is conducted usually at a temperature of from 50° C. to a boiling point of a solvent used, preferably from 80° C. to 150° C., for from 0.5 to 30 hours.

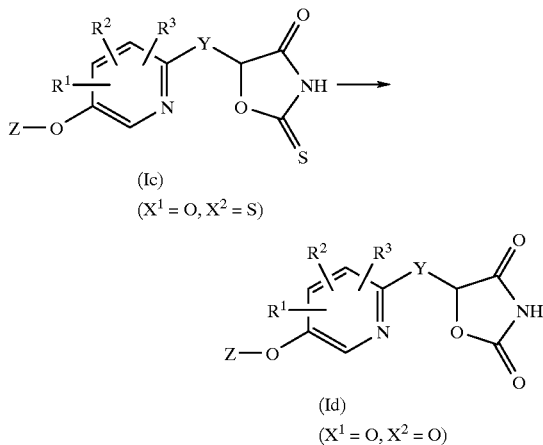

(wherein $R^1$, $R^2$, $R^3$, Y and Z are as defined above).

A compound of the formula (Ic) (Xl=O, $X^2$=S) can be modified into a compound of the formula (Id) ($X^1$=O, $X^2$=O) by oxidizing a thioxo group at the 2-position of thiazolidine in accordance with a well known method.

This reaction is conducted by using an appropriate oxidizing agent (such as hydrogen peroxide, an organic peroxide including peracetic acid, perbenzoic acid, methachloroperbenzoic acid, monopermaleic acid, monoperphthalic acid and the like, mercury ion, bromine, chlorine and meta-periodic acid) generally in water or in a solvent such as aprotic polar organic solvents (e.g. dimethylformamide, dimethylsulfoxide, dimethylacetamide, tetramethylurea, sulfolane and N,N-dimethylimidazolidinone), ethers (e.g. tetrahydrofuran and dioxane), and alkoxyalkanes (e.g. dimethoxyethane and diethoxyethane). These materials are selected appropriately depending on the reactivity of the aimed reaction, and are used respectively alone or in combination.

This reaction is conducted generally at a temperature ranging from 0° C. to a boiling point of a solvent used, preferably from 20° C. to 100° C., for from 0.5 to 30 hours.

A compound of the formula (I) can be converted into the corresponding N-oxide form by oxidizing a nitrogen atom on a pyridine ring with an appropriate oxidizing agent in accordance with a well known method. Examples of the oxidizing agent used in this method include hydrogen peroxide (used in acetic acid or trifluoroacetic acid at a temperature of from 0° C. to 100° C., preferably from 50° C. to 80° C., for from 1 to 20 hours, preferably from 3 to 10 hours, optionally in the presence of a catalytic a mount of sulfuric acid to accelerate the reaction), peracetic acid (used in water or acetic acid, optionally in an organic solvent such as tetrahydrofuran or ethyl acetate, at a temperature of from 0° C. to 100° C., preferably from 40° C. to 80° C., for from 1 to 10 hours, preferably from 3 to 5 hours), perbenzoic acid or methachloroperbenzoic acid (used in an organic solvent such as chloroform or benzene, at a temperature of from 0° C. to 50° C., preferably from 10° C. to 30° C., for from 0.1 to 3 hours, optionally more than 2 weeks), and monoper-maleic acid or monoperphthalic acid (used in an organic solvent such as chloroform or ethanol, at a temperature of from –10° C. to 50° C., preferably from 0° C. to 30° C., for from 0.5 to 50 hours, preferably from 1 to 10 hours). These oxidizing agents can be used in combination. Also, these N-oxide products can be converted into the corresponding pyridine products by reducing a nitrogen atom on a pyridine ring with an appropriate reducing agent in accordance with a well known method. Examples of the reducing agent used in this method include catalytic hydrogenation (used in an organic solvent such as acetic acid, acetic anhydride, methanol or ethanol, optionally a mixture thereof, at a temperature of from 0° C. to 100° C., preferably from 10° C. to 70° C., under from atmospheric pressure to 30 atoms, preferably from normal pressure to 10 atoms, in the presence of a catalyst such as Raney nickel, Urushibara nickel, palladium carbon or platinum oxide), iron (used in acetic acid at a temperature of from 50° C. to 100° C., preferably from 70° C. to 80° C., for from 0.5 to 5 hours, preferably from 1 to 2 hours), zinc (used in acetic acid, optionally in the presence of a catalytic amount of sulfuric acid), phosphorus trichloride, phosphorus pentachloride and phosphorus tribromide (used in an organic solvent such as chloroform or ethyl acetate, at a temperature of from 0° C. to 100° C., preferably from 20° C. to 80° C., for from 0.5 to 5 hours, preferably from 1 to 3 hours), triethylphosphine, triphenylphosphine and triethyl phosphite (used in an organic solvent such as ethyl acetate, at a temperature of from 150° C. to 300° C. for from 0.5 to 10 hours), and sulfur and sulfur dioxide (used in an organic solvent such as benzene or chlorobenzene, at a temperature of from 150° C. to 200° C. for from 0.5 to 30 hours).

The above-mentioned compounds (II), (III), (IV), (VI), (VII), (VIII), (IX) and (X) are novel compounds, and are useful as intermediate products for preparing the compound of the formula (I) of the present invention.

The following Tables 1 to 16 illustrate examples of the compounds having the formulas (I-1), (I-2) and (I-3) of the present invention. Furthermore, the pyridine-N-oxides obtained by oxidizing a nitrogen atom on a pyridine ring and the salts derived by treating a basic nitrogen on a thiazolidine ring by means of a well known method are also the compounds of the present invention.

TABLE 1

| Y | $R^4$ | $X^1$ | $X^2$ |
|---|---|---|---|
| —C(Me)= | bond with $R^7$ | S | O |
| —CH$_2$— | Me | S | O |
| —CH(Me)— | H | S | O |
| —CH(Me)— | Me | S | O |
| —SO$_2$— | H | S | O |
| —SO$_2$— | Me | S | O |
| —CH= | bond with $R^7$ | S | O |
| —CH= | bond with $R^7$ | S | S |
| —CH= | bond with $R^7$ | O | S |
| —CH= | bond with $R^7$ | O | O |
| —CH= | bond with $R^7$ | S | NH |
| —CH$_2$— | H | S | O |
| —CH$_2$— | H | S | S |

TABLE 1-continued

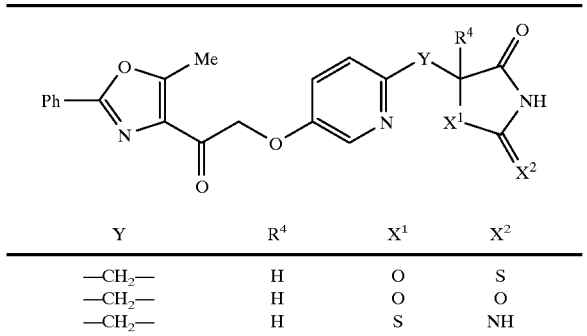

| Y | R⁴ | X¹ | X² |
|---|----|----|----|
| —CH₂— | H | O | S |
| —CH₂— | H | O | O |
| —CH₂— | H | S | NH |

TABLE 2

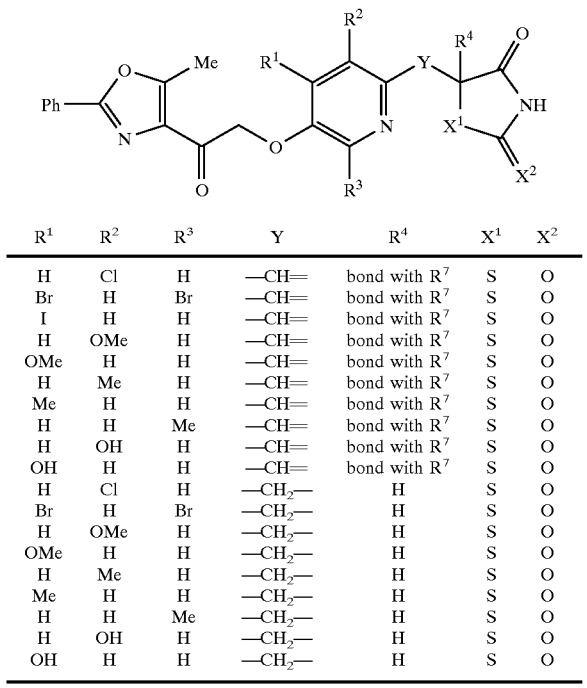

| R¹ | R² | R³ | Y | R⁴ | X¹ | X² |
|----|----|----|---|----|----|----|
| H | Cl | H | —CH= | bond with R⁷ | S | O |
| Br | H | Br | —CH= | bond with R⁷ | S | O |
| I | H | H | —CH= | bond with R⁷ | S | O |
| H | OMe | H | —CH= | bond with R⁷ | S | O |
| OMe | H | H | —CH= | bond with R⁷ | S | O |
| H | Me | H | —CH= | bond with R⁷ | S | O |
| Me | H | H | —CH= | bond with R⁷ | S | O |
| H | H | Me | —CH= | bond with R⁷ | S | O |
| H | OH | H | —CH= | bond with R⁷ | S | O |
| OH | H | H | —CH= | bond with R⁷ | S | O |
| H | Cl | H | —CH₂— | H | S | O |
| Br | H | Br | —CH₂— | H | S | O |
| H | OMe | H | —CH₂— | H | S | O |
| OMe | H | H | —CH₂— | H | S | O |
| H | Me | H | —CH₂— | H | S | O |
| Me | H | H | —CH₂— | H | S | O |
| H | H | Me | —CH₂— | H | S | O |
| H | OH | H | —CH₂— | H | S | O |
| OH | H | H | —CH₂— | H | S | O |

TABLE 3

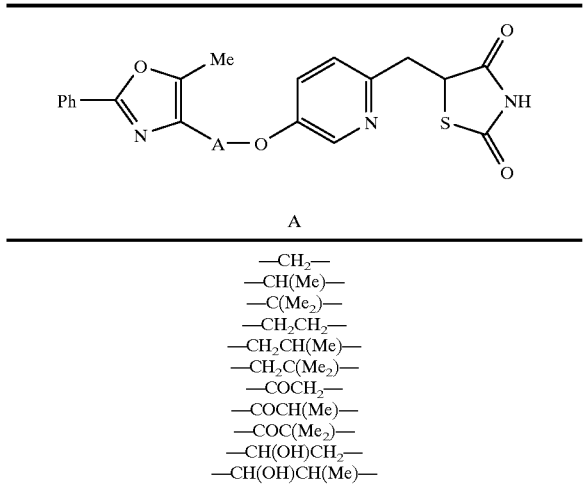

| A |
|---|
| —CH₂— |
| —CH(Me)— |
| —C(Me₂)— |
| —CH₂CH₂— |
| —CH₂CH(Me)— |
| —CH₂C(Me₂)— |
| —COCH₂— |
| —COCH(Me)— |
| —COC(Me₂)— |
| —CH(OH)CH₂— |
| —CH(OH)CH(Me)— |

TABLE 3-continued

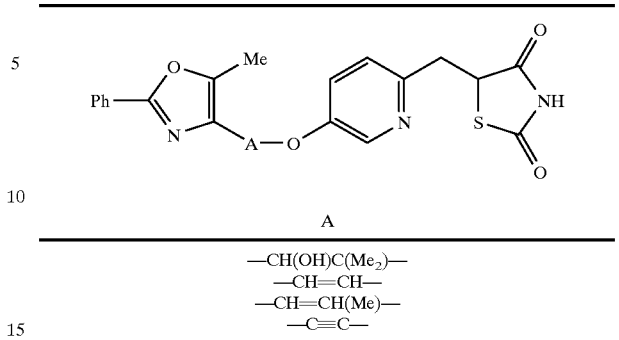

| A |
|---|
| —CH(OH)C(Me₂)— |
| —CH=CH— |
| —CH=CH(Me)— |
| —C≡C— |

TABLE 4

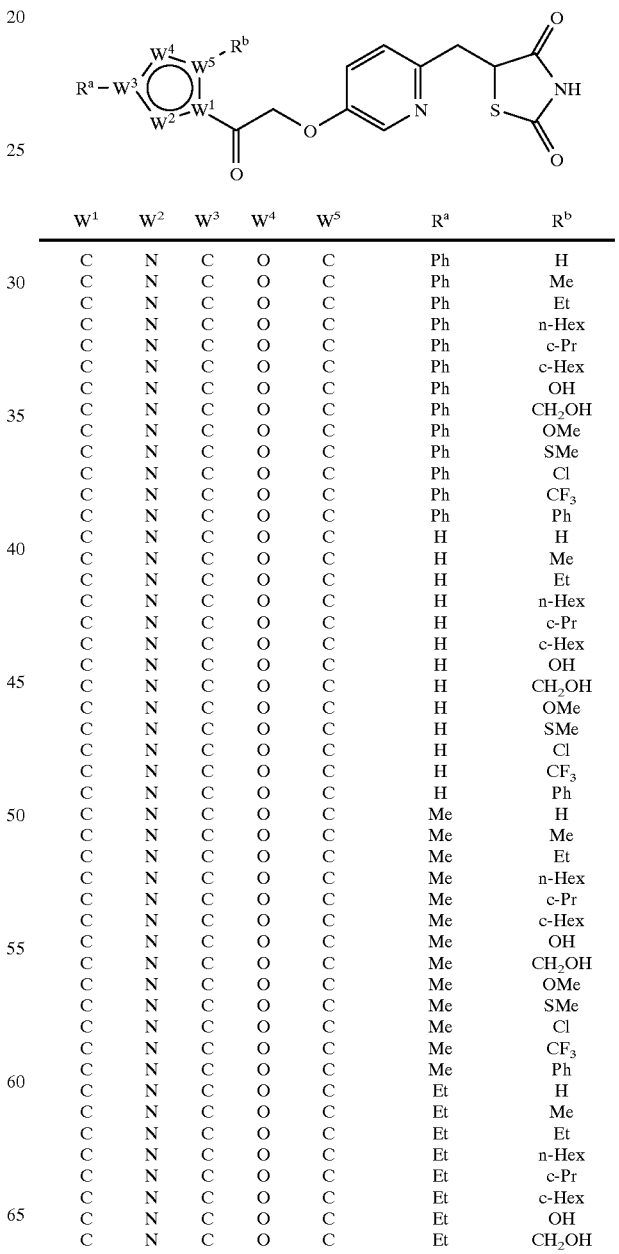

| W¹ | W² | W³ | W⁴ | W⁵ | Rᵃ | Rᵇ |
|----|----|----|----|----|-----|-----|
| C | N | C | O | C | Ph | H |
| C | N | C | O | C | Ph | Me |
| C | N | C | O | C | Ph | Et |
| C | N | C | O | C | Ph | n-Hex |
| C | N | C | O | C | Ph | c-Pr |
| C | N | C | O | C | Ph | c-Hex |
| C | N | C | O | C | Ph | OH |
| C | N | C | O | C | Ph | CH₂OH |
| C | N | C | O | C | Ph | OMe |
| C | N | C | O | C | Ph | SMe |
| C | N | C | O | C | Ph | Cl |
| C | N | C | O | C | Ph | CF₃ |
| C | N | C | O | C | Ph | Ph |
| C | N | C | O | C | H | H |
| C | N | C | O | C | H | Me |
| C | N | C | O | C | H | Et |
| C | N | C | O | C | H | n-Hex |
| C | N | C | O | C | H | c-Pr |
| C | N | C | O | C | H | c-Hex |
| C | N | C | O | C | H | OH |
| C | N | C | O | C | H | CH₂OH |
| C | N | C | O | C | H | OMe |
| C | N | C | O | C | H | SMe |
| C | N | C | O | C | H | Cl |
| C | N | C | O | C | H | CF₃ |
| C | N | C | O | C | H | Ph |
| C | N | C | O | C | Me | H |
| C | N | C | O | C | Me | Me |
| C | N | C | O | C | Me | Et |
| C | N | C | O | C | Me | n-Hex |
| C | N | C | O | C | Me | c-Pr |
| C | N | C | O | C | Me | c-Hex |
| C | N | C | O | C | Me | OH |
| C | N | C | O | C | Me | CH₂OH |
| C | N | C | O | C | Me | OMe |
| C | N | C | O | C | Me | SMe |
| C | N | C | O | C | Me | Cl |
| C | N | C | O | C | Me | CF₃ |
| C | N | C | O | C | Me | Ph |
| C | N | C | O | C | Et | H |
| C | N | C | O | C | Et | Me |
| C | N | C | O | C | Et | Et |
| C | N | C | O | C | Et | n-Hex |
| C | N | C | O | C | Et | c-Pr |
| C | N | C | O | C | Et | c-Hex |
| C | N | C | O | C | Et | OH |
| C | N | C | O | C | Et | CH₂OH |

TABLE 4-continued

| W¹ | W² | W³ | W⁴ | W⁵ | Rᵃ | Rᵇ |
|----|----|----|----|----|----|----|
| C | N | C | O | C | Et | OMe |
| C | N | C | O | C | Et | SMe |
| C | N | C | O | C | Et | Cl |
| C | N | C | O | C | Et | $CF_3$ |
| C | N | C | O | C | Et | Ph |
| C | N | C | O | C | n-Pr | H |
| C | N | C | O | C | n-Pr | Me |
| C | N | C | O | C | n-Pr | Et |
| C | N | C | O | C | n-Pr | n-Hex |
| C | N | C | O | C | n-Pr | c-Pr |
| C | N | C | O | C | n-Pr | c-Hex |
| C | N | C | O | C | n-Pr | OH |
| C | N | C | O | C | n-Pr | $CH_2OH$ |
| C | N | C | O | C | n-Pr | OMe |
| C | N | C | O | C | n-Pr | SMe |
| C | N | C | O | C | n-Pr | Cl |
| C | N | C | O | C | n-Pr | $CF_3$ |
| C | N | C | O | C | n-Pr | Ph |
| C | N | C | O | C | n-Hex | H |
| C | N | C | O | C | n-Hex | Me |
| C | N | C | O | C | n-Hex | Et |
| C | N | C | O | C | n-Hex | n-Hex |
| C | N | C | O | C | n-Hex | c-Pr |
| C | N | C | O | C | n-Hex | c-Hex |
| C | N | C | O | C | n-Hex | OH |
| C | N | C | O | C | n-Hex | $CH_2OH$ |
| C | N | C | O | C | n-Hex | OMe |
| C | N | C | O | C | n-Hex | SMe |
| C | N | C | O | C | n-Hex | Cl |
| C | N | C | O | C | n-Hex | $CF_3$ |
| C | N | C | O | C | n-Hex | Ph |
| C | N | C | O | C | i-Pr | H |
| C | N | C | O | C | i-Pr | Me |
| C | N | C | O | C | i-Pr | Et |
| C | N | C | O | C | i-Pr | n-Hex |
| C | N | C | O | C | i-Pr | c-Pr |
| C | N | C | O | C | i-Pr | c-Hex |
| C | N | C | O | C | i-Pr | OH |
| C | N | C | O | C | i-Pr | $CH_2OH$ |
| C | N | C | O | C | i-Pr | OMe |
| C | N | C | O | C | i-Pr | SMe |
| C | N | C | O | C | i-Pr | Cl |
| C | N | C | O | C | i-Pr | $CF_3$ |
| C | N | C | O | C | i-Pr | Ph |
| C | N | C | O | C | t-Bu | H |
| C | N | C | O | C | t-Bu | Me |
| C | N | C | O | C | t-Bu | Et |
| C | N | C | O | C | t-Bu | n-Hex |
| C | N | C | O | C | t-Bu | c-Pr |
| C | N | C | O | C | t-Bu | c-Hex |
| C | N | C | O | C | t-Bu | OH |
| C | N | C | O | C | t-Bu | $CH_2OH$ |
| C | N | C | O | C | t-Bu | OMe |
| C | N | C | O | C | t-Bu | SMe |
| C | N | C | O | C | t-Bu | Cl |
| C | N | C | O | C | t-Bu | $CF_3$ |
| C | N | C | O | C | t-Bu | Ph |
| C | N | C | O | C | c-Hex | H |
| C | N | C | O | C | c-Hex | Me |
| C | N | C | O | C | c-Hex | Et |
| C | N | C | O | C | c-Hex | n-Hex |
| C | N | C | O | C | c-Hex | c-Pr |
| C | N | C | O | C | c-Hex | c-Hex |
| C | N | C | O | C | c-Hex | OH |
| C | N | C | O | C | c-Hex | $CH_2OH$ |
| C | N | C | O | C | c-Hex | OMe |
| C | N | C | O | C | c-Hex | SMe |
| C | N | C | O | C | c-Hex | Cl |
| C | N | C | O | C | c-Hex | $CF_3$ |
| C | N | C | O | C | c-Hex | Ph |
| C | N | C | O | C | 3-c-hexenyl | H |
| C | N | C | O | C | 3-c-hexenyl | Me |
| C | N | C | O | C | 3-c-hexenyl | Et |
| C | N | C | O | C | 3-c-hexenyl | n-Hex |
| C | N | C | O | C | 3-c-hexenyl | c-Pr |
| C | N | C | O | C | 3-c-hexenyl | c-Hex |
| C | N | C | O | C | 3-c-hexenyl | OH |
| C | N | C | O | C | 3-c-hexenyl | $CH_2OH$ |
| C | N | C | O | C | 3-c-hexenyl | OMe |
| C | N | C | O | C | 3-c-hexenyl | SMe |
| C | N | C | O | C | 3-c-hexenyl | Cl |
| C | N | C | O | C | 3-c-hexenyl | $CF_3$ |
| C | N | C | O | C | 3-c-hexenyl | Ph |
| C | N | C | O | C | $CH_2OH$ | H |
| C | N | C | O | C | $CH_2OH$ | Me |
| C | N | C | O | C | $CH_2OH$ | Et |
| C | N | C | O | C | $CH_2OH$ | n-Hex |
| C | N | C | O | C | $CH_2OH$ | c-Pr |
| C | N | C | O | C | $CH_2OH$ | c-Hex |
| C | N | C | O | C | $CH_2OH$ | OH |
| C | N | C | O | C | $CH_2OH$ | $CH_2OH$ |
| C | N | C | O | C | $CH_2OH$ | OMe |
| C | N | C | O | C | $CH_2OH$ | SMe |
| C | N | C | O | C | $CH_2OH$ | Cl |
| C | N | C | O | C | $CH_2OH$ | $CF_3$ |
| C | N | C | O | C | $CH_2OH$ | Ph |
| C | N | C | O | C | $CH_2Ph$ | H |
| C | N | C | O | C | $CH_2Ph$ | Me |
| C | N | C | O | C | $CH_2Ph$ | Et |
| C | N | C | O | C | $CH_2Ph$ | n-Hex |
| C | N | C | O | C | $CH_2Ph$ | c-Pr |
| C | N | C | O | C | $CH_2Ph$ | c-Hex |
| C | N | C | O | C | $CH_2Ph$ | OH |
| C | N | C | O | C | $CH_2Ph$ | $CH_2OH$ |
| C | N | C | O | C | $CH_2Ph$ | OMe |
| C | N | C | O | C | $CH_2Ph$ | SMe |
| C | N | C | O | C | $CH_2Ph$ | Cl |
| C | N | C | O | C | $CH_2Ph$ | $CF_3$ |
| C | N | C | O | C | $CH_2Ph$ | Ph |
| C | N | C | O | C | α-naphthyl | H |
| C | N | C | O | C | α-naphthyl | Me |
| C | N | C | O | C | α-naphthyl | Et |
| C | N | C | O | C | α-naphthyl | n-Hex |
| C | N | C | O | C | α-naphthyl | c-Pr |
| C | N | C | O | C | α-naphthyl | c-Hex |
| C | N | C | O | C | α-naphthyl | OH |
| C | N | C | O | C | α-naphthyl | $CH_2OH$ |
| C | N | C | O | C | α-naphthyl | OMe |
| C | N | C | O | C | α-naphthyl | SMe |
| C | N | C | O | C | α-naphthyl | Cl |
| C | N | C | O | C | α-naphthyl | $CF_3$ |
| C | N | C | O | C | α-naphthyl | Ph |
| C | N | C | O | C | β-naphthyl | H |
| C | N | C | O | C | β-naphthyl | Me |
| C | N | C | O | C | β-naphthyl | Et |
| C | N | C | O | C | β-naphthyl | n-Hex |
| C | N | C | O | C | β-naphthyl | c-Pr |
| C | N | C | O | C | β-naphthyl | c-Hex |
| C | N | C | O | C | β-naphthyl | OH |
| C | N | C | O | C | β-naphthyl | $CH_2OH$ |
| C | N | C | O | C | β-naphthyl | OMe |
| C | N | C | O | C | β-naphthyl | SMe |
| C | N | C | O | C | β-naphthyl | Cl |
| C | N | C | O | C | β-naphthyl | $CF_3$ |

TABLE 4-continued

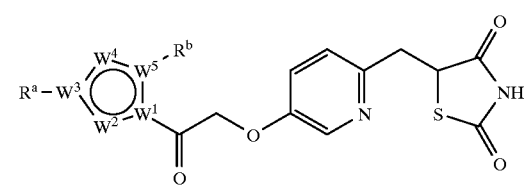

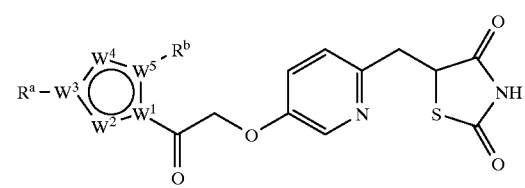

| $W^1$ | $W^2$ | $W^3$ | $W^4$ | $W^5$ | $R^a$ | $R^b$ | $W^1$ | $W^2$ | $W^3$ | $W^4$ | $W^5$ | $R^a$ | $R^b$ |
|---|---|---|---|---|---|---|---|---|---|---|---|---|---|
| C | N | C | O | C | β-naphthyl | Ph | C | N | C | O | C | 2-tolyl | Me |
| C | N | C | O | C | 2-pyridyl | H | C | N | C | O | C | 2-tolyl | Et |
| C | N | C | O | C | 2-pyridyl | Me | C | N | C | O | C | 2-tolyl | n-Hex |
| C | N | C | O | C | 2-pyridyl | Et | C | N | C | O | C | 2-tolyl | c-Pr |
| C | N | C | O | C | 2-pyridyl | n-Hex | C | N | C | O | C | 2-tolyl | c-Hex |
| C | N | C | O | C | 2-pyridyl | c-Pr | C | N | C | O | C | 2-tolyl | OH |
| C | N | C | O | C | 2-pyridyl | c-Hex | C | N | C | O | C | 2-tolyl | $CH_2OH$ |
| C | N | C | O | C | 2-pyridyl | OH | C | N | C | O | C | 2-tolyl | OMe |
| C | N | C | O | C | 2-pyridyl | $CH_2OH$ | C | N | C | O | C | 2-tolyl | SMe |
| C | N | C | O | C | 2-pyridyl | OMe | C | N | C | O | C | 2-tolyl | Cl |
| C | N | C | O | C | 2-pyridyl | SMe | C | N | C | O | C | 2-tolyl | $CF_3$ |
| C | N | C | O | C | 2-pyridyl | Cl | C | N | C | O | C | 2-tolyl | Ph |
| C | N | C | O | C | 2-pyridyl | $CF_3$ | C | N | C | O | C | 3-tolyl | H |
| C | N | C | O | C | 2-pyridyl | Ph | C | N | C | O | C | 3-tolyl | Me |
| C | N | C | O | C | 3-pyridyl | H | C | N | C | O | C | 3-tolyl | Et |
| C | N | C | O | C | 3-pyridyl | Me | C | N | C | O | C | 3-tolyl | n-Hex |
| C | N | C | O | C | 3-pyridyl | Et | C | N | C | O | C | 3-tolyl | c-Pr |
| C | N | C | O | C | 3-pyridyl | n-Hex | C | N | C | O | C | 3-tolyl | c-Hex |
| C | N | C | O | C | 3-pyridyl | c-Pr | C | N | C | O | C | 3-tolyl | OH |
| C | N | C | O | C | 3-pyridyl | c-Hex | C | N | C | O | C | 3-tolyl | $CH_2OH$ |
| C | N | C | O | C | 3-pyridyl | OH | C | N | C | O | C | 3-tolyl | OMe |
| C | N | C | O | C | 3-pyridyl | $CH_2OH$ | C | N | C | O | C | 3-tolyl | SMe |
| C | N | C | O | C | 3-pyridyl | OMe | C | N | C | O | C | 3-tolyl | Cl |
| C | N | C | O | C | 3-pyridyl | SMe | C | N | C | O | C | 3-tolyl | $CF_3$ |
| C | N | C | O | C | 3-pyridyl | Cl | C | N | C | O | C | 3-tolyl | Ph |
| C | N | C | O | C | 3-pyridyl | $CF_3$ | C | N | C | O | C | 4-tolyl | H |
| C | N | C | O | C | 3-pyridyl | Ph | C | N | C | O | C | 4-tolyl | Me |
| C | N | C | O | C | 4-pyridyl | H | C | N | C | O | C | 4-tolyl | Et |
| C | N | C | O | C | 4-pyridyl | Me | C | N | C | O | C | 4-tolyl | n-Hex |
| C | N | C | O | C | 4-pyridyl | Et | C | N | C | O | C | 4-tolyl | c-Pr |
| C | N | C | O | C | 4-pyridyl | n-Hex | C | N | C | O | C | 4-tolyl | c-Hex |
| C | N | C | O | C | 4-pyridyl | c-Pr | C | N | C | O | C | 4-tolyl | OH |
| C | N | C | O | C | 4-pyridyl | c-Hex | C | N | C | O | C | 4-tolyl | $CH_2OH$ |
| C | N | C | O | C | 4-pyridyl | OH | C | N | C | O | C | 4-tolyl | OMe |
| C | N | C | O | C | 4-pyridyl | $CH_2OH$ | C | N | C | O | C | 4-tolyl | SMe |
| C | N | C | O | C | 4-pyridyl | OMe | C | N | C | O | C | 4-tolyl | Cl |
| C | N | C | O | C | 4-pyridyl | SMe | C | N | C | O | C | 4-tolyl | $CF_3$ |
| C | N | C | O | C | 4-pyridyl | Cl | C | N | C | O | C | 4-tolyl | Ph |
| C | N | C | O | C | 4-pyridyl | $CF_3$ | C | N | C | O | C | Ph-2,3-$Me_2$ | H |
| C | N | C | O | C | 4-pyridyl | Ph | C | N | C | O | C | Ph-2,3-$Me_2$ | Me |
| C | N | C | O | C | 2-furanyl | H | C | N | C | O | C | Ph-2,3-$Me_2$ | Et |
| C | N | C | O | C | 2-furanyl | Me | C | N | C | O | C | Ph-2,3-$Me_2$ | n-Hex |
| C | N | C | O | C | 2-furanyl | Et | C | N | C | O | C | Ph-2,3-$Me_2$ | c-Pr |
| C | N | C | O | C | 2-furanyl | n-Hex | C | N | C | O | C | Ph-2,3-$Me_2$ | c-Hex |
| C | N | C | O | C | 2-furanyl | c-Pr | C | N | C | O | C | Ph-2,3-$Me_2$ | OH |
| C | N | C | O | C | 2-furanyl | c-Hex | C | N | C | O | C | Ph-2,3-$Me_2$ | $CH_2OH$ |
| C | N | C | O | C | 2-furanyl | OH | C | N | C | O | C | Ph-2,3-$Me_2$ | OMe |
| C | N | C | O | C | 2-furanyl | $CH_2OH$ | C | N | C | O | C | Ph-2,3-$Me_2$ | SMe |
| C | N | C | O | C | 2-furanyl | OMe | C | N | C | O | C | Ph-2,3-$Me_2$ | Cl |
| C | N | C | O | C | 2-furanyl | SMe | C | N | C | O | C | Ph-2,3-$Me_2$ | $CF_3$ |
| C | N | C | O | C | 2-furanyl | Cl | C | N | C | O | C | Ph-2,3-$Me_2$ | Ph |
| C | N | C | O | C | 2-furanyl | $CF_3$ | C | N | C | O | C | Ph-3,4-$Me_2$ | H |
| C | N | C | O | C | 2-furanyl | Ph | C | N | C | O | C | Ph-3,4-$Me_2$ | Me |
| C | N | C | O | C | 2-thienyl | H | C | N | C | O | C | Ph-3,4-$Me_2$ | Et |
| C | N | C | O | C | 2-thienyl | Me | C | N | C | O | C | Ph-3,4-$Me_2$ | n-Hex |
| C | N | C | O | C | 2-thienyl | Et | C | N | C | O | C | Ph-3,4-$Me_2$ | c-Pr |
| C | N | C | O | C | 2-thienyl | n-Hex | C | N | C | O | C | Ph-3,4-$Me_2$ | c-Hex |
| C | N | C | O | C | 2-thienyl | c-Pr | C | N | C | O | C | Ph-3,4-$Me_2$ | OH |
| C | N | C | O | C | 2-thienyl | c-Hex | C | N | C | O | C | Ph-3,4-$Me_2$ | $CH_2OH$ |
| C | N | C | O | C | 2-thienyl | OH | C | N | C | O | C | Ph-3,4-$Me_2$ | OMe |
| C | N | C | O | C | 2-thienyl | $CH_2OH$ | C | N | C | O | C | Ph-3,4-$Me_2$ | SMe |
| C | N | C | O | C | 2-thienyl | OMe | C | N | C | O | C | Ph-3,4-$Me_2$ | Cl |
| C | N | C | O | C | 2-thienyl | SMe | C | N | C | O | C | Ph-3,4-$Me_2$ | $CF_3$ |
| C | N | C | O | C | 2-thienyl | Cl | C | N | C | O | C | Ph-3,4-$Me_2$ | Ph |
| C | N | C | O | C | 2-thienyl | $CF_3$ | C | N | C | O | C | Ph-3,5-$Me_2$ | H |
| C | N | C | O | C | 2-thienyl | Ph | C | N | C | O | C | Ph-3,5-$Me_2$ | Me |
| C | N | C | O | C | 2-tolyl | H | C | N | C | O | C | Ph-3,5-$Me_2$ | Et |

TABLE 4-continued

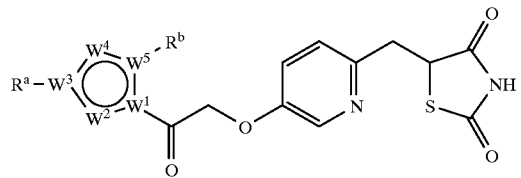

| W¹ | W² | W³ | W⁴ | W⁵ | Rᵃ | Rᵇ |
|---|---|---|---|---|---|---|
| C | N | C | O | C | Ph-3,5-Me₂ | n-Hex |
| C | N | C | O | C | Ph-3,5-Me₂ | c-Pr |
| C | N | C | O | C | Ph-3,5-Me₂ | c-Hex |
| C | N | C | O | C | Ph-3,5-Me₂ | OH |
| C | N | C | O | C | Ph-3,5-Me₂ | CH₂OH |
| C | N | C | O | C | Ph-3,5-Me₂ | OMe |
| C | N | C | O | C | Ph-3,5-Me₂ | SMe |
| C | N | C | O | C | Ph-3,5-Me₂ | Cl |
| C | N | C | O | C | Ph-3,5-Me₂ | CF₃ |
| C | N | C | O | C | Ph-3,5-Me₂ | Ph |
| C | N | C | O | C | Ph-2,6-Me₂ | H |
| C | N | C | O | C | Ph-2,6-Me₂ | Me |
| C | N | C | O | C | Ph-2,6-Me₂ | Et |
| C | N | C | O | C | Ph-2,6-Me₂ | n-Hex |
| C | N | C | O | C | Ph-2,6-Me₂ | c-Pr |
| C | N | C | O | C | Ph-2,6-Me₂ | c-Hex |
| C | N | C | O | C | Ph-2,6-Me₂ | OH |
| C | N | C | O | C | Ph-2,6-Me₂ | CH₂OH |
| C | N | C | O | C | Ph-2,6-Me₂ | OMe |
| C | N | C | O | C | Ph-2,6-Me₂ | SMe |
| C | N | C | O | C | Ph-2,6-Me₂ | Cl |
| C | N | C | O | C | Ph-2,6-Me₂ | CF₃ |
| C | N | C | O | C | Ph-2,6-Me₂ | Ph |
| C | N | C | O | C | Ph-2-Cl | H |
| C | N | C | O | C | Ph-2-Cl | Me |
| C | N | C | O | C | Ph-2-Cl | Et |
| C | N | C | O | C | Ph-2-Cl | n-Hex |
| C | N | C | O | C | Ph-2-Cl | c-Pr |
| C | N | C | O | C | Ph-2-Cl | c-Hex |
| C | N | C | O | C | Ph-2-Cl | OH |
| C | N | C | O | C | Ph-2-Cl | CH₂OH |
| C | N | C | O | C | Ph-2-Cl | OMe |
| C | N | C | O | C | Ph-2-Cl | SMe |
| C | N | C | O | C | Ph-2-Cl | Cl |
| C | N | C | O | C | Ph-2-Cl | CF₃ |
| C | N | C | O | C | Ph-2-Cl | Ph |
| C | N | C | O | C | Ph-3-Cl | H |
| C | N | C | O | C | Ph-3-Cl | Me |
| C | N | C | O | C | Ph-3-Cl | Et |
| C | N | C | O | C | Ph-3-Cl | n-Hex |
| C | N | C | O | C | Ph-3-Cl | c-Pr |
| C | N | C | O | C | Ph-3-Cl | c-Hex |
| C | N | C | O | C | Ph-3-Cl | OH |
| C | N | C | O | C | Ph-3-Cl | CH₂OH |
| C | N | C | O | C | Ph-3-Cl | OMe |
| C | N | C | O | C | Ph-3-Cl | SMe |
| C | N | C | O | C | Ph-3-Cl | Cl |
| C | N | C | O | C | Ph-3-Cl | CF₃ |
| C | N | C | O | C | Ph-3-Cl | Ph |
| C | N | C | O | C | Ph-4-Cl | H |
| C | N | C | O | C | Ph-4-Cl | Me |
| C | N | C | O | C | Ph-4-Cl | Et |
| C | N | C | O | C | Ph-4-Cl | n-Hex |
| C | N | C | O | C | Ph-4-Cl | c-Pr |
| C | N | C | O | C | Ph-4-Cl | c-Hex |
| C | N | C | O | C | Ph-4-Cl | OH |
| C | N | C | O | C | Ph-4-Cl | CH₂OH |
| C | N | C | O | C | Ph-4-Cl | OMe |
| C | N | C | O | C | Ph-4-Cl | SMe |
| C | N | C | O | C | Ph-4-Cl | Cl |
| C | N | C | O | C | Ph-4-Cl | CF₃ |
| C | N | C | O | C | Ph-4-Cl | Ph |
| C | N | C | O | C | Ph-3,4-Cl₂ | H |
| C | N | C | O | C | Ph-3,4-Cl₂ | Me |
| C | N | C | O | C | Ph-3,4-Cl₂ | Et |
| C | N | C | O | C | Ph-3,4-Cl₂ | n-Hex |
| C | N | C | O | C | Ph-3,4-Cl₂ | c-Pr |

TABLE 4-continued

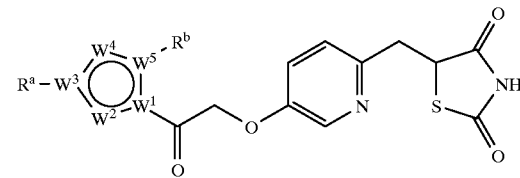

| W¹ | W² | W³ | W⁴ | W⁵ | Rᵃ | Rᵇ |
|---|---|---|---|---|---|---|
| C | N | C | O | C | Ph-3,4-Cl₂ | c-Hex |
| C | N | C | O | C | Ph-3,4-Cl₂ | OH |
| C | N | C | O | C | Ph-3,4-Cl₂ | CH₂OH |
| C | N | C | O | C | Ph-3,4-Cl₂ | OMe |
| C | N | C | O | C | Ph-3,4-Cl₂ | SMe |
| C | N | C | O | C | Ph-3,4-Cl₂ | Cl |
| C | N | C | O | C | Ph-3,4-Cl₂ | CF₃ |
| C | N | C | O | C | Ph-3,4-Cl₂ | Ph |
| C | N | C | O | C | Ph-4-F | H |
| C | N | C | O | C | Ph-4-F | Me |
| C | N | C | O | C | Ph-4-F | Et |
| C | N | C | O | C | Ph-4-F | n-Hex |
| C | N | C | O | C | Ph-4-F | c-Pr |
| C | N | C | O | C | Ph-4-F | c-Hex |
| C | N | C | O | C | Ph-4-F | OH |
| C | N | C | O | C | Ph-4-F | CH₂OH |
| C | N | C | O | C | Ph-4-F | OMe |
| C | N | C | O | C | Ph-4-F | SMe |
| C | N | C | O | C | Ph-4-F | Cl |
| C | N | C | O | C | Ph-4-F | CF₃ |
| C | N | C | O | C | Ph-4-F | Ph |
| C | N | C | O | C | Ph-4-Br | H |
| C | N | C | O | C | Ph-4-Br | Me |
| C | N | C | O | C | Ph-4-Br | Et |
| C | N | C | O | C | Ph-4-Br | n-Hex |
| C | N | C | O | C | Ph-4-Br | c-Pr |
| C | N | C | O | C | Ph-4-Br | c-Hex |
| C | N | C | O | C | Ph-4-Br | OH |
| C | N | C | O | C | Ph-4-Br | CH₂OH |
| C | N | C | O | C | Ph-4-Br | OMe |
| C | N | C | O | C | Ph-4-Br | SMe |
| C | N | C | O | C | Ph-4-Br | Cl |
| C | N | C | O | C | Ph-4-Br | CF₃ |
| C | N | C | O | C | Ph-4-Br | Ph |
| C | N | C | O | C | Ph-2-OMe | H |
| C | N | C | O | C | Ph-2-OMe | Me |
| C | N | C | O | C | Ph-2-OMe | Et |
| C | N | C | O | C | Ph-2-OMe | n-Hex |
| C | N | C | O | C | Ph-2-OMe | c-Pr |
| C | N | C | O | C | Ph-2-OMe | c-Hex |
| C | N | C | O | C | Ph-2-OMe | OH |
| C | N | C | O | C | Ph-2-OMe | CH₂OH |
| C | N | C | O | C | Ph-2-OMe | OMe |
| C | N | C | O | C | Ph-2-OMe | SMe |
| C | N | C | O | C | Ph-2-OMe | Cl |
| C | N | C | O | C | Ph-2-OMe | CF₃ |
| C | N | C | O | C | Ph-2-OMe | Ph |
| C | N | C | O | C | Ph-3-OMe | H |
| C | N | C | O | C | Ph-3-OMe | Me |
| C | N | C | O | C | Ph-3-OMe | Et |
| C | N | C | O | C | Ph-3-OMe | n-Hex |
| C | N | C | O | C | Ph-3-OMe | c-Pr |
| C | N | C | O | C | Ph-3-OMe | c-Hex |
| C | N | C | O | C | Ph-3-OMe | OH |
| C | N | C | O | C | Ph-3-OMe | CH₂OH |
| C | N | C | O | C | Ph-3-OMe | OMe |
| C | N | C | O | C | Ph-3-OMe | SMe |
| C | N | C | O | C | Ph-3-OMe | Cl |
| C | N | C | O | C | Ph-3-OMe | CF₃ |
| C | N | C | O | C | Ph-3-OMe | Ph |
| C | N | C | O | C | Ph-4-OMe | H |
| C | N | C | O | C | Ph-4-OMe | Me |
| C | N | C | O | C | Ph-4-OMe | Et |
| C | N | C | O | C | Ph-4-OMe | n-Hex |
| C | N | C | O | C | Ph-4-OMe | c-Pr |
| C | N | C | O | C | Ph-4-OMe | c-Hex |
| C | N | C | O | C | Ph-4-OMe | OH |

TABLE 4-continued

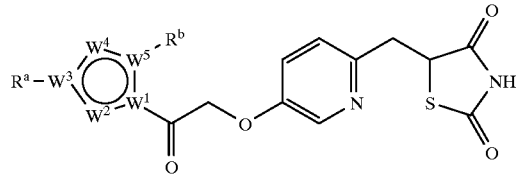

| W¹ | W² | W³ | W⁴ | W⁵ | Rᵃ | Rᵇ |
|---|---|---|---|---|---|---|
| C | N | C | O | C | Ph-4-OMe | CH$_2$OH |
| C | N | C | O | C | Ph-4-OMe | OMe |
| C | N | C | O | C | Ph-4-OMe | SMe |
| C | N | C | O | C | Ph-4-OMe | Cl |
| C | N | C | O | C | Ph-4-OMe | CF$_3$ |
| C | N | C | O | C | Ph-4-OMe | Ph |
| C | N | C | O | C | Ph-3,4-(OMe)$_2$ | H |
| C | N | C | O | C | Ph-3,4-(OMe)$_2$ | Me |
| C | N | C | O | C | Ph-3,4-(OMe)$_2$ | Et |
| C | N | C | O | C | Ph-3,4-(OMe)$_2$ | n-Hex |
| C | N | C | O | C | Ph-3,4-(OMe)$_2$ | c-Pr |
| C | N | C | O | C | Ph-3,4-(OMe)$_2$ | c-Hex |
| C | N | C | O | C | Ph-3,4-(OMe)$_2$ | OH |
| C | N | C | O | C | Ph-3,4-(OMe)$_2$ | CH$_2$OH |
| C | N | C | O | C | Ph-3,4-(OMe)$_2$ | OMe |
| C | N | C | O | C | Ph-3,4-(OMe)$_2$ | SMe |
| C | N | C | O | C | Ph-3,4-(OMe)$_2$ | Cl |
| C | N | C | O | C | Ph-3,4-(OMe)$_2$ | CF$_3$ |
| C | N | C | O | C | Ph-3,4-(OMe)$_2$ | Ph |
| C | N | C | O | C | Ph-2-OH | H |
| C | N | C | O | C | Ph-2-OH | Me |
| C | N | C | O | C | Ph-2-OH | Et |
| C | N | C | O | C | Ph-2-OH | n-Hex |
| C | N | C | O | C | Ph-2-OH | c-Pr |
| C | N | C | O | C | Ph-2-OH | c-Hex |
| C | N | C | O | C | Ph-2-OH | OH |
| C | N | C | O | C | Ph-2-OH | CH$_2$OH |
| C | N | C | O | C | Ph-2-OH | OMe |
| C | N | C | O | C | Ph-2-OH | SMe |
| C | N | C | O | C | Ph-2-OH | Cl |
| C | N | C | O | C | Ph-2-OH | CF$_3$ |
| C | N | C | O | C | Ph-2-OH | Ph |
| C | N | C | O | C | Ph-3-OH | H |
| C | N | C | O | C | Ph-3-OH | Me |
| C | N | C | O | C | Ph-3-OH | Et |
| C | N | C | O | C | Ph-3-OH | n-Hex |
| C | N | C | O | C | Ph-3-OH | c-Pr |
| C | N | C | O | C | Ph-3-OH | c-Hex |
| C | N | C | O | C | Ph-3-OH | OH |
| C | N | C | O | C | Ph-3-OH | CH$_2$OH |
| C | N | C | O | C | Ph-3-OH | OMe |
| C | N | C | O | C | Ph-3-OH | SMe |
| C | N | C | O | C | Ph-3-OH | Cl |
| C | N | C | O | C | Ph-3-OH | CF$_3$ |
| C | N | C | O | C | Ph-3-OH | Ph |
| C | N | C | O | C | Ph-4-OH | H |
| C | N | C | O | C | Ph-4-OH | Me |
| C | N | C | O | C | Ph-4-OH | Et |
| C | N | C | O | C | Ph-4-OH | n-Hex |
| C | N | C | O | C | Ph-4-OH | c-Pr |
| C | N | C | O | C | Ph-4-OH | c-Hex |
| C | N | C | O | C | Ph-4-OH | OH |
| C | N | C | O | C | Ph-4-OH | CH$_2$OH |
| C | N | C | O | C | Ph-4-OH | OMe |
| C | N | C | O | C | Ph-4-OH | SMe |
| C | N | C | O | C | Ph-4-OH | Cl |
| C | N | C | O | C | Ph-4-OH | CF$_3$ |
| C | N | C | O | C | Ph-4-OH | Ph |
| C | N | C | O | C | Ph-3,4-(OH)$_2$ | H |
| C | N | C | O | C | Ph-3,4-(OH)$_2$ | Me |
| C | N | C | O | C | Ph-3,4-(OH)$_2$ | Et |
| C | N | C | O | C | Ph-3,4-(OH)$_2$ | n-Hex |
| C | N | C | O | C | Ph-3,4-(OH)$_2$ | c-Pr |
| C | N | C | O | C | Ph-3,4-(OH)$_2$ | c-Hex |
| C | N | C | O | C | Ph-3,4-(OH)$_2$ | OH |
| C | N | C | O | C | Ph-3,4-(OH)$_2$ | CH$_2$OH |
| C | N | C | O | C | Ph-3,4-(OH)$_2$ | OMe |

TABLE 4-continued

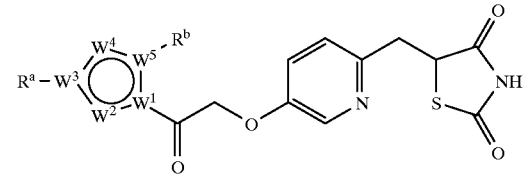

| W¹ | W² | W³ | W⁴ | W⁵ | Rᵃ | Rᵇ |
|---|---|---|---|---|---|---|
| C | N | C | O | C | Ph-3,4-(OH)$_2$ | SMe |
| C | N | C | O | C | Ph-3,4-(OH)$_2$ | Cl |
| C | N | C | O | C | Ph-3,4-(OH)$_2$ | CF$_3$ |
| C | N | C | O | C | Ph-3,4-(OH)$_2$ | Ph |
| C | N | C | O | C | Ph-3-SMe | H |
| C | N | C | O | C | Ph-3-SMe | Me |
| C | N | C | O | C | Ph-3-SMe | Et |
| C | N | C | O | C | Ph-3-SMe | n-Hex |
| C | N | C | O | C | Ph-3-SMe | c-Pr |
| C | N | C | O | C | Ph-3-SMe | c-Hex |
| C | N | C | O | C | Ph-3-SMe | OH |
| C | N | C | O | C | Ph-3-SMe | CH$_2$OH |
| C | N | C | O | C | Ph-3-SMe | OMe |
| C | N | C | O | C | Ph-3-SMe | SMe |
| C | N | C | O | C | Ph-3-SMe | Cl |
| C | N | C | O | C | Ph-3-SMe | CF$_3$ |
| C | N | C | O | C | Ph-3-SMe | Ph |
| C | N | C | O | C | Ph-3-CF$_3$ | H |
| C | N | C | O | C | Ph-3-CF$_3$ | Me |
| C | N | C | O | C | Ph-3-CF$_3$ | Et |
| C | N | C | O | C | Ph-3-CF$_3$ | n-Hex |
| C | N | C | O | C | Ph-3-CF$_3$ | c-Pr |
| C | N | C | O | C | Ph-3-CF$_3$ | c-Hex |
| C | N | C | O | C | Ph-3-CF$_3$ | OH |
| C | N | C | O | C | Ph-3-CF$_3$ | CH$_2$OH |
| C | N | C | O | C | Ph-3-CF$_3$ | OMe |
| C | N | C | O | C | Ph-3-CF$_3$ | SMe |
| C | N | C | O | C | Ph-3-CF$_3$ | Cl |
| C | N | C | O | C | Ph-3-CF$_3$ | CF$_3$ |
| C | N | C | O | C | Ph-3-CF$_3$ | Ph |
| C | N | C | O | C | Ph-3-NO$_2$ | H |
| C | N | C | O | C | Ph-3-NO$_2$ | Me |
| C | N | C | O | C | Ph-3-NO$_2$ | Et |
| C | N | C | O | C | Ph-3-NO$_2$ | n-Hex |
| C | N | C | O | C | Ph-3-NO$_2$ | c-Pr |
| C | N | C | O | C | Ph-3-NO$_2$ | c-Hex |
| C | N | C | O | C | Ph-3-NO$_2$ | OH |
| C | N | C | O | C | Ph-3-NO$_2$ | CH$_2$OH |
| C | N | C | O | C | Ph-3-NO$_2$ | OMe |
| C | N | C | O | C | Ph-3-NO$_2$ | SMe |
| C | N | C | O | C | Ph-3-NO$_2$ | Cl |
| C | N | C | O | C | Ph-3-NO$_2$ | CF$_3$ |
| C | N | C | O | C | Ph-3-NO$_2$ | Ph |
| C | N | C | O | C | Ph-4-NMe$_2$ | H |
| C | N | C | O | C | Ph-4-NMe$_2$ | Me |
| C | N | C | O | C | Ph-4-NMe$_2$ | Et |
| C | N | C | O | C | Ph-4-NMe$_2$ | n-Hex |
| C | N | C | O | C | Ph-4-NMe$_2$ | c-Pr |
| C | N | C | O | C | Ph-4-NMe$_2$ | c-Hex |
| C | N | C | O | C | Ph-4-NMe$_2$ | OH |
| C | N | C | O | C | Ph-4-NMe$_2$ | CH$_2$OH |
| C | N | C | O | C | Ph-4-NMe$_2$ | OMe |
| C | N | C | O | C | Ph-4-NMe$_2$ | SMe |
| C | N | C | O | C | Ph-4-NMe$_2$ | Cl |
| C | N | C | O | C | Ph-4-NMe$_2$ | CF$_3$ |
| C | N | C | O | C | Ph-4-NMe$_2$ | Ph |
| C | N | C | S | C | Ph | H |
| C | N | C | S | C | Ph | Me |
| C | N | C | S | C | Ph | Et |
| C | N | C | S | C | Ph | n-Hex |
| C | N | C | S | C | Ph | c-Pr |
| C | N | C | S | C | Ph | c-Hex |
| C | N | C | S | C | Ph | OH |
| C | N | C | S | C | Ph | CH$_2$OH |
| C | N | C | S | C | Ph | OMe |
| C | N | C | S | C | Ph | SMe |
| C | N | C | S | C | Ph | Cl |

TABLE 4-continued

| W¹ | W² | W³ | W⁴ | W⁵ | Rᵃ | Rᵇ |
|---|---|---|---|---|---|---|
| C | N | C | S | C | Ph | CF$_3$ |
| C | N | C | S | C | Ph | Ph |
| C | N | C | S | C | H | H |
| C | N | C | S | C | H | Me |
| C | N | C | S | C | H | Et |
| C | N | C | S | C | H | n-Hex |
| C | N | C | S | C | H | c-Pr |
| C | N | C | S | C | H | c-Hex |
| C | N | C | S | C | H | OH |
| C | N | C | S | C | H | CH$_2$OH |
| C | N | C | S | C | H | OMe |
| C | N | C | S | C | H | SMe |
| C | N | C | S | C | H | Cl |
| C | N | C | S | C | H | CF$_3$ |
| C | N | C | S | C | H | Ph |
| C | N | C | S | C | Me | H |
| C | N | C | S | C | Me | Me |
| C | N | C | S | C | Me | Et |
| C | N | C | S | C | Me | n-Hex |
| C | N | C | S | C | Me | c-Pr |
| C | N | C | S | C | Me | c-Hex |
| C | N | C | S | C | Me | OH |
| C | N | C | S | C | Me | CH$_2$OH |
| C | N | C | S | C | Me | OMe |
| C | N | C | S | C | Me | SMe |
| C | N | C | S | C | Me | Cl |
| C | N | C | S | C | Me | CF$_3$ |
| C | N | C | S | C | Me | Ph |
| C | N | C | S | C | Et | H |
| C | N | C | S | C | Et | Me |
| C | N | C | S | C | Et | Et |
| C | N | C | S | C | Et | n-Hex |
| C | N | C | S | C | Et | c-Pr |
| C | N | C | S | C | Et | c-Hex |
| C | N | C | S | C | Et | OH |
| C | N | C | S | C | Et | CH$_2$OH |
| C | N | C | S | C | Et | OMe |
| C | N | C | S | C | Et | SMe |
| C | N | C | S | C | Et | Cl |
| C | N | C | S | C | Et | CF$_3$ |
| C | N | C | S | C | Et | Ph |
| C | N | C | S | C | n-Pr | H |
| C | N | C | S | C | n-Pr | Me |
| C | N | C | S | C | n-Pr | Et |
| C | N | C | S | C | n-Pr | n-Hex |
| C | N | C | S | C | n-Pr | c-Pr |
| C | N | C | S | C | n-Pr | c-Hex |
| C | N | C | S | C | n-Pr | OH |
| C | N | C | S | C | n-Pr | CH$_2$OH |
| C | N | C | S | C | n-Pr | OMe |
| C | N | C | S | C | n-Pr | SMe |
| C | N | C | S | C | n-Pr | Cl |
| C | N | C | S | C | n-Pr | CF$_3$ |
| C | N | C | S | C | n-Pr | Ph |
| C | N | C | S | C | n-Hex | H |
| C | N | C | S | C | n-Hex | Me |
| C | N | C | S | C | n-Hex | Et |
| C | N | C | S | C | n-Hex | n-Hex |
| C | N | C | S | C | n-Hex | c-Pr |
| C | N | C | S | C | n-Hex | c-Hex |
| C | N | C | S | C | n-Hex | OH |
| C | N | C | S | C | n-Hex | CH$_2$OH |
| C | N | C | S | C | n-Hex | OMe |
| C | N | C | S | C | n-Hex | SMe |
| C | N | C | S | C | n-Hex | Cl |
| C | N | C | S | C | n-Hex | CF$_3$ |
| C | N | C | S | C | n-Hex | Ph |
| C | N | C | S | C | i-Pr | H |
| C | N | C | S | C | i-Pr | Me |
| C | N | C | S | C | i-Pr | n-Hex |
| C | N | C | S | C | i-Pr | c-Pr |
| C | N | C | S | C | i-Pr | c-Hex |
| C | N | C | S | C | i-Pr | OH |
| C | N | C | S | C | i-Pr | CH$_2$OH |
| C | N | C | S | C | i-Pr | OMe |
| C | N | C | S | C | i-Pr | SMe |
| C | N | C | S | C | i-Pr | Cl |
| C | N | C | S | C | i-Pr | CF$_3$ |
| C | N | C | S | C | i-Pr | Ph |
| C | N | C | S | C | t-Bu | H |
| C | N | C | S | C | t-Bu | Me |
| C | N | C | S | C | t-Bu | Et |
| C | N | C | S | C | t-Bu | n-Hex |
| C | N | C | S | C | t-Bu | c-Pr |
| C | N | C | S | C | t-Bu | c-Hex |
| C | N | C | S | C | t-Bu | OH |
| C | N | C | S | C | t-Bu | CH$_2$OH |
| C | N | C | S | C | t-Bu | OMe |
| C | N | C | S | C | t-Bu | SMe |
| C | N | C | S | C | t-Bu | Cl |
| C | N | C | S | C | t-Bu | CF$_3$ |
| C | N | C | S | C | t-Bu | Ph |
| C | N | C | S | C | c-Hex | H |
| C | N | C | S | C | c-Hex | Me |
| C | N | C | S | C | c-Hex | Et |
| C | N | C | S | C | c-Hex | n-Hex |
| C | N | C | S | C | c-Hex | c-Pr |
| C | N | C | S | C | c-Hex | c-Hex |
| C | N | C | S | C | c-Hex | OH |
| C | N | C | S | C | c-Hex | CH$_2$OH |
| C | N | C | S | C | c-Hex | OMe |
| C | N | C | S | C | c-Hex | SMe |
| C | N | C | S | C | c-Hex | Cl |
| C | N | C | S | C | c-Hex | CF$_3$ |
| C | N | C | S | C | c-Hex | Ph |
| C | N | C | S | C | 3-c-hexenyl | H |
| C | N | C | S | C | 3-c-hexenyl | Me |
| C | N | C | S | C | 3-c-hexenyl | Et |
| C | N | C | S | C | 3-c-hexenyl | n-Hex |
| C | N | C | S | C | 3-c-hexenyl | c-Pr |
| C | N | C | S | C | 3-c-hexenyl | c-Hex |
| C | N | C | S | C | 3-c-hexenyl | OH |
| C | N | C | S | C | 3-c-hexenyl | CH$_2$OH |
| C | N | C | S | C | 3-c-hexenyl | OMe |
| C | N | C | S | C | 3-c-hexenyl | SMe |
| C | N | C | S | C | 3-c-hexenyl | Cl |
| C | N | C | S | C | 3-c-hexenyl | CF$_3$ |
| C | N | C | S | C | 3-c-hexenyl | Ph |
| C | N | C | S | C | CH$_2$OH | H |
| C | N | C | S | C | CH$_2$OH | Me |
| C | N | C | S | C | CH$_2$OH | Et |
| C | N | C | S | C | CH$_2$OH | n-Hex |
| C | N | C | S | C | CH$_2$OH | c-Pr |
| C | N | C | S | C | CH$_2$OH | c-Hex |
| C | N | C | S | C | CH$_2$OH | OH |
| C | N | C | S | C | CH$_2$OH | CH$_2$OH |
| C | N | C | S | C | CH$_2$OH | OMe |
| C | N | C | S | C | CH$_2$OH | SMe |
| C | N | C | S | C | CH$_2$OH | Cl |
| C | N | C | S | C | CH$_2$OH | CF$_3$ |
| C | N | C | S | C | CH$_2$OH | Ph |
| C | N | C | S | C | CH$_2$Ph | H |
| C | N | C | S | C | CH$_2$Ph | Me |

TABLE 4-continued

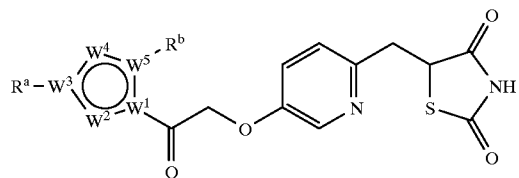
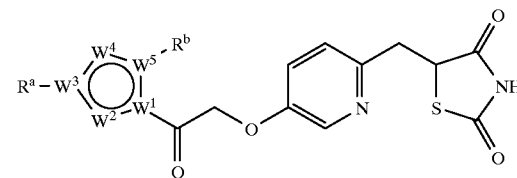

| W¹ | W² | W³ | W⁴ | W⁵ | Rᵃ | Rᵇ |
|---|---|---|---|---|---|---|
| C | N | C | S | C | CH₂Ph | Et |
| C | N | C | S | C | CH₂Ph | n-Hex |
| C | N | C | S | C | CH₂Ph | c-Pr |
| C | N | C | S | C | CH₂Ph | c-Hex |
| C | N | C | S | C | CH₂Ph | OH |
| C | N | C | S | C | CH₂Ph | CH₂OH |
| C | N | C | S | C | CH₂Ph | OMe |
| C | N | C | S | C | CH₂Ph | SMe |
| C | N | C | S | C | CH₂Ph | Cl |
| C | N | C | S | C | CH₂Ph | CF₃ |
| C | N | C | S | C | CH₂Ph | Ph |
| C | N | C | S | C | α-naphthyl | H |
| C | N | C | S | C | α-naphthyl | Me |
| C | N | C | S | C | α-naphthyl | Et |
| C | N | C | S | C | α-naphthyl | n-Hex |
| C | N | C | S | C | α-naphthyl | c-Pr |
| C | N | C | S | C | α-naphthyl | c-Hex |
| C | N | C | S | C | α-naphthyl | OH |
| C | N | C | S | C | α-naphthyl | CH₂OH |
| C | N | C | S | C | α-naphthyl | OMe |
| C | N | C | S | C | α-naphthyl | SMe |
| C | N | C | S | C | α-naphthyl | Cl |
| C | N | C | S | C | α-naphthyl | CF₃ |
| C | N | C | S | C | α-naphthyl | Ph |
| C | N | C | S | C | β-naphthyl | H |
| C | N | C | S | C | β-naphthyl | Me |
| C | N | C | S | C | β-naphthyl | Et |
| C | N | C | S | C | β-naphthyl | n-Hex |
| C | N | C | S | C | β-naphthyl | c-Pr |
| C | N | C | S | C | β-naphthyl | c-Hex |
| C | N | C | S | C | β-naphthyl | OH |
| C | N | C | S | C | β-naphthyl | CH₂OH |
| C | N | C | S | C | β-naphthyl | OMe |
| C | N | C | S | C | β-naphthyl | SMe |
| C | N | C | S | C | β-naphthyl | Cl |
| C | N | C | S | C | β-naphthyl | CF₃ |
| C | N | C | S | C | β-naphthyl | Ph |
| C | N | C | S | C | 2-pyridyl | H |
| C | N | C | S | C | 2-pyridyl | Me |
| C | N | C | S | C | 2-pyridyl | Et |
| C | N | C | S | C | 2-pyridyl | n-Hex |
| C | N | C | S | C | 2-pyridyl | c-Pr |
| C | N | C | S | C | 2-pyridyl | c-Hex |
| C | N | C | S | C | 2-pyridyl | OH |
| C | N | C | S | C | 2-pyridyl | CH₂OH |
| C | N | C | S | C | 2-pyridyl | OMe |
| C | N | C | S | C | 2-pyridyl | SMe |
| C | N | C | S | C | 2-pyridyl | Cl |
| C | N | C | S | C | 2-pyridyl | CF₃ |
| C | N | C | S | C | 2-pyridyl | Ph |
| C | N | C | S | C | 3-pyridyl | H |
| C | N | C | S | C | 3-pyridyl | Me |
| C | N | C | S | C | 3-pyridyl | Et |
| C | N | C | S | C | 3-pyridyl | n-Hex |
| C | N | C | S | C | 3-pyridyl | c-Pr |
| C | N | C | S | C | 3-pyridyl | c-Hex |
| C | N | C | S | C | 3-pyridyl | OH |
| C | N | C | S | C | 3-pyridyl | CH₂OH |
| C | N | C | S | C | 3-pyridyl | OMe |
| C | N | C | S | C | 3-pyridyl | SMe |
| C | N | C | S | C | 3-pyridyl | Cl |
| C | N | C | S | C | 3-pyridyl | CF₃ |
| C | N | C | S | C | 3-pyridyl | Ph |
| C | N | C | S | C | 4-pyridyl | H |
| C | N | C | S | C | 4-pyridyl | Me |
| C | N | C | S | C | 4-pyridyl | Et |
| C | N | C | S | C | 4-pyridyl | n-Hex |
| C | N | C | S | C | 4-pyridyl | c-Pr |
| C | N | C | S | C | 4-pyridyl | c-Hex |
| C | N | C | S | C | 4-pyridyl | OH |
| C | N | C | S | C | 4-pyridyl | CH₂OH |
| C | N | C | S | C | 4-pyridyl | OMe |
| C | N | C | S | C | 4-pyridyl | SMe |
| C | N | C | S | C | 4-pyridyl | Cl |
| C | N | C | S | C | 4-pyridyl | CF₃ |
| C | N | C | S | C | 4-pyridyl | Ph |
| C | N | C | S | C | 2-furanyl | H |
| C | N | C | S | C | 2-furanyl | Me |
| C | N | C | S | C | 2-furanyl | Et |
| C | N | C | S | C | 2-furanyl | n-Hex |
| C | N | C | S | C | 2-furanyl | c-Pr |
| C | N | C | S | C | 2-furanyl | c-Hex |
| C | N | C | S | C | 2-furanyl | OH |
| C | N | C | S | C | 2-furanyl | CH₂OH |
| C | N | C | S | C | 2-furanyl | OMe |
| C | N | C | S | C | 2-furanyl | SMe |
| C | N | C | S | C | 2-furanyl | Cl |
| C | N | C | S | C | 2-furanyl | CF₃ |
| C | N | C | S | C | 2-furanyl | Ph |
| C | N | C | S | C | 2-thienyl | H |
| C | N | C | S | C | 2-thienyl | Me |
| C | N | C | S | C | 2-thienyl | Et |
| C | N | C | S | C | 2-thienyl | n-Hex |
| C | N | C | S | C | 2-thienyl | c-Pr |
| C | N | C | S | C | 2-thienyl | c-Hex |
| C | N | C | S | C | 2-thienyl | OH |
| C | N | C | S | C | 2-thienyl | CH₂OH |
| C | N | C | S | C | 2-thienyl | OMe |
| C | N | C | S | C | 2-thienyl | SMe |
| C | N | C | S | C | 2-thienyl | Cl |
| C | N | C | S | C | 2-thienyl | CF₃ |
| C | N | C | S | C | 2-thienyl | Ph |
| C | N | C | S | C | 2-tolyl | H |
| C | N | C | S | C | 2-tolyl | Me |
| C | N | C | S | C | 2-tolyl | Et |
| C | N | C | S | C | 2-tolyl | n-Hex |
| C | N | C | S | C | 2-tolyl | c-Pr |
| C | N | C | S | C | 2-tolyl | c-Hex |
| C | N | C | S | C | 2-tolyl | OH |
| C | N | C | S | C | 2-tolyl | CH₂OH |
| C | N | C | S | C | 2-tolyl | OMe |
| C | N | C | S | C | 2-tolyl | SMe |
| C | N | C | S | C | 2-tolyl | Cl |
| C | N | C | S | C | 2-tolyl | CF₃ |
| C | N | C | S | C | 2-tolyl | Ph |
| C | N | C | S | C | 3-tolyl | H |
| C | N | C | S | C | 3-tolyl | Me |
| C | N | C | S | C | 3-tolyl | Et |
| C | N | C | S | C | 3-tolyl | n-Hex |
| C | N | C | S | C | 3-tolyl | c-Pr |
| C | N | C | S | C | 3-tolyl | c-Hex |
| C | N | C | S | C | 3-tolyl | OH |
| C | N | C | S | C | 3-tolyl | CH₂OH |
| C | N | C | S | C | 3-tolyl | OMe |
| C | N | C | S | C | 3-tolyl | SMe |
| C | N | C | S | C | 3-tolyl | Cl |
| C | N | C | S | C | 3-tolyl | CF₃ |
| C | N | C | S | C | 3-tolyl | Ph |
| C | N | C | S | C | 4-tolyl | H |
| C | N | C | S | C | 4-tolyl | Me |
| C | N | C | S | C | 4-tolyl | Et |
| C | N | C | S | C | 4-tolyl | n-Hex |
| C | N | C | S | C | 4-tolyl | c-Pr |
| C | N | C | S | C | 4-tolyl | c-Hex |

TABLE 4-continued

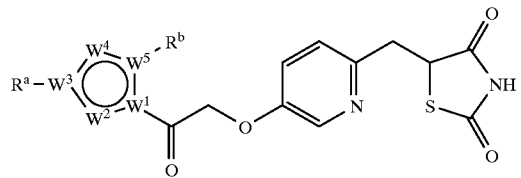

| W¹ | W² | W³ | W⁴ | W⁵ | Rᵃ | Rᵇ |
|---|---|---|---|---|---|---|
| C | N | C | S | C | 4-tolyl | OH |
| C | N | C | S | C | 4-tolyl | CH₂OH |
| C | N | C | S | C | 4-tolyl | OMe |
| C | N | C | S | C | 4-tolyl | SMe |
| C | N | C | S | C | 4-tolyl | Cl |
| C | N | C | S | C | 4-tolyl | CF₃ |
| C | N | C | S | C | 4-tolyl | Ph |
| C | N | C | S | C | Ph-2,3-Me₂ | H |
| C | N | C | S | C | Ph-2,3-Me₂ | Me |
| C | N | C | S | C | Ph-2,3-Me₂ | Et |
| C | N | C | S | C | Ph-2,3-Me₂ | n-Hex |
| C | N | C | S | C | Ph-2,3-Me₂ | c-Pr |
| C | N | C | S | C | Ph-2,3-Me₂ | c-Hex |
| C | N | C | S | C | Ph-2,3-Me₂ | OH |
| C | N | C | S | C | Ph-2,3-Me₂ | CH₂OH |
| C | N | C | S | C | Ph-2,3-Me₂ | OMe |
| C | N | C | S | C | Ph-2,3-Me₂ | SMe |
| C | N | C | S | C | Ph-2,3-Me₂ | Cl |
| C | N | C | S | C | Ph-2,3-Me₂ | CF₃ |
| C | N | C | S | C | Ph-2,3-Me₂ | Ph |
| C | N | C | S | C | Ph-3,4-Me₂ | H |
| C | N | C | S | C | Ph-3,4-Me₂ | Me |
| C | N | C | S | C | Ph-3,4-Me₂ | Et |
| C | N | C | S | C | Ph-3,4-Me₂ | n-Hex |
| C | N | C | S | C | Ph-3,4-Me₂ | c-Pr |
| C | N | C | S | C | Ph-3,4-Me₂ | c-Hex |
| C | N | C | S | C | Ph-3,4-Me₂ | OH |
| C | N | C | S | C | Ph-3,4-Me₂ | CH₂OH |
| C | N | C | S | C | Ph-3,4-Me₂ | OMe |
| C | N | C | S | C | Ph-3,4-Me₂ | SMe |
| C | N | C | S | C | Ph-3,4-Me₂ | Cl |
| C | N | C | S | C | Ph-3,4-Me₂ | CF₃ |
| C | N | C | S | C | Ph-3,4-Me₂ | Ph |
| C | N | C | S | C | Ph-3,5-Me₂ | H |
| C | N | C | S | C | Ph-3,5-Me₂ | Me |
| C | N | C | S | C | Ph-3,5-Me₂ | Et |
| C | N | C | S | C | Ph-3,5-Me₂ | n-Hex |
| C | N | C | S | C | Ph-3,5-Me₂ | c-Pr |
| C | N | C | S | C | Ph-3,5-Me₂ | c-Hex |
| C | N | C | S | C | Ph-3,5-Me₂ | OH |
| C | N | C | S | C | Ph-3,5-Me₂ | CH₂OH |
| C | N | C | S | C | Ph-3,5-Me₂ | OMe |
| C | N | C | S | C | Ph-3,5-Me₂ | SMe |
| C | N | C | S | C | Ph-3,5-Me₂ | Cl |
| C | N | C | S | C | Ph-3,5-Me₂ | CF₃ |
| C | N | C | S | C | Ph-3,5-Me₂ | Ph |
| C | N | C | S | C | Ph-2,6-Me₂ | H |
| C | N | C | S | C | Ph-2,6-Me₂ | Me |
| C | N | C | S | C | Ph-2,6-Me₂ | Et |
| C | N | C | S | C | Ph-2,6-Me₂ | n-Hex |
| C | N | C | S | C | Ph-2,6-Me₂ | c-Pr |
| C | N | C | S | C | Ph-2,6-Me₂ | c-Hex |
| C | N | C | S | C | Ph-2,6-Me₂ | OH |
| C | N | C | S | C | Ph-2,6-Me₂ | CH₂OH |
| C | N | C | S | C | Ph-2,6-Me₂ | OMe |
| C | N | C | S | C | Ph-2,6-Me₂ | SMe |
| C | N | C | S | C | Ph-2,6-Me₂ | Cl |
| C | N | C | S | C | Ph-2,6-Me₂ | CF₃ |
| C | N | C | S | C | Ph-2,6-Me₂ | Ph |
| C | N | C | S | C | Ph-2-Cl | H |
| C | N | C | S | C | Ph-2-Cl | Me |
| C | N | C | S | C | Ph-2-Cl | Et |
| C | N | C | S | C | Ph-2-Cl | n-Hex |
| C | N | C | S | C | Ph-2-Cl | c-Pr |
| C | N | C | S | C | Ph-2-Cl | c-Hex |
| C | N | C | S | C | Ph-2-Cl | OH |
| C | N | C | S | C | Ph-2-Cl | CH₂OH |

TABLE 4-continued

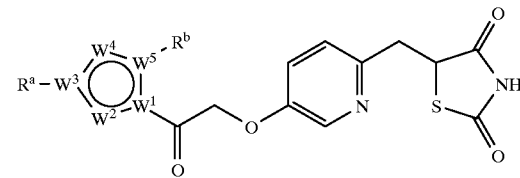

| W¹ | W² | W³ | W⁴ | W⁵ | Rᵃ | Rᵇ |
|---|---|---|---|---|---|---|
| C | N | C | S | C | Ph-2-Cl | OMe |
| C | N | C | S | C | Ph-2-Cl | SMe |
| C | N | C | S | C | Ph-2-Cl | Cl |
| C | N | C | S | C | Ph-2-Cl | CF₃ |
| C | N | C | S | C | Ph-2-Cl | Ph |
| C | N | C | S | C | Ph-3-Cl | H |
| C | N | C | S | C | Ph-3-Cl | Me |
| C | N | C | S | C | Ph-3-Cl | Et |
| C | N | C | S | C | Ph-3-Cl | n-Hex |
| C | N | C | S | C | Ph-3-Cl | c-Pr |
| C | N | C | S | C | Ph-3-Cl | c-Hex |
| C | N | C | S | C | Ph-3-Cl | OH |
| C | N | C | S | C | Ph-3-Cl | CH₂OH |
| C | N | C | S | C | Ph-3-Cl | OMe |
| C | N | C | S | C | Ph-3-Cl | SMe |
| C | N | C | S | C | Ph-3-Cl | Cl |
| C | N | C | S | C | Ph-3-Cl | CF₃ |
| C | N | C | S | C | Ph-3-Cl | Ph |
| C | N | C | S | C | Ph-4-Cl | H |
| C | N | C | S | C | Ph-4-Cl | Me |
| C | N | C | S | C | Ph-4-Cl | Et |
| C | N | C | S | C | Ph-4-Cl | n-Hex |
| C | N | C | S | C | Ph-4-Cl | c-Pr |
| C | N | C | S | C | Ph-4-Cl | c-Hex |
| C | N | C | S | C | Ph-4-Cl | OH |
| C | N | C | S | C | Ph-4-Cl | CH₂OH |
| C | N | C | S | C | Ph-4-Cl | OMe |
| C | N | C | S | C | Ph-4-Cl | SMe |
| C | N | C | S | C | Ph-4-Cl | Cl |
| C | N | C | S | C | Ph-4-Cl | CF₃ |
| C | N | C | S | C | Ph-4-Cl | Ph |
| C | N | C | S | C | Ph-3,4-Cl₂ | H |
| C | N | C | S | C | Ph-3,4-Cl₂ | Me |
| C | N | C | S | C | Ph-3,4-Cl₂ | Et |
| C | N | C | S | C | Ph-3,4-Cl₂ | n-Hex |
| C | N | C | S | C | Ph-3,4-Cl₂ | c-Pr |
| C | N | C | S | C | Ph-3,4-Cl₂ | c-Hex |
| C | N | C | S | C | Ph-3,4-Cl₂ | OH |
| C | N | C | S | C | Ph-3,4-Cl₂ | CH₂OH |
| C | N | C | S | C | Ph-3,4-Cl₂ | OMe |
| C | N | C | S | C | Ph-3,4-Cl₂ | SMe |
| C | N | C | S | C | Ph-3,4-Cl₂ | Cl |
| C | N | C | S | C | Ph-3,4-Cl₂ | CF₃ |
| C | N | C | S | C | Ph-3,4-Cl₂ | Ph |
| C | N | C | S | C | Ph-4-F | H |
| C | N | C | S | C | Ph-4-F | Me |
| C | N | C | S | C | Ph-4-F | Et |
| C | N | C | S | C | Ph-4-F | n-Hex |
| C | N | C | S | C | Ph-4-F | c-Pr |
| C | N | C | S | C | Ph-4-F | c-Hex |
| C | N | C | S | C | Ph-4-F | OH |
| C | N | C | S | C | Ph-4-F | CH₂OH |
| C | N | C | S | C | Ph-4-F | OMe |
| C | N | C | S | C | Ph-4-F | SMe |
| C | N | C | S | C | Ph-4-F | Cl |
| C | N | C | S | C | Ph-4-F | CF₃ |
| C | N | C | S | C | Ph-4-F | Ph |
| C | N | C | S | C | Ph-4-Br | H |
| C | N | C | S | C | Ph-4-Br | Me |
| C | N | C | S | C | Ph-4-Br | Et |
| C | N | C | S | C | Ph-4-Br | n-Hex |
| C | N | C | S | C | Ph-4-Br | c-Pr |
| C | N | C | S | C | Ph-4-Br | c-Hex |
| C | N | C | S | C | Ph-4-Br | OH |
| C | N | C | S | C | Ph-4-Br | CH₂OH |
| C | N | C | S | C | Ph-4-Br | OMe |
| C | N | C | S | C | Ph-4-Br | SMe |

TABLE 4-continued

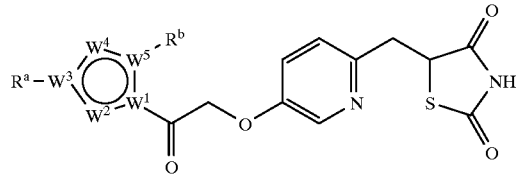
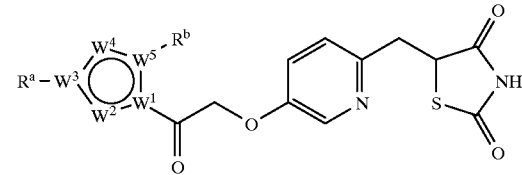

| W¹ | W² | W³ | W⁴ | W⁵ | Rᵃ | Rᵇ |
|---|---|---|---|---|---|---|
| C | N | C | S | C | Ph-4-Br | Cl |
| C | N | C | S | C | Ph-4-Br | $CF_3$ |
| C | N | C | S | C | Ph-4-Br | Ph |
| C | N | C | S | C | Ph-2-OMe | H |
| C | N | C | S | C | Ph-2-OMe | Me |
| C | N | C | S | C | Ph-2-OMe | Et |
| C | N | C | S | C | Ph-2-OMe | n-Hex |
| C | N | C | S | C | Ph-2-OMe | c-Pr |
| C | N | C | S | C | Ph-2-OMe | c-Hex |
| C | N | C | S | C | Ph-2-OMe | OH |
| C | N | C | S | C | Ph-2-OMe | $CH_2OH$ |
| C | N | C | S | C | Ph-2-OMe | OMe |
| C | N | C | S | C | Ph-2-OMe | SMe |
| C | N | C | S | C | Ph-2-OMe | Cl |
| C | N | C | S | C | Ph-2-OMe | $CF_3$ |
| C | N | C | S | C | Ph-2-OMe | Ph |
| C | N | C | S | C | Ph-3-OMe | H |
| C | N | C | S | C | Ph-3-OMe | Me |
| C | N | C | S | C | Ph-3-OMe | Et |
| C | N | C | S | C | Ph-3-OMe | n-Hex |
| C | N | C | S | C | Ph-3-OMe | c-Pr |
| C | N | C | S | C | Ph-3-OMe | c-Hex |
| C | N | C | S | C | Ph-3-OMe | OH |
| C | N | C | S | C | Ph-3-OMe | $CH_2OH$ |
| C | N | C | S | C | Ph-3-OMe | OMe |
| C | N | C | S | C | Ph-3-OMe | SMe |
| C | N | C | S | C | Ph-3-OMe | Cl |
| C | N | C | S | C | Ph-3-OMe | $CF_3$ |
| C | N | C | S | C | Ph-3-OMe | Ph |
| C | N | C | S | C | Ph-4-OMe | H |
| C | N | C | S | C | Ph-4-OMe | Me |
| C | N | C | S | C | Ph-4-OMe | Et |
| C | N | C | S | C | Ph-4-OMe | n-Hex |
| C | N | C | S | C | Ph-4-OMe | c-Pr |
| C | N | C | S | C | Ph-4-OMe | c-Hex |
| C | N | C | S | C | Ph-4-OMe | OH |
| C | N | C | S | C | Ph-4-OMe | $CH_2OH$ |
| C | N | C | S | C | Ph-4-OMe | OMe |
| C | N | C | S | C | Ph-4-OMe | SMe |
| C | N | C | S | C | Ph-4-OMe | Cl |
| C | N | C | S | C | Ph-4-OMe | $CF_3$ |
| C | N | C | S | C | Ph-4-OMe | Ph |
| C | N | C | S | C | Ph-3,4-(OMe)₂ | H |
| C | N | C | S | C | Ph-3,4-(OMe)₂ | Me |
| C | N | C | S | C | Ph-3,4-(OMe)₂ | Et |
| C | N | C | S | C | Ph-3,4-(OMe)₂ | n-Hex |
| C | N | C | S | C | Ph-3,4-(OMe)₂ | c-Pr |
| C | N | C | S | C | Ph-3,4-(OMe)₂ | c-Hex |
| C | N | C | S | C | Ph-3,4-(OMe)₂ | OH |
| C | N | C | S | C | Ph-3,4-(OMe)₂ | $CH_2OH$ |
| C | N | C | S | C | Ph-3,4-(OMe)₂ | OMe |
| C | N | C | S | C | Ph-3,4-(OMe)₂ | SMe |
| C | N | C | S | C | Ph-3,4-(OMe)₂ | Cl |
| C | N | C | S | C | Ph-3,4-(OMe)₂ | $CF_3$ |
| C | N | C | S | C | Ph-3,4-(OMe)₂ | Ph |
| C | N | C | S | C | Ph-2-OH | H |
| C | N | C | S | C | Ph-2-OH | Me |
| C | N | C | S | C | Ph-2-OH | Et |
| C | N | C | S | C | Ph-2-OH | n-Hex |
| C | N | C | S | C | Ph-2-OH | c-Pr |
| C | N | C | S | C | Ph-2-OH | c-Hex |
| C | N | C | S | C | Ph-2-OH | OH |
| C | N | C | S | C | Ph-2-OH | $CH_2OH$ |
| C | N | C | S | C | Ph-2-OH | OMe |
| C | N | C | S | C | Ph-2-OH | SMe |
| C | N | C | S | C | Ph-2-OH | Cl |
| C | N | C | S | C | Ph-2-OH | $CF_3$ |
| C | N | C | S | C | Ph-2-OH | Ph |
| C | N | C | S | C | Ph-3-OH | H |
| C | N | C | S | C | Ph-3-OH | Me |
| C | N | C | S | C | Ph-3-OH | Et |
| C | N | C | S | C | Ph-3-OH | n-Hex |
| C | N | C | S | C | Ph-3-OH | c-Pr |
| C | N | C | S | C | Ph-3-OH | c-Hex |
| C | N | C | S | C | Ph-3-OH | OH |
| C | N | C | S | C | Ph-3-OH | $CH_2OH$ |
| C | N | C | S | C | Ph-3-OH | OMe |
| C | N | C | S | C | Ph-3-OH | SMe |
| C | N | C | S | C | Ph-3-OH | Cl |
| C | N | C | S | C | Ph-3-OH | $CF_3$ |
| C | N | C | S | C | Ph-3-OH | Ph |
| C | N | C | S | C | Ph-4-OH | H |
| C | N | C | S | C | Ph-4-OH | Me |
| C | N | C | S | C | Ph-4-OH | Et |
| C | N | C | S | C | Ph-4-OH | n-Hex |
| C | N | C | S | C | Ph-4-OH | c-Pr |
| C | N | C | S | C | Ph-4-OH | c-Hex |
| C | N | C | S | C | Ph-4-OH | OH |
| C | N | C | S | C | Ph-4-OH | $CH_2OH$ |
| C | N | C | S | C | Ph-4-OH | OMe |
| C | N | C | S | C | Ph-4-OH | SMe |
| C | N | C | S | C | Ph-4-OH | Cl |
| C | N | C | S | C | Ph-4-OH | $CF_3$ |
| C | N | C | S | C | Ph-4-OH | Ph |
| C | N | C | S | C | Ph-3,4-(OH)₂ | H |
| C | N | C | S | C | Ph-3,4-(OH)₂ | Me |
| C | N | C | S | C | Ph-3,4-(OH)₂ | Et |
| C | N | C | S | C | Ph-3,4-(OH)₂ | n-Hex |
| C | N | C | S | C | Ph-3,4-(OH)₂ | c-Pr |
| C | N | C | S | C | Ph-3,4-(OH)₂ | c-Hex |
| C | N | C | S | C | Ph-3,4-(OH)₂ | OH |
| C | N | C | S | C | Ph-3,4-(OH)₂ | $CH_2OH$ |
| C | N | C | S | C | Ph-3,4-(OH)₂ | OMe |
| C | N | C | S | C | Ph-3,4-(OH)₂ | SMe |
| C | N | C | S | C | Ph-3,4-(OH)₂ | Cl |
| C | N | C | S | C | Ph-3,4-(OH)₂ | $CF_3$ |
| C | N | C | S | C | Ph-3,4-(OH)₂ | Ph |
| C | N | C | S | C | Ph-3-SMe | H |
| C | N | C | S | C | Ph-3-SMe | Me |
| C | N | C | S | C | Ph-3-SMe | Et |
| C | N | C | S | C | Ph-3-SMe | n-Hex |
| C | N | C | S | C | Ph-3-SMe | c-Pr |
| C | N | C | S | C | Ph-3-SMe | c-Hex |
| C | N | C | S | C | Ph-3-SMe | OH |
| C | N | C | S | C | Ph-3-SMe | $CH_2OH$ |
| C | N | C | S | C | Ph-3-SMe | OMe |
| C | N | C | S | C | Ph-3-SMe | SMe |
| C | N | C | S | C | Ph-3-SMe | Cl |
| C | N | C | S | C | Ph-3-SMe | $CF_3$ |
| C | N | C | S | C | Ph-3-SMe | Ph |
| C | N | C | S | C | Ph-3-$CF_3$ | H |
| C | N | C | S | C | Ph-3-$CF_3$ | Me |
| C | N | C | S | C | Ph-3-$CF_3$ | Et |
| C | N | C | S | C | Ph-3-$CF_3$ | n-Hex |
| C | N | C | S | C | Ph-3-$CF_3$ | c-Pr |
| C | N | C | S | C | Ph-3-$CF_3$ | c-Hex |
| C | N | C | S | C | Ph-3-$CF_3$ | OH |
| C | N | C | S | C | Ph-3-$CF_3$ | $CH_2OH$ |
| C | N | C | S | C | Ph-3-$CF_3$ | OMe |
| C | N | C | S | C | Ph-3-$CF_3$ | SMe |
| C | N | C | S | C | Ph-3-$CF_3$ | Cl |
| C | N | C | S | C | Ph-3-$CF_3$ | $CF_3$ |
| C | N | C | S | C | Ph-3-$CF_3$ | Ph |
| C | N | C | S | C | Ph-3-$NO_2$ | H |

TABLE 4-continued

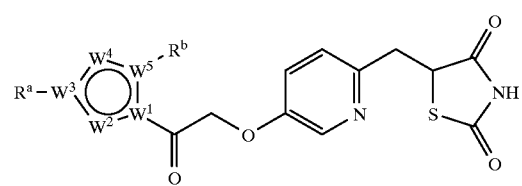
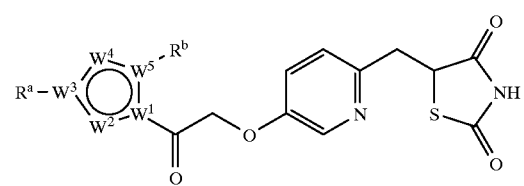

| W¹ | W² | W³ | W⁴ | W⁵ | Rᵃ | Rᵇ |
|---|---|---|---|---|---|---|
| C | N | C | S | C | Ph-3-NO₂ | Me |
| C | N | C | S | C | Ph-3-NO₂ | Et |
| C | N | C | S | C | Ph-3-NO₂ | n-Hex |
| C | N | C | S | C | Ph-3-NO₂ | c-Pr |
| C | N | C | S | C | Ph-3-NO₂ | c-Hex |
| C | N | C | S | C | Ph-3-NO₂ | OH |
| C | N | C | S | C | Ph-3-NO₂ | CH₂OH |
| C | N | C | S | C | Ph-3-NO₂ | OMe |
| C | N | C | S | C | Ph-3-NO₂ | SMe |
| C | N | C | S | C | Ph-3-NO₂ | Cl |
| C | N | C | S | C | Ph-3-NO₂ | CF₃ |
| C | N | C | S | C | Ph-3-NO₂ | Ph |
| C | N | C | S | C | Ph-4-NMe₂ | H |
| C | N | C | S | C | Ph-4-NMe₂ | Me |
| C | N | C | S | C | Ph-4-NMe₂ | Et |
| C | N | C | S | C | Ph-4-NMe₂ | n-Hex |
| C | N | C | S | C | Ph-4-NMe₂ | c-Pr |
| C | N | C | S | C | Ph-4-NMe₂ | c-Hex |
| C | N | C | S | C | Ph-4-NMe₂ | OH |
| C | N | C | S | C | Ph-4-NMe₂ | CH₂OH |
| C | N | C | S | C | Ph-4-NMe₂ | OMe |
| C | N | C | S | C | Ph-4-NMe₂ | SMe |
| C | N | C | S | C | Ph-4-NMe₂ | Cl |
| C | N | C | S | C | Ph-4-NMe₂ | CF₃ |
| C | N | C | S | C | Ph-4-NMe₂ | Ph |
| C | O | C | N | C | Ph | H |
| C | O | C | N | C | Ph | Me |
| C | O | C | N | C | Ph | Et |
| C | O | C | N | C | Ph | n-Hex |
| C | O | C | N | C | Ph | c-Pr |
| C | O | C | N | C | Ph | c-Hex |
| C | O | C | N | C | Ph | OH |
| C | O | C | N | C | Ph | CH₂OH |
| C | O | C | N | C | Ph | OMe |
| C | O | C | N | C | Ph | SMe |
| C | O | C | N | C | Ph | Cl |
| C | O | C | N | C | Ph | CF₃ |
| C | O | C | N | C | Ph | Ph |
| C | O | C | N | C | H | H |
| C | O | C | N | C | H | Me |
| C | O | C | N | C | H | Et |
| C | O | C | N | C | H | n-Hex |
| C | O | C | N | C | H | c-Pr |
| C | O | C | N | C | H | c-Hex |
| C | O | C | N | C | H | OH |
| C | O | C | N | C | H | CH₂OH |
| C | O | C | N | C | H | OMe |
| C | O | C | N | C | H | SMe |
| C | O | C | N | C | H | Cl |
| C | O | C | N | C | H | CF₃ |
| C | O | C | N | C | H | Ph |
| C | O | C | N | C | Me | H |
| C | O | C | N | C | Me | Me |
| C | O | C | N | C | Me | Et |
| C | O | C | N | C | Me | n-Hex |
| C | O | C | N | C | Me | c-Pr |
| C | O | C | N | C | Me | c-Hex |
| C | O | C | N | C | Me | OH |
| C | O | C | N | C | Me | CH₂OH |
| C | O | C | N | C | Me | OMe |
| C | O | C | N | C | Me | SMe |
| C | O | C | N | C | Me | Cl |
| C | O | C | N | C | Me | CF₃ |
| C | O | C | N | C | Me | Ph |
| C | O | C | N | C | Et | H |
| C | O | C | N | C | Et | Me |
| C | O | C | N | C | Et | Et |
| C | O | C | N | C | Et | n-Hex |
| C | O | C | N | C | Et | c-Pr |
| C | O | C | N | C | Et | c-Hex |
| C | O | C | N | C | Et | OH |
| C | O | C | N | C | Et | CH₂OH |
| C | O | C | N | C | Et | OMe |
| C | O | C | N | C | Et | SMe |
| C | O | C | N | C | Et | Cl |
| C | O | C | N | C | Et | CF₃ |
| C | O | C | N | C | Et | Ph |
| C | O | C | N | C | n-Pr | H |
| C | O | C | N | C | n-Pr | Me |
| C | O | C | N | C | n-Pr | Et |
| C | O | C | N | C | n-Pr | n-Hex |
| C | O | C | N | C | n-Pr | c-Pr |
| C | O | C | N | C | n-Pr | c-Hex |
| C | O | C | N | C | n-Pr | OH |
| C | O | C | N | C | n-Pr | CH₂OH |
| C | O | C | N | C | n-Pr | OMe |
| C | O | C | N | C | n-Pr | SMe |
| C | O | C | N | C | n-Pr | Cl |
| C | O | C | N | C | n-Pr | CF₃ |
| C | O | C | N | C | n-Pr | Ph |
| C | O | C | N | C | n-Hex | H |
| C | O | C | N | C | n-Hex | Me |
| C | O | C | N | C | n-Hex | Et |
| C | O | C | N | C | n-Hex | n-Hex |
| C | O | C | N | C | n-Hex | c-Pr |
| C | O | C | N | C | n-Hex | c-Hex |
| C | O | C | N | C | n-Hex | OH |
| C | O | C | N | C | n-Hex | CH₂OH |
| C | O | C | N | C | n-Hex | OMe |
| C | O | C | N | C | n-Hex | SMe |
| C | O | C | N | C | n-Hex | Cl |
| C | O | C | N | C | n-Hex | CF₃ |
| C | O | C | N | C | n-Hex | Ph |
| C | O | C | N | C | i-Pr | H |
| C | O | C | N | C | i-Pr | Me |
| C | O | C | N | C | i-Pr | Et |
| C | O | C | N | C | i-Pr | n-Hex |
| C | O | C | N | C | i-Pr | c-Pr |
| C | O | C | N | C | i-Pr | c-Hex |
| C | O | C | N | C | i-Pr | OH |
| C | O | C | N | C | i-Pr | CH₂OH |
| C | O | C | N | C | i-Pr | OMe |
| C | O | C | N | C | i-Pr | SMe |
| C | O | C | N | C | i-Pr | Cl |
| C | O | C | N | C | i-Pr | CF₃ |
| C | O | C | N | C | i-Pr | Ph |
| C | O | C | N | C | t-Bu | H |
| C | O | C | N | C | t-Bu | Me |
| C | O | C | N | C | t-Bu | Et |
| C | O | C | N | C | t-Bu | n-Hex |
| C | O | C | N | C | t-Bu | c-Pr |
| C | O | C | N | C | t-Bu | c-Hex |
| C | O | C | N | C | t-Bu | OH |
| C | O | C | N | C | t-Bu | CH₂OH |
| C | O | C | N | C | t-Bu | OMe |
| C | O | C | N | C | t-Bu | SMe |
| C | O | C | N | C | t-Bu | Cl |
| C | O | C | N | C | t-Bu | CF₃ |
| C | O | C | N | C | t-Bu | Ph |
| C | O | C | N | C | c-Hex | H |
| C | O | C | N | C | c-Hex | Me |
| C | O | C | N | C | c-Hex | Et |
| C | O | C | N | C | c-Hex | n-Hex |
| C | O | C | N | C | c-Hex | c-Pr |

TABLE 4-continued

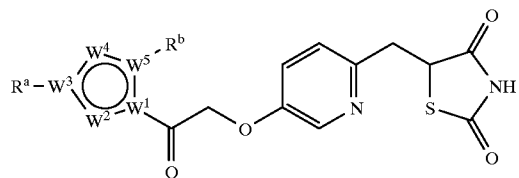

| W¹ | W² | W³ | W⁴ | W⁵ | Rᵃ | Rᵇ |
|---|---|---|---|---|---|---|
| C | O | C | N | C | c-Hex | c-Hex |
| C | O | C | N | C | c-Hex | OH |
| C | O | C | N | C | c-Hex | CH₂OH |
| C | O | C | N | C | c-Hex | OMe |
| C | O | C | N | C | c-Hex | SMe |
| C | O | C | N | C | c-Hex | Cl |
| C | O | C | N | C | c-Hex | CF₃ |
| C | O | C | N | C | c-Hex | Ph |
| C | O | C | N | C | 3-c-hexenyl | H |
| C | O | C | N | C | 3-c-hexenyl | Me |
| C | O | C | N | C | 3-c-hexenyl | Et |
| C | O | C | N | C | 3-c-hexenyl | n-Hex |
| C | O | C | N | C | 3-c-hexenyl | c-Pr |
| C | O | C | N | C | 3-c-hexenyl | c-Hex |
| C | O | C | N | C | 3-c-hexenyl | OH |
| C | O | C | N | C | 3-c-hexenyl | CH₂OH |
| C | O | C | N | C | 3-c-hexenyl | OMe |
| C | O | C | N | C | 3-c-hexenyl | SMe |
| C | O | C | N | C | 3-c-hexenyl | Cl |
| C | O | C | N | C | 3-c-hexenyl | CF₃ |
| C | O | C | N | C | 3-c-hexenyl | Ph |
| C | O | C | N | C | CH₂OH | H |
| C | O | C | N | C | CH₂OH | Me |
| C | O | C | N | C | CH₂OH | Et |
| C | O | C | N | C | CH₂OH | n-Hex |
| C | O | C | N | C | CH₂OH | c-Pr |
| C | O | C | N | C | CH₂OH | c-Hex |
| C | O | C | N | C | CH₂OH | OH |
| C | O | C | N | C | CH₂OH | CH₂OH |
| C | O | C | N | C | CH₂OH | OMe |
| C | O | C | N | C | CH₂OH | SMe |
| C | O | C | N | C | CH₂OH | Cl |
| C | O | C | N | C | CH₂OH | CF₃ |
| C | O | C | N | C | CH₂OH | Ph |
| C | O | C | N | C | CH₂Ph | H |
| C | O | C | N | C | CH₂Ph | Me |
| C | O | C | N | C | CH₂Ph | Et |
| C | O | C | N | C | CH₂Ph | n-Hex |
| C | O | C | N | C | CH₂Ph | c-Pr |
| C | O | C | N | C | CH₂Ph | c-Hex |
| C | O | C | N | C | CH₂Ph | OH |
| C | O | C | N | C | CH₂Ph | CH₂OH |
| C | O | C | N | C | CH₂Ph | OMe |
| C | O | C | N | C | CH₂Ph | SMe |
| C | O | C | N | C | CH₂Ph | Cl |
| C | O | C | N | C | CH₂Ph | CF₃ |
| C | O | C | N | C | CH₂Ph | Ph |
| C | O | C | N | C | α-naphthyl | H |
| C | O | C | N | C | α-naphthyl | Me |
| C | O | C | N | C | α-naphthyl | Et |
| C | O | C | N | C | α-naphthyl | n-Hex |
| C | O | C | N | C | α-naphthyl | c-Pr |
| C | O | C | N | C | α-naphthyl | c-Hex |
| C | O | C | N | C | α-naphthyl | OH |
| C | O | C | N | C | α-naphthyl | CH₂OH |
| C | O | C | N | C | α-naphthyl | OMe |
| C | O | C | N | C | α-naphthyl | SMe |
| C | O | C | N | C | α-naphthyl | Cl |
| C | O | C | N | C | α-naphthyl | CF₃ |
| C | O | C | N | C | α-naphthyl | Ph |
| C | O | C | N | C | β-naphthyl | H |
| C | O | C | N | C | β-naphthyl | Me |
| C | O | C | N | C | β-naphthyl | Et |
| C | O | C | N | C | β-naphthyl | n-Hex |
| C | O | C | N | C | β-naphthyl | c-Pr |
| C | O | C | N | C | β-naphthyl | c-Hex |
| C | O | C | N | C | β-naphthyl | OH |

TABLE 4-continued

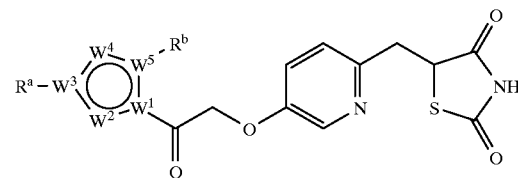

| W¹ | W² | W³ | W⁴ | W⁵ | Rᵃ | Rᵇ |
|---|---|---|---|---|---|---|
| C | O | C | N | C | β-naphthyl | CH₂OH |
| C | O | C | N | C | β-naphthyl | OMe |
| C | O | C | N | C | β-naphthyl | SMe |
| C | O | C | N | C | β-naphthyl | Cl |
| C | O | C | N | C | β-naphthyl | CF₃ |
| C | O | C | N | C | β-naphthyl | Ph |
| C | O | C | N | C | 2-pyridyl | H |
| C | O | C | N | C | 2-pyridyl | Me |
| C | O | C | N | C | 2-pyridyl | Et |
| C | O | C | N | C | 2-pyridyl | n-Hex |
| C | O | C | N | C | 2-pyridyl | c-Pr |
| C | O | C | N | C | 2-pyridyl | c-Hex |
| C | O | C | N | C | 2-pyridyl | OH |
| C | O | C | N | C | 2-pyridyl | CH₂OH |
| C | O | C | N | C | 2-pyridyl | OMe |
| C | O | C | N | C | 2-pyridyl | SMe |
| C | O | C | N | C | 2-pyridyl | Cl |
| C | O | C | N | C | 2-pyridyl | CF₃ |
| C | O | C | N | C | 2-pyridyl | Ph |
| C | O | C | N | C | 3-pyridyl | H |
| C | O | C | N | C | 3-pyridyl | Me |
| C | O | C | N | C | 3-pyridyl | Et |
| C | O | C | N | C | 3-pyridyl | n-Hex |
| C | O | C | N | C | 3-pyridyl | c-Pr |
| C | O | C | N | C | 3-pyridyl | c-Hex |
| C | O | C | N | C | 3-pyridyl | OH |
| C | O | C | N | C | 3-pyridyl | CH₂OH |
| C | O | C | N | C | 3-pyridyl | OMe |
| C | O | C | N | C | 3-pyridyl | SMe |
| C | O | C | N | C | 3-pyridyl | Cl |
| C | O | C | N | C | 3-pyridyl | CF₃ |
| C | O | C | N | C | 3-pyridyl | Ph |
| C | O | C | N | C | 4-pyridyl | H |
| C | O | C | N | C | 4-pyridyl | Me |
| C | O | C | N | C | 4-pyridyl | Et |
| C | O | C | N | C | 4-pyridyl | n-Hex |
| C | O | C | N | C | 4-pyridyl | c-Pr |
| C | O | C | N | C | 4-pyridyl | c-Hex |
| C | O | C | N | C | 4-pyridyl | OH |
| C | O | C | N | C | 4-pyridyl | CH₂OH |
| C | O | C | N | C | 4-pyridyl | OMe |
| C | O | C | N | C | 4-pyridyl | SMe |
| C | O | C | N | C | 4-pyridyl | Cl |
| C | O | C | N | C | 4-pyridyl | CF₃ |
| C | O | C | N | C | 4-pyridyl | Ph |
| C | O | C | N | C | 2-furanyl | H |
| C | O | C | N | C | 2-furanyl | Me |
| C | O | C | N | C | 2-furanyl | Et |
| C | O | C | N | C | 2-furanyl | n-Hex |
| C | O | C | N | C | 2-furanyl | c-Pr |
| C | O | C | N | C | 2-furanyl | c-Hex |
| C | O | C | N | C | 2-furanyl | OH |
| C | O | C | N | C | 2-furanyl | CH₂OH |
| C | O | C | N | C | 2-furanyl | OMe |
| C | O | C | N | C | 2-furanyl | SMe |
| C | O | C | N | C | 2-furanyl | Cl |
| C | O | C | N | C | 2-furanyl | CF₃ |
| C | O | C | N | C | 2-furanyl | Ph |
| C | O | C | N | C | 2-thienyl | H |
| C | O | C | N | C | 2-thienyl | Me |
| C | O | C | N | C | 2-thienyl | Et |
| C | O | C | N | C | 2-thienyl | n-Hex |
| C | O | C | N | C | 2-thienyl | c-Pr |
| C | O | C | N | C | 2-thienyl | c-Hex |
| C | O | C | N | C | 2-thienyl | OH |
| C | O | C | N | C | 2-thienyl | CH₂OH |
| C | O | C | N | C | 2-thienyl | OMe |

TABLE 4-continued

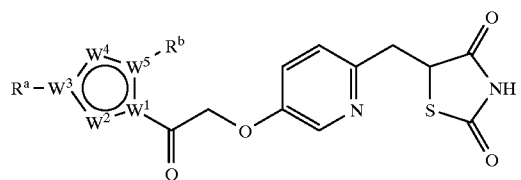

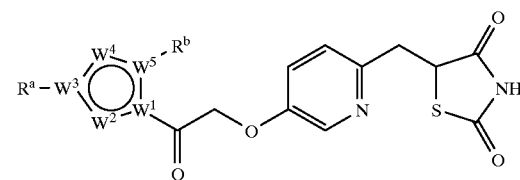

| $W^1$ | $W^2$ | $W^3$ | $W^4$ | $W^5$ | $R^a$ | $R^b$ |
|---|---|---|---|---|---|---|
| C | O | C | N | C | 2-thienyl | SMe |
| C | O | C | N | C | 2-thienyl | Cl |
| C | O | C | N | C | 2-thienyl | $CF_3$ |
| C | O | C | N | C | 2-thienyl | Ph |
| C | O | C | N | C | 2-tolyl | H |
| C | O | C | N | C | 2-tolyl | Me |
| C | O | C | N | C | 2-tolyl | Et |
| C | O | C | N | C | 2-tolyl | n-Hex |
| C | O | C | N | C | 2-tolyl | c-Pr |
| C | O | C | N | C | 2-tolyl | c-Hex |
| C | O | C | N | C | 2-tolyl | OH |
| C | O | C | N | C | 2-tolyl | $CH_2OH$ |
| C | O | C | N | C | 2-tolyl | OMe |
| C | O | C | N | C | 2-tolyl | SMe |
| C | O | C | N | C | 2-tolyl | Cl |
| C | O | C | N | C | 2-tolyl | $CF_3$ |
| C | O | C | N | C | 2-tolyl | Ph |
| C | O | C | N | C | 3-tolyl | H |
| C | O | C | N | C | 3-tolyl | Me |
| C | O | C | N | C | 3-tolyl | Et |
| C | O | C | N | C | 3-tolyl | n-Hex |
| C | O | C | N | C | 3-tolyl | c-Pr |
| C | O | C | N | C | 3-tolyl | c-Hex |
| C | O | C | N | C | 3-tolyl | OH |
| C | O | C | N | C | 3-tolyl | $CH_2OH$ |
| C | O | C | N | C | 3-tolyl | OMe |
| C | O | C | N | C | 3-tolyl | SMe |
| C | O | C | N | C | 3-tolyl | Cl |
| C | O | C | N | C | 3-tolyl | $CF_3$ |
| C | O | C | N | C | 3-tolyl | Ph |
| C | O | C | N | C | 4-tolyl | H |
| C | O | C | N | C | 4-tolyl | Me |
| C | O | C | N | C | 4-tolyl | Et |
| C | O | C | N | C | 4-tolyl | n-Hex |
| C | O | C | N | C | 4-tolyl | c-Pr |
| C | O | C | N | C | 4-tolyl | c-Hex |
| C | O | C | N | C | 4-tolyl | OH |
| C | O | C | N | C | 4-tolyl | $CH_2OH$ |
| C | O | C | N | C | 4-tolyl | OMe |
| C | O | C | N | C | 4-tolyl | SMe |
| C | O | C | N | C | 4-tolyl | Cl |
| C | O | C | N | C | 4-tolyl | $CF_3$ |
| C | O | C | N | C | 4-tolyl | Ph |
| C | O | C | N | C | Ph-2,3-$Me_2$ | H |
| C | O | C | N | C | Ph-2,3-$Me_2$ | Me |
| C | O | C | N | C | Ph-2,3-$Me_2$ | Et |
| C | O | C | N | C | Ph-2,3-$Me_2$ | n-Hex |
| C | O | C | N | C | Ph-2,3-$Me_2$ | c-Pr |
| C | O | C | N | C | Ph-2,3-$Me_2$ | c-Hex |
| C | O | C | N | C | Ph-2,3-$Me_2$ | OH |
| C | O | C | N | C | Ph-2,3-$Me_2$ | $CH_2OH$ |
| C | O | C | N | C | Ph-2,3-$Me_2$ | OMe |
| C | O | C | N | C | Ph-2,3-$Me_2$ | SMe |
| C | O | C | N | C | Ph-2,3-$Me_2$ | Cl |
| C | O | C | N | C | Ph-2,3-$Me_2$ | $CF_3$ |
| C | O | C | N | C | Ph-2,3-$Me_2$ | Ph |
| C | O | C | N | C | Ph-3,4-$Me_2$ | H |
| C | O | C | N | C | Ph-3,4-$Me_2$ | Me |
| C | O | C | N | C | Ph-3,4-$Me_2$ | Et |
| C | O | C | N | C | Ph-3,4-$Me_2$ | n-Hex |
| C | O | C | N | C | Ph-3,4-$Me_2$ | c-Pr |
| C | O | C | N | C | Ph-3,4-$Me_2$ | c-Hex |
| C | O | C | N | C | Ph-3,4-$Me_2$ | OH |
| C | O | C | N | C | Ph-3,4-$Me_2$ | $CH_2OH$ |
| C | O | C | N | C | Ph-3,4-$Me_2$ | OMe |
| C | O | C | N | C | Ph-3,4-$Me_2$ | SMe |
| C | O | C | N | C | Ph-3,4-$Me_2$ | Cl |
| C | O | C | N | C | Ph-3,4-$Me_2$ | $CF_3$ |
| C | O | C | N | C | Ph-3,4-$Me_2$ | Ph |
| C | O | C | N | C | Ph-3,5-$Me_2$ | H |
| C | O | C | N | C | Ph-3,5-$Me_2$ | Me |
| C | O | C | N | C | Ph-3,5-$Me_2$ | Et |
| C | O | C | N | C | Ph-3,5-$Me_2$ | n-Hex |
| C | O | C | N | C | Ph-3,5-$Me_2$ | c-Pr |
| C | O | C | N | C | Ph-3,5-$Me_2$ | c-Hex |
| C | O | C | N | C | Ph-3,5-$Me_2$ | OH |
| C | O | C | N | C | Ph-3,5-$Me_2$ | $CH_2OH$ |
| C | O | C | N | C | Ph-3,5-$Me_2$ | OMe |
| C | O | C | N | C | Ph-3,5-$Me_2$ | SMe |
| C | O | C | N | C | Ph-3,5-$Me_2$ | Cl |
| C | O | C | N | C | Ph-3,5-$Me_2$ | $CF_3$ |
| C | O | C | N | C | Ph-3,5-$Me_2$ | Ph |
| C | O | C | N | C | Ph-2,6-$Me_2$ | H |
| C | O | C | N | C | Ph-2,6-$Me_2$ | Me |
| C | O | C | N | C | Ph-2,6-$Me_2$ | Et |
| C | O | C | N | C | Ph-2,6-$Me_2$ | n-Hex |
| C | O | C | N | C | Ph-2,6-$Me_2$ | c-Pr |
| C | O | C | N | C | Ph-2,6-$Me_2$ | c-Hex |
| C | O | C | N | C | Ph-2,6-$Me_2$ | OH |
| C | O | C | N | C | Ph-2,6-$Me_2$ | $CH_2OH$ |
| C | O | C | N | C | Ph-2,6-$Me_2$ | OMe |
| C | O | C | N | C | Ph-2,6-$Me_2$ | SMe |
| C | O | C | N | C | Ph-2,6-$Me_2$ | Cl |
| C | O | C | N | C | Ph-2,6-$Me_2$ | $CF_3$ |
| C | O | C | N | C | Ph-2,6-$Me_2$ | Ph |
| C | O | C | N | C | Ph-2-Cl | H |
| C | O | C | N | C | Ph-2-Cl | Me |
| C | O | C | N | C | Ph-2-Cl | Et |
| C | O | C | N | C | Ph-2-Cl | n-Hex |
| C | O | C | N | C | Ph-2-Cl | c-Pr |
| C | O | C | N | C | Ph-2-Cl | c-Hex |
| C | O | C | N | C | Ph-2-Cl | OH |
| C | O | C | N | C | Ph-2-Cl | $CH_2OH$ |
| C | O | C | N | C | Ph-2-Cl | OMe |
| C | O | C | N | C | Ph-2-Cl | SMe |
| C | O | C | N | C | Ph-2-Cl | Cl |
| C | O | C | N | C | Ph-2-Cl | $CF_3$ |
| C | O | C | N | C | Ph-2-Cl | Ph |
| C | O | C | N | C | Ph-3-Cl | H |
| C | O | C | N | C | Ph-3-Cl | Me |
| C | O | C | N | C | Ph-3-Cl | Et |
| C | O | C | N | C | Ph-3-Cl | n-Hex |
| C | O | C | N | C | Ph-3-Cl | c-Pr |
| C | O | C | N | C | Ph-3-Cl | c-Hex |
| C | O | C | N | C | Ph-3-Cl | OH |
| C | O | C | N | C | Ph-3-Cl | $CH_2OH$ |
| C | O | C | N | C | Ph-3-Cl | OMe |
| C | O | C | N | C | Ph-3-Cl | SMe |
| C | O | C | N | C | Ph-3-Cl | Cl |
| C | O | C | N | C | Ph-3-Cl | $CF_3$ |
| C | O | C | N | C | Ph-3-Cl | Ph |
| C | O | C | N | C | Ph-4-Cl | H |
| C | O | C | N | C | Ph-4-Cl | Me |
| C | O | C | N | C | Ph-4-Cl | Et |
| C | O | C | N | C | Ph-4-Cl | n-Hex |
| C | O | C | N | C | Ph-4-Cl | c-Pr |
| C | O | C | N | C | Ph-4-Cl | c-Hex |
| C | O | C | N | C | Ph-4-Cl | OH |
| C | O | C | N | C | Ph-4-Cl | $CH_2OH$ |
| C | O | C | N | C | Ph-4-Cl | OMe |
| C | O | C | N | C | Ph-4-Cl | SMe |
| C | O | C | N | C | Ph-4-Cl | Cl |
| C | O | C | N | C | Ph-4-Cl | $CF_3$ |
| C | O | C | N | C | Ph-4-Cl | Ph |

TABLE 4-continued

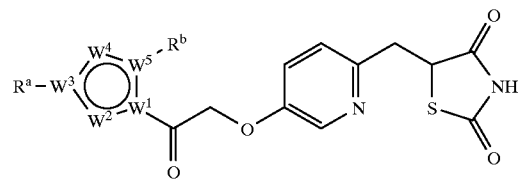

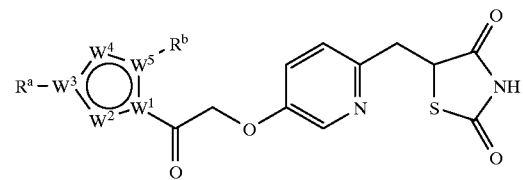

| W¹ | W² | W³ | W⁴ | W⁵ | Rᵃ | Rᵇ |
|---|---|---|---|---|---|---|
| C | O | C | N | C | Ph-3,4-Cl$_2$ | H |
| C | O | C | N | C | Ph-3,4-Cl$_2$ | Me |
| C | O | C | N | C | Ph-3,4-Cl$_2$ | Et |
| C | O | C | N | C | Ph-3,4-Cl$_2$ | n-Hex |
| C | O | C | N | C | Ph-3,4-Cl$_2$ | c-Pr |
| C | O | C | N | C | Ph-3,4-Cl$_2$ | c-Hex |
| C | O | C | N | C | Ph-3,4-Cl$_2$ | OH |
| C | O | C | N | C | Ph-3,4-Cl$_2$ | CH$_2$OH |
| C | O | C | N | C | Ph-3,4-Cl$_2$ | OMe |
| C | O | C | N | C | Ph-3,4-Cl$_2$ | SMe |
| C | O | C | N | C | Ph-3,4-Cl$_2$ | Cl |
| C | O | C | N | C | Ph-3,4-Cl$_2$ | CF$_3$ |
| C | O | C | N | C | Ph-3,4-Cl$_2$ | Ph |
| C | O | C | N | C | Ph-4-F | H |
| C | O | C | N | C | Ph-4-F | Me |
| C | O | C | N | C | Ph-4-F | Et |
| C | O | C | N | C | Ph-4-F | n-Hex |
| C | O | C | N | C | Ph-4-F | c-Pr |
| C | O | C | N | C | Ph-4-F | c-Hex |
| C | O | C | N | C | Ph-4-F | OH |
| C | O | C | N | C | Ph-4-F | CH$_2$OH |
| C | O | C | N | C | Ph-4-F | OMe |
| C | O | C | N | C | Ph-4-F | SMe |
| C | O | C | N | C | Ph-4-F | Cl |
| C | O | C | N | C | Ph-4-F | CF$_3$ |
| C | O | C | N | C | Ph-4-F | Ph |
| C | O | C | N | C | Ph-4-Br | H |
| C | O | C | N | C | Ph-4-Br | Me |
| C | O | C | N | C | Ph-4-Br | Et |
| C | O | C | N | C | Ph-4-Br | n-Hex |
| C | O | C | N | C | Ph-4-Br | c-Pr |
| C | O | C | N | C | Ph-4-Br | c-Hex |
| C | O | C | N | C | Ph-4-Br | OH |
| C | O | C | N | C | Ph-4-Br | CH$_2$OH |
| C | O | C | N | C | Ph-4-Br | OMe |
| C | O | C | N | C | Ph-4-Br | SMe |
| C | O | C | N | C | Ph-4-Br | Cl |
| C | O | C | N | C | Ph-4-Br | CF$_3$ |
| C | O | C | N | C | Ph-4-Br | Ph |
| C | O | C | N | C | Ph-2-OMe | H |
| C | O | C | N | C | Ph-2-OMe | Me |
| C | O | C | N | C | Ph-2-OMe | Et |
| C | O | C | N | C | Ph-2-OMe | n-Hex |
| C | O | C | N | C | Ph-2-OMe | c-Pr |
| C | O | C | N | C | Ph-2-OMe | c-Hex |
| C | O | C | N | C | Ph-2-OMe | OH |
| C | O | C | N | C | Ph-2-OMe | CH$_2$OH |
| C | O | C | N | C | Ph-2-OMe | OMe |
| C | O | C | N | C | Ph-2-OMe | SMe |
| C | O | C | N | C | Ph-2-OMe | Cl |
| C | O | C | N | C | Ph-2-OMe | CF$_3$ |
| C | O | C | N | C | Ph-2-OMe | Ph |
| C | O | C | N | C | Ph-3-OMe | H |
| C | O | C | N | C | Ph-3-OMe | Me |
| C | O | C | N | C | Ph-3-OMe | Et |
| C | O | C | N | C | Ph-3-OMe | n-Hex |
| C | O | C | N | C | Ph-3-OMe | c-Pr |
| C | O | C | N | C | Ph-3-OMe | c-Hex |
| C | O | C | N | C | Ph-3-OMe | OH |
| C | O | C | N | C | Ph-3-OMe | CH$_2$OH |
| C | O | C | N | C | Ph-3-OMe | OMe |
| C | O | C | N | C | Ph-3-OMe | SMe |
| C | O | C | N | C | Ph-3-OMe | Cl |
| C | O | C | N | C | Ph-3-OMe | CF$_3$ |
| C | O | C | N | C | Ph-3-OMe | Ph |
| C | O | C | N | C | Ph-4-OMe | H |
| C | O | C | N | C | Ph-4-OMe | Me |
| C | O | C | N | C | Ph-4-OMe | Et |
| C | O | C | N | C | Ph-4-OMe | n-Hex |
| C | O | C | N | C | Ph-4-OMe | c-Pr |
| C | O | C | N | C | Ph-4-OMe | c-Hex |
| C | O | C | N | C | Ph-4-OMe | OH |
| C | O | C | N | C | Ph-4-OMe | CH$_2$OH |
| C | O | C | N | C | Ph-4-OMe | OMe |
| C | O | C | N | C | Ph-4-OMe | SMe |
| C | O | C | N | C | Ph-4-OMe | Cl |
| C | O | C | N | C | Ph-4-OMe | CF$_3$ |
| C | O | C | N | C | Ph-4-OMe | Ph |
| C | O | C | N | C | Ph-3,4-(OMe)$_2$ | H |
| C | O | C | N | C | Ph-3,4-(OMe)$_2$ | Me |
| C | O | C | N | C | Ph-3,4-(OMe)$_2$ | Et |
| C | O | C | N | C | Ph-3,4-(OMe)$_2$ | n-Hex |
| C | O | C | N | C | Ph-3,4-(OMe)$_2$ | c-Pr |
| C | O | C | N | C | Ph-3,4-(OMe)$_2$ | c-Hex |
| C | O | C | N | C | Ph-3,4-(OMe)$_2$ | OH |
| C | O | C | N | C | Ph-3,4-(OMe)$_2$ | CH$_2$OH |
| C | O | C | N | C | Ph-3,4-(OMe)$_2$ | OMe |
| C | O | C | N | C | Ph-3,4-(OMe)$_2$ | SMe |
| C | O | C | N | C | Ph-3,4-(OMe)$_2$ | Cl |
| C | O | C | N | C | Ph-3,4-(OMe)$_2$ | CF$_3$ |
| C | O | C | N | C | Ph-3,4-(OMe)$_2$ | Ph |
| C | O | C | N | C | Ph-2-OH | H |
| C | O | C | N | C | Ph-2-OH | Me |
| C | O | C | N | C | Ph-2-OH | Et |
| C | O | C | N | C | Ph-2-OH | n-Hex |
| C | O | C | N | C | Ph-2-OH | c-Pr |
| C | O | C | N | C | Ph-2-OH | c-Hex |
| C | O | C | N | C | Ph-2-OH | OH |
| C | O | C | N | C | Ph-2-OH | CH$_2$OH |
| C | O | C | N | C | Ph-2-OH | OMe |
| C | O | C | N | C | Ph-2-OH | SMe |
| C | O | C | N | C | Ph-2-OH | Cl |
| C | O | C | N | C | Ph-2-OH | CF$_3$ |
| C | O | C | N | C | Ph-2-OH | Ph |
| C | O | C | N | C | Ph-3-OH | H |
| C | O | C | N | C | Ph-3-OH | Me |
| C | O | C | N | C | Ph-3-OH | Et |
| C | O | C | N | C | Ph-3-OH | n-Hex |
| C | O | C | N | C | Ph-3-OH | c-Pr |
| C | O | C | N | C | Ph-3-OH | c-Hex |
| C | O | C | N | C | Ph-3-OH | OH |
| C | O | C | N | C | Ph-3-OH | CH$_2$OH |
| C | O | C | N | C | Ph-3-OH | OMe |
| C | O | C | N | C | Ph-3-OH | SMe |
| C | O | C | N | C | Ph-3-OH | Cl |
| C | O | C | N | C | Ph-3-OH | CF$_3$ |
| C | O | C | N | C | Ph-3-OH | Ph |
| C | O | C | N | C | Ph-4-OH | H |
| C | O | C | N | C | Ph-4-OH | Me |
| C | O | C | N | C | Ph-4-OH | Et |
| C | O | C | N | C | Ph-4-OH | n-Hex |
| C | O | C | N | C | Ph-4-OH | c-Pr |
| C | O | C | N | C | Ph-4-OH | c-Hex |
| C | O | C | N | C | Ph-4-OH | OH |
| C | O | C | N | C | Ph-4-OH | CH$_2$OH |
| C | O | C | N | C | Ph-4-OH | OMe |
| C | O | C | N | C | Ph-4-OH | SMe |
| C | O | C | N | C | Ph-4-OH | Cl |
| C | O | C | N | C | Ph-4-OH | CF$_3$ |
| C | O | C | N | C | Ph-4-OH | Ph |
| C | O | C | N | C | Ph-3,4-(OH)$_2$ | H |
| C | O | C | N | C | Ph-3,4-(OH)$_2$ | Me |
| C | O | C | N | C | Ph-3,4-(OH)$_2$ | Et |
| C | O | C | N | C | Ph-3,4-(OH)$_2$ | n-Hex |

TABLE 4-continued

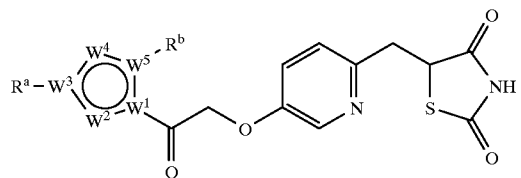
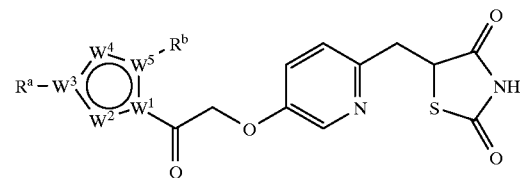

| W¹ | W² | W³ | W⁴ | W⁵ | Rᵃ | Rᵇ |
|---|---|---|---|---|---|---|
| C | O | C | N | C | Ph-3,4-(OH)₂ | c-Pr |
| C | O | C | N | C | Ph-3,4-(OH)₂ | c-Hex |
| C | O | C | N | C | Ph-3,4-(OH)₂ | OH |
| C | O | C | N | C | Ph-3,4-(OH)₂ | CH₂OH |
| C | O | C | N | C | Ph-3,4-(OH)₂ | OMe |
| C | O | C | N | C | Ph-3,4-(OH)₂ | SMe |
| C | O | C | N | C | Ph-3,4-(OH)₂ | Cl |
| C | O | C | N | C | Ph-3,4-(OH)₂ | CF₃ |
| C | O | C | N | C | Ph-3,4-(OH)₂ | Ph |
| C | O | C | N | C | Ph-3-SMe | H |
| C | O | C | N | C | Ph-3-SMe | Me |
| C | O | C | N | C | Ph-3-SMe | Et |
| C | O | C | N | C | Ph-3-SMe | n-Hex |
| C | O | C | N | C | Ph-3-SMe | c-Pr |
| C | O | C | N | C | Ph-3-SMe | c-Hex |
| C | O | C | N | C | Ph-3-SMe | OH |
| C | O | C | N | C | Ph-3-SMe | CH₂OH |
| C | O | C | N | C | Ph-3-SMe | OMe |
| C | O | C | N | C | Ph-3-SMe | SMe |
| C | O | C | N | C | Ph-3-SMe | Cl |
| C | O | C | N | C | Ph-3-SMe | CF₃ |
| C | O | C | N | C | Ph-3-SMe | Ph |
| C | O | C | N | C | Ph-3-CF₃ | H |
| C | O | C | N | C | Ph-3-CF₃ | Me |
| C | O | C | N | C | Ph-3-CF₃ | Et |
| C | O | C | N | C | Ph-3-CF₃ | n-Hex |
| C | O | C | N | C | Ph-3-CF₃ | c-Pr |
| C | O | C | N | C | Ph-3-CF₃ | c-Hex |
| C | O | C | N | C | Ph-3-CF₃ | OH |
| C | O | C | N | C | Ph-3-CF₃ | CH₂OH |
| C | O | C | N | C | Ph-3-CF₃ | OMe |
| C | O | C | N | C | Ph-3-CF₃ | SMe |
| C | O | C | N | C | Ph-3-CF₃ | Cl |
| C | O | C | N | C | Ph-3-CF₃ | CF₃ |
| C | O | C | N | C | Ph-3-CF₃ | Ph |
| C | O | C | N | C | Ph-3-NO₂ | H |
| C | O | C | N | C | Ph-3-NO₂ | Me |
| C | O | C | N | C | Ph-3-NO₂ | Et |
| C | O | C | N | C | Ph-3-NO₂ | n-Hex |
| C | O | C | N | C | Ph-3-NO₂ | c-Pr |
| C | O | C | N | C | Ph-3-NO₂ | c-Hex |
| C | O | C | N | C | Ph-3-NO₂ | OH |
| C | O | C | N | C | Ph-3-NO₂ | CH₂OH |
| C | O | C | N | C | Ph-3-NO₂ | OMe |
| C | O | C | N | C | Ph-3-NO₂ | SMe |
| C | O | C | N | C | Ph-3-NO₂ | Cl |
| C | O | C | N | C | Ph-3-NO₂ | CF₃ |
| C | O | C | N | C | Ph-3-NO₂ | Ph |
| C | O | C | N | C | Ph-4-NMe₂ | H |
| C | O | C | N | C | Ph-4-NMe₂ | Me |
| C | O | C | N | C | Ph-4-NMe₂ | Et |
| C | O | C | N | C | Ph-4-NMe₂ | n-Hex |
| C | O | C | N | C | Ph-4-NMe₂ | c-Pr |
| C | O | C | N | C | Ph-4-NMe₂ | c-Hex |
| C | O | C | N | C | Ph-4-NMe₂ | OH |
| C | O | C | N | C | Ph-4-NMe₂ | CH₂OH |
| C | O | C | N | C | Ph-4-NMe₂ | OMe |
| C | O | C | N | C | Ph-4-NMe₂ | SMe |
| C | O | C | N | C | Ph-4-NMe₂ | Cl |
| C | O | C | N | C | Ph-4-NMe₂ | CF₃ |
| C | O | C | N | C | Ph-4-NMe₂ | Ph |
| C | S | C | N | C | Ph | H |
| C | S | C | N | C | Ph | Me |
| C | S | C | N | C | Ph | Et |
| C | S | C | N | C | Ph | n-Hex |
| C | S | C | N | C | Ph | c-Pr |
| C | S | C | N | C | Ph | c-Hex |
| C | S | C | N | C | Ph | OH |
| C | S | C | N | C | Ph | CH₂OH |
| C | S | C | N | C | Ph | OMe |
| C | S | C | N | C | Ph | SMe |
| C | S | C | N | C | Ph | Cl |
| C | S | C | N | C | Ph | CF₃ |
| C | S | C | N | C | Ph | Ph |
| C | S | C | N | C | H | H |
| C | S | C | N | C | H | Me |
| C | S | C | N | C | H | Et |
| C | S | C | N | C | H | n-Hex |
| C | S | C | N | C | H | c-Pr |
| C | S | C | N | C | H | c-Hex |
| C | S | C | N | C | H | OH |
| C | S | C | N | C | H | CH₂OH |
| C | S | C | N | C | H | OMe |
| C | S | C | N | C | H | SMe |
| C | S | C | N | C | H | Cl |
| C | S | C | N | C | H | CF₃ |
| C | S | C | N | C | H | Ph |
| C | S | C | N | C | Me | H |
| C | S | C | N | C | Me | Me |
| C | S | C | N | C | Me | Et |
| C | S | C | N | C | Me | n-Hex |
| C | S | C | N | C | Me | c-Pr |
| C | S | C | N | C | Me | c-Hex |
| C | S | C | N | C | Me | OH |
| C | S | C | N | C | Me | CH₂OH |
| C | S | C | N | C | Me | OMe |
| C | S | C | N | C | Me | SMe |
| C | S | C | N | C | Me | Cl |
| C | S | C | N | C | Me | CF₃ |
| C | S | C | N | C | Me | Ph |
| C | S | C | N | C | Et | H |
| C | S | C | N | C | Et | Me |
| C | S | C | N | C | Et | Et |
| C | S | C | N | C | Et | n-Hex |
| C | S | C | N | C | Et | c-Pr |
| C | S | C | N | C | Et | c-Hex |
| C | S | C | N | C | Et | OH |
| C | S | C | N | C | Et | CH₂OH |
| C | S | C | N | C | Et | OMe |
| C | S | C | N | C | Et | SMe |
| C | S | C | N | C | Et | Cl |
| C | S | C | N | C | Et | CF₃ |
| C | S | C | N | C | Et | Ph |
| C | S | C | N | C | n-Pr | H |
| C | S | C | N | C | n-Pr | Me |
| C | S | C | N | C | n-Pr | Et |
| C | S | C | N | C | n-Pr | n-Hex |
| C | S | C | N | C | n-Pr | c-Pr |
| C | S | C | N | C | n-Pr | c-Hex |
| C | S | C | N | C | n-Pr | OH |
| C | S | C | N | C | n-Pr | CH₂OH |
| C | S | C | N | C | n-Pr | OMe |
| C | S | C | N | C | n-Pr | SMe |
| C | S | C | N | C | n-Pr | Cl |
| C | S | C | N | C | n-Pr | CF₃ |
| C | S | C | N | C | n-Pr | Ph |
| C | S | C | N | C | n-Hex | H |
| C | S | C | N | C | n-Hex | Me |
| C | S | C | N | C | n-Hex | Et |
| C | S | C | N | C | n-Hex | n-Hex |
| C | S | C | N | C | n-Hex | c-Pr |
| C | S | C | N | C | n-Hex | c-Hex |
| C | S | C | N | C | n-Hex | OH |
| C | S | C | N | C | n-Hex | CH₂OH |

TABLE 4-continued

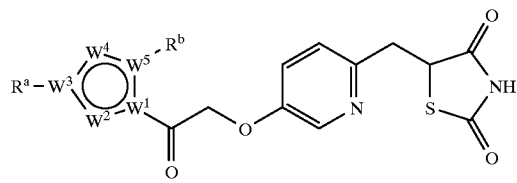
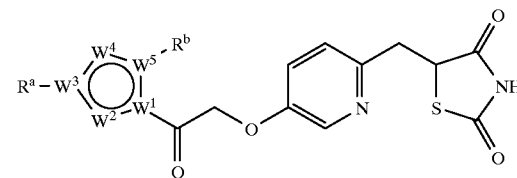

| W¹ | W² | W³ | W⁴ | W⁵ | Rᵃ | Rᵇ |
|---|---|---|---|---|---|---|
| C | S | C | N | C | n-Hex | OMe |
| C | S | C | N | C | n-Hex | SMe |
| C | S | C | N | C | n-Hex | Cl |
| C | S | C | N | C | n-Hex | CF₃ |
| C | S | C | N | C | n-Hex | Ph |
| C | S | C | N | C | i-Pr | H |
| C | S | C | N | C | i-Pr | Me |
| C | S | C | N | C | i-Pr | Et |
| C | S | C | N | C | i-Pr | n-Hex |
| C | S | C | N | C | i-Pr | c-Pr |
| C | S | C | N | C | i-Pr | c-Hex |
| C | S | C | N | C | i-Pr | OH |
| C | S | C | N | C | i-Pr | CH₂OH |
| C | S | C | N | C | i-Pr | OMe |
| C | S | C | N | C | i-Pr | SMe |
| C | S | C | N | C | i-Pr | Cl |
| C | S | C | N | C | i-Pr | CF₃ |
| C | S | C | N | C | i-Pr | Ph |
| C | S | C | N | C | t-Bu | H |
| C | S | C | N | C | t-Bu | Me |
| C | S | C | N | C | t-Bu | Et |
| C | S | C | N | C | t-Bu | n-Hex |
| C | S | C | N | C | t-Bu | c-Pr |
| C | S | C | N | C | t-Bu | c-Hex |
| C | S | C | N | C | t-Bu | OH |
| C | S | C | N | C | t-Bu | CH₂OH |
| C | S | C | N | C | t-Bu | OMe |
| C | S | C | N | C | t-Bu | SMe |
| C | S | C | N | C | t-Bu | Cl |
| C | S | C | N | C | t-Bu | CF₃ |
| C | S | C | N | C | t-Bu | Ph |
| C | S | C | N | C | c-Hex | H |
| C | S | C | N | C | c-Hex | Me |
| C | S | C | N | C | c-Hex | Et |
| C | S | C | N | C | c-Hex | n-Hex |
| C | S | C | N | C | c-Hex | c-Pr |
| C | S | C | N | C | c-Hex | c-Hex |
| C | S | C | N | C | c-Hex | OH |
| C | S | C | N | C | c-Hex | CH₂OH |
| C | S | C | N | C | c-Hex | OMe |
| C | S | C | N | C | c-Hex | SMe |
| C | S | C | N | C | c-Hex | Cl |
| C | S | C | N | C | c-Hex | CF₃ |
| C | S | C | N | C | c-Hex | Ph |
| C | S | C | N | C | 3-c-hexenyl | H |
| C | S | C | N | C | 3-c-hexenyl | Me |
| C | S | C | N | C | 3-c-hexenyl | Et |
| C | S | C | N | C | 3-c-hexenyl | n-Hex |
| C | S | C | N | C | 3-c-hexenyl | c-Pr |
| C | S | C | N | C | 3-c-hexenyl | c-Hex |
| C | S | C | N | C | 3-c-hexenyl | OH |
| C | S | C | N | C | 3-c-hexenyl | CH₂OH |
| C | S | C | N | C | 3-c-hexenyl | OMe |
| C | S | C | N | C | 3-c-hexenyl | SMe |
| C | S | C | N | C | 3-c-hexenyl | Cl |
| C | S | C | N | C | 3-c-hexenyl | CF₃ |
| C | S | C | N | C | 3-c-hexenyl | Ph |
| C | S | C | N | C | CH₂OH | H |
| C | S | C | N | C | CH₂OH | Me |
| C | S | C | N | C | CH₂OH | Et |
| C | S | C | N | C | CH₂OH | n-Hex |
| C | S | C | N | C | CH₂OH | c-Pr |
| C | S | C | N | C | CH₂OH | c-Hex |
| C | S | C | N | C | CH₂OH | OH |
| C | S | C | N | C | CH₂OH | CH₂OH |
| C | S | C | N | C | CH₂OH | OMe |
| C | S | C | N | C | CH₂OH | SMe |
| C | S | C | N | C | CH₂OH | Cl |
| C | S | C | N | C | CH₂OH | CF₃ |
| C | S | C | N | C | CH₂OH | Ph |
| C | S | C | N | C | CH₂Ph | H |
| C | S | C | N | C | CH₂Ph | Me |
| C | S | C | N | C | CH₂Ph | Et |
| C | S | C | N | C | CH₂Ph | n-Hex |
| C | S | C | N | C | CH₂Ph | c-Pr |
| C | S | C | N | C | CH₂Ph | c-Hex |
| C | S | C | N | C | CH₂Ph | OH |
| C | S | C | N | C | CH₂Ph | CH₂OH |
| C | S | C | N | C | CH₂Ph | OMe |
| C | S | C | N | C | CH₂Ph | SMe |
| C | S | C | N | C | CH₂Ph | Cl |
| C | S | C | N | C | CH₂Ph | CF₃ |
| C | S | C | N | C | CH₂Ph | Ph |
| C | S | C | N | C | α-naphthyl | H |
| C | S | C | N | C | α-naphthyl | Me |
| C | S | C | N | C | α-naphthyl | Et |
| C | S | C | N | C | α-naphthyl | n-Hex |
| C | S | C | N | C | α-naphthyl | c-Pr |
| C | S | C | N | C | α-naphthyl | c-Hex |
| C | S | C | N | C | α-naphthyl | OH |
| C | S | C | N | C | α-naphthyl | CH₂OH |
| C | S | C | N | C | α-naphthyl | OMe |
| C | S | C | N | C | α-naphthyl | SMe |
| C | S | C | N | C | α-naphthyl | Cl |
| C | S | C | N | C | α-naphthyl | CF₃ |
| C | S | C | N | C | α-naphthyl | Ph |
| C | S | C | N | C | β-naphthyl | H |
| C | S | C | N | C | β-naphthyl | Me |
| C | S | C | N | C | β-naphthyl | Et |
| C | S | C | N | C | β-naphthyl | n-Hex |
| C | S | C | N | C | β-naphthyl | c-Pr |
| C | S | C | N | C | β-naphthyl | c-Hex |
| C | S | C | N | C | β-naphthyl | OH |
| C | S | C | N | C | β-naphthyl | CH₂OH |
| C | S | C | N | C | β-naphthyl | OMe |
| C | S | C | N | C | β-naphthyl | SMe |
| C | S | C | N | C | β-naphthyl | Cl |
| C | S | C | N | C | β-naphthyl | CF₃ |
| C | S | C | N | C | β-naphthyl | Ph |
| C | S | C | N | C | 2-pyridyl | H |
| C | S | C | N | C | 2-pyridyl | Me |
| C | S | C | N | C | 2-pyridyl | Et |
| C | S | C | N | C | 2-pyridyl | n-Hex |
| C | S | C | N | C | 2-pyridyl | c-Pr |
| C | S | C | N | C | 2-pyridyl | c-Hex |
| C | S | C | N | C | 2-pyridyl | OH |
| C | S | C | N | C | 2-pyridyl | CH₂OH |
| C | S | C | N | C | 2-pyridyl | OMe |
| C | S | C | N | C | 2-pyridyl | SMe |
| C | S | C | N | C | 2-pyridyl | Cl |
| C | S | C | N | C | 2-pyridyl | CF₃ |
| C | S | C | N | C | 2-pyridyl | Ph |
| C | S | C | N | C | 3-pyridyl | H |
| C | S | C | N | C | 3-pyridyl | Me |
| C | S | C | N | C | 3-pyridyl | Et |
| C | S | C | N | C | 3-pyridyl | n-Hex |
| C | S | C | N | C | 3-pyridyl | c-Pr |
| C | S | C | N | C | 3-pyridyl | c-Hex |
| C | S | C | N | C | 3-pyridyl | OH |
| C | S | C | N | C | 3-pyridyl | CH₂OH |
| C | S | C | N | C | 3-pyridyl | OMe |
| C | S | C | N | C | 3-pyridyl | SMe |
| C | S | C | N | C | 3-pyridyl | Cl |
| C | S | C | N | C | 3-pyridyl | CF₃ |

TABLE 4-continued

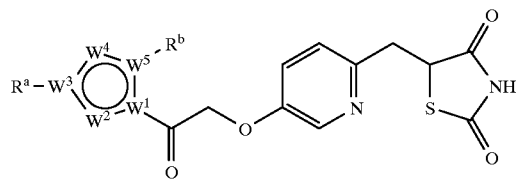
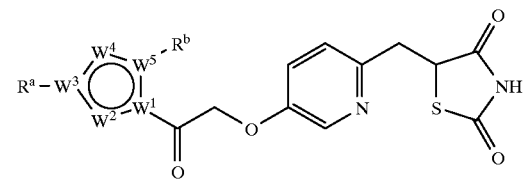

| W¹ | W² | W³ | W⁴ | W⁵ | Rᵃ | Rᵇ |
|---|---|---|---|---|---|---|
| C | S | C | N | C | 3-pyridyl | Ph |
| C | S | C | N | C | 4-pyridyl | H |
| C | S | C | N | C | 4-pyridyl | Me |
| C | S | C | N | C | 4-pyridyl | Et |
| C | S | C | N | C | 4-pyridyl | n-Hex |
| C | S | C | N | C | 4-pyridyl | c-Pr |
| C | S | C | N | C | 4-pyridyl | c-Hex |
| C | S | C | N | C | 4-pyridyl | OH |
| C | S | C | N | C | 4-pyridyl | CH₂OH |
| C | S | C | N | C | 4-pyridyl | OMe |
| C | S | C | N | C | 4-pyridyl | SMe |
| C | S | C | N | C | 4-pyridyl | Cl |
| C | S | C | N | C | 4-pyridyl | CF₃ |
| C | S | C | N | C | 4-pyridyl | Ph |
| C | S | C | N | C | 2-furanyl | H |
| C | S | C | N | C | 2-furanyl | Me |
| C | S | C | N | C | 2-furanyl | Et |
| C | S | C | N | C | 2-furanyl | n-Hex |
| C | S | C | N | C | 2-furanyl | c-Pr |
| C | S | C | N | C | 2-furanyl | c-Hex |
| C | S | C | N | C | 2-furanyl | OH |
| C | S | C | N | C | 2-furanyl | CH₂OH |
| C | S | C | N | C | 2-furanyl | OMe |
| C | S | C | N | C | 2-furanyl | SMe |
| C | S | C | N | C | 2-furanyl | Cl |
| C | S | C | N | C | 2-furanyl | CF₃ |
| C | S | C | N | C | 2-furanyl | Ph |
| C | S | C | N | C | 2-thienyl | H |
| C | S | C | N | C | 2-thienyl | Me |
| C | S | C | N | C | 2-thienyl | Et |
| C | S | C | N | C | 2-thienyl | n-Hex |
| C | S | C | N | C | 2-thienyl | c-Pr |
| C | S | C | N | C | 2-thienyl | c-Hex |
| C | S | C | N | C | 2-thienyl | OH |
| C | S | C | N | C | 2-thienyl | CH₂OH |
| C | S | C | N | C | 2-thienyl | OMe |
| C | S | C | N | C | 2-thienyl | SMe |
| C | S | C | N | C | 2-thienyl | Cl |
| C | S | C | N | C | 2-thienyl | CF₃ |
| C | S | C | N | C | 2-thienyl | Ph |
| C | S | C | N | C | 2-tolyl | H |
| C | S | C | N | C | 2-tolyl | Me |
| C | S | C | N | C | 2-tolyl | Et |
| C | S | C | N | C | 2-tolyl | n-Hex |
| C | S | C | N | C | 2-tolyl | c-Pr |
| C | S | C | N | C | 2-tolyl | c-Hex |
| C | S | C | N | C | 2-tolyl | OH |
| C | S | C | N | C | 2-tolyl | CH₂OH |
| C | S | C | N | C | 2-tolyl | OMe |
| C | S | C | N | C | 2-tolyl | SMe |
| C | S | C | N | C | 2-tolyl | Cl |
| C | S | C | N | C | 2-tolyl | CF₃ |
| C | S | C | N | C | 2-tolyl | Ph |
| C | S | C | N | C | 3-tolyl | H |
| C | S | C | N | C | 3-tolyl | Me |
| C | S | C | N | C | 3-tolyl | Et |
| C | S | C | N | C | 3-tolyl | n-Hex |
| C | S | C | N | C | 3-tolyl | c-Pr |
| C | S | C | N | C | 3-tolyl | c-Hex |
| C | S | C | N | C | 3-tolyl | OH |
| C | S | C | N | C | 3-tolyl | CH₂OH |
| C | S | C | N | C | 3-tolyl | OMe |
| C | S | C | N | C | 3-tolyl | SMe |
| C | S | C | N | C | 3-tolyl | Cl |
| C | S | C | N | C | 3-tolyl | CF₃ |
| C | S | C | N | C | 3-tolyl | Ph |
| C | S | C | N | C | 4-tolyl | H |
| C | S | C | N | C | 4-tolyl | Me |
| C | S | C | N | C | 4-tolyl | Et |
| C | S | C | N | C | 4-tolyl | n-Hex |
| C | S | C | N | C | 4-tolyl | c-Pr |
| C | S | C | N | C | 4-tolyl | c-Hex |
| C | S | C | N | C | 4-tolyl | OH |
| C | S | C | N | C | 4-tolyl | CH₂OH |
| C | S | C | N | C | 4-tolyl | OMe |
| C | S | C | N | C | 4-tolyl | SMe |
| C | S | C | N | C | 4-tolyl | Cl |
| C | S | C | N | C | 4-tolyl | CF₃ |
| C | S | C | N | C | 4-tolyl | Ph |
| C | S | C | N | C | Ph-2,3-Me₂ | H |
| C | S | C | N | C | Ph-2,3-Me₂ | Me |
| C | S | C | N | C | Ph-2,3-Me₂ | Et |
| C | S | C | N | C | Ph-2,3-Me₂ | n-Hex |
| C | S | C | N | C | Ph-2,3-Me₂ | c-Pr |
| C | S | C | N | C | Ph-2,3-Me₂ | c-Hex |
| C | S | C | N | C | Ph-2,3-Me₂ | OH |
| C | S | C | N | C | Ph-2,3-Me₂ | CH₂OH |
| C | S | C | N | C | Ph-2,3-Me₂ | OMe |
| C | S | C | N | C | Ph-2,3-Me₂ | SMe |
| C | S | C | N | C | Ph-2,3-Me₂ | Cl |
| C | S | C | N | C | Ph-2,3-Me₂ | CF₃ |
| C | S | C | N | C | Ph-2,3-Me₂ | Ph |
| C | S | C | N | C | Ph-3,4-Me₂ | H |
| C | S | C | N | C | Ph-3,4-Me₂ | Me |
| C | S | C | N | C | Ph-3,4-Me₂ | Et |
| C | S | C | N | C | Ph-3,4-Me₂ | n-Hex |
| C | S | C | N | C | Ph-3,4-Me₂ | c-Pr |
| C | S | C | N | C | Ph-3,4-Me₂ | c-Hex |
| C | S | C | N | C | Ph-3,4-Me₂ | OH |
| C | S | C | N | C | Ph-3,4-Me₂ | CH₂OH |
| C | S | C | N | C | Ph-3,4-Me₂ | OMe |
| C | S | C | N | C | Ph-3,4-Me₂ | SMe |
| C | S | C | N | C | Ph-3,4-Me₂ | Cl |
| C | S | C | N | C | Ph-3,4-Me₂ | CF₃ |
| C | S | C | N | C | Ph-3,4-Me₂ | Ph |
| C | S | C | N | C | Ph-3,5-Me₂ | H |
| C | S | C | N | C | Ph-3,5-Me₂ | Me |
| C | S | C | N | C | Ph-3,5-Me₂ | Et |
| C | S | C | N | C | Ph-3,5-Me₂ | n-Hex |
| C | S | C | N | C | Ph-3,5-Me₂ | c-Pr |
| C | S | C | N | C | Ph-3,5-Me₂ | c-Hex |
| C | S | C | N | C | Ph-3,5-Me₂ | OH |
| C | S | C | N | C | Ph-3,5-Me₂ | CH₂OH |
| C | S | C | N | C | Ph-3,5-Me₂ | OMe |
| C | S | C | N | C | Ph-3,5-Me₂ | SMe |
| C | S | C | N | C | Ph-3,5-Me₂ | Cl |
| C | S | C | N | C | Ph-3,5-Me₂ | CF₃ |
| C | S | C | N | C | Ph-3,5-Me₂ | Ph |
| C | S | C | N | C | Ph-2,6-Me₂ | H |
| C | S | C | N | C | Ph-2,6-Me₂ | Me |
| C | S | C | N | C | Ph-2,6-Me₂ | Et |
| C | S | C | N | C | Ph-2,6-Me₂ | n-Hex |
| C | S | C | N | C | Ph-2,6-Me₂ | c-Pr |
| C | S | C | N | C | Ph-2,6-Me₂ | c-Hex |
| C | S | C | N | C | Ph-2,6-Me₂ | OH |
| C | S | C | N | C | Ph-2,6-Me₂ | CH₂OH |
| C | S | C | N | C | Ph-2,6-Me₂ | OMe |
| C | S | C | N | C | Ph-2,6-Me₂ | SMe |
| C | S | C | N | C | Ph-2,6-Me₂ | Cl |
| C | S | C | N | C | Ph-2,6-Me₂ | CF₃ |
| C | S | C | N | C | Ph-2,6-Me₂ | Ph |
| C | S | C | N | C | Ph-2-Cl | H |
| C | S | C | N | C | Ph-2-Cl | Me |
| C | S | C | N | C | Ph-2-Cl | Et |

TABLE 4-continued

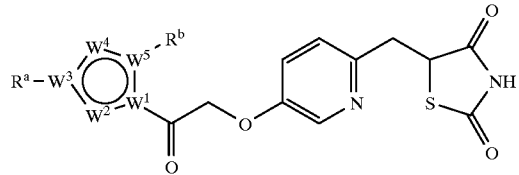

| W¹ | W² | W³ | W⁴ | W⁵ | Rᵃ | Rᵇ |
|---|---|---|---|---|---|---|
| C | S | C | N | C | Ph-2-Cl | n-Hex |
| C | S | C | N | C | Ph-2-Cl | c-Pr |
| C | S | C | N | C | Ph-2-Cl | c-Hex |
| C | S | C | N | C | Ph-2-Cl | OH |
| C | S | C | N | C | Ph-2-Cl | $CH_2OH$ |
| C | S | C | N | C | Ph-2-Cl | OMe |
| C | S | C | N | C | Ph-2-Cl | SMe |
| C | S | C | N | C | Ph-2-Cl | Cl |
| C | S | C | N | C | Ph-2-Cl | $CF_3$ |
| C | S | C | N | C | Ph-2-Cl | Ph |
| C | S | C | N | C | Ph-3-Cl | H |
| C | S | C | N | C | Ph-3-Cl | Me |
| C | S | C | N | C | Ph-3-Cl | Et |
| C | S | C | N | C | Ph-3-Cl | n-Hex |
| C | S | C | N | C | Ph-3-Cl | c-Pr |
| C | S | C | N | C | Ph-3-Cl | c-Hex |
| C | S | C | N | C | Ph-3-Cl | OH |
| C | S | C | N | C | Ph-3-Cl | $CH_2OH$ |
| C | S | C | N | C | Ph-3-Cl | OMe |
| C | S | C | N | C | Ph-3-Cl | SMe |
| C | S | C | N | C | Ph-3-Cl | Cl |
| C | S | C | N | C | Ph-3-Cl | $CF_3$ |
| C | S | C | N | C | Ph-3-Cl | Ph |
| C | S | C | N | C | Ph-4-Cl | H |
| C | S | C | N | C | Ph-4-Cl | Me |
| C | S | C | N | C | Ph-4-Cl | Et |
| C | S | C | N | C | Ph-4-Cl | n-Hex |
| C | S | C | N | C | Ph-4-Cl | c-Pr |
| C | S | C | N | C | Ph-4-Cl | c-Hex |
| C | S | C | N | C | Ph-4-Cl | OH |
| C | S | C | N | C | Ph-4-Cl | $CH_2OH$ |
| C | S | C | N | C | Ph-4-Cl | OMe |
| C | S | C | N | C | Ph-4-Cl | SMe |
| C | S | C | N | C | Ph-4-Cl | Cl |
| C | S | C | N | C | Ph-4-Cl | $CF_3$ |
| C | S | C | N | C | Ph-4-Cl | Ph |
| C | S | C | N | C | Ph-3,4-$Cl_2$ | H |
| C | S | C | N | C | Ph-3,4-$Cl_2$ | Me |
| C | S | C | N | C | Ph-3,4-$Cl_2$ | Et |
| C | S | C | N | C | Ph-3,4-$Cl_2$ | n-Hex |
| C | S | C | N | C | Ph-3,4-$Cl_2$ | c-Pr |
| C | S | C | N | C | Ph-3,4-$Cl_2$ | c-Hex |
| C | S | C | N | C | Ph-3,4-$Cl_2$ | OH |
| C | S | C | N | C | Ph-3,4-$Cl_2$ | $CH_2OH$ |
| C | S | C | N | C | Ph-3,4-$Cl_2$ | OMe |
| C | S | C | N | C | Ph-3,4-$Cl_2$ | SMe |
| C | S | C | N | C | Ph-3,4-$Cl_2$ | Cl |
| C | S | C | N | C | Ph-3,4-$Cl_2$ | $CF_3$ |
| C | S | C | N | C | Ph-3,4-$Cl_2$ | Ph |
| C | S | C | N | C | Ph-4-F | H |
| C | S | C | N | C | Ph-4-F | Me |
| C | S | C | N | C | Ph-4-F | Et |
| C | S | C | N | C | Ph-4-F | n-Hex |
| C | S | C | N | C | Ph-4-F | c-Pr |
| C | S | C | N | C | Ph-4-F | c-Hex |
| C | S | C | N | C | Ph-4-F | OH |
| C | S | C | N | C | Ph-4-F | $CH_2OH$ |
| C | S | C | N | C | Ph-4-F | OMe |
| C | S | C | N | C | Ph-4-F | SMe |
| C | S | C | N | C | Ph-4-F | Cl |
| C | S | C | N | C | Ph-4-F | $CF_3$ |
| C | S | C | N | C | Ph-4-F | Ph |
| C | S | C | N | C | Ph-4-Br | H |
| C | S | C | N | C | Ph-4-Br | Me |
| C | S | C | N | C | Ph-4-Br | Et |
| C | S | C | N | C | Ph-4-Br | n-Hex |
| C | S | C | N | C | Ph-4-Br | c-Pr |
| C | S | C | N | C | Ph-4-Br | c-Hex |
| C | S | C | N | C | Ph-4-Br | OH |
| C | S | C | N | C | Ph-4-Br | $CH_2OH$ |
| C | S | C | N | C | Ph-4-Br | OMe |
| C | S | C | N | C | Ph-4-Br | SMe |
| C | S | C | N | C | Ph-4-Br | Cl |
| C | S | C | N | C | Ph-4-Br | $CF_3$ |
| C | S | C | N | C | Ph-4-Br | Ph |
| C | S | C | N | C | Ph-2-OMe | H |
| C | S | C | N | C | Ph-2-OMe | Me |
| C | S | C | N | C | Ph-2-OMe | Et |
| C | S | C | N | C | Ph-2-OMe | n-Hex |
| C | S | C | N | C | Ph-2-OMe | c-Pr |
| C | S | C | N | C | Ph-2-OMe | c-Hex |
| C | S | C | N | C | Ph-2-OMe | OH |
| C | S | C | N | C | Ph-2-OMe | $CH_2OH$ |
| C | S | C | N | C | Ph-2-OMe | OMe |
| C | S | C | N | C | Ph-2-OMe | SMe |
| C | S | C | N | C | Ph-2-OMe | Cl |
| C | S | C | N | C | Ph-2-OMe | $CF_3$ |
| C | S | C | N | C | Ph-2-OMe | Ph |
| C | S | C | N | C | Ph-3-OMe | H |
| C | S | C | N | C | Ph-3-OMe | Me |
| C | S | C | N | C | Ph-3-OMe | Et |
| C | S | C | N | C | Ph-3-OMe | n-Hex |
| C | S | C | N | C | Ph-3-OMe | c-Pr |
| C | S | C | N | C | Ph-3-OMe | c-Hex |
| C | S | C | N | C | Ph-3-OMe | OH |
| C | S | C | N | C | Ph-3-OMe | $CH_2OH$ |
| C | S | C | N | C | Ph-3-OMe | OMe |
| C | S | C | N | C | Ph-3-OMe | SMe |
| C | S | C | N | C | Ph-3-OMe | Cl |
| C | S | C | N | C | Ph-3-OMe | $CF_3$ |
| C | S | C | N | C | Ph-3-OMe | Ph |
| C | S | C | N | C | Ph-4-OMe | H |
| C | S | C | N | C | Ph-4-OMe | Me |
| C | S | C | N | C | Ph-4-OMe | Et |
| C | S | C | N | C | Ph-4-OMe | n-Hex |
| C | S | C | N | C | Ph-4-OMe | c-Pr |
| C | S | C | N | C | Ph-4-OMe | c-Hex |
| C | S | C | N | C | Ph-4-OMe | OH |
| C | S | C | N | C | Ph-4-OMe | $CH_2OH$ |
| C | S | C | N | C | Ph-4-OMe | OMe |
| C | S | C | N | C | Ph-4-OMe | SMe |
| C | S | C | N | C | Ph-4-OMe | Cl |
| C | S | C | N | C | Ph-4-OMe | $CF_3$ |
| C | S | C | N | C | Ph-4-OMe | Ph |
| C | S | C | N | C | Ph-3,4-$(OMe)_2$ | H |
| C | S | C | N | C | Ph-3,4-$(OMe)_2$ | Me |
| C | S | C | N | C | Ph-3,4-$(OMe)_2$ | Et |
| C | S | C | N | C | Ph-3,4-$(OMe)_2$ | n-Hex |
| C | S | C | N | C | Ph-3,4-$(OMe)_2$ | c-Pr |
| C | S | C | N | C | Ph-3,4-$(OMe)_2$ | c-Hex |
| C | S | C | N | C | Ph-3,4-$(OMe)_2$ | OH |
| C | S | C | N | C | Ph-3,4-$(OMe)_2$ | $CH_2OH$ |
| C | S | C | N | C | Ph-3,4-$(OMe)_2$ | OMe |
| C | S | C | N | C | Ph-3,4-$(OMe)_2$ | SMe |
| C | S | C | N | C | Ph-3,4-$(OMe)_2$ | Cl |
| C | S | C | N | C | Ph-3,4-$(OMe)_2$ | $CF_3$ |
| C | S | C | N | C | Ph-3,4-$(OMe)_2$ | Ph |
| C | S | C | N | C | Ph-2-OH | H |
| C | S | C | N | C | Ph-2-OH | Me |
| C | S | C | N | C | Ph-2-OH | Et |
| C | S | C | N | C | Ph-2-OH | n-Hex |
| C | S | C | N | C | Ph-2-OH | c-Pr |
| C | S | C | N | C | Ph-2-OH | c-Hex |
| C | S | C | N | C | Ph-2-OH | OH |

TABLE 4-continued

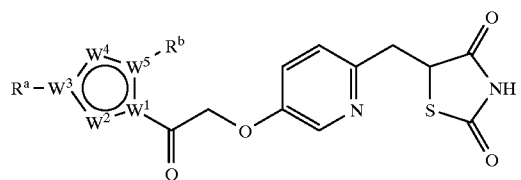
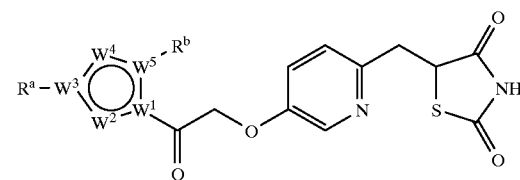

| W¹ | W² | W³ | W⁴ | W⁵ | Rᵃ | Rᵇ |
|---|---|---|---|---|---|---|
| C | S | C | N | C | Ph-2-OH | CH$_2$OH |
| C | S | C | N | C | Ph-2-OH | OMe |
| C | S | C | N | C | Ph-2-OH | SMe |
| C | S | C | N | C | Ph-2-OH | Cl |
| C | S | C | N | C | Ph-2-OH | CF$_3$ |
| C | S | C | N | C | Ph-2-OH | Ph |
| C | S | C | N | C | Ph-3-OH | H |
| C | S | C | N | C | Ph-3-OH | Me |
| C | S | C | N | C | Ph-3-OH | Et |
| C | S | C | N | C | Ph-3-OH | n-Hex |
| C | S | C | N | C | Ph-3-OH | c-Pr |
| C | S | C | N | C | Ph-3-OH | c-Hex |
| C | S | C | N | C | Ph-3-OH | OH |
| C | S | C | N | C | Ph-3-OH | CH$_2$OH |
| C | S | C | N | C | Ph-3-OH | OMe |
| C | S | C | N | C | Ph-3-OH | SMe |
| C | S | C | N | C | Ph-3-OH | Cl |
| C | S | C | N | C | Ph-3-OH | CF$_3$ |
| C | S | C | N | C | Ph-3-OH | Ph |
| C | S | C | N | C | Ph-4-OH | H |
| C | S | C | N | C | Ph-4-OH | Me |
| C | S | C | N | C | Ph-4-OH | Et |
| C | S | C | N | C | Ph-4-OH | n-Hex |
| C | S | C | N | C | Ph-4-OH | c-Pr |
| C | S | C | N | C | Ph-4-OH | c-Hex |
| C | S | C | N | C | Ph-4-OH | OH |
| C | S | C | N | C | Ph-4-OH | CH$_2$OH |
| C | S | C | N | C | Ph-4-OH | OMe |
| C | S | C | N | C | Ph-4-OH | SMe |
| C | S | C | N | C | Ph-4-OH | Cl |
| C | S | C | N | C | Ph-4-OH | CF$_3$ |
| C | S | C | N | C | Ph-4-OH | Ph |
| C | S | C | N | C | Ph-3,4-(OH)$_2$ | H |
| C | S | C | N | C | Ph-3,4-(OH)$_2$ | Me |
| C | S | C | N | C | Ph-3,4-(OH)$_2$ | Et |
| C | S | C | N | C | Ph-3,4-(OH)$_2$ | n-Hex |
| C | S | C | N | C | Ph-3,4-(OH)$_2$ | c-Pr |
| C | S | C | N | C | Ph-3,4-(OH)$_2$ | c-Hex |
| C | S | C | N | C | Ph-3,4-(OH)$_2$ | OH |
| C | S | C | N | C | Ph-3,4-(OH)$_2$ | CH$_2$OH |
| C | S | C | N | C | Ph-3,4-(OH)$_2$ | OMe |
| C | S | C | N | C | Ph-3,4-(OH)$_2$ | SMe |
| C | S | C | N | C | Ph-3,4-(OH)$_2$ | Cl |
| C | S | C | N | C | Ph-3,4-(OH)$_2$ | CF$_3$ |
| C | S | C | N | C | Ph-3,4-(OH)$_2$ | Ph |
| C | S | C | N | C | Ph-3-SMe | H |
| C | S | C | N | C | Ph-3-SMe | Me |
| C | S | C | N | C | Ph-3-SMe | Et |
| C | S | C | N | C | Ph-3-SMe | n-Hex |
| C | S | C | N | C | Ph-3-SMe | c-Pr |
| C | S | C | N | C | Ph-3-SMe | c-Hex |
| C | S | C | N | C | Ph-3-SMe | OH |
| C | S | C | N | C | Ph-3-SMe | CH$_2$OH |
| C | S | C | N | C | Ph-3-SMe | OMe |
| C | S | C | N | C | Ph-3-SMe | SMe |
| C | S | C | N | C | Ph-3-SMe | Cl |
| C | S | C | N | C | Ph-3-SMe | CF$_3$ |
| C | S | C | N | C | Ph-3-SMe | Ph |
| C | S | C | N | C | Ph-3-CF$_3$ | H |
| C | S | C | N | C | Ph-3-CF$_3$ | Me |
| C | S | C | N | C | Ph-3-CF$_3$ | Et |
| C | S | C | N | C | Ph-3-CF$_3$ | n-Hex |
| C | S | C | N | C | Ph-3-CF$_3$ | c-Pr |
| C | S | C | N | C | Ph-3-CF$_3$ | c-Hex |
| C | S | C | N | C | Ph-3-CF$_3$ | OH |
| C | S | C | N | C | Ph-3-CF$_3$ | CH$_2$OH |
| C | S | C | N | C | Ph-3-CF$_3$ | OMe |
| C | S | C | N | C | Ph-3-CF$_3$ | SMe |
| C | S | C | N | C | Ph-3-CF$_3$ | Cl |
| C | S | C | N | C | Ph-3-CF$_3$ | CF$_3$ |
| C | S | C | N | C | Ph-3-CF$_3$ | Ph |
| C | S | C | N | C | Ph-3-NO$_2$ | H |
| C | S | C | N | C | Ph-3-NO$_2$ | Me |
| C | S | C | N | C | Ph-3-NO$_2$ | Et |
| C | S | C | N | C | Ph-3-NO$_2$ | n-Hex |
| C | S | C | N | C | Ph-3-NO$_2$ | c-Pr |
| C | S | C | N | C | Ph-3-NO$_2$ | c-Hex |
| C | S | C | N | C | Ph-3-NO$_2$ | OH |
| C | S | C | N | C | Ph-3-NO$_2$ | CH$_2$OH |
| C | S | C | N | C | Ph-3-NO$_2$ | OMe |
| C | S | C | N | C | Ph-3-NO$_2$ | SMe |
| C | S | C | N | C | Ph-3-NO$_2$ | Cl |
| C | S | C | N | C | Ph-3-NO$_2$ | CF$_3$ |
| C | S | C | N | C | Ph-3-NO$_2$ | Ph |
| C | S | C | N | C | Ph-4-NMe$_2$ | H |
| C | S | C | N | C | Ph-4-NMe$_2$ | Me |
| C | S | C | N | C | Ph-4-NMe$_2$ | Et |
| C | S | C | N | C | Ph-4-NMe$_2$ | n-Hex |
| C | S | C | N | C | Ph-4-NMe$_2$ | c-Pr |
| C | S | C | N | C | Ph-4-NMe$_2$ | c-Hex |
| C | S | C | N | C | Ph-4-NMe$_2$ | OH |
| C | S | C | N | C | Ph-4-NMe$_2$ | CH$_2$OH |
| C | S | C | N | C | Ph-4-NMe$_2$ | OMe |
| C | S | C | N | C | Ph-4-NMe$_2$ | SMe |
| C | S | C | N | C | Ph-4-NMe$_2$ | Cl |
| C | S | C | N | C | Ph-4-NMe$_2$ | CF$_3$ |
| C | S | C | N | C | Ph-4-NMe$_2$ | Ph |
| C | N | N | N | C | Ph | H |
| C | N | N | N | C | Ph | Me |
| C | N | N | N | C | Ph | Et |
| C | N | N | N | C | Ph | n-Hex |
| C | N | N | N | C | Ph | c-Pr |
| C | N | N | N | C | Ph | c-Hex |
| C | N | N | N | C | Ph | OH |
| C | N | N | N | C | Ph | CH$_2$OH |
| C | N | N | N | C | Ph | OMe |
| C | N | N | N | C | Ph | SMe |
| C | N | N | N | C | Ph | Cl |
| C | N | N | N | C | Ph | CF$_3$ |
| C | N | N | N | C | Ph | Ph |
| C | N | N | N | C | H | H |
| C | N | N | N | C | H | Me |
| C | N | N | N | C | H | Et |
| C | N | N | N | C | H | n-Hex |
| C | N | N | N | C | H | c-Pr |
| C | N | N | N | C | H | c-Hex |
| C | N | N | N | C | H | OH |
| C | N | N | N | C | H | CH$_2$OH |
| C | N | N | N | C | H | OMe |
| C | N | N | N | C | H | SMe |
| C | N | N | N | C | H | Cl |
| C | N | N | N | C | H | CF$_3$ |
| C | N | N | N | C | H | Ph |
| C | N | N | N | C | Me | H |
| C | N | N | N | C | Me | Me |
| C | N | N | N | C | Me | Et |
| C | N | N | N | C | Me | n-Hex |
| C | N | N | N | C | Me | c-Pr |
| C | N | N | N | C | Me | c-Hex |
| C | N | N | N | C | Me | OH |
| C | N | N | N | C | Me | CH$_2$OH |
| C | N | N | N | C | Me | OMe |
| C | N | N | N | C | Me | SMe |
| C | N | N | N | C | Me | Cl |

TABLE 4-continued

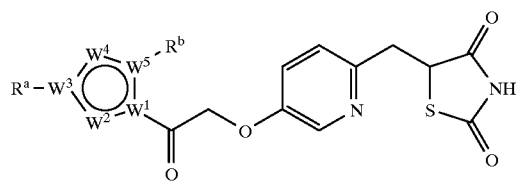
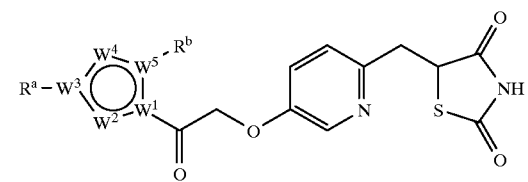

| $W^1$ | $W^2$ | $W^3$ | $W^4$ | $W^5$ | $R^a$ | $R^b$ | $W^1$ | $W^2$ | $W^3$ | $W^4$ | $W^5$ | $R^a$ | $R^b$ |
|---|---|---|---|---|---|---|---|---|---|---|---|---|---|
| C | N | N | N | C | Me | $CF_3$ | C | N | N | N | C | c-Hex | H |
| C | N | N | N | C | Me | Ph | C | N | N | N | C | c-Hex | Me |
| C | N | N | N | C | Et | H | C | N | N | N | C | c-Hex | Et |
| C | N | N | N | C | Et | Me | C | N | N | N | C | c-Hex | n-Hex |
| C | N | N | N | C | Et | Et | C | N | N | N | C | c-Hex | c-Pr |
| C | N | N | N | C | Et | n-Hex | C | N | N | N | C | c-Hex | c-Hex |
| C | N | N | N | C | Et | c-Pr | C | N | N | N | C | c-Hex | OH |
| C | N | N | N | C | Et | c-Hex | C | N | N | N | C | c-Hex | $CH_2OH$ |
| C | N | N | N | C | Et | OH | C | N | N | N | C | c-Hex | OMe |
| C | N | N | N | C | Et | $CH_2OH$ | C | N | N | N | C | c-Hex | SMe |
| C | N | N | N | C | Et | OMe | C | N | N | N | C | c-Hex | Cl |
| C | N | N | N | C | Et | SMe | C | N | N | N | C | c-Hex | $CF_3$ |
| C | N | N | N | C | Et | Cl | C | N | N | N | C | c-Hex | Ph |
| C | N | N | N | C | Et | $CF_3$ | C | N | N | N | C | 3-c-hexenyl | H |
| C | N | N | N | C | Et | Ph | C | N | N | N | C | 3-c-hexenyl | Me |
| C | N | N | N | C | n-Pr | H | C | N | N | N | C | 3-c-hexenyl | Et |
| C | N | N | N | C | n-Pr | Me | C | N | N | N | C | 3-c-hexenyl | n-Hex |
| C | N | N | N | C | n-Pr | Et | C | N | N | N | C | 3-c-hexenyl | c-Pr |
| C | N | N | N | C | n-Pr | n-Hex | C | N | N | N | C | 3-c-hexenyl | c-Hex |
| C | N | N | N | C | n-Pr | c-Pr | C | N | N | N | C | 3-c-hexenyl | OH |
| C | N | N | N | C | n-Pr | c-Hex | C | N | N | N | C | 3-c-hexenyl | $CH_2OH$ |
| C | N | N | N | C | n-Pr | OH | C | N | N | N | C | 3-c-hexenyl | OMe |
| C | N | N | N | C | n-Pr | $CH_2OH$ | C | N | N | N | C | 3-c-hexenyl | SMe |
| C | N | N | N | C | n-Pr | OMe | C | N | N | N | C | 3-c-hexenyl | Cl |
| C | N | N | N | C | n-Pr | SMe | C | N | N | N | C | 3-c-hexenyl | $CF_3$ |
| C | N | N | N | C | n-Pr | Cl | C | N | N | N | C | 3-c-hexenyl | Ph |
| C | N | N | N | C | n-Pr | $CF_3$ | C | N | N | N | C | $CH_2OH$ | H |
| C | N | N | N | C | n-Pr | Ph | C | N | N | N | C | $CH_2OH$ | Me |
| C | N | N | N | C | n-Hex | H | C | N | N | N | C | $CH_2OH$ | Et |
| C | N | N | N | C | n-Hex | Me | C | N | N | N | C | $CH_2OH$ | n-Hex |
| C | N | N | N | C | n-Hex | Et | C | N | N | N | C | $CH_2OH$ | c-Pr |
| C | N | N | N | C | n-Hex | n-Hex | C | N | N | N | C | $CH_2OH$ | c-Hex |
| C | N | N | N | C | n-Hex | c-Pr | C | N | N | N | C | $CH_2OH$ | OH |
| C | N | N | N | C | n-Hex | c-Hex | C | N | N | N | C | $CH_2OH$ | $CH_2OH$ |
| C | N | N | N | C | n-Hex | OH | C | N | N | N | C | $CH_2OH$ | OMe |
| C | N | N | N | C | n-Hex | $CH_2OH$ | C | N | N | N | C | $CH_2OH$ | SMe |
| C | N | N | N | C | n-Hex | OMe | C | N | N | N | C | $CH_2OH$ | Cl |
| C | N | N | N | C | n-Hex | SMe | C | N | N | N | C | $CH_2OH$ | $CF_3$ |
| C | N | N | N | C | n-Hex | Cl | C | N | N | N | C | $CH_2OH$ | Ph |
| C | N | N | N | C | n-Hex | $CF_3$ | C | N | N | N | C | $CH_2Ph$ | H |
| C | N | N | N | C | n-Hex | Ph | C | N | N | N | C | $CH_2Ph$ | Me |
| C | N | N | N | C | i-Pr | H | C | N | N | N | C | $CH_2Ph$ | Et |
| C | N | N | N | C | i-Pr | Me | C | N | N | N | C | $CH_2Ph$ | n-Hex |
| C | N | N | N | C | i-Pr | Et | C | N | N | N | C | $CH_2Ph$ | c-Pr |
| C | N | N | N | C | i-Pr | n-Hex | C | N | N | N | C | $CH_2Ph$ | c-Hex |
| C | N | N | N | C | i-Pr | c-Pr | C | N | N | N | C | $CH_2Ph$ | OH |
| C | N | N | N | C | i-Pr | c-Hex | C | N | N | N | C | $CH_2Ph$ | $CH_2OH$ |
| C | N | N | N | C | i-Pr | OH | C | N | N | N | C | $CH_2Ph$ | OMe |
| C | N | N | N | C | i-Pr | $CH_2OH$ | C | N | N | N | C | $CH_2Ph$ | SMe |
| C | N | N | N | C | i-Pr | OMe | C | N | N | N | C | $CH_2Ph$ | Cl |
| C | N | N | N | C | i-Pr | SMe | C | N | N | N | C | $CH_2Ph$ | $CF_3$ |
| C | N | N | N | C | i-Pr | Cl | C | N | N | N | C | $CH_2Ph$ | Ph |
| C | N | N | N | C | i-Pr | $CF_3$ | C | N | N | N | C | α-naphthyl | H |
| C | N | N | N | C | i-Pr | Ph | C | N | N | N | C | α-naphthyl | Me |
| C | N | N | N | C | t-Bu | H | C | N | N | N | C | α-naphthyl | Et |
| C | N | N | N | C | t-Bu | Me | C | N | N | N | C | α-naphthyl | n-Hex |
| C | N | N | N | C | t-Bu | Et | C | N | N | N | C | α-naphthyl | c-Pr |
| C | N | N | N | C | t-Bu | n-Hex | C | N | N | N | C | α-naphthyl | c-Hex |
| C | N | N | N | C | t-Bu | c-Pr | C | N | N | N | C | α-naphthyl | OH |
| C | N | N | N | C | t-Bu | c-Hex | C | N | N | N | C | α-naphthyl | $CH_2OH$ |
| C | N | N | N | C | t-Bu | OH | C | N | N | N | C | α-naphthyl | OMe |
| C | N | N | N | C | t-Bu | $CH_2OH$ | C | N | N | N | C | α-naphthyl | SMe |
| C | N | N | N | C | t-Bu | OMe | C | N | N | N | C | α-naphthyl | Cl |
| C | N | N | N | C | t-Bu | SMe | C | N | N | N | C | α-naphthyl | $CF_3$ |
| C | N | N | N | C | t-Bu | Cl | C | N | N | N | C | α-naphthyl | Ph |
| C | N | N | N | C | t-Bu | $CF_3$ | C | N | N | N | C | β-naphthyl | H |
| C | N | N | N | C | t-Bu | Ph | C | N | N | N | C | β-naphthyl | Me |

TABLE 4-continued

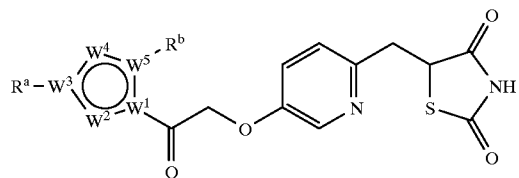

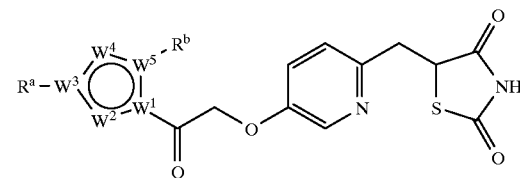

| W¹ | W² | W³ | W⁴ | W⁵ | Rᵃ | Rᵇ |
|---|---|---|---|---|---|---|
| C | N | N | N | C | β-naphthyl | Et |
| C | N | N | N | C | β-naphthyl | n-Hex |
| C | N | N | N | C | β-naphthyl | c-Pr |
| C | N | N | N | C | β-naphthyl | c-Hex |
| C | N | N | N | C | β-naphthyl | OH |
| C | N | N | N | C | β-naphthyl | $CH_2OH$ |
| C | N | N | N | C | β-naphthyl | OMe |
| C | N | N | N | C | β-naphthyl | SMe |
| C | N | N | N | C | β-naphthyl | Cl |
| C | N | N | N | C | β-naphthyl | $CF_3$ |
| C | N | N | N | C | β-naphthyl | Ph |
| C | N | N | N | C | 2-pyridyl | H |
| C | N | N | N | C | 2-pyridyl | Me |
| C | N | N | N | C | 2-pyridyl | Et |
| C | N | N | N | C | 2-pyridyl | n-Hex |
| C | N | N | N | C | 2-pyridyl | c-Pr |
| C | N | N | N | C | 2-pyridyl | c-Hex |
| C | N | N | N | C | 2-pyridyl | OH |
| C | N | N | N | C | 2-pyridyl | $CH_2OH$ |
| C | N | N | N | C | 2-pyridyl | OMe |
| C | N | N | N | C | 2-pyridyl | SMe |
| C | N | N | N | C | 2-pyridyl | Cl |
| C | N | N | N | C | 2-pyridyl | $CF_3$ |
| C | N | N | N | C | 2-pyridyl | Ph |
| C | N | N | N | C | 3-pyridyl | H |
| C | N | N | N | C | 3-pyridyl | Me |
| C | N | N | N | C | 3-pyridyl | Et |
| C | N | N | N | C | 3-pyridyl | n-Hex |
| C | N | N | N | C | 3-pyridyl | c-Pr |
| C | N | N | N | C | 3-pyridyl | c-Hex |
| C | N | N | N | C | 3-pyridyl | OH |
| C | N | N | N | C | 3-pyridyl | $CH_2OH$ |
| C | N | N | N | C | 3-pyridyl | OMe |
| C | N | N | N | C | 3-pyridyl | SMe |
| C | N | N | N | C | 3-pyridyl | Cl |
| C | N | N | N | C | 3-pyridyl | $CF_3$ |
| C | N | N | N | C | 3-pyridyl | Ph |
| C | N | N | N | C | 4-pyridyl | H |
| C | N | N | N | C | 4-pyridyl | Me |
| C | N | N | N | C | 4-pyridyl | Et |
| C | N | N | N | C | 4-pyridyl | n-Hex |
| C | N | N | N | C | 4-pyridyl | c-Pr |
| C | N | N | N | C | 4-pyridyl | c-Hex |
| C | N | N | N | C | 4-pyridyl | OH |
| C | N | N | N | C | 4-pyridyl | $CH_2OH$ |
| C | N | N | N | C | 4-pyridyl | OMe |
| C | N | N | N | C | 4-pyridyl | SMe |
| C | N | N | N | C | 4-pyridyl | Cl |
| C | N | N | N | C | 4-pyridyl | $CF_3$ |
| C | N | N | N | C | 4-pyridyl | Ph |
| C | N | N | N | C | 2-furanyl | H |
| C | N | N | N | C | 2-furanyl | Me |
| C | N | N | N | C | 2-furanyl | Et |
| C | N | N | N | C | 2-furanyl | n-Hex |
| C | N | N | N | C | 2-furanyl | c-Pr |
| C | N | N | N | C | 2-furanyl | c-Hex |
| C | N | N | N | C | 2-furanyl | OH |
| C | N | N | N | C | 2-furanyl | $CH_2OH$ |
| C | N | N | N | C | 2-furanyl | OMe |
| C | N | N | N | C | 2-furanyl | SMe |
| C | N | N | N | C | 2-furanyl | Cl |
| C | N | N | N | C | 2-furanyl | $CF_3$ |
| C | N | N | N | C | 2-furanyl | Ph |
| C | N | N | N | C | 2-thienyl | H |
| C | N | N | N | C | 2-thienyl | Me |
| C | N | N | N | C | 2-thienyl | Et |
| C | N | N | N | C | 2-thienyl | n-Hex |
| C | N | N | N | C | 2-thienyl | c-Pr |
| C | N | N | N | C | 2-thienyl | c-Hex |
| C | N | N | N | C | 2-thienyl | OH |
| C | N | N | N | C | 2-thienyl | $CH_2OH$ |
| C | N | N | N | C | 2-thienyl | OMe |
| C | N | N | N | C | 2-thienyl | SMe |
| C | N | N | N | C | 2-thienyl | Cl |
| C | N | N | N | C | 2-thienyl | $CF_3$ |
| C | N | N | N | C | 2-thienyl | Ph |
| C | N | N | N | C | 2-tolyl | H |
| C | N | N | N | C | 2-tolyl | Me |
| C | N | N | N | C | 2-tolyl | Et |
| C | N | N | N | C | 2-tolyl | n-Hex |
| C | N | N | N | C | 2-tolyl | c-Pr |
| C | N | N | N | C | 2-tolyl | c-Hex |
| C | N | N | N | C | 2-tolyl | OH |
| C | N | N | N | C | 2-tolyl | $CH_2OH$ |
| C | N | N | N | C | 2-tolyl | OMe |
| C | N | N | N | C | 2-tolyl | SMe |
| C | N | N | N | C | 2-tolyl | Cl |
| C | N | N | N | C | 2-tolyl | $CF_3$ |
| C | N | N | N | C | 2-tolyl | Ph |
| C | N | N | N | C | 3-tolyl | H |
| C | N | N | N | C | 3-tolyl | Me |
| C | N | N | N | C | 3-tolyl | Et |
| C | N | N | N | C | 3-tolyl | n-Hex |
| C | N | N | N | C | 3-tolyl | c-Pr |
| C | N | N | N | C | 3-tolyl | c-Hex |
| C | N | N | N | C | 3-tolyl | OH |
| C | N | N | N | C | 3-tolyl | $CH_2OH$ |
| C | N | N | N | C | 3-tolyl | OMe |
| C | N | N | N | C | 3-tolyl | SMe |
| C | N | N | N | C | 3-tolyl | Cl |
| C | N | N | N | C | 3-tolyl | $CF_3$ |
| C | N | N | N | C | 3-tolyl | Ph |
| C | N | N | N | C | 4-tolyl | H |
| C | N | N | N | C | 4-tolyl | Me |
| C | N | N | N | C | 4-tolyl | Et |
| C | N | N | N | C | 4-tolyl | n-Hex |
| C | N | N | N | C | 4-tolyl | c-Pr |
| C | N | N | N | C | 4-tolyl | c-Hex |
| C | N | N | N | C | 4-tolyl | OH |
| C | N | N | N | C | 4-tolyl | $CH_2OH$ |
| C | N | N | N | C | 4-tolyl | OMe |
| C | N | N | N | C | 4-tolyl | SMe |
| C | N | N | N | C | 4-tolyl | Cl |
| C | N | N | N | C | 4-tolyl | $CF_3$ |
| C | N | N | N | C | 4-tolyl | Ph |
| C | N | N | N | C | Ph-2,3-$Me_2$ | H |
| C | N | N | N | C | Ph-2,3-$Me_2$ | Me |
| C | N | N | N | C | Ph-2,3-$Me_2$ | Et |
| C | N | N | N | C | Ph-2,3-$Me_2$ | n-Hex |
| C | N | N | N | C | Ph-2,3-$Me_2$ | c-Pr |
| C | N | N | N | C | Ph-2,3-$Me_2$ | c-Hex |
| C | N | N | N | C | Ph-2,3-$Me_2$ | OH |
| C | N | N | N | C | Ph-2,3-$Me_2$ | $CH_2OH$ |
| C | N | N | N | C | Ph-2,3-$Me_2$ | OMe |
| C | N | N | N | C | Ph-2,3-$Me_2$ | SMe |
| C | N | N | N | C | Ph-2,3-$Me_2$ | Cl |
| C | N | N | N | C | Ph-2,3-$Me_2$ | $CF_3$ |
| C | N | N | N | C | Ph-2,3-$Me_2$ | Ph |
| C | N | N | N | C | Ph-3,4-$Me_2$ | H |
| C | N | N | N | C | Ph-3,4-$Me_2$ | Me |
| C | N | N | N | C | Ph-3,4-$Me_2$ | Et |
| C | N | N | N | C | Ph-3,4-$Me_2$ | n-Hex |
| C | N | N | N | C | Ph-3,4-$Me_2$ | c-Pr |
| C | N | N | N | C | Ph-3,4-$Me_2$ | c-Hex |

TABLE 4-continued

| W¹ | W² | W³ | W⁴ | W⁵ | Rᵃ | Rᵇ |
|---|---|---|---|---|---|---|
| C | N | N | N | C | Ph-3,4-Me₂ | OH |
| C | N | N | N | C | Ph-3,4-Me₂ | CH₂OH |
| C | N | N | N | C | Ph-3,4-Me₂ | OMe |
| C | N | N | N | C | Ph-3,4-Me₂ | SMe |
| C | N | N | N | C | Ph-3,4-Me₂ | Cl |
| C | N | N | N | C | Ph-3,4-Me₂ | CF₃ |
| C | N | N | N | C | Ph-3,4-Me₂ | Ph |
| C | N | N | N | C | Ph-3,5-Me₂ | H |
| C | N | N | N | C | Ph-3,5-Me₂ | Me |
| C | N | N | N | C | Ph-3,5-Me₂ | Et |
| C | N | N | N | C | Ph-3,5-Me₂ | n-Hex |
| C | N | N | N | C | Ph-3,5-Me₂ | c-Pr |
| C | N | N | N | C | Ph-3,5-Me₂ | c-Hex |
| C | N | N | N | C | Ph-3,5-Me₂ | OH |
| C | N | N | N | C | Ph-3,5-Me₂ | CH₂OH |
| C | N | N | N | C | Ph-3,5-Me₂ | OMe |
| C | N | N | N | C | Ph-3,5-Me₂ | SMe |
| C | N | N | N | C | Ph-3,5-Me₂ | Cl |
| C | N | N | N | C | Ph-3,5-Me₂ | CF₃ |
| C | N | N | N | C | Ph-3,5-Me₂ | Ph |
| C | N | N | N | C | Ph-2,6-Me₂ | H |
| C | N | N | N | C | Ph-2,6-Me₂ | Me |
| C | N | N | N | C | Ph-2,6-Me₂ | Et |
| C | N | N | N | C | Ph-2,6-Me₂ | n-Hex |
| C | N | N | N | C | Ph-2,6-Me₂ | c-Pr |
| C | N | N | N | C | Ph-2,6-Me₂ | c-Hex |
| C | N | N | N | C | Ph-2,6-Me₂ | OH |
| C | N | N | N | C | Ph-2,6-Me₂ | CH₂OH |
| C | N | N | N | C | Ph-2,6-Me₂ | OMe |
| C | N | N | N | C | Ph-2,6-Me₂ | SMe |
| C | N | N | N | C | Ph-2,6-Me₂ | Cl |
| C | N | N | N | C | Ph-2,6-Me₂ | CF₃ |
| C | N | N | N | C | Ph-2,6-Me₂ | Ph |
| C | N | N | N | C | Ph-2-Cl | H |
| C | N | N | N | C | Ph-2-Cl | Me |
| C | N | N | N | C | Ph-2-Cl | Et |
| C | N | N | N | C | Ph-2-Cl | n-Hex |
| C | N | N | N | C | Ph-2-Cl | c-Pr |
| C | N | N | N | C | Ph-2-Cl | c-Hex |
| C | N | N | N | C | Ph-2-Cl | OH |
| C | N | N | N | C | Ph-2-Cl | CH₂OH |
| C | N | N | N | C | Ph-2-Cl | OMe |
| C | N | N | N | C | Ph-2-Cl | SMe |
| C | N | N | N | C | Ph-2-Cl | Cl |
| C | N | N | N | C | Ph-2-Cl | CF₃ |
| C | N | N | N | C | Ph-2-Cl | Ph |
| C | N | N | N | C | Ph-3-Cl | H |
| C | N | N | N | C | Ph-3-Cl | Me |
| C | N | N | N | C | Ph-3-Cl | Et |
| C | N | N | N | C | Ph-3-Cl | n-Hex |
| C | N | N | N | C | Ph-3-Cl | c-Pr |
| C | N | N | N | C | Ph-3-Cl | c-Hex |
| C | N | N | N | C | Ph-3-Cl | OH |
| C | N | N | N | C | Ph-3-Cl | CH₂OH |
| C | N | N | N | C | Ph-3-Cl | OMe |
| C | N | N | N | C | Ph-3-Cl | SMe |
| C | N | N | N | C | Ph-3-Cl | Cl |
| C | N | N | N | C | Ph-3-Cl | CF₃ |
| C | N | N | N | C | Ph-3-Cl | Ph |
| C | N | N | N | C | Ph-4-Cl | H |
| C | N | N | N | C | Ph-4-Cl | Me |
| C | N | N | N | C | Ph-4-Cl | Et |
| C | N | N | N | C | Ph-4-Cl | n-Hex |
| C | N | N | N | C | Ph-4-Cl | c-Pr |
| C | N | N | N | C | Ph-4-Cl | c-Hex |
| C | N | N | N | C | Ph-4-Cl | OH |
| C | N | N | N | C | Ph-4-Cl | CH₂OH |
| C | N | N | N | C | Ph-4-Cl | OMe |
| C | N | N | N | C | Ph-4-Cl | SMe |
| C | N | N | N | C | Ph-4-Cl | Cl |
| C | N | N | N | C | Ph-4-Cl | CF₃ |
| C | N | N | N | C | Ph-4-Cl | Ph |
| C | N | N | N | C | Ph-3,4-Cl₂ | H |
| C | N | N | N | C | Ph-3,4-Cl₂ | Me |
| C | N | N | N | C | Ph-3,4-Cl₂ | Et |
| C | N | N | N | C | Ph-3,4-Cl₂ | n-Hex |
| C | N | N | N | C | Ph-3,4-Cl₂ | c-Pr |
| C | N | N | N | C | Ph-3,4-Cl₂ | c-Hex |
| C | N | N | N | C | Ph-3,4-Cl₂ | OH |
| C | N | N | N | C | Ph-3,4-Cl₂ | CH₂OH |
| C | N | N | N | C | Ph-3,4-Cl₂ | OMe |
| C | N | N | N | C | Ph-3,4-Cl₂ | SMe |
| C | N | N | N | C | Ph-3,4-Cl₂ | Cl |
| C | N | N | N | C | Ph-3,4-Cl₂ | CF₃ |
| C | N | N | N | C | Ph-3,4-Cl₂ | Ph |
| C | N | N | N | C | Ph-4-F | H |
| C | N | N | N | C | Ph-4-F | Me |
| C | N | N | N | C | Ph-4-F | Et |
| C | N | N | N | C | Ph-4-F | n-Hex |
| C | N | N | N | C | Ph-4-F | c-Pr |
| C | N | N | N | C | Ph-4-F | c-Hex |
| C | N | N | N | C | Ph-4-F | OH |
| C | N | N | N | C | Ph-4-F | CH₂OH |
| C | N | N | N | C | Ph-4-F | OMe |
| C | N | N | N | C | Ph-4-F | SMe |
| C | N | N | N | C | Ph-4-F | Cl |
| C | N | N | N | C | Ph-4-F | CF₃ |
| C | N | N | N | C | Ph-4-F | Ph |
| C | N | N | N | C | Ph-4-Br | H |
| C | N | N | N | C | Ph-4-Br | Me |
| C | N | N | N | C | Ph-4-Br | Et |
| C | N | N | N | C | Ph-4-Br | n-Hex |
| C | N | N | N | C | Ph-4-Br | c-Pr |
| C | N | N | N | C | Ph-4-Br | c-Hex |
| C | N | N | N | C | Ph-4-Br | OH |
| C | N | N | N | C | Ph-4-Br | CH₂OH |
| C | N | N | N | C | Ph-4-Br | OMe |
| C | N | N | N | C | Ph-4-Br | SMe |
| C | N | N | N | C | Ph-4-Br | Cl |
| C | N | N | N | C | Ph-4-Br | CF₃ |
| C | N | N | N | C | Ph-4-Br | Ph |
| C | N | N | N | C | Ph-2-OMe | H |
| C | N | N | N | C | Ph-2-OMe | Me |
| C | N | N | N | C | Ph-2-OMe | Et |
| C | N | N | N | C | Ph-2-OMe | n-Hex |
| C | N | N | N | C | Ph-2-OMe | c-Pr |
| C | N | N | N | C | Ph-2-OMe | c-Hex |
| C | N | N | N | C | Ph-2-OMe | OH |
| C | N | N | N | C | Ph-2-OMe | CH₂OH |
| C | N | N | N | C | Ph-2-OMe | OMe |
| C | N | N | N | C | Ph-2-OMe | SMe |
| C | N | N | N | C | Ph-2-OMe | Cl |
| C | N | N | N | C | Ph-2-OMe | CF₃ |
| C | N | N | N | C | Ph-2-OMe | Ph |
| C | N | N | N | C | Ph-3-OMe | H |
| C | N | N | N | C | Ph-3-OMe | Me |
| C | N | N | N | C | Ph-3-OMe | Et |
| C | N | N | N | C | Ph-3-OMe | n-Hex |
| C | N | N | N | C | Ph-3-OMe | c-Pr |
| C | N | N | N | C | Ph-3-OMe | c-Hex |
| C | N | N | N | C | Ph-3-OMe | OH |
| C | N | N | N | C | Ph-3-OMe | CH₂OH |
| C | N | N | N | C | Ph-3-OMe | OMe |
| C | N | N | N | C | Ph-3-OMe | SMe |

TABLE 4-continued

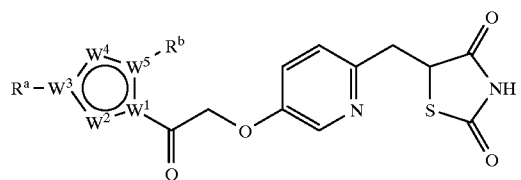

| W¹ | W² | W³ | W⁴ | W⁵ | Rᵃ | Rᵇ |
|---|---|---|---|---|---|---|
| C | N | N | N | C | Ph-3-OMe | Cl |
| C | N | N | N | C | Ph-3-OMe | CF₃ |
| C | N | N | N | C | Ph-3-OMe | Ph |
| C | N | N | N | C | Ph-4-OMe | H |
| C | N | N | N | C | Ph-4-OMe | Me |
| C | N | N | N | C | Ph-4-OMe | Et |
| C | N | N | N | C | Ph-4-OMe | n-Hex |
| C | N | N | N | C | Ph-4-OMe | c-Pr |
| C | N | N | N | C | Ph-4-OMe | c-Hex |
| C | N | N | N | C | Ph-4-OMe | OH |
| C | N | N | N | C | Ph-4-OMe | CH₂OH |
| C | N | N | N | C | Ph-4-OMe | OMe |
| C | N | N | N | C | Ph-4-OMe | SMe |
| C | N | N | N | C | Ph-4-OMe | Cl |
| C | N | N | N | C | Ph-4-OMe | CF₃ |
| C | N | N | N | C | Ph-4-OMe | Ph |
| C | N | N | N | C | Ph-3,4-(OMe)₂ | H |
| C | N | N | N | C | Ph-3,4-(OMe)₂ | Me |
| C | N | N | N | C | Ph-3,4-(OMe)₂ | Et |
| C | N | N | N | C | Ph-3,4-(OMe)₂ | n-Hex |
| C | N | N | N | C | Ph-3,4-(OMe)₂ | c-Pr |
| C | N | N | N | C | Ph-3,4-(OMe)₂ | c-Hex |
| C | N | N | N | C | Ph-3,4-(OMe)₂ | OH |
| C | N | N | N | C | Ph-3,4-(OMe)₂ | CH₂OH |
| C | N | N | N | C | Ph-3,4-(OMe)₂ | OMe |
| C | N | N | N | C | Ph-3,4-(OMe)₂ | SMe |
| C | N | N | N | C | Ph-3,4-(OMe)₂ | Cl |
| C | N | N | N | C | Ph-3,4-(OMe)₂ | CF₃ |
| C | N | N | N | C | Ph-3,4-(OMe)₂ | Ph |
| C | N | N | N | C | Ph-2-OH | H |
| C | N | N | N | C | Ph-2-OH | Me |
| C | N | N | N | C | Ph-2-OH | Et |
| C | N | N | N | C | Ph-2-OH | n-Hex |
| C | N | N | N | C | Ph-2-OH | c-Pr |
| C | N | N | N | C | Ph-2-OH | c-Hex |
| C | N | N | N | C | Ph-2-OH | OH |
| C | N | N | N | C | Ph-2-OH | CH₂OH |
| C | N | N | N | C | Ph-2-OH | OMe |
| C | N | N | N | C | Ph-2-OH | SMe |
| C | N | N | N | C | Ph-2-OH | Cl |
| C | N | N | N | C | Ph-2-OH | CF₃ |
| C | N | N | N | C | Ph-2-OH | Ph |
| C | N | N | N | C | Ph-3-OH | H |
| C | N | N | N | C | Ph-3-OH | Me |
| C | N | N | N | C | Ph-3-OH | Et |
| C | N | N | N | C | Ph-3-OH | n-Hex |
| C | N | N | N | C | Ph-3-OH | c-Pr |
| C | N | N | N | C | Ph-3-OH | c-Hex |
| C | N | N | N | C | Ph-3-OH | OH |
| C | N | N | N | C | Ph-3-OH | CH₂OH |
| C | N | N | N | C | Ph-3-OH | OMe |
| C | N | N | N | C | Ph-3-OH | SMe |
| C | N | N | N | C | Ph-3-OH | Cl |
| C | N | N | N | C | Ph-3-OH | CF₃ |
| C | N | N | N | C | Ph-3-OH | Ph |
| C | N | N | N | C | Ph-4-OH | H |
| C | N | N | N | C | Ph-4-OH | Me |
| C | N | N | N | C | Ph-4-OH | Et |
| C | N | N | N | C | Ph-4-OH | n-Hex |
| C | N | N | N | C | Ph-4-OH | c-Pr |
| C | N | N | N | C | Ph-4-OH | c-Hex |
| C | N | N | N | C | Ph-4-OH | OH |
| C | N | N | N | C | Ph-4-OH | CH₂OH |
| C | N | N | N | C | Ph-4-OH | OMe |
| C | N | N | N | C | Ph-4-OH | SMe |
| C | N | N | N | C | Ph-4-OH | Cl |
| C | N | N | N | C | Ph-4-OH | CF₃ |
| C | N | N | N | C | Ph-4-OH | Ph |
| C | N | N | N | C | Ph-3,4-(OH)₂ | H |
| C | N | N | N | C | Ph-3,4-(OH)₂ | Me |
| C | N | N | N | C | Ph-3,4-(OH)₂ | Et |
| C | N | N | N | C | Ph-3,4-(OH)₂ | n-Hex |
| C | N | N | N | C | Ph-3,4-(OH)₂ | c-Pr |
| C | N | N | N | C | Ph-3,4-(OH)₂ | c-Hex |
| C | N | N | N | C | Ph-3,4-(OH)₂ | OH |
| C | N | N | N | C | Ph-3,4-(OH)₂ | CH₂OH |
| C | N | N | N | C | Ph-3,4-(OH)₂ | OMe |
| C | N | N | N | C | Ph-3,4-(OH)₂ | SMe |
| C | N | N | N | C | Ph-3,4-(OH)₂ | Cl |
| C | N | N | N | C | Ph-3,4-(OH)₂ | CF₃ |
| C | N | N | N | C | Ph-3,4-(OH)₂ | Ph |
| C | N | N | N | C | Ph-3-SMe | H |
| C | N | N | N | C | Ph-3-SMe | Me |
| C | N | N | N | C | Ph-3-SMe | Et |
| C | N | N | N | C | Ph-3-SMe | n-Hex |
| C | N | N | N | C | Ph-3-SMe | c-Pr |
| C | N | N | N | C | Ph-3-SMe | c-Hex |
| C | N | N | N | C | Ph-3-SMe | OH |
| C | N | N | N | C | Ph-3-SMe | CH₂OH |
| C | N | N | N | C | Ph-3-SMe | OMe |
| C | N | N | N | C | Ph-3-SMe | SMe |
| C | N | N | N | C | Ph-3-SMe | Cl |
| C | N | N | N | C | Ph-3-SMe | CF₃ |
| C | N | N | N | C | Ph-3-SMe | Ph |
| C | N | N | N | C | Ph-3-CF₃ | H |
| C | N | N | N | C | Ph-3-CF₃ | Me |
| C | N | N | N | C | Ph-3-CF₃ | Et |
| C | N | N | N | C | Ph-3-CF₃ | n-Hex |
| C | N | N | N | C | Ph-3-CF₃ | c-Pr |
| C | N | N | N | C | Ph-3-CF₃ | c-Hex |
| C | N | N | N | C | Ph-3-CF₃ | OH |
| C | N | N | N | C | Ph-3-CF₃ | CH₂OH |
| C | N | N | N | C | Ph-3-CF₃ | OMe |
| C | N | N | N | C | Ph-3-CF₃ | SMe |
| C | N | N | N | C | Ph-3-CF₃ | Cl |
| C | N | N | N | C | Ph-3-CF₃ | CF₃ |
| C | N | N | N | C | Ph-3-CF₃ | Ph |
| C | N | N | N | C | Ph-3-NO₂ | H |
| C | N | N | N | C | Ph-3-NO₂ | Me |
| C | N | N | N | C | Ph-3-NO₂ | Et |
| C | N | N | N | C | Ph-3-NO₂ | n-Hex |
| C | N | N | N | C | Ph-3-NO₂ | c-Pr |
| C | N | N | N | C | Ph-3-NO₂ | c-Hex |
| C | N | N | N | C | Ph-3-NO₂ | OH |
| C | N | N | N | C | Ph-3-NO₂ | CH₂OH |
| C | N | N | N | C | Ph-3-NO₂ | OMe |
| C | N | N | N | C | Ph-3-NO₂ | SMe |
| C | N | N | N | C | Ph-3-NO₂ | Cl |
| C | N | N | N | C | Ph-3-NO₂ | CF₃ |
| C | N | N | N | C | Ph-3-NO₂ | Ph |
| C | N | N | N | C | Ph-4-NMe₂ | H |
| C | N | N | N | C | Ph-4-NMe₂ | Me |
| C | N | N | N | C | Ph-4-NMe₂ | Et |
| C | N | N | N | C | Ph-4-NMe₂ | n-Hex |
| C | N | N | N | C | Ph-4-NMe₂ | c-Pr |
| C | N | N | N | C | Ph-4-NMe₂ | c-Hex |
| C | N | N | N | C | Ph-4-NMe₂ | OH |
| C | N | N | N | C | Ph-4-NMe₂ | CH₂OH |
| C | N | N | N | C | Ph-4-NMe₂ | OMe |
| C | N | N | N | C | Ph-4-NMe₂ | SMe |
| C | N | N | N | C | Ph-4-NMe₂ | Cl |
| C | N | N | N | C | Ph-4-NMe₂ | CF₃ |
| C | N | N | N | C | Ph-4-NMe₂ | Ph |
| C | N | C | N | N | Ph | H |

TABLE 4-continued

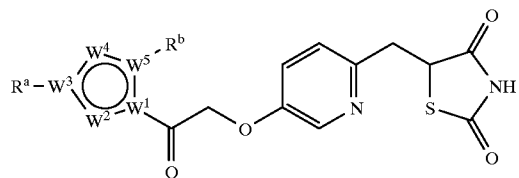

| W¹ | W² | W³ | W⁴ | W⁵ | Rᵃ | Rᵇ |
|---|---|---|---|---|---|---|
| C | N | C | N | N | Ph | Me |
| C | N | C | N | N | Ph | Et |
| C | N | C | N | N | Ph | n-Hex |
| C | N | C | N | N | Ph | c-Pr |
| C | N | C | N | N | Ph | c-Hex |
| C | N | C | N | N | Ph | OH |
| C | N | C | N | N | Ph | CH₂OH |
| C | N | C | N | N | Ph | OMe |
| C | N | C | N | N | Ph | SMe |
| C | N | C | N | N | Ph | Cl |
| C | N | C | N | N | Ph | CF₃ |
| C | N | C | N | N | Ph | Ph |
| C | N | C | N | N | H | H |
| C | N | C | N | N | H | Me |
| C | N | C | N | N | H | Et |
| C | N | C | N | N | H | n-Hex |
| C | N | C | N | N | H | c-Pr |
| C | N | C | N | N | H | c-Hex |
| C | N | C | N | N | H | OH |
| C | N | C | N | N | H | CH₂OH |
| C | N | C | N | N | H | OMe |
| C | N | C | N | N | H | SMe |
| C | N | C | N | N | H | Cl |
| C | N | C | N | N | H | CF₃ |
| C | N | C | N | N | H | Ph |
| C | N | C | N | N | Me | H |
| C | N | C | N | N | Me | Me |
| C | N | C | N | N | Me | Et |
| C | N | C | N | N | Me | n-Hex |
| C | N | C | N | N | Me | c-Pr |
| C | N | C | N | N | Me | c-Hex |
| C | N | C | N | N | Me | OH |
| C | N | C | N | N | Me | CH₂OH |
| C | N | C | N | N | Me | OMe |
| C | N | C | N | N | Me | SMe |
| C | N | C | N | N | Me | Cl |
| C | N | C | N | N | Me | CF₃ |
| C | N | C | N | N | Me | Ph |
| C | N | C | N | N | Et | H |
| C | N | C | N | N | Et | Me |
| C | N | C | N | N | Et | Et |
| C | N | C | N | N | Et | n-Hex |
| C | N | C | N | N | Et | c-Pr |
| C | N | C | N | N | Et | c-Hex |
| C | N | C | N | N | Et | OH |
| C | N | C | N | N | Et | CH₂OH |
| C | N | C | N | N | Et | OMe |
| C | N | C | N | N | Et | SMe |
| C | N | C | N | N | Et | Cl |
| C | N | C | N | N | Et | CF₃ |
| C | N | C | N | N | Et | Ph |
| C | N | C | N | N | n-Pr | H |
| C | N | C | N | N | n-Pr | Me |
| C | N | C | N | N | n-Pr | Et |
| C | N | C | N | N | n-Pr | n-Hex |
| C | N | C | N | N | n-Pr | c-Pr |
| C | N | C | N | N | n-Pr | c-Hex |
| C | N | C | N | N | n-Pr | OH |
| C | N | C | N | N | n-Pr | CH₂OH |
| C | N | C | N | N | n-Pr | OMe |
| C | N | C | N | N | n-Pr | SMe |
| C | N | C | N | N | n-Pr | Cl |
| C | N | C | N | N | n-Pr | CF₃ |
| C | N | C | N | N | n-Pr | Ph |
| C | N | C | N | N | n-Hex | H |
| C | N | C | N | N | n-Hex | Me |
| C | N | C | N | N | n-Hex | Et |

TABLE 4-continued

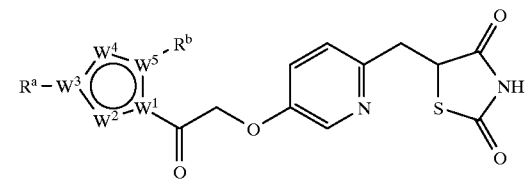

| W¹ | W² | W³ | W⁴ | W⁵ | Rᵃ | Rᵇ |
|---|---|---|---|---|---|---|
| C | N | C | N | N | n-Hex | n-Hex |
| C | N | C | N | N | n-Hex | c-Pr |
| C | N | C | N | N | n-Hex | c-Hex |
| C | N | C | N | N | n-Hex | OH |
| C | N | C | N | N | n-Hex | CH₂OH |
| C | N | C | N | N | n-Hex | OMe |
| C | N | C | N | N | n-Hex | SMe |
| C | N | C | N | N | n-Hex | Cl |
| C | N | C | N | N | n-Hex | CF₃ |
| C | N | C | N | N | n-Hex | Ph |
| C | N | C | N | N | i-Pr | H |
| C | N | C | N | N | i-Pr | Me |
| C | N | C | N | N | i-Pr | Et |
| C | N | C | N | N | i-Pr | n-Hex |
| C | N | C | N | N | i-Pr | c-Pr |
| C | N | C | N | N | i-Pr | c-Hex |
| C | N | C | N | N | i-Pr | OH |
| C | N | C | N | N | i-Pr | CH₂OH |
| C | N | C | N | N | i-Pr | OMe |
| C | N | C | N | N | i-Pr | SMe |
| C | N | C | N | N | i-Pr | Cl |
| C | N | C | N | N | i-Pr | CF₃ |
| C | N | C | N | N | i-Pr | Ph |
| C | N | C | N | N | t-Bu | H |
| C | N | C | N | N | t-Bu | Me |
| C | N | C | N | N | t-Bu | Et |
| C | N | C | N | N | t-Bu | n-Hex |
| C | N | C | N | N | t-Bu | c-Pr |
| C | N | C | N | N | t-Bu | c-Hex |
| C | N | C | N | N | t-Bu | OH |
| C | N | C | N | N | t-Bu | CH₂OH |
| C | N | C | N | N | t-Bu | OMe |
| C | N | C | N | N | t-Bu | SMe |
| C | N | C | N | N | t-Bu | Cl |
| C | N | C | N | N | t-Bu | CF₃ |
| C | N | C | N | N | t-Bu | Ph |
| C | N | C | N | N | c-Hex | H |
| C | N | C | N | N | c-Hex | Me |
| C | N | C | N | N | c-Hex | Et |
| C | N | C | N | N | c-Hex | n-Hex |
| C | N | C | N | N | c-Hex | c-Pr |
| C | N | C | N | N | c-Hex | c-Hex |
| C | N | C | N | N | c-Hex | OH |
| C | N | C | N | N | c-Hex | CH₂OH |
| C | N | C | N | N | c-Hex | OMe |
| C | N | C | N | N | c-Hex | SMe |
| C | N | C | N | N | c-Hex | Cl |
| C | N | C | N | N | c-Hex | CF₃ |
| C | N | C | N | N | c-Hex | Ph |
| C | N | C | N | N | 3-c-hexenyl | H |
| C | N | C | N | N | 3-c-hexenyl | Me |
| C | N | C | N | N | 3-c-hexenyl | Et |
| C | N | C | N | N | 3-c-hexenyl | n-Hex |
| C | N | C | N | N | 3-c-hexenyl | c-Pr |
| C | N | C | N | N | 3-c-hexenyl | c-Hex |
| C | N | C | N | N | 3-c-hexenyl | OH |
| C | N | C | N | N | 3-c-hexenyl | CH₂OH |
| C | N | C | N | N | 3-c-hexenyl | OMe |
| C | N | C | N | N | 3-c-hexenyl | SMe |
| C | N | C | N | N | 3-c-hexenyl | Cl |
| C | N | C | N | N | 3-c-hexenyl | CF₃ |
| C | N | C | N | N | 3-c-hexenyl | Ph |
| C | N | C | N | N | CH₂OH | H |
| C | N | C | N | N | CH₂OH | Me |
| C | N | C | N | N | CH₂OH | Et |
| C | N | C | N | N | CH₂OH | n-Hex |
| C | N | C | N | N | CH₂OH | c-Pr |

TABLE 4-continued

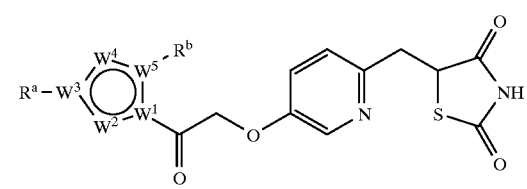

| W¹ | W² | W³ | W⁴ | W⁵ | Rᵃ | Rᵇ |
|---|---|---|---|---|---|---|
| C | N | C | N | N | CH₂OH | c-Hex |
| C | N | C | N | N | CH₂OH | OH |
| C | N | C | N | N | CH₂OH | CH₂OH |
| C | N | C | N | N | CH₂OH | OMe |
| C | N | C | N | N | CH₂OH | SMe |
| C | N | C | N | N | CH₂OH | Cl |
| C | N | C | N | N | CH₂OH | CF₃ |
| C | N | C | N | N | CH₂OH | Ph |
| C | N | C | N | N | CH₂Ph | H |
| C | N | C | N | N | CH₂Ph | Me |
| C | N | C | N | N | CH₂Ph | Et |
| C | N | C | N | N | CH₂Ph | n-Hex |
| C | N | C | N | N | CH₂Ph | c-Pr |
| C | N | C | N | N | CH₂Ph | c-Hex |
| C | N | C | N | N | CH₂Ph | OH |
| C | N | C | N | N | CH₂Ph | CH₂OH |
| C | N | C | N | N | CH₂Ph | OMe |
| C | N | C | N | N | CH₂Ph | SMe |
| C | N | C | N | N | CH₂Ph | Cl |
| C | N | C | N | N | CH₂Ph | CF₃ |
| C | N | C | N | N | CH₂Ph | Ph |
| C | N | C | N | N | α-naphthyl | H |
| C | N | C | N | N | α-naphthyl | Me |
| C | N | C | N | N | α-naphthyl | Et |
| C | N | C | N | N | α-naphthyl | n-Hex |
| C | N | C | N | N | α-naphthyl | c-Pr |
| C | N | C | N | N | α-naphthyl | c-Hex |
| C | N | C | N | N | α-naphthyl | OH |
| C | N | C | N | N | α-naphthyl | CH₂OH |
| C | N | C | N | N | α-naphthyl | OMe |
| C | N | C | N | N | α-naphthyl | SMe |
| C | N | C | N | N | α-naphthyl | Cl |
| C | N | C | N | N | α-naphthyl | CF₃ |
| C | N | C | N | N | α-naphthyl | Ph |
| C | N | C | N | N | β-naphthyl | H |
| C | N | C | N | N | β-naphthyl | Me |
| C | N | C | N | N | β-naphthyl | Et |
| C | N | C | N | N | β-naphthyl | n-Hex |
| C | N | C | N | N | β-naphthyl | c-Pr |
| C | N | C | N | N | β-naphthyl | c-Hex |
| C | N | C | N | N | β-naphthyl | OH |
| C | N | C | N | N | β-naphthyl | CH₂OH |
| C | N | C | N | N | β-naphthyl | OMe |
| C | N | C | N | N | β-naphthyl | SMe |
| C | N | C | N | N | β-naphthyl | Cl |
| C | N | C | N | N | β-naphthyl | CF₃ |
| C | N | C | N | N | β-naphthyl | Ph |
| C | N | C | N | N | 2-pyridyl | H |
| C | N | C | N | N | 2-pyridyl | Me |
| C | N | C | N | N | 2-pyridyl | Et |
| C | N | C | N | N | 2-pyridyl | n-Hex |
| C | N | C | N | N | 2-pyridyl | c-Pr |
| C | N | C | N | N | 2-pyridyl | c-Hex |
| C | N | C | N | N | 2-pyridyl | OH |
| C | N | C | N | N | 2-pyridyl | CH₂OH |
| C | N | C | N | N | 2-pyridyl | OMe |
| C | N | C | N | N | 2-pyridyl | SMe |
| C | N | C | N | N | 2-pyridyl | Cl |
| C | N | C | N | N | 2-pyridyl | CF₃ |
| C | N | C | N | N | 2-pyridyl | Ph |
| C | N | C | N | N | 3-pyridyl | H |
| C | N | C | N | N | 3-pyridyl | Me |
| C | N | C | N | N | 3-pyridyl | Et |
| C | N | C | N | N | 3-pyridyl | n-Hex |
| C | N | C | N | N | 3-pyridyl | c-Pr |
| C | N | C | N | N | 3-pyridyl | c-Hex |
| C | N | C | N | N | 3-pyridyl | OH |

TABLE 4-continued

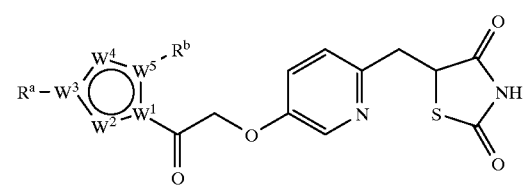

| W¹ | W² | W³ | W⁴ | W⁵ | Rᵃ | Rᵇ |
|---|---|---|---|---|---|---|
| C | N | C | N | N | 3-pyridyl | CH₂OH |
| C | N | C | N | N | 3-pyridyl | OMe |
| C | N | C | N | N | 3-pyridyl | SMe |
| C | N | C | N | N | 3-pyridyl | Cl |
| C | N | C | N | N | 3-pyridyl | CF₃ |
| C | N | C | N | N | 3-pyridyl | Ph |
| C | N | C | N | N | 4-pyridyl | H |
| C | N | C | N | N | 4-pyridyl | Me |
| C | N | C | N | N | 4-pyridyl | Et |
| C | N | C | N | N | 4-pyridyl | n-Hex |
| C | N | C | N | N | 4-pyridyl | c-Pr |
| C | N | C | N | N | 4-pyridyl | c-Hex |
| C | N | C | N | N | 4-pyridyl | OH |
| C | N | C | N | N | 4-pyridyl | CH₂OH |
| C | N | C | N | N | 4-pyridyl | OMe |
| C | N | C | N | N | 4-pyridyl | SMe |
| C | N | C | N | N | 4-pyridyl | Cl |
| C | N | C | N | N | 4-pyridyl | CF₃ |
| C | N | C | N | N | 4-pyridyl | Ph |
| C | N | C | N | N | 2-furanyl | H |
| C | N | C | N | N | 2-furanyl | Me |
| C | N | C | N | N | 2-furanyl | Et |
| C | N | C | N | N | 2-furanyl | n-Hex |
| C | N | C | N | N | 2-furanyl | c-Pr |
| C | N | C | N | N | 2-furanyl | c-Hex |
| C | N | C | N | N | 2-furanyl | OH |
| C | N | C | N | N | 2-furanyl | CH₂OH |
| C | N | C | N | N | 2-furanyl | OMe |
| C | N | C | N | N | 2-furanyl | SMe |
| C | N | C | N | N | 2-furanyl | Cl |
| C | N | C | N | N | 2-furanyl | CF₃ |
| C | N | C | N | N | 2-furanyl | Ph |
| C | N | C | N | N | 2-thienyl | H |
| C | N | C | N | N | 2-thienyl | Me |
| C | N | C | N | N | 2-thienyl | Et |
| C | N | C | N | N | 2-thienyl | n-Hex |
| C | N | C | N | N | 2-thienyl | c-Pr |
| C | N | C | N | N | 2-thienyl | c-Hex |
| C | N | C | N | N | 2-thienyl | OH |
| C | N | C | N | N | 2-thienyl | CH₂OH |
| C | N | C | N | N | 2-thienyl | OMe |
| C | N | C | N | N | 2-thienyl | SMe |
| C | N | C | N | N | 2-thienyl | Cl |
| C | N | C | N | N | 2-thienyl | CF₃ |
| C | N | C | N | N | 2-thienyl | Ph |
| C | N | C | N | N | 2-tolyl | H |
| C | N | C | N | N | 2-tolyl | Me |
| C | N | C | N | N | 2-tolyl | Et |
| C | N | C | N | N | 2-tolyl | n-Hex |
| C | N | C | N | N | 2-tolyl | c-Pr |
| C | N | C | N | N | 2-tolyl | c-Hex |
| C | N | C | N | N | 2-tolyl | OH |
| C | N | C | N | N | 2-tolyl | CH₂OH |
| C | N | C | N | N | 2-tolyl | OMe |
| C | N | C | N | N | 2-tolyl | SMe |
| C | N | C | N | N | 2-tolyl | Cl |
| C | N | C | N | N | 2-tolyl | CF₃ |
| C | N | C | N | N | 2-tolyl | Ph |
| C | N | C | N | N | 3-tolyl | H |
| C | N | C | N | N | 3-tolyl | Me |
| C | N | C | N | N | 3-tolyl | Et |
| C | N | C | N | N | 3-tolyl | n-Hex |
| C | N | C | N | N | 3-tolyl | c-Pr |
| C | N | C | N | N | 3-tolyl | c-Hex |
| C | N | C | N | N | 3-tolyl | OH |
| C | N | C | N | N | 3-tolyl | CH₂OH |
| C | N | C | N | N | 3-tolyl | OMe |

TABLE 4-continued

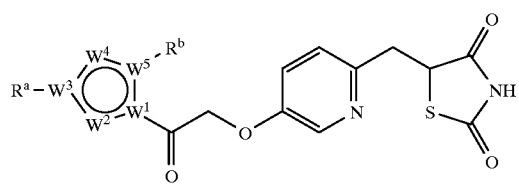 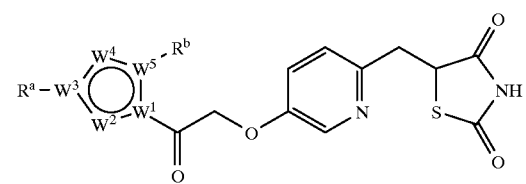

| W¹ | W² | W³ | W⁴ | W⁵ | Rᵃ | Rᵇ |
|---|---|---|---|---|---|---|
| C | N | C | N | N | 3-tolyl | SMe |
| C | N | C | N | N | 3-tolyl | Cl |
| C | N | C | N | N | 3-tolyl | CF$_3$ |
| C | N | C | N | N | 3-tolyl | Ph |
| C | N | C | N | N | 4-tolyl | H |
| C | N | C | N | N | 4-tolyl | Me |
| C | N | C | N | N | 4-tolyl | Et |
| C | N | C | N | N | 4-tolyl | n-Hex |
| C | N | C | N | N | 4-tolyl | c-Pr |
| C | N | C | N | N | 4-tolyl | c-Hex |
| C | N | C | N | N | 4-tolyl | OH |
| C | N | C | N | N | 4-tolyl | CH$_2$OH |
| C | N | C | N | N | 4-tolyl | OMe |
| C | N | C | N | N | 4-tolyl | SMe |
| C | N | C | N | N | 4-tolyl | Cl |
| C | N | C | N | N | 4-tolyl | CF$_3$ |
| C | N | C | N | N | 4-tolyl | Ph |
| C | N | C | N | N | Ph-2,3-Me$_2$ | H |
| C | N | C | N | N | Ph-2,3-Me$_2$ | Me |
| C | N | C | N | N | Ph-2,3-Me$_2$ | Et |
| C | N | C | N | N | Ph-2,3-Me$_2$ | n-Hex |
| C | N | C | N | N | Ph-2,3-Me$_2$ | c-Pr |
| C | N | C | N | N | Ph-2,3-Me$_2$ | c-Hex |
| C | N | C | N | N | Ph-2,3-Me$_2$ | OH |
| C | N | C | N | N | Ph-2,3-Me$_2$ | CH$_2$OH |
| C | N | C | N | N | Ph-2,3-Me$_2$ | OMe |
| C | N | C | N | N | Ph-2,3-Me$_2$ | SMe |
| C | N | C | N | N | Ph-2,3-Me$_2$ | Cl |
| C | N | C | N | N | Ph-2,3-Me$_2$ | CF$_3$ |
| C | N | C | N | N | Ph-2,3-Me$_2$ | Ph |
| C | N | C | N | N | Ph-3,4-Me$_2$ | H |
| C | N | C | N | N | Ph-3,4-Me$_2$ | Me |
| C | N | C | N | N | Ph-3,4-Me$_2$ | Et |
| C | N | C | N | N | Ph-3,4-Me$_2$ | n-Hex |
| C | N | C | N | N | Ph-3,4-Me$_2$ | c-Pr |
| C | N | C | N | N | Ph-3,4-Me$_2$ | c-Hex |
| C | N | C | N | N | Ph-3,4-Me$_2$ | OH |
| C | N | C | N | N | Ph-3,4-Me$_2$ | CH$_2$OH |
| C | N | C | N | N | Ph-3,4-Me$_2$ | OMe |
| C | N | C | N | N | Ph-3,4-Me$_2$ | SMe |
| C | N | C | N | N | Ph-3,4-Me$_2$ | Cl |
| C | N | C | N | N | Ph-3,4-Me$_2$ | CF$_3$ |
| C | N | C | N | N | Ph-3,4-Me$_2$ | Ph |
| C | N | C | N | N | Ph-3,5-Me$_2$ | H |
| C | N | C | N | N | Ph-3,5-Me$_2$ | Me |
| C | N | C | N | N | Ph-3,5-Me$_2$ | Et |
| C | N | C | N | N | Ph-3,5-Me$_2$ | n-Hex |
| C | N | C | N | N | Ph-3,5-Me$_2$ | c-Pr |
| C | N | C | N | N | Ph-3,5-Me$_2$ | c-Hex |
| C | N | C | N | N | Ph-3,5-Me$_2$ | OH |
| C | N | C | N | N | Ph-3,5-Me$_2$ | CH$_2$OH |
| C | N | C | N | N | Ph-3,5-Me$_2$ | OMe |
| C | N | C | N | N | Ph-3,5-Me$_2$ | SMe |
| C | N | C | N | N | Ph-3,5-Me$_2$ | Cl |
| C | N | C | N | N | Ph-3,5-Me$_2$ | CF$_3$ |
| C | N | C | N | N | Ph-3,5-Me$_2$ | Ph |
| C | N | C | N | N | Ph-2,6-Me$_2$ | H |
| C | N | C | N | N | Ph-2,6-Me$_2$ | Me |
| C | N | C | N | N | Ph-2,6-Me$_2$ | Et |
| C | N | C | N | N | Ph-2,6-Me$_2$ | n-Hex |
| C | N | C | N | N | Ph-2,6-Me$_2$ | c-Pr |
| C | N | C | N | N | Ph-2,6-Me$_2$ | c-Hex |
| C | N | C | N | N | Ph-2,6-Me$_2$ | OH |
| C | N | C | N | N | Ph-2,6-Me$_2$ | CH$_2$OH |
| C | N | C | N | N | Ph-2,6-Me$_2$ | OMe |
| C | N | C | N | N | Ph-2,6-Me$_2$ | SMe |
| C | N | C | N | N | Ph-2,6-Me$_2$ | Cl |
| C | N | C | N | N | Ph-2,6-Me$_2$ | CF$_3$ |
| C | N | C | N | N | Ph-2,6-Me$_2$ | Ph |
| C | N | C | N | N | Ph-2-Cl | H |
| C | N | C | N | N | Ph-2-Cl | Me |
| C | N | C | N | N | Ph-2-Cl | Et |
| C | N | C | N | N | Ph-2-Cl | n-Hex |
| C | N | C | N | N | Ph-2-Cl | c-Pr |
| C | N | C | N | N | Ph-2-Cl | c-Hex |
| C | N | C | N | N | Ph-2-Cl | OH |
| C | N | C | N | N | Ph-2-Cl | CH$_2$OH |
| C | N | C | N | N | Ph-2-Cl | OMe |
| C | N | C | N | N | Ph-2-Cl | SMe |
| C | N | C | N | N | Ph-2-Cl | Cl |
| C | N | C | N | N | Ph-2-Cl | CF$_3$ |
| C | N | C | N | N | Ph-2-Cl | Ph |
| C | N | C | N | N | Ph-3-Cl | H |
| C | N | C | N | N | Ph-3-Cl | Me |
| C | N | C | N | N | Ph-3-Cl | Et |
| C | N | C | N | N | Ph-3-Cl | n-Hex |
| C | N | C | N | N | Ph-3-Cl | c-Pr |
| C | N | C | N | N | Ph-3-Cl | c-Hex |
| C | N | C | N | N | Ph-3-Cl | OH |
| C | N | C | N | N | Ph-3-Cl | CH$_2$OH |
| C | N | C | N | N | Ph-3-Cl | OMe |
| C | N | C | N | N | Ph-3-Cl | SMe |
| C | N | C | N | N | Ph-3-Cl | Cl |
| C | N | C | N | N | Ph-3-Cl | CF$_3$ |
| C | N | C | N | N | Ph-3-Cl | Ph |
| C | N | C | N | N | Ph-4-Cl | H |
| C | N | C | N | N | Ph-4-Cl | Me |
| C | N | C | N | N | Ph-4-Cl | Et |
| C | N | C | N | N | Ph-4-Cl | n-Hex |
| C | N | C | N | N | Ph-4-Cl | c-Pr |
| C | N | C | N | N | Ph-4-Cl | c-Hex |
| C | N | C | N | N | Ph-4-Cl | OH |
| C | N | C | N | N | Ph-4-Cl | CH$_2$OH |
| C | N | C | N | N | Ph-4-Cl | OMe |
| C | N | C | N | N | Ph-4-Cl | SMe |
| C | N | C | N | N | Ph-4-Cl | Cl |
| C | N | C | N | N | Ph-4-Cl | CF$_3$ |
| C | N | C | N | N | Ph-4-Cl | Ph |
| C | N | C | N | N | Ph-3,4-Cl$_2$ | H |
| C | N | C | N | N | Ph-3,4-Cl$_2$ | Me |
| C | N | C | N | N | Ph-3,4-Cl$_2$ | Et |
| C | N | C | N | N | Ph-3,4-Cl$_2$ | n-Hex |
| C | N | C | N | N | Ph-3,4-Cl$_2$ | c-Pr |
| C | N | C | N | N | Ph-3,4-Cl$_2$ | c-Hex |
| C | N | C | N | N | Ph-3,4-Cl$_2$ | OH |
| C | N | C | N | N | Ph-3,4-Cl$_2$ | CH$_2$OH |
| C | N | C | N | N | Ph-3,4-Cl$_2$ | OMe |
| C | N | C | N | N | Ph-3,4-Cl$_2$ | SMe |
| C | N | C | N | N | Ph-3,4-Cl$_2$ | Cl |
| C | N | C | N | N | Ph-3,4-Cl$_2$ | CF$_3$ |
| C | N | C | N | N | Ph-3,4-Cl$_2$ | Ph |
| C | N | C | N | N | Ph-4-F | H |
| C | N | C | N | N | Ph-4-F | Me |
| C | N | C | N | N | Ph-4-F | Et |
| C | N | C | N | N | Ph-4-F | n-Hex |
| C | N | C | N | N | Ph-4-F | c-Pr |
| C | N | C | N | N | Ph-4-F | c-Hex |
| C | N | C | N | N | Ph-4-F | OH |
| C | N | C | N | N | Ph-4-F | CH$_2$OH |
| C | N | C | N | N | Ph-4-F | OMe |
| C | N | C | N | N | Ph-4-F | SMe |
| C | N | C | N | N | Ph-4-F | Cl |
| C | N | C | N | N | Ph-4-F | CF$_3$ |
| C | N | C | N | N | Ph-4-F | Ph |

TABLE 4-continued

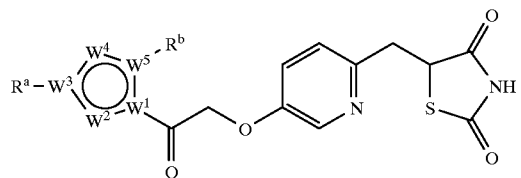

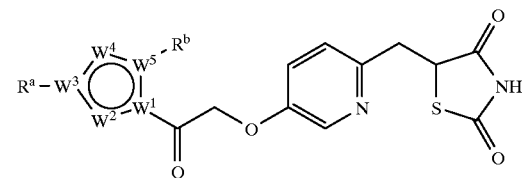

| W¹ | W² | W³ | W⁴ | W⁵ | Rᵃ | Rᵇ |
|---|---|---|---|---|---|---|
| C | N | C | N | N | Ph-4-Br | H |
| C | N | C | N | N | Ph-4-Br | Me |
| C | N | C | N | N | Ph-4-Br | Et |
| C | N | C | N | N | Ph-4-Br | n-Hex |
| C | N | C | N | N | Ph-4-Br | c-Pr |
| C | N | C | N | N | Ph-4-Br | c-Hex |
| C | N | C | N | N | Ph-4-Br | OH |
| C | N | C | N | N | Ph-4-Br | $CH_2OH$ |
| C | N | C | N | N | Ph-4-Br | OMe |
| C | N | C | N | N | Ph-4-Br | SMe |
| C | N | C | N | N | Ph-4-Br | Cl |
| C | N | C | N | N | Ph-4-Br | $CF_3$ |
| C | N | C | N | N | Ph-4-Br | Ph |
| C | N | C | N | N | Ph-2-OMe | H |
| C | N | C | N | N | Ph-2-OMe | Me |
| C | N | C | N | N | Ph-2-OMe | Et |
| C | N | C | N | N | Ph-2-OMe | n-Hex |
| C | N | C | N | N | Ph-2-OMe | c-Pr |
| C | N | C | N | N | Ph-2-OMe | c-Hex |
| C | N | C | N | N | Ph-2-OMe | OH |
| C | N | C | N | N | Ph-2-OMe | $CH_2OH$ |
| C | N | C | N | N | Ph-2-OMe | OMe |
| C | N | C | N | N | Ph-2-OMe | SMe |
| C | N | C | N | N | Ph-2-OMe | Cl |
| C | N | C | N | N | Ph-2-OMe | $CF_3$ |
| C | N | C | N | N | Ph-2-OMe | Ph |
| C | N | C | N | N | Ph-3-OMe | H |
| C | N | C | N | N | Ph-3-OMe | Me |
| C | N | C | N | N | Ph-3-OMe | Et |
| C | N | C | N | N | Ph-3-OMe | n-Hex |
| C | N | C | N | N | Ph-3-OMe | c-Pr |
| C | N | C | N | N | Ph-3-OMe | c-Hex |
| C | N | C | N | N | Ph-3-OMe | OH |
| C | N | C | N | N | Ph-3-OMe | $CH_2OH$ |
| C | N | C | N | N | Ph-3-OMe | OMe |
| C | N | C | N | N | Ph-3-OMe | SMe |
| C | N | C | N | N | Ph-3-OMe | Cl |
| C | N | C | N | N | Ph-3-OMe | $CF_3$ |
| C | N | C | N | N | Ph-3-OMe | Ph |
| C | N | C | N | N | Ph-4-OMe | H |
| C | N | C | N | N | Ph-4-OMe | Me |
| C | N | C | N | N | Ph-4-OMe | Et |
| C | N | C | N | N | Ph-4-OMe | n-Hex |
| C | N | C | N | N | Ph-4-OMe | c-Pr |
| C | N | C | N | N | Ph-4-OMe | c-Hex |
| C | N | C | N | N | Ph-4-OMe | OH |
| C | N | C | N | N | Ph-4-OMe | $CH_2OH$ |
| C | N | C | N | N | Ph-4-OMe | OMe |
| C | N | C | N | N | Ph-4-OMe | SMe |
| C | N | C | N | N | Ph-4-OMe | Cl |
| C | N | C | N | N | Ph-4-OMe | $CF_3$ |
| C | N | C | N | N | Ph-4-OMe | Ph |
| C | N | C | N | N | Ph-3,4-$(OMe)_2$ | H |
| C | N | C | N | N | Ph-3,4-$(OMe)_2$ | Me |
| C | N | C | N | N | Ph-3,4-$(OMe)_2$ | Et |
| C | N | C | N | N | Ph-3,4-$(OMe)_2$ | n-Hex |
| C | N | C | N | N | Ph-3,4-$(OMe)_2$ | c-Pr |
| C | N | C | N | N | Ph-3,4-$(OMe)_2$ | c-Hex |
| C | N | C | N | N | Ph-3,4-$(OMe)_2$ | OH |
| C | N | C | N | N | Ph-3,4-$(OMe)_2$ | $CH_2OH$ |
| C | N | C | N | N | Ph-3,4-$(OMe)_2$ | OMe |
| C | N | C | N | N | Ph-3,4-$(OMe)_2$ | SMe |
| C | N | C | N | N | Ph-3,4-$(OMe)_2$ | Cl |
| C | N | C | N | N | Ph-3,4-$(OMe)_2$ | $CF_3$ |
| C | N | C | N | N | Ph-3,4-$(OMe)_2$ | Ph |
| C | N | C | N | N | Ph-2-OH | H |
| C | N | C | N | N | Ph-2-OH | Me |
| C | N | C | N | N | Ph-2-OH | Et |
| C | N | C | N | N | Ph-2-OH | n-Hex |
| C | N | C | N | N | Ph-2-OH | c-Pr |
| C | N | C | N | N | Ph-2-OH | c-Hex |
| C | N | C | N | N | Ph-2-OH | OH |
| C | N | C | N | N | Ph-2-OH | $CH_2OH$ |
| C | N | C | N | N | Ph-2-OH | OMe |
| C | N | C | N | N | Ph-2-OH | SMe |
| C | N | C | N | N | Ph-2-OH | Cl |
| C | N | C | N | N | Ph-2-OH | $CF_3$ |
| C | N | C | N | N | Ph-2-OH | Ph |
| C | N | C | N | N | Ph-3-OH | H |
| C | N | C | N | N | Ph-3-OH | Me |
| C | N | C | N | N | Ph-3-OH | Et |
| C | N | C | N | N | Ph-3-OH | n-Hex |
| C | N | C | N | N | Ph-3-OH | c-Pr |
| C | N | C | N | N | Ph-3-OH | c-Hex |
| C | N | C | N | N | Ph-3-OH | OH |
| C | N | C | N | N | Ph-3-OH | $CH_2OH$ |
| C | N | C | N | N | Ph-3-OH | OMe |
| C | N | C | N | N | Ph-3-OH | SMe |
| C | N | C | N | N | Ph-3-OH | Cl |
| C | N | C | N | N | Ph-3-OH | $CF_3$ |
| C | N | C | N | N | Ph-3-OH | Ph |
| C | N | C | N | N | Ph-4-OH | H |
| C | N | C | N | N | Ph-4-OH | Me |
| C | N | C | N | N | Ph-4-OH | Et |
| C | N | C | N | N | Ph-4-OH | n-Hex |
| C | N | C | N | N | Ph-4-OH | c-Pr |
| C | N | C | N | N | Ph-4-OH | c-Hex |
| C | N | C | N | N | Ph-4-OH | OH |
| C | N | C | N | N | Ph-4-OH | $CH_2OH$ |
| C | N | C | N | N | Ph-4-OH | OMe |
| C | N | C | N | N | Ph-4-OH | SMe |
| C | N | C | N | N | Ph-4-OH | Cl |
| C | N | C | N | N | Ph-4-OH | $CF_3$ |
| C | N | C | N | N | Ph-4-OH | Ph |
| C | N | C | N | N | Ph-3,4-$(OH)_2$ | H |
| C | N | C | N | N | Ph-3,4-$(OH)_2$ | Me |
| C | N | C | N | N | Ph-3,4-$(OH)_2$ | Et |
| C | N | C | N | N | Ph-3,4-$(OH)_2$ | n-Hex |
| C | N | C | N | N | Ph-3,4-$(OH)_2$ | c-Pr |
| C | N | C | N | N | Ph-3,4-$(OH)_2$ | c-Hex |
| C | N | C | N | N | Ph-3,4-$(OH)_2$ | OH |
| C | N | C | N | N | Ph-3,4-$(OH)_2$ | $CH_2OH$ |
| C | N | C | N | N | Ph-3,4-$(OH)_2$ | OMe |
| C | N | C | N | N | Ph-3,4-$(OH)_2$ | SMe |
| C | N | C | N | N | Ph-3,4-$(OH)_2$ | Cl |
| C | N | C | N | N | Ph-3,4-$(OH)_2$ | $CF_3$ |
| C | N | C | N | N | Ph-3,4-$(OH)_2$ | Ph |
| C | N | C | N | N | Ph-3-SMe | H |
| C | N | C | N | N | Ph-3-SMe | Me |
| C | N | C | N | N | Ph-3-SMe | Et |
| C | N | C | N | N | Ph-3-SMe | n-Hex |
| C | N | C | N | N | Ph-3-SMe | c-Pr |
| C | N | C | N | N | Ph-3-SMe | c-Hex |
| C | N | C | N | N | Ph-3-SMe | OH |
| C | N | C | N | N | Ph-3-SMe | $CH_2OH$ |
| C | N | C | N | N | Ph-3-SMe | OMe |
| C | N | C | N | N | Ph-3-SMe | SMe |
| C | N | C | N | N | Ph-3-SMe | Cl |
| C | N | C | N | N | Ph-3-SMe | $CF_3$ |
| C | N | C | N | N | Ph-3-SMe | Ph |
| C | N | C | N | N | Ph-3-$CF_3$ | H |
| C | N | C | N | N | Ph-3-$CF_3$ | Me |
| C | N | C | N | N | Ph-3-$CF_3$ | Et |
| C | N | C | N | N | Ph-3-$CF_3$ | n-Hex |

TABLE 4-continued

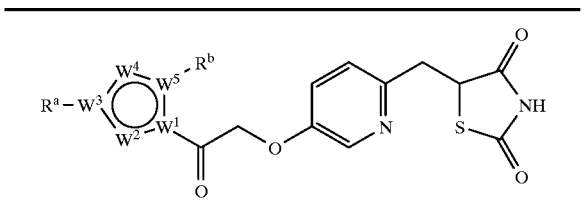

| W¹ | W² | W³ | W⁴ | W⁵ | Rᵃ | Rᵇ |
|---|---|---|---|---|---|---|
| C | N | C | N | N | Ph-3-CF₃ | c-Pr |
| C | N | C | N | N | Ph-3-CF₃ | c-Hex |
| C | N | C | N | N | Ph-3-CF₃ | OH |
| C | N | C | N | N | Ph-3-CF₃ | CH₂OH |
| C | N | C | N | N | Ph-3-CF₃ | OMe |
| C | N | C | N | N | Ph-3-CF₃ | SMe |
| C | N | C | N | N | Ph-3-CF₃ | Cl |
| C | N | C | N | N | Ph-3-CF₃ | CF₃ |
| C | N | C | N | N | Ph-3-CF₃ | Ph |
| C | N | C | N | N | Ph-3-NO₂ | H |
| C | N | C | N | N | Ph-3-NO₂ | Me |
| C | N | C | N | N | Ph-3-NO₂ | Et |
| C | N | C | N | N | Ph-3-NO₂ | n-Hex |
| C | N | C | N | N | Ph-3-NO₂ | c-Pr |
| C | N | C | N | N | Ph-3-NO₂ | c-Hex |
| C | N | C | N | N | Ph-3-NO₂ | OH |
| C | N | C | N | N | Ph-3-NO₂ | CH₂OH |
| C | N | C | N | N | Ph-3-NO₂ | OMe |
| C | N | C | N | N | Ph-3-NO₂ | SMe |
| C | N | C | N | N | Ph-3-NO₂ | Cl |
| C | N | C | N | N | Ph-3-NO₂ | CF₃ |
| C | N | C | N | N | Ph-3-NO₂ | Ph |
| C | N | C | N | N | Ph-4-NMe₂ | H |
| C | N | C | N | N | Ph-4-NMe₂ | Me |
| C | N | C | N | N | Ph-4-NMe₂ | Et |
| C | N | C | N | N | Ph-4-NMe₂ | n-Hex |
| C | N | C | N | N | Ph-4-NMe₂ | c-Pr |
| C | N | C | N | N | Ph-4-NMe₂ | c-Hex |
| C | N | C | N | N | Ph-4-NMe₂ | OH |
| C | N | C | N | N | Ph-4-NMe₂ | CH₂OH |
| C | N | C | N | N | Ph-4-NMe₂ | OMe |
| C | N | C | N | N | Ph-4-NMe₂ | SMe |
| C | N | C | N | N | Ph-4-NMe₂ | Cl |
| C | N | C | N | N | Ph-4-NMe₂ | CF₃ |
| C | N | C | N | N | Ph-4-NMe₂ | Ph |

TABLE 5

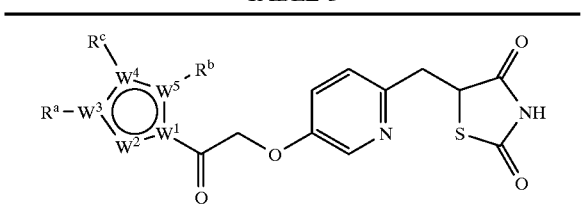

| W¹ | W² | W³ | W⁴ | W⁵ | Rᵃ | Rᵇ | Rᶜ |
|---|---|---|---|---|---|---|---|
| C | N | C | C | N | Ph | Me | Me |
| C | N | C | C | N | Ph | Me | Et |
| C | N | C | C | N | Ph | Me | n-Hex |
| C | N | C | C | N | Ph | Me | c-Pr |
| C | N | C | C | N | Ph | Me | c-Hex |
| C | N | C | C | N | Ph | Me | OH |
| C | N | C | C | N | Ph | Me | CH₂OH |
| C | N | C | C | N | Ph | Me | OMe |
| C | N | C | C | N | Ph | Me | SMe |
| C | N | C | C | N | Ph | Me | Cl |
| C | N | C | C | N | Ph | Me | CF₃ |
| C | N | C | C | N | Ph | Me | Ph |
| C | N | C | C | N | Ph | Me | H |
| C | N | C | C | N | H | Me | Me |
| C | N | C | C | N | H | Me | Et |

TABLE 5-continued

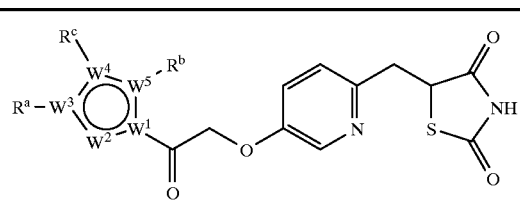

| W¹ | W² | W³ | W⁴ | W⁵ | Rᵃ | Rᵇ | Rᶜ |
|---|---|---|---|---|---|---|---|
| C | N | C | C | N | H | Me | n-Hex |
| C | N | C | C | N | H | Me | c-Pr |
| C | N | C | C | N | H | Me | c-Hex |
| C | N | C | C | N | H | Me | OH |
| C | N | C | C | N | H | Me | CH₂OH |
| C | N | C | C | N | H | Me | OMe |
| C | N | C | C | N | H | Me | SMe |
| C | N | C | C | N | H | Me | Cl |
| C | N | C | C | N | H | Me | CF₃ |
| C | N | C | C | N | H | Me | Ph |
| C | N | C | C | N | Me | Me | H |
| C | N | C | C | N | Me | Me | Me |
| C | N | C | C | N | Me | Me | Et |
| C | N | C | C | N | Me | Me | n-Hex |
| C | N | C | C | N | Me | Me | c-Pr |
| C | N | C | C | N | Me | Me | c-Hex |
| C | N | C | C | N | Me | Me | OH |
| C | N | C | C | N | Me | Me | CH₂OH |
| C | N | C | C | N | Me | Me | OMe |
| C | N | C | C | N | Me | Me | SMe |
| C | N | C | C | N | Me | Me | Cl |
| C | N | C | C | N | Me | Me | CF₃ |
| C | N | C | C | N | Me | Me | Ph |
| C | N | C | C | N | Et | Me | H |
| C | N | C | C | N | Et | Me | Me |
| C | N | C | C | N | Et | Me | Et |
| C | N | C | C | N | Et | Me | n-Hex |
| C | N | C | C | N | Et | Me | c-Pr |
| C | N | C | C | N | Et | Me | c-Hex |
| C | N | C | C | N | Et | Me | OH |
| C | N | C | C | N | Et | Me | CH₂OH |
| C | N | C | C | N | Et | Me | OMe |
| C | N | C | C | N | Et | Me | SMe |
| C | N | C | C | N | Et | Me | Cl |
| C | N | C | C | N | Et | Me | CF₃ |
| C | N | C | C | N | Et | Me | Ph |
| C | N | C | C | N | n-Pr | Me | H |
| C | N | C | C | N | n-Pr | Me | Me |
| C | N | C | C | N | n-Pr | Me | Et |
| C | N | C | C | N | n-Pr | Me | n-Hex |
| C | N | C | C | N | n-Pr | Me | c-Pr |
| C | N | C | C | N | n-Pr | Me | c-Hex |
| C | N | C | C | N | n-Pr | Me | OH |
| C | N | C | C | N | n-Pr | Me | CH₂OH |
| C | N | C | C | N | n-Pr | Me | OMe |
| C | N | C | C | N | n-Pr | Me | SMe |
| C | N | C | C | N | n-Pr | Me | Cl |
| C | N | C | C | N | n-Pr | Me | CF₃ |
| C | N | C | C | N | n-Pr | Me | Ph |
| C | N | C | C | N | n-Hex | Me | H |
| C | N | C | C | N | n-Hex | Me | Me |
| C | N | C | C | N | n-Hex | Me | Et |
| C | N | C | C | N | n-Hex | Me | n-Hex |
| C | N | C | C | N | n-Hex | Me | c-Pr |
| C | N | C | C | N | n-Hex | Me | c-Hex |
| C | N | C | C | N | n-Hex | Me | OH |
| C | N | C | C | N | n-Hex | Me | CH₂OH |
| C | N | C | C | N | n-Hex | Me | OMe |
| C | N | C | C | N | n-Hex | Me | SMe |
| C | N | C | C | N | n-Hex | Me | Cl |
| C | N | C | C | N | n-Hex | Me | CF₃ |
| C | N | C | C | N | n-Hex | Me | Ph |
| C | N | C | C | N | i-Pr | Me | H |
| C | N | C | C | N | i-Pr | Me | Me |
| C | N | C | C | N | i-Pr | Me | Et |
| C | N | C | C | N | i-Pr | Me | n-Hex |
| C | N | C | C | N | i-Pr | Me | c-Pr |

TABLE 5-continued

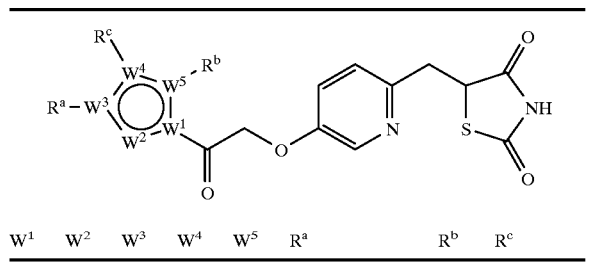

| W¹ | W² | W³ | W⁴ | W⁵ | Rᵃ | Rᵇ | Rᶜ |
|---|---|---|---|---|---|---|---|
| C | N | C | C | N | i-Pr | Me | c-Hex |
| C | N | C | C | N | i-Pr | Me | OH |
| C | N | C | C | N | i-Pr | Me | CH₂OH |
| C | N | C | C | N | i-Pr | Me | OMe |
| C | N | C | C | N | i-Pr | Me | SMe |
| C | N | C | C | N | i-Pr | Me | Cl |
| C | N | C | C | N | i-Pr | Me | CF₃ |
| C | N | C | C | N | i-Pr | Me | Ph |
| C | N | C | C | N | t-Bu | Me | H |
| C | N | C | C | N | t-Bu | Me | Me |
| C | N | C | C | N | t-Bu | Me | Et |
| C | N | C | C | N | t-Bu | Me | n-Hex |
| C | N | C | C | N | t-Bu | Me | c-Pr |
| C | N | C | C | N | t-Bu | Me | c-Hex |
| C | N | C | C | N | t-Bu | Me | OH |
| C | N | C | C | N | t-Bu | Me | CH₂OH |
| C | N | C | C | N | t-Bu | Me | OMe |
| C | N | C | C | N | t-Bu | Me | SMe |
| C | N | C | C | N | t-Bu | Me | Cl |
| C | N | C | C | N | t-Bu | Me | CF₃ |
| C | N | C | C | N | t-Bu | Me | Ph |
| C | N | C | C | N | c-Hex | Me | H |
| C | N | C | C | N | c-Hex | Me | Me |
| C | N | C | C | N | c-Hex | Me | Et |
| C | N | C | C | N | c-Hex | Me | n-Hex |
| C | N | C | C | N | c-Hex | Me | c-Pr |
| C | N | C | C | N | c-Hex | Me | c-Hex |
| C | N | C | C | N | c-Hex | Me | OH |
| C | N | C | C | N | c-Hex | Me | CH₂OH |
| C | N | C | C | N | c-Hex | Me | OMe |
| C | N | C | C | N | c-Hex | Me | SMe |
| C | N | C | C | N | c-Hex | Me | Cl |
| C | N | C | C | N | c-Hex | Me | CF₃ |
| C | N | C | C | N | c-Hex | Me | Ph |
| C | N | C | C | N | 3-c-hexenyl | Me | H |
| C | N | C | C | N | 3-c-hexenyl | Me | Me |
| C | N | C | C | N | 3-c-hexenyl | Me | Et |
| C | N | C | C | N | 3-c-hexenyl | Me | n-Hex |
| C | N | C | C | N | 3-c-hexenyl | Me | c-Pr |
| C | N | C | C | N | 3-c-hexenyl | Me | c-Hex |
| C | N | C | C | N | 3-c-hexenyl | Me | OH |
| C | N | C | C | N | 3-c-hexenyl | Me | CH₂OH |
| C | N | C | C | N | 3-c-hexenyl | Me | OMe |
| C | N | C | C | N | 3-c-hexenyl | Me | SMe |
| C | N | C | C | N | 3-c-hexenyl | Me | Cl |
| C | N | C | C | N | 3-c-hexenyl | Me | CF₃ |
| C | N | C | C | N | 3-c-hexenyl | Me | Ph |
| C | N | C | C | N | CH₂OH | Me | H |
| C | N | C | C | N | CH₂OH | Me | Me |
| C | N | C | C | N | CH₂OH | Me | Et |
| C | N | C | C | N | CH₂OH | Me | n-Hex |
| C | N | C | C | N | CH₂OH | Me | c-Pr |
| C | N | C | C | N | CH₂OH | Me | c-Hex |
| C | N | C | C | N | CH₂OH | Me | OH |
| C | N | C | C | N | CH₂OH | Me | CH₂OH |
| C | N | C | C | N | CH₂OH | Me | OMe |
| C | N | C | C | N | CH₂OH | Me | SMe |
| C | N | C | C | N | CH₂OH | Me | Cl |
| C | N | C | C | N | CH₂OH | Me | CF₃ |
| C | N | C | C | N | CH₂OH | Me | Ph |
| C | N | C | C | N | CH₂Ph | Me | H |
| C | N | C | C | N | CH₂Ph | Me | Me |
| C | N | C | C | N | CH₂Ph | Me | Et |
| C | N | C | C | N | CH₂Ph | Me | n-Hex |
| C | N | C | C | N | CH₂Ph | Me | c-Pr |
| C | N | C | C | N | CH₂Ph | Me | c-Hex |
| C | N | C | C | N | CH₂Ph | Me | OH |
| C | N | C | C | N | CH₂Ph | Me | CH₂OH |
| C | N | C | C | N | CH₂Ph | Me | OMe |
| C | N | C | C | N | CH₂Ph | Me | SMe |
| C | N | C | C | N | CH₂Ph | Me | Cl |
| C | N | C | C | N | CH₂Ph | Me | CF₃ |
| C | N | C | C | N | CH₂Ph | Me | Ph |
| C | N | C | C | N | α-naphthyl | Me | H |
| C | N | C | C | N | α-naphthyl | Me | Me |
| C | N | C | C | N | α-naphthyl | Me | Et |
| C | N | C | C | N | α-naphthyl | Me | n-Hex |
| C | N | C | C | N | α-naphthyl | Me | c-Pr |
| C | N | C | C | N | α-naphthyl | Me | c-Hex |
| C | N | C | C | N | α-naphthyl | Me | OH |
| C | N | C | C | N | α-naphthyl | Me | CH₂OH |
| C | N | C | C | N | α-naphthyl | Me | OMe |
| C | N | C | C | N | α-naphthyl | Me | SMe |
| C | N | C | C | N | α-naphthyl | Me | Cl |
| C | N | C | C | N | α-naphthyl | Me | CF₃ |
| C | N | C | C | N | α-naphthyl | Me | Ph |
| C | N | C | C | N | β-naphthyl | Me | H |
| C | N | C | C | N | β-naphthyl | Me | Me |
| C | N | C | C | N | β-naphthyl | Me | Et |
| C | N | C | C | N | β-naphthyl | Me | n-Hex |
| C | N | C | C | N | β-naphthyl | Me | c-Pr |
| C | N | C | C | N | β-naphthyl | Me | c-Hex |
| C | N | C | C | N | β-naphthyl | Me | OH |
| C | N | C | C | N | β-naphthyl | Me | CH₂OH |
| C | N | C | C | N | β-naphthyl | Me | OMe |
| C | N | C | C | N | β-naphthyl | Me | SMe |
| C | N | C | C | N | β-naphthyl | Me | Cl |
| C | N | C | C | N | β-naphthyl | Me | CF₃ |
| C | N | C | C | N | β-naphthyl | Me | Ph |
| C | N | C | C | N | 2-pyridyl | Me | H |
| C | N | C | C | N | 2-pyridyl | Me | Me |
| C | N | C | C | N | 2-pyridyl | Me | Et |
| C | N | C | C | N | 2-pyridyl | Me | n-Hex |
| C | N | C | C | N | 2-pyridyl | Me | c-Pr |
| C | N | C | C | N | 2-pyridyl | Me | c-Hex |
| C | N | C | C | N | 2-pyridyl | Me | OH |
| C | N | C | C | N | 2-pyridyl | Me | CH₂OH |
| C | N | C | C | N | 2-pyridyl | Me | OMe |
| C | N | C | C | N | 2-pyridyl | Me | SMe |
| C | N | C | C | N | 2-pyridyl | Me | Cl |
| C | N | C | C | N | 2-pyridyl | Me | CF₃ |
| C | N | C | C | N | 2-pyridyl | Me | Ph |
| C | N | C | C | N | 3-pyridyl | Me | H |
| C | N | C | C | N | 3-pyridyl | Me | Me |
| C | N | C | C | N | 3-pyridyl | Me | Et |
| C | N | C | C | N | 3-pyridyl | Me | n-Hex |
| C | N | C | C | N | 3-pyridyl | Me | c-Pr |
| C | N | C | C | N | 3-pyridyl | Me | c-Hex |
| C | N | C | C | N | 3-pyridyl | Me | OH |
| C | N | C | C | N | 3-pyridyl | Me | CH₂OH |
| C | N | C | C | N | 3-pyridyl | Me | OMe |
| C | N | C | C | N | 3-pyridyl | Me | SMe |
| C | N | C | C | N | 3-pyridyl | Me | Cl |
| C | N | C | C | N | 3-pyridyl | Me | CF₃ |
| C | N | C | C | N | 3-pyridyl | Me | Ph |
| C | N | C | C | N | 4-pyridyl | Me | H |
| C | N | C | C | N | 4-pyridyl | Me | Me |
| C | N | C | C | N | 4-pyridyl | Me | Et |
| C | N | C | C | N | 4-pyridyl | Me | n-Hex |
| C | N | C | C | N | 4-pyridyl | Me | c-Pr |
| C | N | C | C | N | 4-pyridyl | Me | c-Hex |
| C | N | C | C | N | 4-pyridyl | Me | OH |
| C | N | C | C | N | 4-pyridyl | Me | CH₂OH |
| C | N | C | C | N | 4-pyridyl | Me | OMe |

TABLE 5-continued

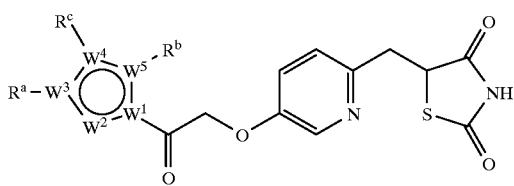

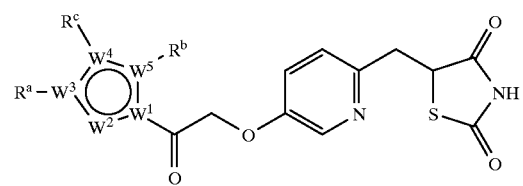

| W¹ | W² | W³ | W⁴ | W⁵ | Rᵃ | Rᵇ | Rᶜ |
|---|---|---|---|---|---|---|---|
| C | N | C | C | N | 4-pyridyl | Me | SMe |
| C | N | C | C | N | 4-pyridyl | Me | Cl |
| C | N | C | C | N | 4-pyridyl | Me | CF$_3$ |
| C | N | C | C | N | 4-pyridyl | Me | Ph |
| C | N | C | C | N | 2-furanyl | Me | H |
| C | N | C | C | N | 2-furanyl | Me | Me |
| C | N | C | C | N | 2-furanyl | Me | Et |
| C | N | C | C | N | 2-furanyl | Me | n-Hex |
| C | N | C | C | N | 2-furanyl | Me | c-Pr |
| C | N | C | C | N | 2-furanyl | Me | c-Hex |
| C | N | C | C | N | 2-furanyl | Me | OH |
| C | N | C | C | N | 2-furanyl | Me | CH$_2$OH |
| C | N | C | C | N | 2-furanyl | Me | OMe |
| C | N | C | C | N | 2-furanyl | Me | SMe |
| C | N | C | C | N | 2-furanyl | Me | Cl |
| C | N | C | C | N | 2-furanyl | Me | CF$_3$ |
| C | N | C | C | N | 2-furanyl | Me | Ph |
| C | N | C | C | N | 2-thienyl | Me | H |
| C | N | C | C | N | 2-thienyl | Me | Me |
| C | N | C | C | N | 2-thienyl | Me | Et |
| C | N | C | C | N | 2-thienyl | Me | n-Hex |
| C | N | C | C | N | 2-thienyl | Me | c-Pr |
| C | N | C | C | N | 2-thienyl | Me | c-Hex |
| C | N | C | C | N | 2-thienyl | Me | OH |
| C | N | C | C | N | 2-thienyl | Me | CH$_2$OH |
| C | N | C | C | N | 2-thienyl | Me | OMe |
| C | N | C | C | N | 2-thienyl | Me | SMe |
| C | N | C | C | N | 2-thienyl | Me | Cl |
| C | N | C | C | N | 2-thienyl | Me | CF$_3$ |
| C | N | C | C | N | 2-thienyl | Me | Ph |
| C | N | C | C | N | 2-tolyl | Me | H |
| C | N | C | C | N | 2-tolyl | Me | Me |
| C | N | C | C | N | 2-tolyl | Me | Et |
| C | N | C | C | N | 2-tolyl | Me | n-Hex |
| C | N | C | C | N | 2-tolyl | Me | c-Pr |
| C | N | C | C | N | 2-tolyl | Me | c-Hex |
| C | N | C | C | N | 2-tolyl | Me | OH |
| C | N | C | C | N | 2-tolyl | Me | CH$_2$OH |
| C | N | C | C | N | 2-tolyl | Me | OMe |
| C | N | C | C | N | 2-tolyl | Me | SMe |
| C | N | C | C | N | 2-tolyl | Me | Cl |
| C | N | C | C | N | 2-tolyl | Me | CF$_3$ |
| C | N | C | C | N | 2-tolyl | Me | Ph |
| C | N | C | C | N | 3-tolyl | Me | H |
| C | N | C | C | N | 3-tolyl | Me | Me |
| C | N | C | C | N | 3-tolyl | Me | Et |
| C | N | C | C | N | 3-tolyl | Me | n-Hex |
| C | N | C | C | N | 3-tolyl | Me | c-Pr |
| C | N | C | C | N | 3-tolyl | Me | c-Hex |
| C | N | C | C | N | 3-tolyl | Me | OH |
| C | N | C | C | N | 3-tolyl | Me | CH$_2$OH |
| C | N | C | C | N | 3-tolyl | Me | OMe |
| C | N | C | C | N | 3-tolyl | Me | SMe |
| C | N | C | C | N | 3-tolyl | Me | Cl |
| C | N | C | C | N | 3-tolyl | Me | CF$_3$ |
| C | N | C | C | N | 3-tolyl | Me | Ph |
| C | N | C | C | N | 4-tolyl | Me | H |
| C | N | C | C | N | 4-tolyl | Me | Me |
| C | N | C | C | N | 4-tolyl | Me | Et |
| C | N | C | C | N | 4-tolyl | Me | n-Hex |
| C | N | C | C | N | 4-tolyl | Me | c-Pr |
| C | N | C | C | N | 4-tolyl | Me | c-Hex |
| C | N | C | C | N | 4-tolyl | Me | OH |
| C | N | C | C | N | 4-tolyl | Me | CH$_2$OH |
| C | N | C | C | N | 4-tolyl | Me | OMe |
| C | N | C | C | N | 4-tolyl | Me | SMe |
| C | N | C | C | N | 4-tolyl | Me | Cl |
| C | N | C | C | N | 4-tolyl | Me | CF$_3$ |
| C | N | C | C | N | 4-tolyl | Me | Ph |
| C | N | C | C | N | Ph-2,3-Me$_2$ | Me | H |
| C | N | C | C | N | Ph-2,3-Me$_2$ | Me | Me |
| C | N | C | C | N | Ph-2,3-Me$_2$ | Me | Et |
| C | N | C | C | N | Ph-2,3-Me$_2$ | Me | n-Hex |
| C | N | C | C | N | Ph-2,3-Me$_2$ | Me | c-Pr |
| C | N | C | C | N | Ph-2,3-Me$_2$ | Me | c-Hex |
| C | N | C | C | N | Ph-2,3-Me$_2$ | Me | OH |
| C | N | C | C | N | Ph-2,3-Me$_2$ | Me | CH$_2$OH |
| C | N | C | C | N | Ph-2,3-Me$_2$ | Me | OMe |
| C | N | C | C | N | Ph-2,3-Me$_2$ | Me | SMe |
| C | N | C | C | N | Ph-2,3-Me$_2$ | Me | Cl |
| C | N | C | C | N | Ph-2,3-Me$_2$ | Me | CF$_3$ |
| C | N | C | C | N | Ph-2,3-Me$_2$ | Me | Ph |
| C | N | C | C | N | Ph-3,4-Me$_2$ | Me | H |
| C | N | C | C | N | Ph-3,4-Me$_2$ | Me | Me |
| C | N | C | C | N | Ph-3,4-Me$_2$ | Me | Et |
| C | N | C | C | N | Ph-3,4-Me$_2$ | Me | n-Hex |
| C | N | C | C | N | Ph-3,4-Me$_2$ | Me | c-Pr |
| C | N | C | C | N | Ph-3,4-Me$_2$ | Me | c-Hex |
| C | N | C | C | N | Ph-3,4-Me$_2$ | Me | OH |
| C | N | C | C | N | Ph-3,4-Me$_2$ | Me | CH$_2$OH |
| C | N | C | C | N | Ph-3,4-Me$_2$ | Me | OMe |
| C | N | C | C | N | Ph-3,4-Me$_2$ | Me | SMe |
| C | N | C | C | N | Ph-3,4-Me$_2$ | Me | Cl |
| C | N | C | C | N | Ph-3,4-Me$_2$ | Me | CF$_3$ |
| C | N | C | C | N | Ph-3,4-Me$_2$ | Me | Ph |
| C | N | C | C | N | Ph-3,5-Me$_2$ | Me | H |
| C | N | C | C | N | Ph-3,5-Me$_2$ | Me | Me |
| C | N | C | C | N | Ph-3,5-Me$_2$ | Me | Et |
| C | N | C | C | N | Ph-3,5-Me$_2$ | Me | n-Hex |
| C | N | C | C | N | Ph-3,5-Me$_2$ | Me | c-Pr |
| C | N | C | C | N | Ph-3,5-Me$_2$ | Me | c-Hex |
| C | N | C | C | N | Ph-3,5-Me$_2$ | Me | OH |
| C | N | C | C | N | Ph-3,5-Me$_2$ | Me | CH$_2$OH |
| C | N | C | C | N | Ph-3,5-Me$_2$ | Me | OMe |
| C | N | C | C | N | Ph-3,5-Me$_2$ | Me | SMe |
| C | N | C | C | N | Ph-3,5-Me$_2$ | Me | Cl |
| C | N | C | C | N | Ph-3,5-Me$_2$ | Me | CF$_3$ |
| C | N | C | C | N | Ph-3,5-Me$_2$ | Me | Ph |
| C | N | C | C | N | Ph-2,6-Me$_2$ | Me | H |
| C | N | C | C | N | Ph-2,6-Me$_2$ | Me | Me |
| C | N | C | C | N | Ph-2,6-Me$_2$ | Me | Et |
| C | N | C | C | N | Ph-2,6-Me$_2$ | Me | n-Hex |
| C | N | C | C | N | Ph-2,6-Me$_2$ | Me | c-Pr |
| C | N | C | C | N | Ph-2,6-Me$_2$ | Me | c-Hex |
| C | N | C | C | N | Ph-2,6-Me$_2$ | Me | OH |
| C | N | C | C | N | Ph-2,6-Me$_2$ | Me | CH$_2$OH |
| C | N | C | C | N | Ph-2,6-Me$_2$ | Me | OMe |
| C | N | C | C | N | Ph-2,6-Me$_2$ | Me | SMe |
| C | N | C | C | N | Ph-2,6-Me$_2$ | Me | Cl |
| C | N | C | C | N | Ph-2,6-Me$_2$ | Me | CF$_3$ |
| C | N | C | C | N | Ph-2,6-Me$_2$ | Me | Ph |
| C | N | C | C | N | Ph-2-Cl | Me | H |
| C | N | C | C | N | Ph-2-Cl | Me | Me |
| C | N | C | C | N | Ph-2-Cl | Me | Et |
| C | N | C | C | N | Ph-2-Cl | Me | n-Hex |
| C | N | C | C | N | Ph-2-Cl | Me | c-Pr |
| C | N | C | C | N | Ph-2-Cl | Me | c-Hex |
| C | N | C | C | N | Ph-2-Cl | Me | OH |
| C | N | C | C | N | Ph-2-Cl | Me | CH$_2$OH |
| C | N | C | C | N | Ph-2-Cl | Me | OMe |
| C | N | C | C | N | Ph-2-Cl | Me | SMe |
| C | N | C | C | N | Ph-2-Cl | Me | Cl |
| C | N | C | C | N | Ph-2-Cl | Me | CF$_3$ |
| C | N | C | C | N | Ph-2-Cl | Me | Ph |

TABLE 5-continued

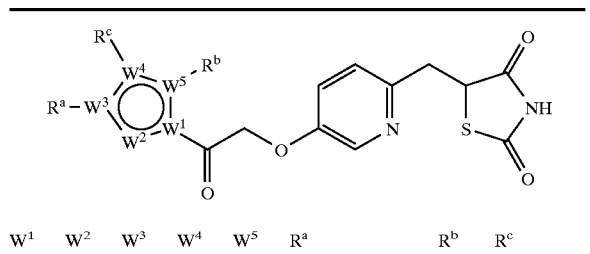
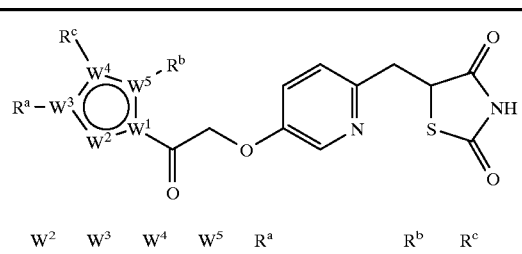

| W¹ | W² | W³ | W⁴ | W⁵ | Rᵃ | Rᵇ | Rᶜ |
|---|---|---|---|---|---|---|---|
| C | N | C | C | N | Ph-3-Cl | Me | H |
| C | N | C | C | N | Ph-3-Cl | Me | Me |
| C | N | C | C | N | Ph-3-Cl | Me | Et |
| C | N | C | C | N | Ph-3-Cl | Me | n-Hex |
| C | N | C | C | N | Ph-3-Cl | Me | c-Pr |
| C | N | C | C | N | Ph-3-Cl | Me | c-Hex |
| C | N | C | C | N | Ph-3-Cl | Me | OH |
| C | N | C | C | N | Ph-3-Cl | Me | CH₂OH |
| C | N | C | C | N | Ph-3-Cl | Me | OMe |
| C | N | C | C | N | Ph-3-Cl | Me | SMe |
| C | N | C | C | N | Ph-3-Cl | Me | Cl |
| C | N | C | C | N | Ph-3-Cl | Me | CF₃ |
| C | N | C | C | N | Ph-3-Cl | Me | Ph |
| C | N | C | C | N | Ph-4-Cl | Me | H |
| C | N | C | C | N | Ph-4-Cl | Me | Me |
| C | N | C | C | N | Ph-4-Cl | Me | Et |
| C | N | C | C | N | Ph-4-Cl | Me | n-Hex |
| C | N | C | C | N | Ph-4-Cl | Me | c-Pr |
| C | N | C | C | N | Ph-4-Cl | Me | c-Hex |
| C | N | C | C | N | Ph-4-Cl | Me | OH |
| C | N | C | C | N | Ph-4-Cl | Me | CH₂OH |
| C | N | C | C | N | Ph-4-Cl | Me | OMe |
| C | N | C | C | N | Ph-4-Cl | Me | SMe |
| C | N | C | C | N | Ph-4-Cl | Me | Cl |
| C | N | C | C | N | Ph-4-Cl | Me | CF₃ |
| C | N | C | C | N | Ph-4-Cl | Me | Ph |
| C | N | C | C | N | Ph-3,4-Cl₂ | Me | H |
| C | N | C | C | N | Ph-3,4-Cl₂ | Me | Me |
| C | N | C | C | N | Ph-3,4-Cl₂ | Me | Et |
| C | N | C | C | N | Ph-3,4-Cl₂ | Me | n-Hex |
| C | N | C | C | N | Ph-3,4-Cl₂ | Me | c-Pr |
| C | N | C | C | N | Ph-3,4-Cl₂ | Me | c-Hex |
| C | N | C | C | N | Ph-3,4-Cl₂ | Me | OH |
| C | N | C | C | N | Ph-3,4-Cl₂ | Me | CH₂OH |
| C | N | C | C | N | Ph-3,4-Cl₂ | Me | OMe |
| C | N | C | C | N | Ph-3,4-Cl₂ | Me | SMe |
| C | N | C | C | N | Ph-3,4-Cl₂ | Me | Cl |
| C | N | C | C | N | Ph-3,4-Cl₂ | Me | CF₃ |
| C | N | C | C | N | Ph-3,4-Cl₂ | Me | Ph |
| C | N | C | C | N | Ph-4-F | Me | H |
| C | N | C | C | N | Ph-4-F | Me | Me |
| C | N | C | C | N | Ph-4-F | Me | Et |
| C | N | C | C | N | Ph-4-F | Me | n-Hex |
| C | N | C | C | N | Ph-4-F | Me | c-Pr |
| C | N | C | C | N | Ph-4-F | Me | c-Hex |
| C | N | C | C | N | Ph-4-F | Me | OH |
| C | N | C | C | N | Ph-4-F | Me | CH₂OH |
| C | N | C | C | N | Ph-4-F | Me | OMe |
| C | N | C | C | N | Ph-4-F | Me | SMe |
| C | N | C | C | N | Ph-4-F | Me | Cl |
| C | N | C | C | N | Ph-4-F | Me | CF₃ |
| C | N | C | C | N | Ph-4-F | Me | Ph |
| C | N | C | C | N | Ph-4-Br | Me | H |
| C | N | C | C | N | Ph-4-Br | Me | Me |
| C | N | C | C | N | Ph-4-Br | Me | Et |
| C | N | C | C | N | Ph-4-Br | Me | n-Hex |
| C | N | C | C | N | Ph-4-Br | Me | c-Pr |
| C | N | C | C | N | Ph-4-Br | Me | c-Hex |
| C | N | C | C | N | Ph-4-Br | Me | OH |
| C | N | C | C | N | Ph-4-Br | Me | CH₂OH |
| C | N | C | C | N | Ph-4-Br | Me | OMe |
| C | N | C | C | N | Ph-4-Br | Me | SMe |
| C | N | C | C | N | Ph-4-Br | Me | Cl |
| C | N | C | C | N | Ph-4-Br | Me | CF₃ |
| C | N | C | C | N | Ph-4-Br | Me | Ph |
| C | N | C | C | N | Ph-2-OMe | Me | H |
| C | N | C | C | N | Ph-2-OMe | Me | Me |
| C | N | C | C | N | Ph-2-OMe | Me | Et |
| C | N | C | C | N | Ph-2-OMe | Me | n-Hex |
| C | N | C | C | N | Ph-2-OMe | Me | c-Pr |
| C | N | C | C | N | Ph-2-OMe | Me | c-Hex |
| C | N | C | C | N | Ph-2-OMe | Me | OH |
| C | N | C | C | N | Ph-2-OMe | Me | CH₂OH |
| C | N | C | C | N | Ph-2-OMe | Me | OMe |
| C | N | C | C | N | Ph-2-OMe | Me | SMe |
| C | N | C | C | N | Ph-2-OMe | Me | Cl |
| C | N | C | C | N | Ph-2-OMe | Me | CF₃ |
| C | N | C | C | N | Ph-2-OMe | Me | Ph |
| C | N | C | C | N | Ph-3-OMe | Me | H |
| C | N | C | C | N | Ph-3-OMe | Me | Me |
| C | N | C | C | N | Ph-3-OMe | Me | Et |
| C | N | C | C | N | Ph-3-OMe | Me | n-Hex |
| C | N | C | C | N | Ph-3-OMe | Me | c-Pr |
| C | N | C | C | N | Ph-3-OMe | Me | c-Hex |
| C | N | C | C | N | Ph-3-OMe | Me | OH |
| C | N | C | C | N | Ph-3-OMe | Me | CH₂OH |
| C | N | C | C | N | Ph-3-OMe | Me | OMe |
| C | N | C | C | N | Ph-3-OMe | Me | SMe |
| C | N | C | C | N | Ph-3-OMe | Me | Cl |
| C | N | C | C | N | Ph-3-OMe | Me | CF₃ |
| C | N | C | C | N | Ph-3-OMe | Me | Ph |
| C | N | C | C | N | Ph-4-OMe | Me | H |
| C | N | C | C | N | Ph-4-OMe | Me | Me |
| C | N | C | C | N | Ph-4-OMe | Me | Et |
| C | N | C | C | N | Ph-4-OMe | Me | n-Hex |
| C | N | C | C | N | Ph-4-OMe | Me | c-Pr |
| C | N | C | C | N | Ph-4-OMe | Me | c-Hex |
| C | N | C | C | N | Ph-4-OMe | Me | OH |
| C | N | C | C | N | Ph-4-OMe | Me | CH₂OH |
| C | N | C | C | N | Ph-4-OMe | Me | OMe |
| C | N | C | C | N | Ph-4-OMe | Me | SMe |
| C | N | C | C | N | Ph-4-OMe | Me | Cl |
| C | N | C | C | N | Ph-4-OMe | Me | CF₃ |
| C | N | C | C | N | Ph-4-OMe | Me | Ph |
| C | N | C | C | N | Ph-3,4-(OMe)₂ | Me | H |
| C | N | C | C | N | Ph-3,4-(OMe)₂ | Me | Me |
| C | N | C | C | N | Ph-3,4-(OMe)₂ | Me | Et |
| C | N | C | C | N | Ph-3,4-(OMe)₂ | Me | n-Hex |
| C | N | C | C | N | Ph-3,4-(OMe)₂ | Me | c-Pr |
| C | N | C | C | N | Ph-3,4-(OMe)₂ | Me | c-Hex |
| C | N | C | C | N | Ph-3,4-(OMe)₂ | Me | OH |
| C | N | C | C | N | Ph-3,4-(OMe)₂ | Me | CH₂OH |
| C | N | C | C | N | Ph-3,4-(OMe)₂ | Me | OMe |
| C | N | C | C | N | Ph-3,4-(OMe)₂ | Me | SMe |
| C | N | C | C | N | Ph-3,4-(OMe)₂ | Me | Cl |
| C | N | C | C | N | Ph-3,4-(OMe)₂ | Me | CF₃ |
| C | N | C | C | N | Ph-3,4-(OMe)₂ | Me | Ph |
| C | N | C | C | N | Ph-2-OH | Me | H |
| C | N | C | C | N | Ph-2-OH | Me | Me |
| C | N | C | C | N | Ph-2-OH | Me | Et |
| C | N | C | C | N | Ph-2-OH | Me | n-Hex |
| C | N | C | C | N | Ph-2-OH | Me | c-Pr |
| C | N | C | C | N | Ph-2-OH | Me | c-Hex |
| C | N | C | C | N | Ph-2-OH | Me | OH |
| C | N | C | C | N | Ph-2-OH | Me | CH₂OH |
| C | N | C | C | N | Ph-2-OH | Me | OMe |
| C | N | C | C | N | Ph-2-OH | Me | SMe |
| C | N | C | C | N | Ph-2-OH | Me | Cl |
| C | N | C | C | N | Ph-2-OH | Me | CF₃ |
| C | N | C | C | N | Ph-2-OH | Me | Ph |
| C | N | C | C | N | Ph-3-OH | Me | H |
| C | N | C | C | N | Ph-3-OH | Me | Me |
| C | N | C | C | N | Ph-3-OH | Me | Et |
| C | N | C | C | N | Ph-3-OH | Me | n-Hex |

TABLE 5-continued

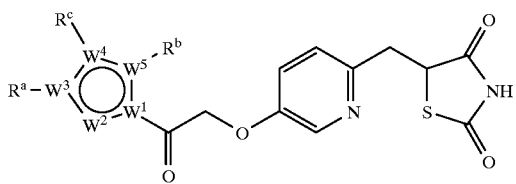

| W¹ | W² | W³ | W⁴ | W⁵ | Rᵃ | Rᵇ | Rᶜ |
|---|---|---|---|---|---|---|---|
| C | N | C | C | N | Ph-3-OH | Me | c-Pr |
| C | N | C | C | N | Ph-3-OH | Me | c-Hex |
| C | N | C | C | N | Ph-3-OH | Me | OH |
| C | N | C | C | N | Ph-3-OH | Me | CH₂OH |
| C | N | C | C | N | Ph-3-OH | Me | OMe |
| C | N | C | C | N | Ph-3-OH | Me | SMe |
| C | N | C | C | N | Ph-3-OH | Me | Cl |
| C | N | C | C | N | Ph-3-OH | Me | CF₃ |
| C | N | C | C | N | Ph-3-OH | Me | Ph |
| C | N | C | C | N | Ph-4-OH | Me | H |
| C | N | C | C | N | Ph-4-OH | Me | Me |
| C | N | C | C | N | Ph-4-OH | Me | Et |
| C | N | C | C | N | Ph-4-OH | Me | n-Hex |
| C | N | C | C | N | Ph-4-OH | Me | c-Pr |
| C | N | C | C | N | Ph-4-OH | Me | c-Hex |
| C | N | C | C | N | Ph-4-OH | Me | OH |
| C | N | C | C | N | Ph-4-OH | Me | CH₂OH |
| C | N | C | C | N | Ph-4-OH | Me | OMe |
| C | N | C | C | N | Ph-4-OH | Me | SMe |
| C | N | C | C | N | Ph-4-OH | Me | Cl |
| C | N | C | C | N | Ph-4-OH | Me | CF₃ |
| C | N | C | C | N | Ph-4-OH | Me | Ph |
| C | N | C | C | N | Ph-3,4-(OH)₂ | Me | H |
| C | N | C | C | N | Ph-3,4-(OH)₂ | Me | Me |
| C | N | C | C | N | Ph-3,4-(OH)₂ | Me | Et |
| C | N | C | C | N | Ph-3,4-(OH)₂ | Me | n-Hex |
| C | N | C | C | N | Ph-3,4-(OH)₂ | Me | c-Pr |
| C | N | C | C | N | Ph-3,4-(OH)₂ | Me | c-Hex |
| C | N | C | C | N | Ph-3,4-(OH)₂ | Me | OH |
| C | N | C | C | N | Ph-3,4-(OH)₂ | Me | CH₂OH |
| C | N | C | C | N | Ph-3,4-(OH)₂ | Me | OMe |
| C | N | C | C | N | Ph-3,4-(OH)₂ | Me | SMe |
| C | N | C | C | N | Ph-3,4-(OH)₂ | Me | Cl |
| C | N | C | C | N | Ph-3,4-(OH)₂ | Me | CF₃ |
| C | N | C | C | N | Ph-3,4-(OH)₂ | Me | Ph |
| C | N | C | C | N | Ph-3-SMe | Me | H |
| C | N | C | C | N | Ph-3-SMe | Me | Me |
| C | N | C | C | N | Ph-3-SMe | Me | Et |
| C | N | C | C | N | Ph-3-SMe | Me | n-Hex |
| C | N | C | C | N | Ph-3-SMe | Me | c-Pr |
| C | N | C | C | N | Ph-3-SMe | Me | c-Hex |
| C | N | C | C | N | Ph-3-SMe | Me | OH |
| C | N | C | C | N | Ph-3-SMe | Me | CH₂OH |
| C | N | C | C | N | Ph-3-SMe | Me | OMe |
| C | N | C | C | N | Ph-3-SMe | Me | SMe |
| C | N | C | C | N | Ph-3-SMe | Me | Cl |
| C | N | C | C | N | Ph-3-SMe | Me | CF₃ |
| C | N | C | C | N | Ph-3-SMe | Me | Ph |
| C | N | C | C | N | Ph-3-CF₃ | Me | H |
| C | N | C | C | N | Ph-3-CF₃ | Me | Me |
| C | N | C | C | N | Ph-3-CF₃ | Me | Et |
| C | N | C | C | N | Ph-3-CF₃ | Me | n-Hex |
| C | N | C | C | N | Ph-3-CF₃ | Me | c-Pr |
| C | N | C | C | N | Ph-3-CF₃ | Me | c-Hex |
| C | N | C | C | N | Ph-3-CF₃ | Me | OH |
| C | N | C | C | N | Ph-3-CF₃ | Me | CH₂OH |
| C | N | C | C | N | Ph-3-CF₃ | Me | OMe |
| C | N | C | C | N | Ph-3-CF₃ | Me | SMe |
| C | N | C | C | N | Ph-3-CF₃ | Me | Cl |
| C | N | C | C | N | Ph-3-CF₃ | Me | CF₃ |
| C | N | C | C | N | Ph-3-CF₃ | Me | Ph |
| C | N | C | C | N | Ph-3-NO₂ | Me | H |
| C | N | C | C | N | Ph-3-NO₂ | Me | Me |
| C | N | C | C | N | Ph-3-NO₂ | Me | Et |
| C | N | C | C | N | Ph-3-NO₂ | Me | n-Hex |
| C | N | C | C | N | Ph-3-NO₂ | Me | c-Pr |
| C | N | C | C | N | Ph-3-NO₂ | Me | c-Hex |

TABLE 5-continued

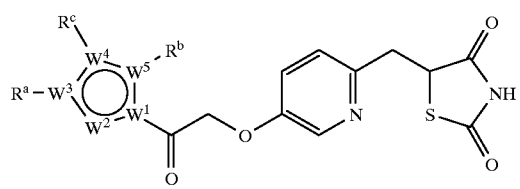

| W¹ | W² | W³ | W⁴ | W⁵ | Rᵃ | Rᵇ | Rᶜ |
|---|---|---|---|---|---|---|---|
| C | N | C | C | N | Ph-3-NO₂ | Me | OH |
| C | N | C | C | N | Ph-3-NO₂ | Me | CH₂OH |
| C | N | C | C | N | Ph-3-NO₂ | Me | OMe |
| C | N | C | C | N | Ph-3-NO₂ | Me | SMe |
| C | N | C | C | N | Ph-3-NO₂ | Me | Cl |
| C | N | C | C | N | Ph-3-NO₂ | Me | CF₃ |
| C | N | C | C | N | Ph-3-NO₂ | Me | Ph |
| C | N | C | C | N | Ph-3-NO₂ | Me | H |
| C | N | C | C | N | Ph-4-NMe₂ | Me | Me |
| C | N | C | C | N | Ph-4-NMe₂ | Me | Et |
| C | N | C | C | N | Ph-4-NMe₂ | Me | n-Hex |
| C | N | C | C | N | Ph-4-NMe₂ | Me | c-Pr |
| C | N | C | C | N | Ph-4-NMe₂ | Me | c-Hex |
| C | N | C | C | N | Ph-4-NMe₂ | Me | OH |
| C | N | C | C | N | Ph-4-NMe₂ | Me | CH₂OH |
| C | N | C | C | N | Ph-4-NMe₂ | Me | OMe |
| C | N | C | C | N | Ph-4-NMe₂ | Me | SMe |
| C | N | C | C | N | Ph-4-NMe₂ | Me | Cl |
| C | N | C | C | N | Ph-4-NMe₂ | Me | CF₃ |
| C | N | C | C | N | Ph-4-NMe₂ | Me | Ph |
| C | N | C | C | N | Ph | Me | H |
| C | N | C | C | N | Ph | Me | H |
| C | O | C | C | C | Ph | Me | H |
| C | S | C | C | C | Ph | Me | H |
| C | N | N | C | C | Ph | Me | H |

TABLE 6

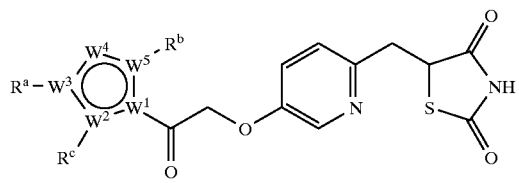

| W¹ | W² | W³ | W⁴ | W⁵ | Rᵃ | Rᵇ | Rᶜ |
|---|---|---|---|---|---|---|---|
| C | C | C | NH | C | Ph | Me | H |
| C | C | C | NH | C | Br | H | H |
| C | C | C | NH | C | Br | H | Me |
| C | C | C | NH | C | Br | Me | Me |
| C | N | C | C | C | Ph | Me | H |
| C | N | C | C | C | Ph | Me | Me |
| C | N | C | C | C | Ph | H | Me |
| C | N | C | C | C | Ph | H | H |
| C | N | C | C | C | H | H | Me |
| C | N | C | C | C | H | Me | Me |
| C | N | C | C | C | H | Me | H |
| C | C | C | O | C | Ph | Me | H |
| C | C | C | O | C | Me | Me | H |
| C | C | C | O | C | H | Me | Me |
| C | C | C | S | C | Ph | Me | H |
| C | C | C | S | C | Me | Me | H |
| C | C | C | S | C | H | H | H |
| C | C | C | N | N | Ph | Me | H |
| C | C | C | N | N | Ph | H | Me |
| C | C | C | N | N | Ph | H | H |
| C | C | C | N | N | Ph | Me | H |
| C | N | C | N | C | Ph | Me | H |

TABLE 6-continued

| W¹ | W² | W³ | W⁴ | W⁵ | Rᵃ | Rᵇ | Rᶜ |
|---|---|---|---|---|---|---|---|
| C | N | C | N | C | Ph | Me | Me |
| C | N | C | N | C | Ph | H | Me |
| C | N | C | N | C | Ph | H | H |

TABLE 7

| W¹ | W² | W³ | W⁴ | W⁵ | Rᵃ | Rᵇ | Rᶜ |
|---|---|---|---|---|---|---|---|
| N | C | C | C | C | Ph | Me | H |
| C | C | C | C | N | Ph | Me | H |
| C | C | N | C | C | Ph | Me | H |
| N | C | C | C | N | Ph | Me | H |
| N | N | N | C | C | Ph | Me | H |
| N | N | C | C | N | Ph | Me | H |
| N | C | C | N | N | Ph | Me | H |
| C | C | N | N | N | Ph | Me | H |

TABLE 8

| W¹ | W² | W³ | W⁴ | W⁵ | Rᵃ |
|---|---|---|---|---|---|
| C | C | C | N | O | Ph |
| C | C | C | N | O | Ph-2,4-Cl₂ |
| C | C | C | N | O | Ph-3,4-Cl₂ |
| C | C | C | N | O | Ph-2,4-Me₂ |
| C | C | N | C | N | Ph |
| C | S | C | C | N | H |
| C | S | C | C | N | Ph |
| C | N | C | C | S | Ph |

TABLE 9

| W¹ | W² | W³ | W⁴ | W⁵ | W⁶ | W⁷ | W⁸ | W⁹ |
|---|---|---|---|---|---|---|---|---|
| CH | CH | CH | C | CH | CH | CH | CH | C |
| C | CMe | NH | C | CH | CH | CH | CH | C |
| C | CMe | NMe | C | CH | CH | CH | CH | C |
| C | CH | NH | C | CH | CH | CH | CH | C |
| C | CH | S | C | CH | CH | CH | CH | C |
| N | CH | N | C | CH | CH | CH | CH | C |
| C | CH | O | C | CH | CH | CH | CH | C |
| C | CH | CH | C | CH | CH | CH | CH | N |
| C | N | NH | C | CH | CH | CH | CH | C |
| C | N | NMe | C | CH | CH | CH | CH | C |
| N | N | N | C | CH | CH | CH | CH | C |
| N | CH | N | C | N | CH | N | CH | C |
| C | CH | N | N | CH | CH | CH | N | C |
| C | CH | N | N | CH | CH | N | N | C |
| C | CMe | S | C | N | CCF₃ | N | —* | N |
| C | CMe | S | C | N | CMe | N | — | N |
| C | CH | S | C | N | CH | N | — | N |

*; covalent bond

TABLE 10

| W¹ | W² | W³ | W⁴ | W⁵ | W⁶ | W⁷ | W⁸ | W⁹ |
|---|---|---|---|---|---|---|---|---|
| CH₂ | C | CMe | C | CH | CH | CH | CH | C |
| CH₂ | C | CH | C | CH | CH | CH | CH | C |
| NMe | C | CH | C | CH | CH | CH | CH | C |
| NH | C | CH | C | CH | CH | CH | CH | C |
| NMe | C | CMe | C | CH | CH | CH | CH | C |
| NH | C | CMe | C | CH | CH | CH | CH | C |
| NH | C | CH | C | CH | CMe | CH | CH | C |
| NH | C | CH | C | CH | CBr | CH | CH | C |
| NH | C | CH | C | CH | CPh | CH | CH | C |
| NMe | C | CH | C | CH | CMe | CH | CH | C |
| NMe | C | CH | C | CH | CBr | CH | CH | C |
| NMe | C | CH | C | CH | CPh | CH | CH | C |
| S | C | CMe | C | CH | CCl | CH | CH | C |
| S | C | CMe | C | CH | CH | CH | CH | C |
| S | C | CH | C | CH | CH | CH | CH | C |
| S | C | CH | C | CH | CPh | CH | CH | C |
| S | C | CMe | C | CH | CPh | CH | CH | C |
| O | C | CH | C | CH | CH | CH | COMe | C |
| O | C | CMe | C | CH | CH | CH | CH | C |
| O | C | CH | C | CH | CH | CH | CH | C |
| O | C | CH | C | CH | CPh | CH | CH | C |
| O | C | CMe | C | CH | CPh | CH | CH | C |
| NH | C | N | C | CH | CH | CH | CH | C |
| NMe | C | N | C | CH | CH | CH | CH | C |
| NH | C | N | C | CH | CMe | CMe | CH | C |
| NMe | C | N | C | CH | CMe | CMe | CH | C |
| NH | C | N | C | CH | CPh | CH | CH | C |
| NMe | C | N | C | CH | CPh | CH | CH | C |
| NMe | C | N | C | CH | CH | CPh | CH | C |
| N | C | O | C | CH | CH | CH | CH | C |
| N | C | O | C | CH | CPh | CH | CH | C |
| N | C | O | C | CH | CH | CPh | CH | C |
| N | C | O | C | CH | CMe | CH | CH | C |

TABLE 10-continued

| W¹ | W² | W³ | W⁴ | W⁵ | W⁶ | W⁷ | W⁸ | W⁹ |
|---|---|---|---|---|---|---|---|---|
| N | C | O | C | CH | CH | CMe | CH | C |
| N | C | S | C | CH | CH | CH | CH | C |
| N | C | S | C | CH | CPh | CH | CH | C |
| N | C | S | C | CH | CH | CPh | CH | C |
| N | C | S | C | CH | CMe | CH | CH | C |
| N | C | S | C | CH | CH | CMe | CH | C |
| CH | C | CH | C | CH | CH | CH | CH | N |
| NH | C | N | C | N | CH | N | CH | C |
| NMe | C | N | C | N | CH | N | CH | C |
| N | C | CH | C | N | CH | CH | CH | N |
| N | C | CH | C | N | N | CH | CH | N |
| S | C | CMe | N | N | CCF₃ | N | —* | C |
| S | C | CMe | N | N | CMe | N | — | C |
| S | C | CH | N | N | CH | N | — | C |

*; covalent bond

TABLE 11

| W¹ | W² | W³ | W⁴ | W⁵ | W⁶ | W⁷ | W⁸ | W⁹ |
|---|---|---|---|---|---|---|---|---|
| CH₂ | CH | CH | C | C | CH | CH | CH | C |
| CH | CH | CH₂ | C | C | CH | CH | CH | C |
| NMe | CH | CH | C | C | CH | CH | CH | C |
| CH | CH | NMe | C | C | CH | CH | CH | C |
| S | CH | CH | C | C | CH | CH | CH | C |
| CH | CH | S | C | C | CH | CH | CH | C |
| O | CH | CH | C | C | CH | CH | CH | C |
| CH | CH | O | C | C | CH | CH | CH | C |
| NH | C | N | C | C | CH | CH | CH | C |
| NMe | C | N | C | C | CH | CH | CH | C |
| N | C | NMe | C | C | CH | CH | CH | C |
| N | C | O | C | C | CH | CH | CH | C |
| O | C | N | C | C | CH | CH | CH | C |
| N | C | S | C | C | CH | CH | CH | C |
| S | C | N | C | C | CH | CH | CH | C |
| CH | CH | CH | C | C | CH | CH | CH | N |
| CH | CH | CH | N | C | CH | CH | CH | C |
| NH | CH | N | C | C | N | CH | N | C |
| CH | CH | N | N | C | CH | CH | N | C |
| CH | CH | N | N | C | CH | N | N | C |

TABLE 12

| W¹ | W² | W³ | W⁴ | W⁵ | W⁶ | W⁷ | W⁸ | W⁹ |
|---|---|---|---|---|---|---|---|---|
| CH₂ | CH | CH | C | CH | C | CH | CH | C |
| CH | CH | CH₂ | C | CH | C | CH | CH | C |
| NMe | CH | CH | C | CH | C | CH | CH | C |
| CH | CH | NMe | C | CH | C | CH | CH | C |
| S | CH | CH | C | CH | C | CH | CH | C |
| CH | CH | S | C | CH | C | CH | CH | C |
| S | CH₂ | CH₂ | C | CH | C | CH | CH | C |
| CH₂ | CH₂ | S | C | CH | C | CH | CH | C |
| O | CH | CH | C | CH | C | CH | CH | C |
| CH | CH | O | C | CH | C | CH | CH | C |
| O | CH₂ | CH₂ | C | CH | C | CH | CH | C |
| CH₂ | CH₂ | O | C | CH | C | CH | CH | C |
| NH | C | N | C | CH | C | CH | CH | C |
| NMe | C | N | C | CH | C | CH | CH | C |
| N | C | NMe | C | CH | C | CH | CH | C |
| N | C | O | C | CH | C | CH | CH | C |
| O | C | N | C | CH | C | CH | CH | C |
| N | C | S | C | CH | C | CH | CH | C |
| S | C | N | C | CH | C | CH | CH | C |
| CH | CH | CH | C | CH | C | CH | CH | N |
| CH | CH | CH | N | CH | C | CH | CH | C |
| NH | CH | N | C | N | C | N | CH | C |
| CH | CH | N | N | C | C | CH | N | C |
| CH | CMe | N | N | CMe | C | CH | N | C |
| CH | CH | N | N | CH | C | N | N | C |
| CH | CMe | N | N | CMe | C | N | N | C |
| CH | CPh | N | N | CMe | C | CH | N | C |
| CH | CPh | N | N | CMe | C | N | N | C |

TABLE 13

| W¹ | W² | W³ | W⁴ | W⁵ | W⁶ | W⁷ | W⁸ |
|---|---|---|---|---|---|---|---|
| C | CH | CH | CH | CH | CH | CH | CH |
| C | CH | CH | CH | CH | CH | CH | N |
| C | CH | CH | CH | N | CH | CH | CH |
| C | CH | CH | N | CH | CH | CH | CH |
| C | CH | CH | CH | CH | CH | N | CH |
| C | CH | CH | CH | CH | N | CH | CH |
| C | CH | N | CH | CH | CH | CH | CH |
| C | N | CH | CH | CH | CH | CH | CH |
| C | CH | CH | CH | O | CH₂ | CH₂ | O |
| C | CH | CH | CH | O | CH | CH | O |
| C | N | N | CH | CH | CH | CH | CH |
| C | CH | CH | CH | CH | N | N | CH |
| C | CH | CH | N | N | CH | CH | CH |
| C | CH | CH | CH | N | CH | CH | N |
| C | CH | CH | CH | CH | N | CH | N |
| C | CH | CH | CH | CH | CH | N | N |
| C | CH | CH | N | N | CH | CH | N |
| C | N | CH | N | N | CH | CH | N |
| N | CH | CH | S | CH | CH | CH | CH |
| C | CH | CH | CH | S | CH | CH | NH |

TABLE 13-continued

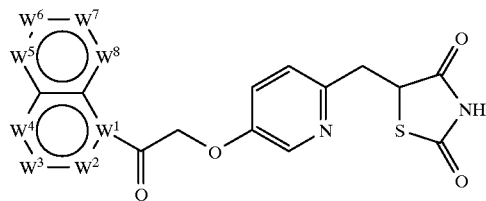

| W¹ | W² | W³ | W⁴ | W⁵ | W⁶ | W⁷ | W⁸ |
|---|---|---|---|---|---|---|---|
| C | CH | CH | CH | S | CH | CH | NMe |
| C | CH | CH | CH | NH | CH | CH | S |
| C | CH | CH | CH | NMe | CH | CH | S |
| N | CO | CH | CH | CH | CH | CH | CH |
| N | CH | CH | CO | CH | CH | CH | CH |
| C | CH | CH | CH | NH | CO | CH | CH |
| C | CH | CH | CH | NMe | CO | CH | CH |
| C | CH | CH | CH | CH | CH | CO | NH |
| C | CH | CH | CH | CH | CH | CO | NMe |
| C | CH | CH | CH | NH | CH | CH | CO |
| C | CH | CH | CH | NMe | CH | CH | CO |
| C | CH | CH | CH | CO | CH | CH | NH |
| C | CH | CH | CH | CO | CH | CH | NMe |
| C | CH | NH | CO | CH | CH | CH | CH |
| C | CH | NMe | CO | CH | CH | CH | CH |
| C | CH | CH | CH | CO | NH | CH | CH |
| C | CH | CH | CH | CO | NMe | CH | CH |
| C | CH | CH | CH | CH | CH | NH | CO |
| C | CH | CH | CH | CH | CH | NMe | CO |
| C | CO | NH | CH | CH | CH | CH | CH |
| C | CO | NMe | CH | CH | CH | CH | CH |
| C | NH | CO | CH | CH | CH | CH | CH |
| C | NMe | CO | CH | CH | CH | CH | CH |
| C | CH | CH | CH | CH | NH | CO | CH |
| C | CH | CH | CH | CH | NMe | CO | CH |
| C | CH | CH | CH | CH | CO | NH | CH |
| C | CH | CH | CH | CH | CO | NMe | CH |
| C | N | NH | CO | CH | CH | CH | CH |
| C | N | NMe | CO | CH | CH | CH | CH |
| C | CH | CH | CH | CH | N | NH | CO |
| C | CH | CH | CH | CH | N | NMe | CO |
| C | CH | CH | CH | CO | NH | N | CH |
| C | CH | CH | CH | CO | NMe | N | CH |

TABLE 14

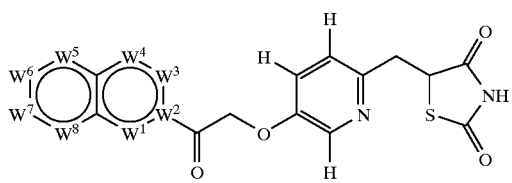

| W¹ | W² | W³ | W⁴ | W⁵ | W⁶ | W⁷ | W⁸ |
|---|---|---|---|---|---|---|---|
| CH | C | CH | CH | CH | CH | CH | CH |
| CH | C | CH | CH | CH | CH | CH | N |
| CH | C | CH | CH | N | CH | CH | CH |
| N | C | CH | CH | CH | CH | CH | CH |
| CH | C | CH | N | CH | CH | CH | CH |
| CH | C | CH | CH | CH | CH | N | CH |
| CH | C | CH | CH | CH | N | CH | CH |
| CH | C | N | CH | CH | CH | CH | CH |
| CH | C | CH | CH | O | CH₂ | CH₂ | O |
| CH | C | CH | CH | O | CH | CH | O |
| CH | C | CH | CH | CH | N | N | CH |
| CH | C | CH | N | N | CH | CH | CH |
| N | C | CH | CH | CH | CH | CH | N |
| N | C | CH | N | CH | CH | CH | CH |
| CH | C | CH | CH | CH | CH | CH | N |
| N | C | N | CH | CH | CH | CH | CH |

TABLE 14-continued

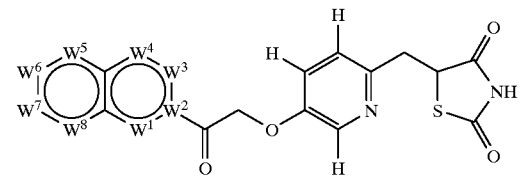

| W¹ | W² | W³ | W⁴ | W⁵ | W⁶ | W⁷ | W⁸ |
|---|---|---|---|---|---|---|---|
| CH | C | CH | CH | CH | N | CH | N |
| CH | C | CH | CH | N | CH | N | CH |
| CH | C | N | N | CH | CH | CH | CH |
| CH | C | CH | CH | CH | CH | N | N |
| CH | C | CH | CH | N | N | CH | CH |
| N | C | N | N | CH | CH | CH | N |
| N | C | CH | N | CH | N | CH | N |
| N | C | CH | N | N | CH | N | CH |
| S | C | CH | NH | CH | CH | CH | CH |
| S | C | CH | NMe | CH | CH | CH | CH |
| NH | C | CH | S | CH | CH | CH | CH |
| NMe | C | CH | S | CH | CH | CH | CH |
| CH | C | CH | CH | NH | CH | CH | S |
| CH | C | CH | CH | NMe | CH | CH | S |
| CH | C | CH | CH | S | CH | CH | NH |
| CH | C | CH | CH | S | CH | CH | NMe |
| S | C | CMe | NH | CH | CH | CH | CH |
| S | C | CMe | NMe | CH | CH | CH | CH |
| CH | C | CO | NH | CH | CH | CH | CH |
| CH | C | CO | NMe | CH | CH | CH | CH |
| CH | C | CH | CH | NH | CO | CH | CH |
| CH | C | CH | CH | NMe | CO | CH | CH |
| CH | C | CH | CH | CH | CH | CO | NH |
| CH | C | CH | CH | CH | CH | CO | NMe |
| NH | C | CH | CO | CH | CH | CH | CH |
| NMe | C | CH | CO | CH | CH | CH | CH |
| CO | C | CH | NH | CH | CH | CH | CH |
| CO | C | CH | NMe | CH | CH | CH | CH |
| CO | N | CH | CH | CH | CH | CH | CH |
| CH | C | NH | CO | CH | CH | CH | CH |
| CH | C | NMe | CO | CH | CH | CH | CH |
| CH | C | CH | CH | CO | NH | CH | CH |
| CH | C | CH | CH | CO | NMe | CH | CH |
| CH | C | CH | CH | CH | CH | NH | CO |
| CH | C | CH | CH | CH | CH | NMe | CO |
| CH | N | CO | CH | CH | CH | CH | CH |
| CH | C | CH | CH | CH | CO | NH | CH |
| CH | C | CH | CH | CH | CO | NMe | CH |
| CH | C | CH | CH | CH | NH | CO | CH |
| CH | C | CH | CH | CH | NMe | CO | CH |
| CO | N | N | CH | CH | CH | CH | CH |
| CH | C | CH | CH | CH | N | NH | CO |
| CH | C | CH | CH | CH | N | NMe | CO |
| CH | C | CH | CH | CO | NH | N | CH |
| CH | C | CH | CH | CO | NMe | N | CH |

TABLE 15

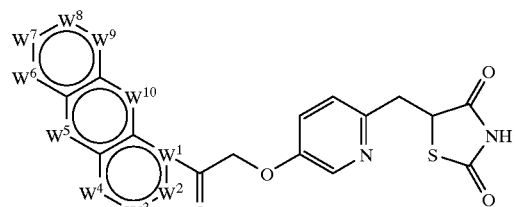

| W¹ | W² | W³ | W⁴ | W⁵ | W⁶ | W⁷ | W⁸ | W⁹ | W¹⁰ |
|---|---|---|---|---|---|---|---|---|---|
| C | CH | CH | CH | O | CH | CH | CH | CH | CH₂ |
| C | CH | CH | CH | CH₂ | CH | CH | CH | CH | O |
| C | CH | CH | CH | O | CH | CH | CH | CH | S |

TABLE 15-continued

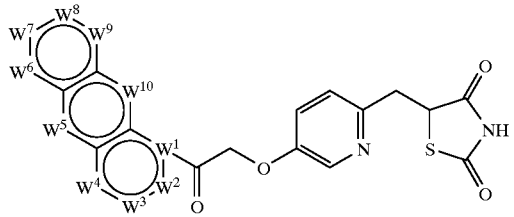

| W¹ | W² | W³ | W⁴ | W⁵ | W⁶ | W⁷ | W⁸ | W⁹ | W¹⁰ |
|---|---|---|---|---|---|---|---|---|---|
| C | CH | CH | CH | S | CH | CH | CH | CH | O |
| C | CH | CH | CH | S | CH | CH | CH | CH | S |
| C | CH | CH | CH | N | CH | CH | CH | CH | CH |
| C | CH | CH | CH | CH | CH | CH | CH | CH | N |
| C | CH | CH | CH | N | CH | CH | CH | CH | N |
| C | CH | CH | CH | S | CH | CH | CH | CH | NH |
| C | CH | CH | CH | S | CH | CH | CH | CH | NMe |
| C | CH | CH | CH | NH | CH | CH | CH | CH | S |
| C | CH | CH | CH | NMe | CH | CH | CH | CH | S |
| C | CH | CH | CH | O | CH | CH | CH | CH | NH |
| C | CH | CH | CH | NH | CH | CH | CH | CH | O |
| C | CH | CH | N | O | CH | CH | CH | CH | CH₂ |
| C | CH | CH | CH | O | N | CH | CH | CH | CH₂ |
| C | CH | CH | CH | CH₂ | CH | CH | CH | N | O |
| C | CH | CH | N | O | CH | CH | CH | CH | CO |
| C | CH | CH | CH | O | N | CH | CH | CH | CO |
| C | CH | CH | CH | CO | CH | CH | CH | N | O |
| C | CH | CH | CH | — | CH | CH | CH | CH | CH₂ |
| C | CH | CH | CH | CH₂ | CH | CH | CH | CH | — |
| C | CH | CH | CH | — | CH | CH | CH | CH | NH |
| C | CH | CH | CH | — | CH | CH | CH | CH | NMe |
| C | CH | CH | CH | NH | CH | CH | CH | CH | — |
| C | CH | CH | CH | NMe | CH | CH | CH | CH | — |

TABLE 16

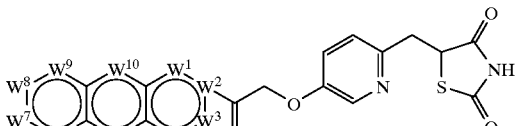

| W¹ | W² | W³ | W⁴ | W⁵ | W⁶ | W⁷ | W⁸ | W⁹ | W¹⁰ |
|---|---|---|---|---|---|---|---|---|---|
| CH | C | CH | CH | O | CH | CH | CH | CH | CH₂ |
| CH | C | CH | CH | CH₂ | CH | CH | CH | CH | O |
| CH | C | CH | CH | O | CH | CH | CH | CH | S |
| CH | C | CH | CH | S | CH | CH | CH | CH | O |
| CH | C | CH | CH | S | CH | CH | CH | CH | S |
| CH | C | CH | CH | N | CH | CH | CH | CH | CH |
| CH | C | CH | CH | CH | CH | CH | CH | CH | N |
| CH | C | CH | CH | N | CH | CH | CH | CH | N |
| CH | C | CH | CH | S | CH | CH | CH | CH | NH |
| CH | C | CH | CH | S | CH | CH | CH | CH | NMe |
| CH | C | CH | CH | NH | CH | CH | CH | CH | S |
| CH | C | CH | CH | NMe | CH | CH | CH | CH | S |
| CH | C | CH | CH | O | CH | CH | CH | CH | NH |
| CH | C | CH | CH | NH | CH | CH | CH | CH | O |
| CH | C | CH | N | O | CH | CH | CH | CH | CH₂ |
| N | C | CH | CH | CH₂ | CH | CH | CH | CH | O |
| CH | C | CH | CH | O | N | CH | CH | CH | CH₂ |
| CH | C | CH | CH | CH₂ | CH | CH | CH | N | O |
| CH | C | CH | N | O | CH | CH | CH | CH | CO |
| N | C | CH | CH | CO | CH | CH | CH | CH | O |
| CH | C | CH | CH | O | N | CH | CH | CH | CO |
| CH | C | CH | CH | CO | CH | CH | CH | N | O |
| CH | C | CH | CH | —* | CH | CH | CH | CH | CH₂ |
| CH | C | CH | CH | CH₂ | CH | CH | CH | CH | — |
| CH | C | CH | CH | — | CH | CH | CH | CH | NH |
| CH | C | CH | CH | — | CH | CH | CH | CH | NMe |
| CH | C | CH | CH | NH | CH | CH | CH | CH | — |

TABLE 16-continued

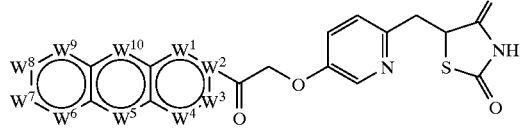

| W¹ | W² | W³ | W⁴ | W⁵ | W⁶ | W⁷ | W⁸ | W⁹ | W¹⁰ |
|---|---|---|---|---|---|---|---|---|---|
| CH | C | CH | CH | NMe | CH | CH | CH | CH | — |
| CH | C | CMe | N | O | CH | CH | CH | CH | CO |
| CH | C | CMe | N | O | CH | CH | CMe | CH | CO |

*; covalent bond

As evident from the following test results, the compound (I) or its pharmaceutically acceptable salt of the present invention has a hypoglycemic activity, and can be used alone or in a mixture with a known pharmaceutically acceptable binder, excipient, lubricant or disintegrator, for preventing or treating diabetes mellitus of mammals including humans, mice, rats, rabbits, dogs, monkeys, cows, horses, pigs and the like. The compound (I) or its pharmaceutically acceptable salt of the present invention can also be used in combination with various oral hypoglycemic agents such as insulin derivatives, sulfonylurea derivatives and biguanide derivatives, and aldose-reductase inhibitory agents.

Furthermore, as evident from the following test results, the compound (I) or its pharmaceutically acceptable salt of the present invention has anti-glycation activities and aldose-reductase inhibitory activities, and is therefore useful for preventing or treating diabetic complications including diabetic eye diseases (diabetic cataract, diabetic retinopathy, etc.), diabetic neuropathy, diabetic nephropathy, diabetic gangrene, and the like.

The compounds (I) of the present invention may be formulated into various suitable formulations depending upon the manner of administration. The compounds of the present invention may be administered in the form of free thiazolidindione or in the form of physiologically hydrolyzable and acceptable pharmaceutically acceptable salts (such as sodium salts or potassium salts).

The pharmaceutical composition of the present invention is preferably administered orally in the form of the compound of the present invention by itself or in the form of powders, granules, tablets or capsules formulated by mixing the compound of the present invention with a suitable pharmaceutically acceptable carrier including a binder (such as hydroxypropyl cellulose, syrup, gum arabic, gelatin, sorbitol, tragacanth gum, polyvinyl pyrrolidone or CMC-Ca), an excipient (such as lactose, sugar, corn starch, calcium phosphate, sorbitol, glycine or microcrystal cellulose powder), a lubricant (such as magnesium stearate, talc, polyethylene glycol or silica), and a disintegrator (such as potato starch).

However, the pharmaceutical composition of the present invention is not limited to such oral administration and it is applicable for parenteral administration. For example, it may be administered in the form of e.g. a suppository formulated by using oily base material such as cacao butter, polyethylene glycol, lanolin or fatty acid triglyceride, a transdermal therapeutic base formulated by using liquid paraffin, white vaseline, a higher alcohol, Macrogol ointment, hydrophilic ointment or hydro-gel base material, an injection formulation formulated by using one or more materials selected from the group consisting of polyethylene glycol, hydro-gel base material, distilled water, distilled water for injection and an excipient such as lactose or corn starch, or a formulation for administration through mucous membranes such as an ocular mucous membrane, a nasal mucous membrane and an oral mucous membrane.

The daily dose of the compound of the present invention is from 0.05 to 50 mg, preferably from 0.1 to 10 mg per kg weight of a patient, and it is administered from once to three times per day. The dose may of course be varied depending upon the age, the weight or the condition of illness of a patient.

BEST MODE FOR CARRYING OUT THE INVENTION

Now, the present invention will be described in further detail with reference to Test Examples for the pharmacological activities of the compounds of the present invention, their Preparation Examples and Formulation Examples. However, it should be understood that the present invention is by no means restricted by such specific Examples.

EXAMPLE 1

Preparation of 5-((5-(2-oxo-2-(2-phenyl-5-methyl-4-oxazolyl)ethoxy)-2-pyridyl)methylidene)thiazolidin-2,4-dione (Compound No. I-1a-1)

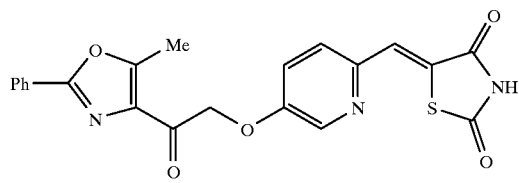

Step 1
Preparation of 5-(2-Oxo-2-(2-phenyl-5-methyl-4-oxazolyl)ethoxy)-2-pyridinemethanol (Compound No. III-1)

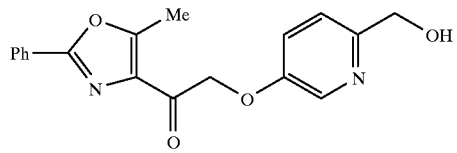

4.04 (25 mmol) of 5-hydroxypyridinemethanol hydrochloride (Compound No. IV-1) (prepared in accordance with a method disclosed in U.S. Pat. No. 4,202,901) and 7.00 g (25 mmol) of 4-bromoacetyl-5-methyl-2-phenyloxazole (prepared by way of 4-acetyl-5-methyl-2-phenyloxazole in accordance with a method disclosed in "J. Chem. Soc. (C), p. 1397 (1968) and Japanese Unexamined patent Publication No. 85372/1986) were dissolved in 100 ml of dimethylformamide dehydrated with molecular sieve. To the resultant solution, was added 5.18 g of anhydrous potassium carbonate, and the resultant solution was stirred at room temperature for 4 hours. The solvent was distilled off from this reaction solution at 60° C. under a reduced pressure by an evaporator, and the viscous residue thus obtained was extracted with 100 ml of chloroform. The solution thus obtained was washed with brine, and was dried over anhydrous magnesium sulfate. After removing the drying agent by filtration, the residue obtained by distilling the solvent off under a reduced pressure was subjected to 5 silica gel column chromatography (eluent: 50% —ethyl acetate/benzene and then ethyl acetate and finally 5% —methanol/chloroform) to obtain 2.58 g (31.9%) of yellow-brown powder of the aimed product (Compound No. III-1).

mp 133–134° C. MS (FAB) m/e: 325 (M+H)$^+$ $^1$H-NMR (CDCl$_3$) δ:2.74 (3H, s), 3.5 (1H), 4.74 (2H, s), 5.44 (2H, s), 7.3–7.4 (2H, m), 7.48–7.51 (3H, m), 8.04–8.06 (2H, m), 8.34–8.35 (1H, m)

The same operation as mentioned above was conducted by using Z-halogenated material as a basic material in 1 5 dimethylformamide or chloroform in the presence of a base such as sodium hydride or triethylamine to obtain the following Compounds Nos. (III-2) to (III-5). (In the following Table, Z corresponds to substituents of the compound of the formula III.)

| Compound No. | Z | properties | melting point (° C.) | MS (m/e) |
|---|---|---|---|---|
| III-2 | MeOCH$_2$ | pale brown oil | | 170 (M + H)$^+$ FAB |
| III-3 | PhCH$_2$ | brown oil | | |
| III-4 | PhCO | pale brown powder | | |
| III-5 | Me$_3$Si | pale brown oil | | |

III-2
$^1$H-NMR(CDCl$_3$) δ:3.45 (3H, s), 4.2 (1H), 4.65(2H, s), 5.15 (2H, S), 7.2–7.4 (2H, m), 8.2–8.3 (1H, m)
III-3
$^1$H-NMR(CDCl$_3$) δ:3.3 (1H, s), 4.65(2H, s), 5.15 (2H, s), 7.1–7.3(2H, m), 7.3–7.5 (5H, m), 8.2–8.3 (1H, m)
III-4
$^1$H-NMR(CDCl$_3$) δ:3.7(1H), 4.75(2H, s), 7.1–8.5 (8H, m)
III-5
$^1$H-NMR(CDCl$_3$) δ:1.1(9H, s), 4.5(2H, s), 6.9–8.2 (13H, m)
Step 2
Preparation of 5-(2-Oxo-2-(2-phenyl-5-methyl-4-oxazolyl) ethoxy-2-pyridinecarbaldehyde (Compound No. II-1)

0.15 g (0.47 mmol) of Compound No. III-1 was dissolved in 5 ml of dehydrated chloroform. 340 mg of active manganese dioxide was added to this solution, and the resultant solution was stirred at room temperature for 5 days. After recognizing disappearance of the starting material by thin layer chromatography, the oxidizing agent residue was removed by filtration. The solution thus obtained was treated with activated carbon, and the solvent was distilled off under a reduced pressure to obtain 0.11 g (72.8%) of brown powder of the aimed product (Compound No. II-1).

mp 115–118° C. MS(FAB) m/e: 323(M+H)$^+$
$^1$H-NMR(CDCl$_3$) δ:2.74(3H, s), 5.54(2H, s), 7.36–7.38 (1H, m), 7.49–7.52(3H, m), 7.97–7.99 (1H, m), 8.0–8.1 (1H, m), 8.53–8.54 (1H, m), 10.04 (1H, s)

In the same manner as mentioned above, the following Compounds Nos. (II-2) to (II-5) were prepared. (In the following Table, Z corresponds to substituents of the compound of the formula II.)

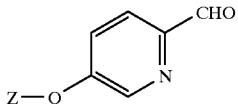

| Compound No. | Z | properties | melting point (°C.) | MS (m/e) |
|---|---|---|---|---|
| II-2 | MeOCH$_2$ | brown oil | | 168(M + H)$^+$ FAB |
| II-3 | PhCH$_2$ | pale yellow wax | 22–23 | |
| II-4 | PhCO | pale brown powder | 85–87 | |
| II-5 | Me$_3$Si | brown oil | | |

II-2
$^1$H-NMR(CDCl$_3$) δ:3.48 (3H, s), 5.25 (2H, s), 7.3–7.6 (1H, m), 7.8–8.0(1H, m), 8.4–8.5(1H, m), 9.90(1H, s)

II-3
$^1$H-NMR(CDCl$_3$) δ:5.17(2H, s), 7.3–7.5(6H, m), 7.8–8.1 (1H, m), 8.4–8.5(1H, m), 9.90(1H, s)

II-4
$^1$H-NMR(CDCl$_3$) δ:7.2–8.3(7H, m), 8.6–8.8(1H, m), 9.97 (1H, s)

0.756 g (6.14 mmol) of 5-hydroxy-2-pyridinecarbaldehyde (Compound No. XIII-1) (prepared in accordance with a method disclosed in Japanese Unexamined patent Publication No. 273659/1990) and 1.72 g (6.14 mmol) of 4-bromoacetyl-5-methyl-2-phenyloxazole were dissolved in 29 ml of dimethylformaldehyde dehydrated with molecular sieve, and the resultant solution was stirred at room temperature. To this solution, was gradually added 1.6 ml (9.21 mmol) of diisopropyl ethylamine, and the resultant solution was stirred at room temperature for 2.5 hours. After recognizing the end of the reaction by thin layer chromatography, 200 ml of chloroform was added to the resultant solution and the resultant solution was washed with brine. The organic layer was dried over anhydrous sodium sulfate. After removing the drying agent by filtration, the solvent was distilled off under a reduced pressure. The residue thus obtained was subjected to silica gel column chromatography (50% —ethyl acetate/hexane) to obtain 1.318 g (61%) of the aimed product (Compound No. II-1).

In the same manner as mentioned above, the following Compounds Nos. (II-6) to (II-34) were prepared. (In the following Table, Z corresponds to substituents of the compound of the formula II.)

| Compound No. | Z | properties | MS(m/e) |
|---|---|---|---|
| II-6 | Me—Ph—oxazole(Me)—C(=O)—Et | colorless wax | 337(M$^+$ + 1) |
| II-7 | m-Me—Ph—oxazole(Me)—C(=O)—Et | pale brown powder | 337(M$^+$ + 1) |
| II-8 | furyl—oxazole(Me)—C(=O)—Et | pale brown powder | 311(M$^+$ − 1) |
| II-9 | Ph—Ph—oxazole(Me)—C(=O)—Et | pale brown powder | 398(M$^+$) |
| II-10 | F—Ph—oxazole(Me)—C(=O)—Et | pale brown powder | 339(M$^+$) |

-continued

| Compound No. | Z | properties | MS(m/e) |
|---|---|---|---|
| II-11 | naphthalen-2-yl-(5-methyloxazol-4-yl) propyl ketone | pale brown powder | 372(M⁺) |
| II-12 | 2-(4-chlorophenyl)-5-methyloxazol-4-yl propyl ketone | pale brown powder | 357(M⁺ + 1) |
| II-13 | 2-(4-methoxyphenyl)-5-methyloxazol-4-yl propyl ketone | pale brown powder | 351(M⁺ − 1) |
| II-14 | 1-(naphthalen-2-yl)propan-1-one | pale yellow crystals 127–129 | 292(M + H)⁺ FAB |
| II-15 | 1-(naphthalen-1-yl)propan-1-one | colorless crystals 137–138 | 292(M + H)⁺ FAB |
| II-16 | 3-propyl-1H-indole | colorless crystals 120–122 | 267(M + H)⁺ FAB |
| II-17 | 1-(3-methylbenzo[b]thiophen-2-yl)propan-1-one | colorless crystals 136–138 | 312(M + H)⁺ FAB |
| II-18 | 1-(benzofuran-2-yl)propan-1-one | colorless crystals 134–136 | 282(M + H)⁺ FAB |
| II-19 | 1-(5-methyl-1-phenyl-1H-pyrazol-4-yl)propan-1-one | colorless crystals 138–140 | 322(M + H)⁺ FAB |

-continued

| Compound No. | Z | properties | MS(m/e) |
|---|---|---|---|
| II-20 | (3-Ph, 5-Me-isoxazol-4-yl)-C(=O)-CH₂CH₃ | pale yellow oil | |
| II-21 | (2,3-dihydro-1,4-benzodioxin-6-yl)-C(=O)-CH₂CH₃ | colorless crystals 173–175 | 300(M + H)⁺ FAB |
| II-22 | (fluoren-2-yl)-C(=O)-CH₂CH₃ | pale yellow crystals 160–163 | 330(M + H)⁺ FAB |
| II-23 | (3-Br-1-Me-indol-2-yl)-C(=O)-CH₂CH₃ | pale yellow crystals 140–143 | 373(M + H)⁺ FAB |
| II-24 | Me₃Si-CH₂CH₂-O-CH₂CH₃ | colorless oil | 254(M + H)⁺ FAB |
| II-25 | (2,5-diMe-furan-3-yl)-C(=O)-CH₂CH₃ | pale yellow solid | 259(M)⁺ EI |
| II-26 | (1-Me-3-Ph-pyrazol-5-yl)-C(=O)-CH₂CH₃ | pale yellow solid | 321(M)⁺ EI |
| II-27 | (2-Ph-4-Me-1,2,3-triazol-5-yl)-C(=O)-CH₂CH₃ | pale brown solid | 322(M)⁺ EI |
| II-28 | (2-Ph-5-Et-1,2,3-triazol-4-yl)-C(=O)-Me | brown solid | 323(M + H)⁺ FAB |
| II-29 | (6-Me-pyridin-2-yl)-CH₂CH₂CH₃ | pale yellow oil | 242(M)⁺ EI |

-continued

| Compound No. | Z | properties | MS(m/e) |
|---|---|---|---|
| II-30 | 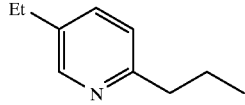 | yellow amorphous | 256(M)+ EI |
| II-31 | 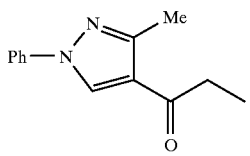 | colorless solid 153–156 | 321(M)+ EI |
| II-32 | 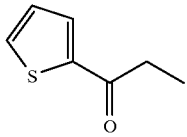 | orange solid | 247(M)+ EI |
| II-33 | 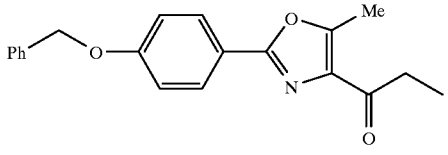 | brown powder 154–155 | |
| II-34 | 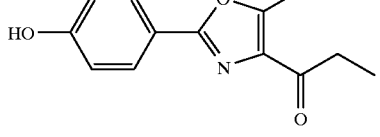 | yellow powder 201–203 | |

II-6

$^1$H-NMR(CDCl$_3$) δ:2.35 (3H, s), 2.61 (3H, s) 5.38 (2H, s) 7.16 (3H, m), 7.8 0(3H, m), 8.40 (1H, m), 9.86 (1H, s)

II-7

$^1$H-NMR(CDCl$_3$) δ:2.42(3H, s), 2.68(3H, s), 5.48(2H, s), 7.33(3H, m), 7.9 0(3H, m), 8.50 (1H, m) 9.96 (1H, s)

II-8

$^1$H-NMR(CDCl$_3$) δ:2.68 (3H, s), 5.44(2H, s), 6.86 (1H, m), 7.55 (1H, m), 7.8 7(1H, m), 8.05 (2H, m), 8.51 (1H, m), 9.99 (1H, s)

II-9

$^1$H-NMR(CDCl$_3$) δ:2.74 (3H, s), 5.51 (2H, s), 7.1–8.5 (12H, m) 10.03(1H, s)

II-10

$^1$H-NMR(CDCl$_3$) δ:2.68(3H, s), 5.46(2H, s), 7.24(3H, m), 7.95(3H, m), 8.5(1H, m), 10.03(1H,s).

II-11

$^1$H-NMR(CDCl$_3$) δ:2.83(3H, s), 5.52 (2H, s), 7.35(3H, m), 7.85(5H, m), 8.5 0(2H, m), 9.97 (1H, s).

II-12

$^1$H-NMR(CDCl$_3$) δ:2.70(3H, s), 5.49(2H, s), 7.40(2H, m), 7.93(4H, m), 8.4 5(1H, m), 9.96 (1H, s).

II-13

$^1$H-NMR(CDCl$_3$) δ:2.70 (3H, s), 3.88(3H, s), 5.51 (2H, s), 6.99(2H, m), 7.3 5(1H, m), 7.97 (3H, m), 8.51 (1H, m), 10.0 (1H, s).

Step 3

Preparation of 5-((5-(2-Oxo-2-(2-phenyl-5-methyl-4-oxazolyl)ethoxy)-2-pyridyl)methylidene)thiazolidin-2,4-dione (Compound No. I-1a-1)

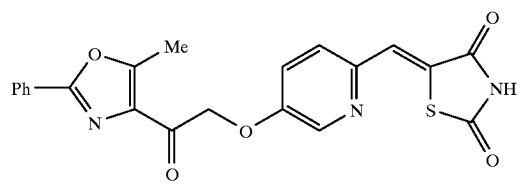

0.15 g (0.47 mmol) of Compound No. (II-1) and 0.11 g of thiazolidindione were suspended in 10 ml of toluene dehydrated with molecular sieve. To this solution, were added 8.4 mg of glacial acetic acid and then 7.9 mg of piperidine, and the resultant solution was stirred at 130° C. for 15 hours. After recognizing disappearance of the starting materials by thin layer chromatography, the precipitated material was dissolved by adding chloroform and methanol to the reaction mixture. The solution thus obtained was washed with brine, and was dried with anhydrous magnesium sulfate. After removing the drying agent by filtration, the solvent was distilled off under a reduced pressure, and the residue thus obtained was subjected to silica gel column chromatography (eluent: chloroform and then 5%—methanol/chloroform) to obtain 0.18 g (94.1%) of pale brown powder of the aimed product (Compound No. I-1a-1).

mp 229–231° C. MS(FAB) m/e: 422(M+H)+

In the same manner as mentioned above, the following Compounds Nos. (I-1a-2) to (I-1a-32) were prepared. (In the following Table, Z corresponds to substituents of the compound of the formula I-1a.)

![structure of formula I-1a]

| Compound No. | Z | properties | melting point (°C.) | MS (m/e) |
|---|---|---|---|---|
| I-1a-2 | MeOCH$_2$ | pale brown powder | 179.5–196 | 267(M + H)+ FAB |
| I-1a-3 | PhCH$_2$ | pale brown powder | 207.5–209.5 | 313(M + H)+ FAB |
| I-1a-4 | PhCO | brown oil | | |
| I-1a-5 | Me$_3$Si | brown oil | | |

I-1a-2

$^1$H-NMR (d$^6$-DMSO) δ:3.14 (3H, s), 5.34 (2H, s), 7.5–7.6 (1H, m), 7.77–7.83(2 H, m), 8.51–8.52(1H, m), 12.3(1H)

I-1a-3

$^1$H-NMR(d$^6$-DMSO) δ:5.27 (2H, s), 7.34–7.49 (5H, m), 7.59–7.61(1H m), 7.78–7.84 (2H, m), 8.54–8.55(m, 1H), 12.3(1H)

| compound No. | Z | melting point (°C.) | MS(m/e) |
|---|---|---|---|
| I-1a-6 | 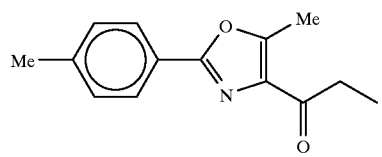 | white powder | 436(M+ + 1) |
| I-1a-7 | 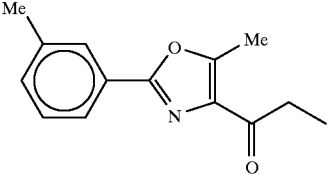 | white powder | 436(M+ + 1) |
| I-1a-8 | 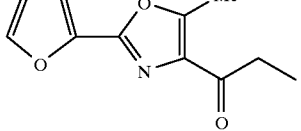 | brown powder | 412(M+ + 1) |
| I-1a-9 | 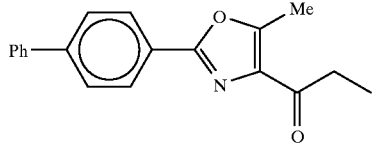 | green brown powder | 497(M+) |
| I-1a-10 | 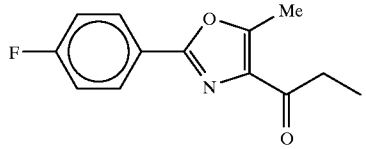 | light gray powder | 440(M+ + 1) |

-continued

| compound No. | Z | melting point (°C.) | MS(m/e) |
|---|---|---|---|
| I-1a-11 | | light gray powder | 471(M⁺) |
| I-1a-12 | | pale brown powder 207–215 | 455, 457(M⁺) |
| I-1a-13 | | pale brown powder 250–(dec.) | 451(M⁺) |
| I-1a-14 | | brown powder >209 (dec.) | 390(M⁺) FD |
| I-1a-15 | | white powder 234–236 | 391(M + H)⁺ FAB |
| I-1a-16 | | colorless crystals 94–98 | 366(M + H)⁺ FAB |
| I-1a-17 | | pale yellow needles 267–269 (dec.) | 410(M⁺) FD |
| I-1a-18 | | yellow brown powder >174 (dec.) | |
| I-1a-19 | | pale yellow poder 249–251 | 421(M + H)⁺ FAB |

-continued

| compound No. | Z | melting point (°C.) | MS(m/e) |
|---|---|---|---|
| I-1a-20 | (3-Ph-5-Me-isoxazol-4-yl)-C(=O)-CH₂CH₂- | colorless powder 205–208 | 422(M + H)⁺ FAB |
| I-1a-21 | (2,3-dihydro-1,4-benzodioxin-6-yl)-C(=O)-CH₂CH₂- | pale brown powder >230 (dec.) | |
| I-1a-22 | (9H-fluoren-2-yl)-C(=O)-CH₂CH₂- | pale yellow powder 268–272 (dec.) | 428(M⁺) FD |
| I-1a-23 | (3-bromo-1-methylindol-2-yl)-C(=O)-CH₂CH₂- | pale yellow powder 230–238 (dec.) | 471(M⁺) FD |
| I-1a-24 | Me₃Si-CH₂CH₂-O-CH₂CH₂- | colorless crystals 124–128 | 353(M + H)⁺ FAB |
| I-1a-25 | (2,5-dimethylfuran-3-yl)-C(=O)-CH₂CH₂- | pale yellow powder 238–240 (dec.) | 359(M + H)⁺ FAB |
| I-1a-26 | (3-Ph-1-Me-pyrazol-5-yl)-C(=O)-CH₂CH₂- | pale yellow powder 244–246 (dec.) | 421(M + H)⁺ FAB |
| I-1a-27 | (4-Me-2-Ph-1,2,3-triazol-5-yl)-C(=O)-CH₂CH₂- | colorless powder 245–249 (dec.) | 422(M + H)⁺ FAB |
| I-1a-28 | (5-ethyl-2-Ph-1,2,3-triazol-4-yl)-C(=O)-CH₂CH₂- | pale brown solid 103–110 (dec.) | 421(M)⁺ EI |
| I-1a-29 | (6-methylpyridin-2-yl)-CH₂CH₂CH₂- | colorless solid 191–193 (dec.) | 341(M)⁺ EI |

-continued

| compound No. | Z | melting point (°C.) | MS(m/e) |
|---|---|---|---|
| I-1a-30 | 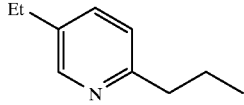 | colorless solid 188–190 (dec.) | 355(M)+ EI |
| I-1a-31 | 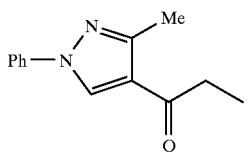 | pale yellow powder 257–259 | 420(M)+ EI |
| I-1a-32 | 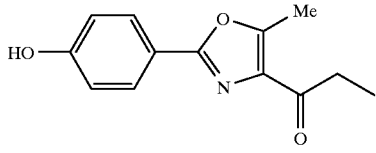 | yellow powder 270 (dec.) | |

I-1a-6

$^1$H-NMR(DMSO, 500 MHz) δ:2.40 (3H, s), 2.68 (3H, s), 5.65 (2H, s), 7.40(2H, m), 7.55(1H, m), 7.80(2H, m), 7.93(2H, m), 8.52(1H, m).

I-1a-7

$^1$H-NMR(CDCl$_3$, 500 MHz) δ:2.46 (3H, s), 2.75 (3H, s), 5.52 (2H, s), 7.35(3H, m), 7.55(2H, m), 7.70(1H, s), 7.88 (2H, m), 8.55(1H, s).

I-1a -8

$^1$H-NMR(CDCl$_3$, 500 MHz) δ:2.70(3H, s), 5.45(2H, s), 6.88(5H, m), 7.46(4H, m, 7.54(1H, m), 7.72(1H, m), 8.06 (2H, m), 8.52(1H, m).

I-1a-9

$^1$H-NMR(CDCl$_3$, 500 MHz) δ:2.76(3H, s), 5.52(2H, s), 7.45(5H, m), 7.75(4H, m), 8.15(3H, m), 8.65(1H, m).

I-1a-10

$^1$H-NMR(CDCl$_3$, 500 MHz) δ:2.74 (3H, s), 5.49(2H, s), 7.21 (2H, m), 7.29(1H, m), 7.46 (1H, m), 7.72(1H, m), 8.05(2H, m), 8.52 (1H, m), 9.4(1H, bs).

I-1a-11

$^1$H-NMR(CDCl$_3$, 500 MHz) δ:2.79(3H, s), 5.55(2H, s), 7.2–7.5(3H, m), 7.56(1H, m), 7.90(4H, m), 8.15(1H, m), 8.55(2H, m).

I-1a-12

$^1$H-NMR(CDCl$_3$, 500 MHz) δ:2.74(3H, s), 5.49(2H, s), 7.16(1H, m), 7.48(3H, m), 7.71(1H, m), 8.00(2H, m), 8.52 (1H, m).

I-1a-13

$^1$H-NMR(CDCl$_3$, 500 MHz) δ:2.72 (3H, s), 3.88 (3H, s), 5.49(2H, m), 6.70 (2H, m), 7.15(1H, m), 7.25(1H, m), 7.35(1H, m), 8.00(2H, m), 8.35 (1H, s).

EXAMPLE 2

Preparation of 5-((5-(2-oxo-2-(2-phenyl-5-methyl-4-oxazolyl )ethoxy-2-pyridyl )methyl) thiazolidin-2, 4-dione (Compound No. I-2a-1)

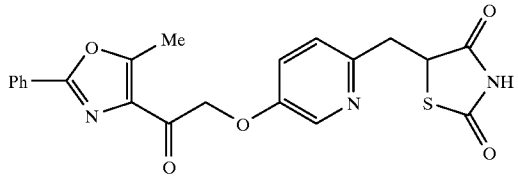

0.48 g (1.1 mmol) of 5-((5-(2-oxo-2-(2-phenyl-5-methyl-4-oxazolyl)ethoxy)-2-pyridyl)methylidene)-thiazolidin-2,4-dione (Compound No. I-1a-1) was dissolved in 50 ml of tetrahydrofuran dehydrated with molecular sieve. To this solution, was added 0.9 g of 10% palladium carbon, and catalytic reduction was conducted at room temperature under 7 atoms of hydrogen for 5 days. After removing the catalyst by filtration, the solvent was distilled off under a reduced pressure to obtain a residue, and the residue thus obtained was subjected to silica gel column chromatography (eluent: 5% —methanol/chloroform) to obtain 0.38 g (26.3%) of pale yellow powder of the aimed product (Compound No. I-2a-1).

mp 56–62° C. MS(FAB) m/e: 424(M+H)+ $^1$H-NMR (CDCl$_3$) δ:2.67 (3H, s), 3.26 (1H, dd, J=10.3, 15.7 Hz), 3.67 (1H, dd, J=3.8, 15.7 Hz), 4.76 (1H, dd, J=3.8, 10.3 Hz), 5.36 (2H, s), 7.06–7.08 (1H, m), 7.1–7.2(1H, m), 7.42–7.44(3H, m), 7.97–7.99 (2H, m), 8.23–8.24(1H, m), 8.4(1H, broad s)

In the same manner as mentioned above, the following Compounds No. (I-2a-2) and Nos. (I-2a-4) to (I-2a-25) were prepared. (In the following Table, Z corresponds to substituents of the compound of the formula I-2a.)

I-2a-2
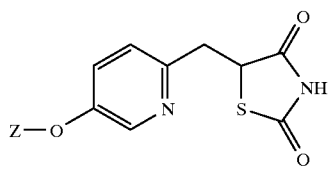
¹H-NMR(d⁶-DMSO) δ:3.34(1H, dd, J=10, 15 Hz), 3.49 (3H, s), 3.73(1H, dd, J=5, 15 Hz), 4.83 (1H, dd, J=5, 10 Hz), 5.19 (2H, s), 7.11–7.14 (1H, m), 7.33–7.36 (1H, m), 8.32–8.35 (1H, m), 9.0 (1H)
| Compound No. | Z | properties | melting point (°C.) | MS (m/e) |
|---|---|---|---|---|
| I-2a-2 | MeOCH₂ | pale yellow oil | | 269(M + H)⁺ FAB |
| compound No. | Z | properties, melting point (°C.) | MS(m/e) |
|---|---|---|---|
| I-2a-4 | 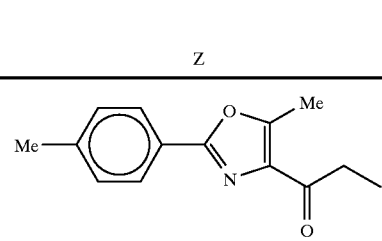 | pale yellow powder 181–185 | 438(M⁺ + 1) FAB |
| I-2a-5 | 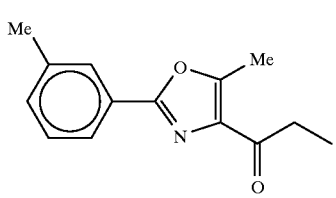 | colorless wax | 437 (M⁺ + 1) |
| I-2a-6 | 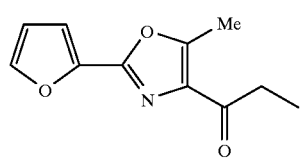 | pale yellow powder 175–178 | |
| I-2a-7 | 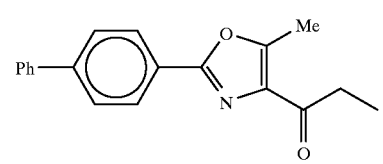 | pale yellow powder 154–156 | 500(M⁺ + H) FAB |
| I-2a-8 | 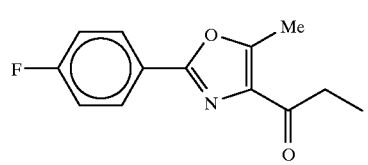 | colorless solid 175–178 | 442(M⁺ + H) FAB |
| I-2a-9 | 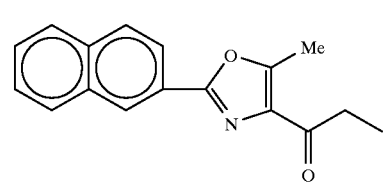 | pale yellow powder 75–80 | |

| compound No. | Z | properties, melting point (°C.) | MS(m/e) |
|---|---|---|---|
| I-2a-10 | 4-Cl-C6H4-oxazole(5-Me)-4-C(O)Et | pale yellow powder 145–152 | |
| I-2a-11 | 4-MeO-C6H4-oxazole(5-Me)-4-C(O)Et | colorless powder 155–162 | |
| I-2a-12 | 1-naphthyl-C(O)Et | colorless powder 151–153(dec.) | 393(M + H)⁻ FAB |
| I-2a-13 | 3-(indol-3-yl)propyl | pale yellow amorphous | 368(M + H)⁺ FAB |
| I-2a-14 | 1-Ph-5-Me-pyrazol-4-yl-C(O)Et | colorless crystals 88–90 | 423(M + H)⁺ FAB |
| I-2a-15 | H2N-C(Ph)=C(C(O)Me)-C(O)Et | colorless amorphous | 426(M + H)⁺ FAB |
| I-2a-16 | 2,3-dihydro-1,4-benzodioxin-6-yl-C(O)Et | pale yellow powder 150–155 | 401(M + H)⁺ FD |
| I-2a-17 | 1-Me-indol-2-yl-C(O)Et | pale yellow amorphous | |
| I-2a-18 | Me3Si-CH2CH2-O-CH2CH3 | colorless oil | 355(M + H)⁺ FAB |

-continued

| compound No. | Z | properties, melting point (°C.) | MS(m/e) |
|---|---|---|---|
| I-2a-19 | (2,5-dimethylfuran-3-yl propanoyl) | colorless crystals 147–149 | 361(M + H)+ FAB |
| I-2a-20 | (1-methyl-3-phenylpyrazol-5-yl propanoyl) | colorless powder 97–105(dec.) | 423(M + H)+ FAB |
| I-2a-21 | (2-phenyl-4-methyl-1,2,3-triazol-5-yl propanoyl) | colorless solid 108–110(dec.) | 424(M + H)+ FAB |
| I-2a-22 | (phenylethyl) | colorless crystals 125–128 | 315(M + H)+ FAB |
| I-2a-23 | (6-methylpyridin-2-yl ethyl) | pale yellow solid 114–116(dec.) | 343(M)+ EI |
| I-2a-24 | (5-ethyl-2-pyridyl) | pcolorless solid 154–156(dec.) | 358(M + H)+ FAB |
| I-2a-25 | (1-phenyl-3-methylpyrazol-4-yl propanoyl) | colorless powder 133–136 | 422(M)+ EI |

I-2a -4

$^1$H-NMR(CDCl$_3$, 90 MHz) δ:2.44(3H, s), 2.72 (3H, s), 3.75 (2H, m), 4.90(1H, m), 5.48 (2H, s), 7.31 (3H, m), 7.92 (3H, m), 8.35 (1H, m).

I-2a -5

$^1$H-NMR(CDCl$_3$, 90 MHz) δ:2.40 (3H, s), 2.70(3H, s), 3.50(2H, m), 4.80(1H, m), 5.38 (2H, s), 7.25 (3H, m), 7.83 (3H, m), 8.29 (1H, m).

EXAMPLE 3

Preparation of 5-((5-(2-hydroxy-2-(2-phenyl-5-methyl-4-oxazolyl)ethoxy)-2-pyridyl)methyl)thiazolidin-2,4-dione (Compound No. (I-2a-3)

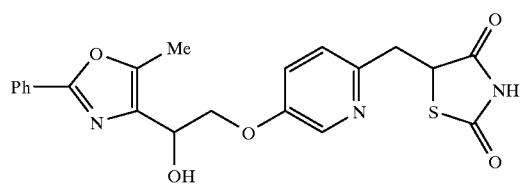

200 mg (0.47 mmol) of 5-((5-(2-oxo-2-(2-phenyl-5-methyl-4-oxazolyl)ethoxy)-2-pyridyl)methyl)thiazolidin-2,4-dione (Compound No. I-2a-1) was dissolved in 5 ml of methanol dehydrated with molecular sieve. To this solution, was added 21.5 mg of sodium borohydride, and the resultant solution was stirred at room temperature for 1 day. The reaction was terminated with a saturated aqueous solution of ammonium chloride, and the reaction mixture was extracted with chloroform. The reaction product thus obtained was washed with brine, and was dried over anhydrous magnesium sulfate. After removing the drying agent by filtration, the solvent was distilled off under a reduced pressure to obtain a residue, and the residue thus obtained was subjected to silica gel column chromatography (eluent: 10%—methanol/chloroform) to obtain 203 mg (quantitative) of pale brown powder of the aimed product (Compound No. I-2a-3).

mp 55–72° C. MS(FAB) m/e: 426(M+H)⁺ $^1$H-NMR(d$^6$-DMSO) δ:2.46 (3H, s), 3.33 (1H, dd, J=10.0, 15.6 Hz), 3.69 (1H, d d, J=3.4, 15.6 Hz), 4.24(1H, dd, J=4.6, 9.5 Hz), 4.37 (1H, dd, J=7.6, 9.5 Hz), 4.81 (1H, dd, J=3.4, 10.0 Hz), 5.10(1H, dd, J=4.6, 7.6 Hz), 7.10–7.15(1H, m), 7.2–7.3 (1H, m), 7.4–7.5 (3H, m), 7.95–8.05 (2H, m), 8.25–8.30 (1H, m), 8.7(1H, broad s)

In the same manner as mentioned above, the following Compounds No. (I-1a-40) to (I-1a-46) were prepared. (In the following Table, Z corresponds to substituents of the compound of the formula I-1a.)

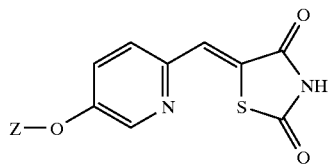

(I-1a)

| compound No. | Z | properties, melting point (°C.) | MS(m/e) |
|---|---|---|---|
| I-1a-40 | Me-C₆H₄-oxazole(Me)-CH(OH)Et | pale yellow powder 231–235 | 437(M⁺) FD |
| I-1a-41 | Ph-oxazole(Me)-CH(OH)Et | colorless powder 263–265(dec.) | 423(M⁺) FD |
| I-1a-42 | F-C₆H₄-oxazole(Me)-CH(OH)Et | colorless powder 254–257(dec.) | 442(M + H)⁺ FAB |
| I-1a-43 | Ph-C₆H₄-oxazole(Me)-CH(OH)Et | pale yellow powder 179–183 | 499(M + H)⁺ FD |
| I-1a-44 | Ph-N-pyrazole(Me)-CH(OH)Et | colorless solid 187–188 | 423(M + H)⁺ FAB |

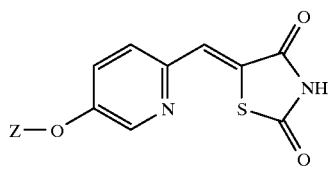

(I-1a)

| compound No. | Z | properties, melting point (°C.) | MS(m/e) |
|---|---|---|---|
| I-1a-45 | Ph—N-N=C(Me)-CH(Et)(OH) (pyrazole) | pale brown crystals 197–198 | 422(M⁺) EI |
| I-1a-46 | HO-C₆H₄-oxazole(Me)-CH(Et)(OH) | pale yellow powder 260–261 | |

In the same manner as mentioned above, the following Compounds No. (I-2a-30) to (I-2a-34) were prepared. (In the following Table, Z corresponds to substituents of the compound of the formula I-2a.)

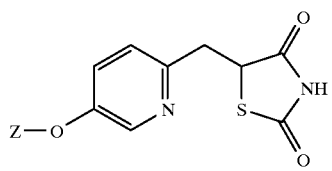

(I-2a)

| compound No. | Z | properties, melting point (°C.) | MS(m/e) |
|---|---|---|---|
| I-2a-30 | F-C₆H₄-oxazole(Me)-CH(Et)(OH) | colorless crystals 189–192 | 444(M + H)⁺ FAB |
| I-2a-31 | Ph-C₆H₄-oxazole(Me)-CH(Et)(OH) | colorless crystals 134–138 | 502(M + H)⁺ FD |
| I-2a-32 | Me-C₆H₄-oxazole(Me)-CH(Et)(OH) | pale yellow powder 181–183 | 440(M + H)⁺ FD |

-continued

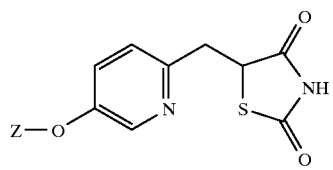
(I-2a)

| compound No. | Z | properties, melting point (°C.) | MS(m/e) |
|---|---|---|---|
| I-2a-33 | Ph—N, N, Me, (CH(OH)Et) | colorless crystals 87–90 (dec.) | 425(M + H)$^+$ FAB |
| I-2a-34 | Ph—N, N, Me, (CH(OH)Et) | colorless amorphous | 425(M + H)$^+$ FAB |

EXAMPLE 4

Preparation of 5-((5-(2-hydroxy-2-(2-phenyl-5-methyl-4-oxazolyl)ethoxy)-2-pyridyl)methylidene)rhodanine (Compound No. (I-1b-1)

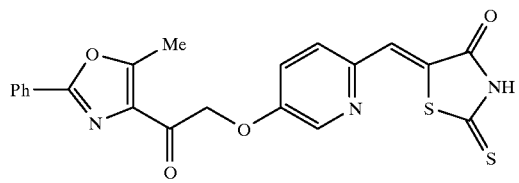

200 mg (0.62 mmol) of Compound No. II-1 and 91 mg of rhodanine was suspended in 10 ml of toluene dehydrated with molecular sieve, and the resultant suspension was dissolved by heating. 11.2 mg of glacial acetic acid and then 10.6 mg of piperidine were added to this solution under cooling by water, and the resultant solution was stirred at room temperature for 2 days. After recognizing disappearance of the starting materials by thin layer chromatography, the precipitated crystal was separated by filtration. The crystal thus obtained was washed with cold toluene, and was dried at 50° C. for 2.5 hours to obtain 220 mg (81.1%) of yellow powder of the aimed product (Compound No. I-1b-1). Also, from the filtrate after removing the crystal, 50 mg of the aimed product was further recovered.

mp 217.5–218.5° C. MS(FAB) m/e: 438(M+H)$^+$
$^1$H-NMR(d$^6$-DMSO)δ:2.69(3H, s), 5.66(2H, s), 7.5–7.7(5H, m), 7.8–7.9(1H, m) 8.0–8.1(2H, m), 8.5–8.6(1H, m), 13.6 (1H, broad s)

EXAMPLE 5

Preparation of 5-((5-(2-oxo-2-(2-phenyl-5-methyl-4-oxazolyl)ethoxy)-2-pyridyl)methyliden)thiazolidin-2,4-dione monomethanesulfonate (Compound No. I-1a-1-1)

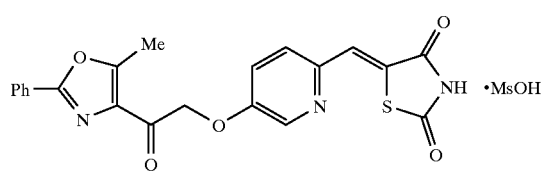

0.2 g (0.48 mmol) of Compound No. I-1a-1 was dissolved in 6 g of tetrahydrofuran at 30–40° C. 1.0 g of methanesulfonic acid was added dropwise to this solution, and the resultant solution was stirred at room temperature. Yellowish precipitate of the methanesulfonate started to separate out around 5 minutes later. After the reaction mixture was stirred at room temperature for 30 minutes, it was stirred at 0–5° C. for further 30 minutes. The precipitated metheanesulfonate was separated by filtration, and was washed with 1 g of cold tetrahydrofuran. After dried in vacuum at 60° C. for 1 hour, 0.2 g (0.39 mmol, 81.4%) of pale yellow powder of the aimed product was obtained.

mp 231° C.

EXAMPLE 6

Preparation of 5-((5-(2-oxo-2-(2-phenyl-5-methyl-4-oxazolyl) ethoxy)-2-pyridyl)methyliden)thiazolidin-2,4-dione monohydrochloride (Compound No. I-1a-1-2)

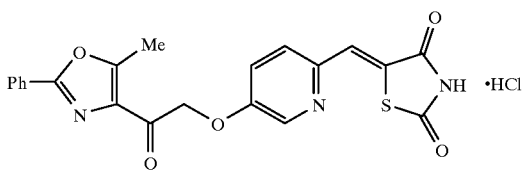

35.0 g (83.1 mmol) of Compound No. I-1a-1 was dissolved in 1751 g of tetrahydrofuran at 60° C. After this solution was cooled to 25° C., 146 g of 41% hydrogen chloride in ethanol was added dropwise, and the resultant solution was stirred at room temperature. Yellowish precipitate of the hydrochloride started to separate out in a few minutes. After the reaction mixture was stirred at room temperature for 30 minutes, 875 g of diethylether was added dropwise in 30 minutes. After the reaction mixture was stirred at room temperature for 30 minutes, it was stirred at 3–5° C. for further 30 minutes. The precipitated hydrochloride was separated by filtration, and dried in vacuum at 30° C. for 2 hour to obtain 32.4 g, (70.8 mmol, 85.6%) of pale yellow powder of the aimed product.

mp 240–242° C.

TEST EXAMPLE 1

Measurement of Hypoglycemic Effect

KK mouse and KKAy mouse, NIDDM models (male, 6–7 weeks old) (Nakamura, Proc. Jpn. Acad. 38, 348–352, 1962; Iwatsuka et al. Endocrinol Jpn, 17, 23–35, 1970) were purchased from Nihon Clea. They were allowed free access to high-calories' chow (CMF, Oriental Yeast) and water. Around 40 g-weighted mice were examined.

Blood (20 μl) collected from the retro-orbital sinus was diluted in 60 units heparin sodium-solution and was centrifuged in a microfuge. The supernatant was assayed. The glucose concentration was determined by glucose oxidase method (Glucose Analyzer II, Beckman). A group of 3 to 4 mice having a blood glucose value of higher than 200 mg/dl, the blood glucose value of which did not reduce by more than 10% for 24 hours after once oral administration of 0.5% carboxymethyl cellulose (CMC)-saline, were tested.

All test-compounds suspended in 0.5% carboxy-methyl cellulose (CMC)-saline were orally administered in mice. Before and 24 hours after the administration, blood was collected from the retro-orbital sinus, and a blood glucose value was measured in the above-mentioned manner. The hypoglycemic activity was expressed by the percentage of reducing blood glucose calculated before and 24 hours after the administration.

| compound No. | dose (mg/kg) | % decrease |
|---|---|---|
| KK mouse | | |
| I-1a-1 | 30 | 48.9 |
| I-2a-1 | 30 | 65.1 |
| glibenclamide | 30 | -3.6 |
| CS-045 | 30 | 24.2 |
| CP-86325 | 30 | 39.4 |
| KKA$^y$ mouse | | |
| I-1a-1 | 30 | 48.6 |
| I-1a-43 | 30 | 47.3 |
| I-2a-1 | 30 | 50.0 |
| I-2a-2 | 30 | 39.9 |
| I-2a-5 | 30 | 47.7 |
| I-2a-30 | 30 | 37.2 |
| I-2a-31 | 30 | 52.2 |
| I-2a-32 | 30 | 35.4 |
| glibenclamide | 30 | -2.5 |
| CS-045 | 30 | -3.0 |
| CP-86325 | 30 | 39.5 |

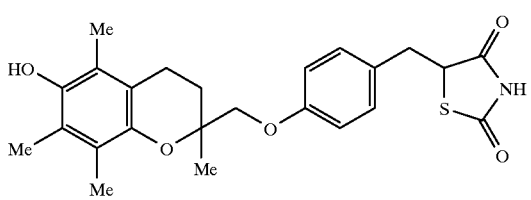

CS-045

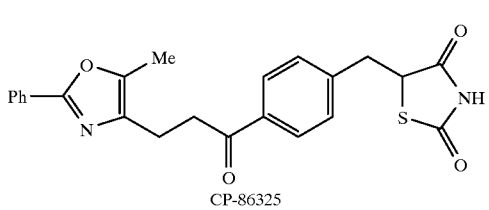

CP-86325

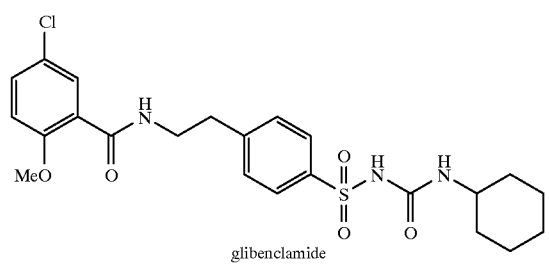

glibenclamide

The compounds of the present invention exhibited hypoglycemic activities at substantially the same or higher degree as compared with CS-045 and CP-86325 used as controls. Glibenclamide (insulin-releasing agent) did not exhibit hypoglycemic activity in this test.

TEST EXAMPLE 2

Measurement of Anti-Glycation Effect

When high-glucose concentrations in diabetic patients sustain for a long time, some kinds of proteins are glycated non-enzymatically. It is considered that the glycated proteins induce diabetic complications (Brownlee, Diabetes, 41 suppl 2, 57–60, 1992).

Because glycated protein is fluorescent, the amount of glycated protein can be determined using fluorescence, according to the previous reports (Doi et al., Proc. Natl. Acad. Sci. U.S.A., 89, 2873–2877, 1992: Mitsuhashi et al., Diabetes, vol. 42, 826–832, 1993). The experimental procedure was modified as follows. Five percent of bovine serum albumin (BSA) containing 0.5M glucose-6- phosphate-2Na (5% BSA-0.5M G6P) was filtration-sterilized (with 0.45 μm-pore size filter) and was incubated at 37° C.; positive control was incubated with 1% dimethyl sulfoxide (DMSO) at 37° C.; blank was incubated at 4° C. All test-compounds dissolved in DMSO (final concentration of DMSO was less than 1%) were added in 5% BSA-0.5M G6P. After 10 day-incubation 5% BSA-0.5M G6P with a compound, positive control and blank were dialyzed against 2L phosphate buffered saline for 24 hours (fractional molecular weight: 12,000–14,000). The dialyzed solution was diluted in water 4 times and was determined the fluorescence (ex. 370 nm-em. 440 nm). The protein concentration of the dialyzed solution (10 μL of which was diluted to 20 times with distilled water) was determined by Lowry-method and the fluorescence was expressed per mg protein. Control (100%) was positive control minus blank. Anti-glycation effect was calculated as the percentage of the control.

| compound No. | concentration | | % decrease |
|---|---|---|---|
| I-1a-1 | 100 μg/ml | (0.24 mM) | 42.3 |
| I-1a-2 | 100 μg/ml | (0.38 mM) | 24.1 |
| I-1a-3 | 100 μg/ml | (0.32 mM) | 34.1 |
| CS-045 | 100 μg/ml | | 10.1 |
| CP-86325 | 100 μg/ml | | 10.3 |
| aminoguanidine | | (1 mM) | 21.4 |
| aminoguanidine | | (10 mM) | 48.9 |
| aminoguanidine | | (100 mM) | 80.2 |

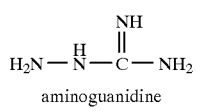

aminoguanidine

The compounds of the present invention exhibited anti-glycation activities stronger than aminoguanidine used as a control. CS-045 and CP-86325 did not exhibit anti-glycation activities.

TEST EXAMPLE 3

Measurement of Aldose-Reductase Inhibitory Activities

Rat kidney AR was prepared as follows; Rat kidney was perfused by ice-cold saline to remove blood and then homogenized in a Teflon homogenizer with 3 time volumes of cold 5 mM Tris-HCl buffer (pH 7.4). The homogenate was centrifuged at 45,000×g for 40 minutes to remove insoluble materials, and the supernatant fraction was used as an aldose reductase sample. Determination of AR and effects of test compounds AR activity was assayed by the modified method of Inukai et al. (Jpn. J. Pharmacol 61, 221–227, 1993). The absorbance of NADPH (340 nm), oxidation of the co-factor for AR, was determined by spectrophotometer (UV-240, Shimadzu, Kyoto). The assay was carried out in 0.1M sodium phosphate (pH 6.2) containing 0.4M lithium sulfate, 0.15 mM NADPH, the enzyme, various concentrations of test compounds and 10 mM DL-glyceraldehyde. The reference blank contained all of the above ingredients, except for DL-glyceraldehyde. The reaction was started by addition of the substrate (DL-glyceraldehyde). The reaction rate was measured at 30° C. for 2 minutes. All test compounds were dissolved in dimethyl sulfoxide (DMSO). The final concentration of DMSO in reaction mixture never exceeded 1%. The effects of inhibitors were estimated as the concentration of test compounds required for 50% inhibition of enzyme activity ($IC_{50}$).

As this result, the compounds of the present invention exhibited satisfactory aldose-reductase inhibitory activities.

FORMULATION EXAMPLE 1

Tablets

| | |
|---|---|
| The compound of the present invention | 1.0 g |
| Lactose | 5.0 g |
| Crystal cellulose powder | 8.0 g |
| Corn starch | 3.0 g |
| Hydroxypropyl cellulose | 1.0 g |
| CMC—Ca | 1.5 g |
| Magnesium stearate | 0.5 g |
| Total | 20.0 g |

The above components were mixed by a usual method and then tabletted to produce 100 tablets each containing 10 mg of the active ingredient.

FORMULATION EXAMPLE 2

Capsules

| | |
|---|---|
| The compound of the present invention | 1.0 g |
| Lactose | 3.5 g |
| Crystal cellulose powder | 10.0 g |
| Magnesium stearate | 0.5 g |
| Total | 15.0 g |

The above components were mixed by a usual method and then packed in No. 4 gelatin capsules to obtain 100 capsules each containing 10 mg of the active ingredient.

FORMULATION EXAMPLE 3

Soft capsules

| | |
|---|---|
| The compound of the present invention | 1.00 g |
| PEG (polyethylene glycol) 400 | 3.89 g |
| Saturated fatty acid triglyceride | 15.00 g |
| Peppermint oil | 0.01 g |
| Polysorbate 80 | 0.10 g |
| Total | 20.00 g |

The above compounds were mixed and packed in No. 3 soft gelatin capsules by a usual method to obtain 100 soft capsules each containing 10 mg of the active ingredient.

FORMULATION EXAMPLE 4

Ointment

| | | |
|---|---|---|
| The compound of the present invention | 1.0 g | (10.0 g) |
| Liquid paraffin | 10.0 g | (10.0 g) |
| Cetanol | 20.0 g | (20.0 g) |
| White vaseline | 68.4 g | (59.4 g) |
| Ethylparaben | 0.1 g | ( 0.1 g) |
| l-menthol | 0.5 g | ( 0.5 g) |
| Total | 100.0 g | |

The above components were mixed by a usual method to obtain a 1% (10%) ointment.

FORMULATION EXAMPLE 5

Suppository

| | |
|---|---|
| The compound of the present invention | 1.0 g |
| Witepsol H15* | 46.9 g |
| Witepsol W35* | 52.0 g |
| Polysorbate 80 | 0.1 g |
| Total | 100.0 g |

*Trademark for triglyceride compound

The above components were melt-mixed by a usual method and poured into suppository containers, followed by cooling for solidification to obtain 100 suppositories of 1 g each containing 10 mg of the active ingredient.

FORMULATION EXAMPLE 6

Granules

| | |
|---|---|
| The compound of the present invention | 1.0 g |
| Lactose | 6.0 g |
| Crystal cellulose powder | 6.5 g |
| Corn starch | 5.0 g |
| Hydroxypropyl cellulose | 1.0 g |
| Magnesium stearate | 0.5 g |
| Total | 20.0 g |

The above components were granulated by a usual method and packaged to obtain 100 packages each containing 200 mg of the granules so that each package contains 10 mg of the active ingredient.

INDUSTRIAL APPLICABILITY

Since the compound of the present invention has a hypoglycemic effect, an anti-glycation activity and an aldose-reductase inhibitory activity and has less toxicity, it is useful for preventing or treating diabetic complications including diabetic eye diseases (such as diabetic cataract and diabetic retinopathy), diabetic neuropathy, diabetic nephropathy, diabetic gangrene, and the like.

We claim:

1. A pyridine type compound or its salt, expressed by the following formula (I):

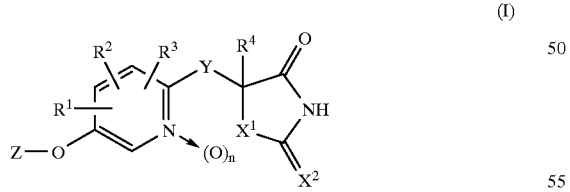

(wherein $X^1$ is S or O);

$X^2$ is S, O or NH;

Y is $CR^6R^7$ (wherein $R^6$ is a hydrogen atom, a $C_1$–$C_7$ alkyl group or a $C_3$–$C_7$ cycloalkyl group, and $R^7$ is a hydrogen atom, a $C_1$–$C_7$ alkyl group or a $C_3$–$C_7$ cycloalkyl group or forms a bond together with $R^4$), or $SO_2$;

Z is a $C_1$–$C_{10}$ alkyl group, a $C_2$–$C_{10}$ alkenyl group, a $C_2$–$C_{10}$ alkynyl group, a $C_3$–$C_7$ cycloalkyl group, a $C_3$–$C_7$ cycloalkenyl group (each of said alkyl, alkenyl, alkynyl, cycloalkyl and cycloalkenyl groups may be substituted with at most 3 of hydroxyl, oxo, $C_1$–$C_7$ alkyl and $C_1$–$C_7$ alkoxy groups), a phenyl group, a biphenyl group, an α-naphthyl group, a β-naphthyl group, a benzyl group, a pyridyl group, a pyrimidinyl group, a pyridazinyl group, a furanyl group, a thienyl group, a pyrrolyl group, a pyrazolyl group, an imidazolyl group, a pyranyl group (each of said phenyl, biphenyl, α-naphthyl, β-naphthyl, benzyl, pyridyl, pyrimidinyl, pyridazinyl, furanyl, thienyl, pyrrolyl, pyrazolyl, imidazolyl and pyranyl groups may be substituted with at most 3 of hydroxyl, $C_1$–$C_7$ alkyl and $C_1$–$C_7$ alkoxy groups and a halogen atom), a substituted silyl group, a $C_1$–$C_{14}$ aliphatic acyl group, a $C_6$–$C_{10}$ aromatic acyl group or -A-B (wherein A is a divalent $C_1$–$C_6$ saturated or $C_2$–$C_6$ unsaturated hydrocarbon group which may be substituted with at most 3 of hydroxyl, oxo and $C_1$–$C_7$ alkyl groups, and B is $C_3$–$C_{10}$ cycloalkyl, $C_3$–$C_7$ cycloalkenyl, $C_6$–$C_{14}$ aromatic and $C_4$–$C_{12}$ heterocyclic aromatic groups, which may have at most 5 substituents in total (said heterocyclic aromatic group may contain at most 5 hetero atoms selected from the group consisting of an oxygen atom, a sulfur atom and a nitrogen atom as constituents for the heterocyclic ring), or a $C_4$–$C_6$ heterocycloaliphatic group (said heterocycloaliphatic group may contain at most 3 hetero atoms selected from the group consisting of an oxygen atom, a sulfur atom and a nitrogen atom as constituents for the heterocyclic ring));

each of $R^1$, $R^2$ and $R^3$ is independently a hydrogen atom, a $C_1$–$C_7$ alkyl group (which may be substituted with a hydroxyl group), a $C_3$–$C_7$ cycloalkyl group, a hydroxyl group or a halogen atom;

$R^4$ is a hydrogen atom or a $C_1$–$C_7$ alkyl group, or forms a bond together with $R^7$; and n is 0 or 1.

2. The pyridine type compound of the formula (I) or its salt according to claim 1, wherein:

$X^2$ is S or O;

Y is $CR^6R^7$ (wherein $R^6$ is a hydrogen atom or a $C_1$–$C_3$ alkyl group and $R^7$ is a hydrogen atom or a $C_1$–$C_3$ alkyl group or forms a bond together with $R^4$);

Z is -A-B (wherein A is a divalent $C_1$–$C_6$ saturated or $C_2$–$C_6$ unsaturated hydrocarbon group which may be substituted with at most 3 hydroxy, oxo and $C_1$–$C_7$ alkyl groups, and B is $C_3$–$C_{10}$ cycloalkyl, $C_3$–$C_7$ cycloalkenyl, $C_6$–$C_{14}$ aromatic and $C_4$–$C_{12}$ heterocyclic aromatic groups, which may have at most 5 substituents in total (said heterocyclic aromatic group may contain at most 5 hetero atoms selected from the group consisting of an oxygen atom, a sulfur atom and a nitrogen atom as constituents for the heterocyclic ring), or a $C_4$–$C_6$ heterocycloaliphatic group (said heterocycloaliphatic group may contain at most 3 hetero atoms selected from the group consisting of an oxygen atom, a sulfur atom and a nitrogen atom as constituents for the heterocyclic ring)), among groups of B, said $C_3$–$C_{10}$ cycloalkyl group being cyclopropyl, cyclobutyl, cyclopentyl, cyclohexyl, cycloheptanyl, cyclooctanyl, cyclononanyl, cyclodecanyl, bicyclo[2.2.1]heptyl, bicyclo[3.1.1] heptyl, bicyclo[2.2.2]octyl, 1-adamantyl or 2-adamantyl, said $C_3$–$C_7$ cycloalkenyl group being 1-cyclohexenyl, 2-cyclohexenyl, 3-cyclohexenyl, cyclpentadienyl, 2-bicylo[2.2.1]heptenyl or 2,5-bicyclo

[2.2.1]heptadienyl, said $C_6$–$C_{14}$ aromatic group being phenyl, α-naphthyl, β-naphthyl, 1-indenyl, 2-indenyl, 3-indenyl, 4-indenyl, 5-indenyl, 6-indenyl, 7-indenyl, 1-indanyl, 2-indanyl, 4-indanyl, 5-indanyl, 1-fluorenyl, 2-fluorenyl, 3-fluorenyl, 4-fluorenyl or 9-fluorenyl, said $C_4$–$C_{12}$ heterocyclic aromatic group being 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 3-furazanyl, 1-pyrazolyl, 3-pyrazolyl, 4-pyrazolyl, 3-oxopyrazol-1-yl, 3-oxopyrazol-2-yl, 3-oxopyrazol-3-yl, 3-oxopyrazol-4-yl, 4-oxopyrazol-3-yl, 1-imidazolyl, 2-imidazolyl, 4-imidazolyl, 2-oxoimidazol-1-yl, 2-oxoimidazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, 1,2,4(2H,4H)-triazol-3-on-2-yl, 1,2,4-(2H,4H)-triazol-3-on-4-yl, 1,2,4(2H,4H)-triazol-3-on-5-yl, 1,2,4(1H,2H)-triazol-3-on-1-yl, 1,2,4(1H,2H)-triazol-3-on-2-yl, 1,2,4(1H,2H)-triazol-3-on-5-yl, 1-tetrazolyl, 2-tetrazolyl, 5-tetrazolyl, 2-pyranyl, 3-pyranyl, 4-pyranyl, 2-pyridyl, 3-pyridyl, 4-pyridyl, 2-pyridon-1-yl, 2-pyridon-3-yl, 2-pyridon-4-yl, 2-pyridon-5-yl, 2-pyridon-6-yl, 4-pyridon-1-yl, 4-pyridon-2-yl, 4-pyridon-3-yl, 3-pyridazinyl, 4-pyridazinyl, 3(2H)-pyridazinon-2-yl, 3(2H)-pyridazinon-4-yl, 3(2H)-pyridazinon-5-yl, 3(2H)-pyridazinon-6-yl, 4(1H)-pyridazinon-1-yl, 4(1H)-pyridazinon-3-yl, 4(1H)-pyridazinon-5-yl, 4(1H)-pyridazinon-6-yl, 2-pyrimidinyl, 4-pyrimidinyl, 5-pyrimidinyl, 2(1H)-pyrimidinon-1-yl, 2(1H)-pyrimidinon-4-yl, 2(1H)-pyrimidinon-5-yl, 2(1H)-pyrimidinon-6-yl, 4(3H)-pyrimidinon-2-yl, 4(3H)-pyrimidinon-3-yl, 4(3H)-pyrimidinon-5-yl, 4(3H)-pyrimidinon-6-yl, 4(1H)-pyrimidinon-1-yl, 4(1H)-pyrimidinon-2-yl, 4(1H)-pyridiminon-5-yl, 4(1H)-pyrimidinon-6-yl, 2-pyrazinyl, 2(1H)-pyrazin-1-yl, 2(1H)-pyrazin-3-yl, 2(1H)-pyrazin-5-yl, 2(1H)-pyrazin-6-yl, 1,2,3-triazin-4-yl, 1,2,3-triazin-5-yl, 1,2,4-triazin-3-yl, 1,2,4-triazin-5-yl, 1,2,4-triazin-6-yl, 1,2,3,4-tetrazin-5-yl, 1,2,4,5-tetrazin-3-yl, 1-indolyl, 2-indolyl, 3-indolyl, 4-indolyl, 5-indolyl, 6-indolyl, 7-indolyl, 2-quinolyl, 3-quinolyl, 4-quinolyl, 5-quinolyl, 6-quinolyl, 7-quinolyl, 8-quinolyl, 2-quinolon-1-yl, 2-quinolon-3-yl, 2-quinolon-4-yl, 2-quinolon-5-yl, 2-quinolon-6-yl, 2-quinolon-7-yl, 2-quinolon-8-yl, 4-quinolon-1-yl, 4-quinolon-2-yl, 4-quinolon-3-yl, 4-quinolon-5-yl, 4-quinolon-6-yl, 4-quinolon-7-yl, 4-quinolon-8-yl, 2-benzofuranyl, 3-benzofuranyl, 4-benzofuranyl, 5-benzofuranyl, 6-benzofuranyl, 7-benzofuranyl, 2-benzothienyl, 3-benzothienyl, 4-benzothienyl, 5-benzothienyl, 6-benzothienyl, 7-benzothienyl, 1-isoquinolyl, 3-isoquinolyl, 4-isoquinolyl, 5-isoquinolyl, 6-isoquinolyl, 7-isoquinolyl, 8-isoquinolyl, 1-isoquinolon-2-yl, 1-isoquinolon-3-yl, 1-isoquinolon-4-yl, 1-isoquinolon-5-yl, 1-isoquinolon-6-yl, 1-isoquinolon-7-yl, 1-isoquinolon-8-yl, 3-isoquinolon-2-yl, 3-isoquinolon-4-yl, 3-isoquinolon-5-yl, 3-isoquinolon-6-yl, 3-isoquinolon-7-yl, 3-isoquinolon-8-yl, 2-benzoxazolyl, 4-benzoxazolyl, 5-benzoxazolyl, 6-benzoxazolyl, 7-benzoxazolyl, 2-benzothiazolyl, 4-benzothiazolyl, 5-benzothiazolyl, 6-benzothiazolyl, 7-benzothiazolyl, 1-benzopyrazolyl, 2-benzopyrazolyl, 3-benzopyrazolyl, 4-benzopyrazolyl, 5-benzopyrazolyl, 6-benzopyrazolyl, 7-benzopyrazolyl, 1-benzimidazolyl, 2-benzimidazolyl, 4-benzimidazolyl, 5-benzimidazolyl, 1-benzotriazolyl, 4-benzotriazolyl, 5-benzotriazolyl, 2-benzopyranyl, 3-benzopyranyl, 4-benzopyranyl, 5-benzopyranyl, 6-benzopyranyl, 7-benzopyranyl, 8-benzopyranyl, 1-indolizinyl, 2-indolizinyl, 3-indolizinyl, 5-indolizinyl, 6-indolizinyl, 7-indolizinyl, 8-indolizinyl, 2-purinyl, 6-purinyl, 7-purinyl, 8-purinyl, 1-phthalazinyl, 5-phthalazinyl, 6-phthalazinyl, 1-oxophthalazin-2-yl, 1-oxophthalazin-4-yl, 1-oxophthalazin-5-yl, 1-oxophthalazin-6-yl, 1-oxophthalazin-7-yl, 1-oxophthalazin-8-yl, 2-naphthyridinyl, 3-naphthyridinyl, 4-naphthyridinyl, 2-quinoxalinyl, 5-quinoxalinyl, 6-quinoxalinyl, 2-quinazolinyl, 4-quinazolinyl, 5-quinazolinyl, 6-quinazolinyl, 7-quinazolinyl, 8-quinazolinyl, 3-cinnolinyl, 4-cinnolinyl, 5-cinnolinyl, 6-cinnolinyl, 7-cinnolinyl, 8-cinnolinyl, 1,4-benzodioxan-2-yl, 1,4-benzodioxan-5-yl, 1,4-benzodioxan-6-yl, 1,4-oxonaphthalen-2-yl, 1,4-oxonaphthalen-5-yl, 1,4-oxonaphthalen-6-yl, 2,3-dihydro-4-benzofuranyl, 2,3-dihydro-5-benzofuranyl, 2,3-dihydro-6-benzofuranyl, 2,3-dihydro-7-benzofuranyl, 1,4-benzothiazin-2-yl, 1,4-benzothiazin-3-yl, 1,4-benzothiazin-4-yl, 1,4-benzothiazin-5-yl, 1,4-benzothiazin-6-yl, 1,4-benzothiazin-7-yl, 1,4-benzothiazin-8-yl, 2-pteridinyl, 4-pteridinyl, 6-pteridinyl, 7-pteridinyl, pyrazolo[1,5-a]pyrimidin-2-yl, pyrazolo[1,5-a]pyrimidin-3-yl, pyrazolo[1,5-a]pyrimidin-5-yl, pyrazolo[1,5-a]pyrimidin-6-yl, pyrazolo[1,5-a]pyrimidin-7-yl, pyrazolo[5,1-c][1,2,4]triazin-3-yl, pyrazolo[5,1-c][1,2,4]triazin-4-yl, pyrazolo[5,1-c][1,2,4]triazin-7-yl, pyrazolo[5,1-c][1,2,4]triazin-8-yl, thiazolo[3,2-b]triazol-2-yl, thiazolo[3,2-b]triazol-5-yl, thiazolo[3,2-b]triazol-6-yl, benzopyrano[2,3-b]pyridin-2-yl, benzopyrano[2,3-b]pyridin-3-yl, benzopyrano[2,3-b]pyridin-4-yl, benzopyrano[2,3-b]pyridin-5-yl, benzopyrano[2,3-b]pyridin-6-yl, benzopyrano[2,3-b]pyridin-7-yl, benzopyrano[2,3-b]pyridin-8-yl, benzopyrano[2,3-b]pyridin-9-yl, 5H-benzopyrano[2,3-b]pyridin-5-on-2-yl, 5H-benzopyrano[2,3-b]pyridin-5-on-3-yl, 5H-benzopyrano[2,3-b]pyridin-5-on-4-yl, 5H-benzopyrano[2,3-b]pyridin-5-on-6-yl, 5H-benzopyrano[2,3-b]pyridin-5-on-7-yl, 5H-benzopyrano[2,3-b]pyridin-5-on-8-yl, 1-xanthenyl, 2-xanthenyl, 3-xanthenyl, 4-xanthenyl, 9-xanthenyl, 1-phenoxathiinyl, 2-phenoxathiinyl, 3-phenoxathiinyl, 4-phenoxathiinyl, 1-carbazolyl, 2-carbazolyl, 3-carbazolyl, 4-carbazolyl, 9-carbazolyl, 1-acridinyl, 2-acridinyl, 3-acridinyl, 4-acridinyl, 9-acridinyl, 1-phenazinyl, 2-phenazinyl, 3-phenazinyl, 4-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 1-thianthrenyl, 2-thianthrenyl, 3-thianthrenyl, 4-thianthrenyl, 6-thianthrenyl, 7-thianthrenyl, 8-thianthrenyl, or 9-thianthrenyl, and said $C_4$–$C_6$ heterocycloaliphatic group being 1-piperidyl, 2-piperidyl, 3-piperidyl, 4-piperidyl, 1-pyrrolidinyl, 2-pyrrolidinyl, 3-pyrrolidinyl, 1-imidazolidinyl, 2-imidazolidinyl, 4-imidazolidinyl, 1-pyrazolidinyl, 3-pyrazolidinyl, 4-pyrazolidinyl, 2-morpholinyl, 3-morpholinyl, 4-morpholinyl, 2-tetrahydrofuranyl, or 3-tetrahydrofuranyl;

each of $R^1$, $R^2$ and $R^3$ is independently a hydrogen atom, a $C_1$–$C_3$ alkyl group (which may be substituted with a hydroxyl group), a hydroxyl group or a halogen atom;

$R^4$ is a hydrogen atom or a $C_1$–$C_3$ alkyl group, or forms a bond together with $R^7$; and
n is 0.
3. The pyridine type compound of the formula (I) or its salt according to claim 1, wherein:
each of $R^1$, $R^2$ and $R^3$ is independently a hydrogen atom, a methyl group, a hydroxy group or a chlorine atom; and
B is
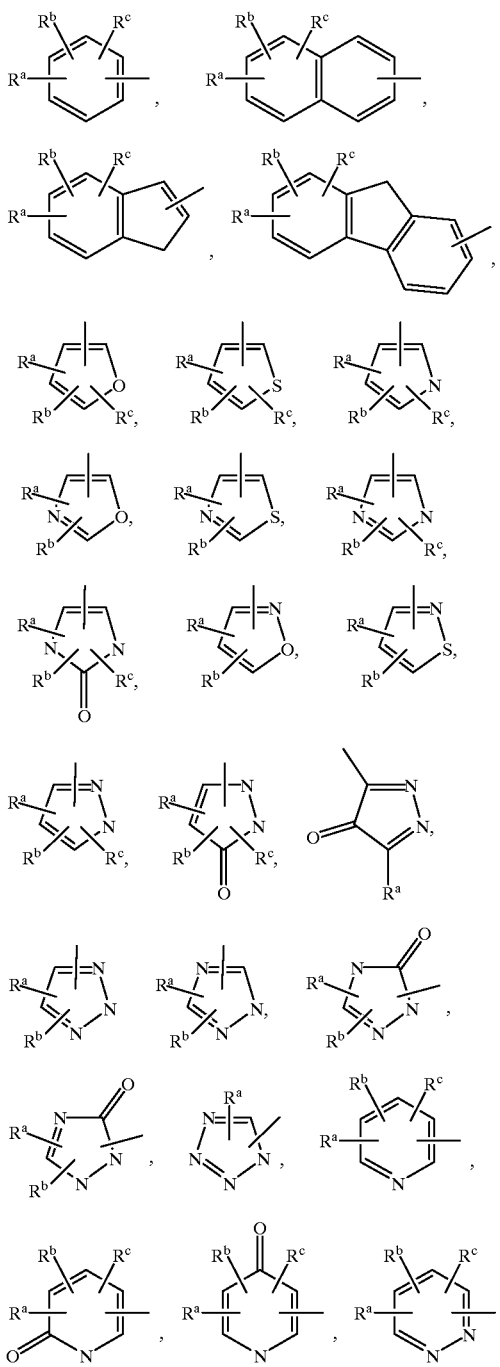
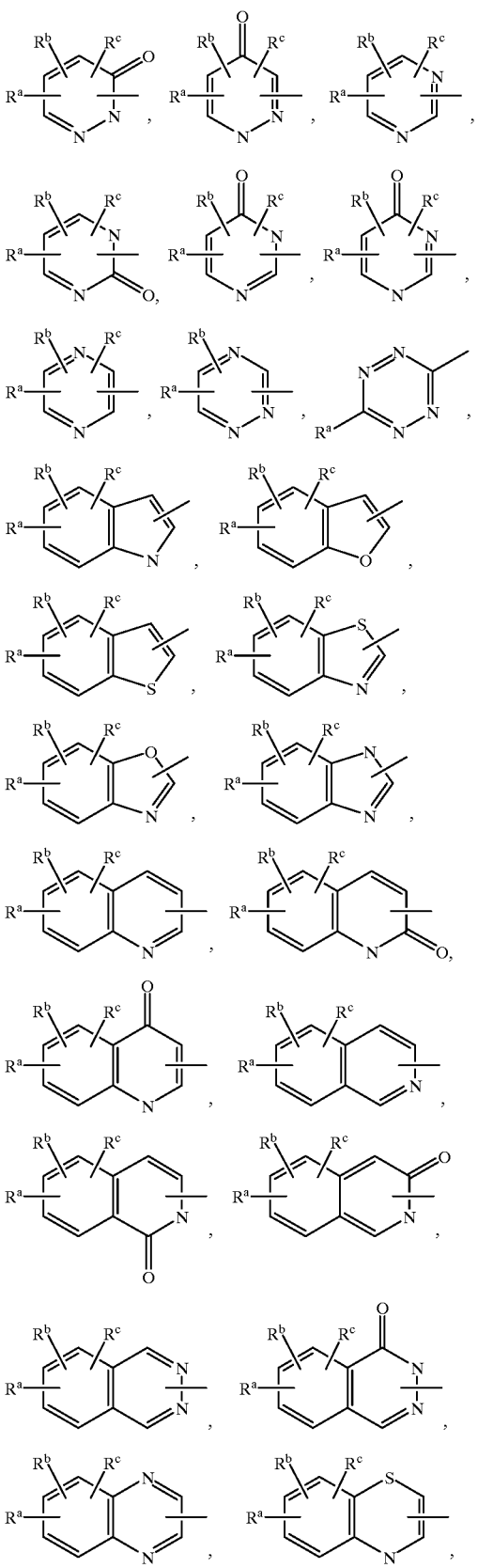

-continued

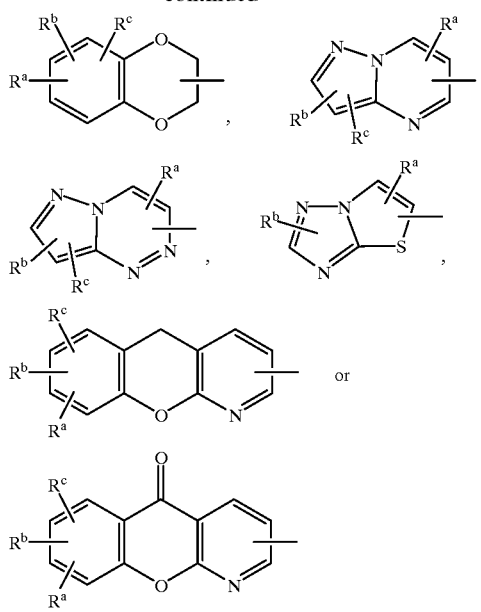

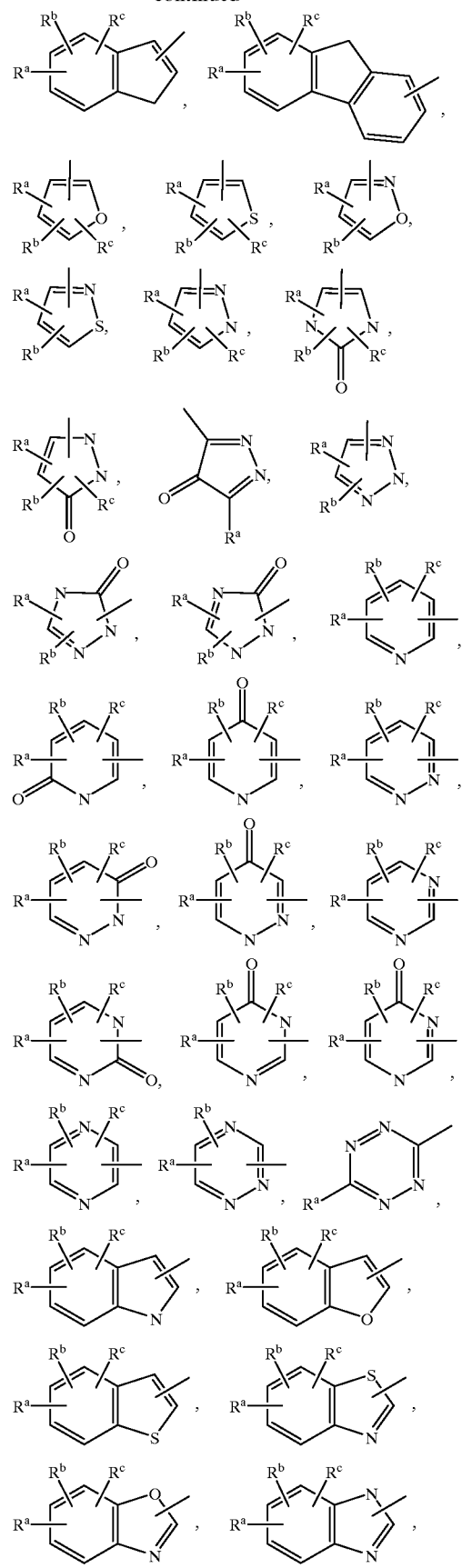

(wherein each $R^a$ and $R^b$ is independently a hydrogen atom, a $C_1$–$C_7$ alkyl group, a $C_3$–$C_7$ cycloalkyl group, a $C_3$–$C_7$ cycloalkenyl group (said alkyl, cycloalkyl and cycloalkenyl groups may be substituted with a hydroxyl group), a hydroxy group, a $C_1$–$C_7$ alkoxy group, a $C_1$–$C_7$ alkylthio group, a fluorine atom, a chlorine atom, a bromine atom, a trifluoromethyl group, a nitro group, an amino group, a methylamino group, a dimethylamino group, an acetamide group, a methanesulfonylamide group, a carboxyl group, a $C_1$–$C_3$ alkoxycarbonyl group, a nitrile group, a carbamoyl group, a sulfamoyl group, a phenoxy group, a benzyloxy group, a phenyl, α-naphthyl, β-naphthyl, furanyl, thienyl, imidazolyl, pyridyl or benzyl group (each of said phenyl, α-naphthyl, β-naphthyl, furanyl, thienyl, imidazolyl, pyridyl and benzyl groups may be substituted with at most 5 substituents selected from the group consisting of phenyl, methyl, ethyl, n-propyl, isopropyl, cyclopropyl, n-butyl, isobutyl, s-butyl, t-butyl, n-hexyl, cyclohexyl, methoxy, ethoxy, n-propoxy, isopropoxy, methylthio, ethylthio, n-propylthio, isopropylthio, hydroxy, fluorine, chlorine, bromine, nitro and dimethylamino groups), a 1-tetrazolyl group, a 3-tetrazolyl group, a 5-tetrazolyl group, a thiazolidindion-5-yl group or a thiazolidindion-5-yl methyl group, and $R^c$ is a hydrogen atom, a $C_1$–$C_7$ alkyl group, a $C_3$–$C_7$ cycloalkyl group or a hydroxymethyl group).

4. The pyridine type compound of the formula (I) or its salt according to claim 1, wherein:
each of $R^1$, $R^2$, and $R^3$ is independently a hydrogen atom, a methyl group, a hydroxyl group or a chlorine atom; and
B is

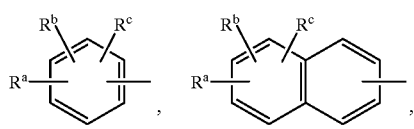

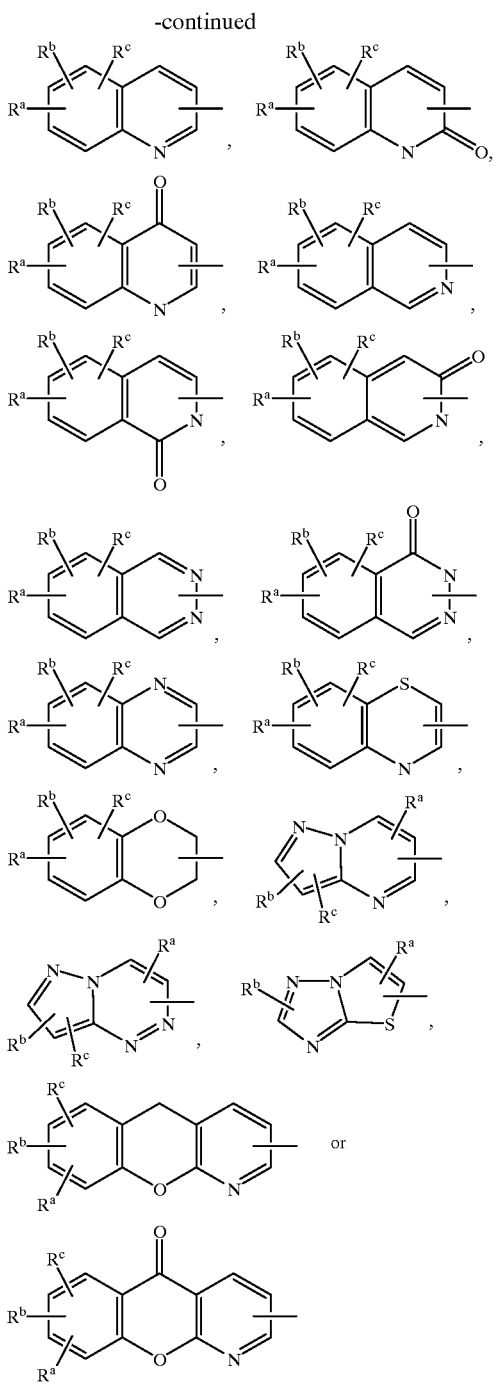

and benzyl groups may be substituted with at most 5 substituents selected from the group consisting of phenyl, methyl, ethyl, n-propyl, isopropyl, cyclopropyl, n-butyl, isobutyl, s-butyl, t-butyl, n-hexyl, cyclohexyl, methoxy, ethoxy, n-propoxy, isopropoxy, methylthio, ethylthio, n-propylthio, isopropylthio, hydroxy, fluorine, chlorine, bromine, nitro and dimethylamino groups), a 1-tetrazolyl group, a 3-tetrazolyl group, a 5-tetrazolyl group, a thiazolidindion-5-yl group or a thiazolidindion-5-yl methyl group, and $R^c$ is a hydrogen atom, a $C_1$–$C_7$ alkyl group, a $C_3$–$C_7$ cycloalkyl group or a hydroxymethyl group).

5. The pyridine type compound of the formula (I) or its salt according to claim 1, wherein:

$X^1$ is S;

$R^1$, $R^2$ and $R^3$ are a hydrogen atom;

Y is $CR^6R^7$ (wherein $R^6$ is a hydrogen atom or a methyl group, and $R^7$ is a hydrogen atom or forms a bond together with $R^4$);

$R^4$ is a hydrogen atom or a methyl group, or forms a bond together with $R^7$; and A is a divalent $C_1$–$C_6$ saturated or $C_2$–$C_6$ unsaturated hydrocarbon group which may be substituted with at most 2 hydroxy, oxo and $C_1$–$C_7$ alkyl groups (provided that the first carbon atom bonded with the oxygen atom at the 5-position of the pyridine ring of the compound of the formula (I) is not substituted with a hydroxy group or an oxo group).

6. The pyridine type compound of the formula (I) or its salt according to claim 1, wherein:

Y is —$CH_2$—; and $R^4$ is a hydrogen atom.

7. The pyridine type compound of the formula (I) or its salt according to claim 1, wherein:

Y is $CHR^7$ ($R^7$ forms a bond together with $R^4$); and $R^4$ forms a bond together with $R^7$.

8. The pyridine type compound of the formula (I) or its salt according to claim 1, wherein:

A is

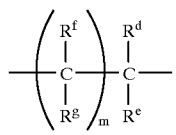

(wherein each of $R^a$ and $R^b$ is independently a hydrogen atom, a $C_1$–$C_7$ alkyl group, a $C_3$–$C_7$ cycloalkyl group, a $C_3$–$C_7$ cycloalkenyl group (said alkyl, cycloalkyl and cycloalkenyl group may be substituted with a hydroxyl group), a hydroxy group, a $C_1$–$C_7$ alkoxy group, a $C_1$–$C_7$ alkylthio group, a fluorine atom, a chlorine atom, a bromine atom, a trifluoromethyl group, a nitro group, an amino group, a methylamino group, a dimethylamino group, an acetamide group, a methanesulfonylamide group, a carboxyl group, a $C_1$–$C_3$ alkoxycarbonyl group, a nitrile group, a carbamoyl group, a sulfamoyl group, a phenoxy group, a benzyloxy group, a phenyl, α-naphthyl, β-naphthyl, furanyl, thienyl, imidazolyl, pyridyl or benzyl group (said phenyl, α-naphthyl, β-naphthyl, furanyl, thienyl, imidazolyl, pyridyl (wherein m is from 0 to 5, each of $R^d$ and $R^e$ is independently a hydrogen atom or a methyl group, and each of $R^f$ and $R^g$ is independently a hydrogen atom, a methyl group or a hydroxyl group, or $R^f$ and $R^g$ together form an oxo group, or adjacent $R^d$ and $R^f$ together form a double bond, or adjacent $R^d$, $R^f$, $R^e$ and $R^g$ together form a triple bond, or adjacent $R^f$'s together form a double bond when m is 2 to 5, or adjacent $R^f$ and $R^g$ together form a triple bond).

9. The pyridine type or compound of the formula (I) or its salt according to claim 1, wherein:

A is

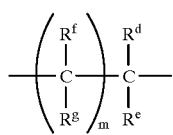

(wherein m is from 0 to 2, each of $R^d$ and $R^e$ is independently a hydrogen atom or a methyl group, and each of $R^f$ and $R^g$ is independently a hydrogen atom, a methyl group or a hydroxyl group, or $R^f$ and $R^g$ together form an oxo group, or adjacent $R^d$ and $R^f$ together form a double bond, or adjacent $R^d$, $R^f$, $R^e$ and $R^g$ together form a triple bond, or adjacent $R^f$'s together form a double bond when m is 2, or adjacent $R^f$ and $R^g$ together form a triple bond).

10. The pyridine type compound of the formula (I) or its salt according to claim 1, wherein;

A is

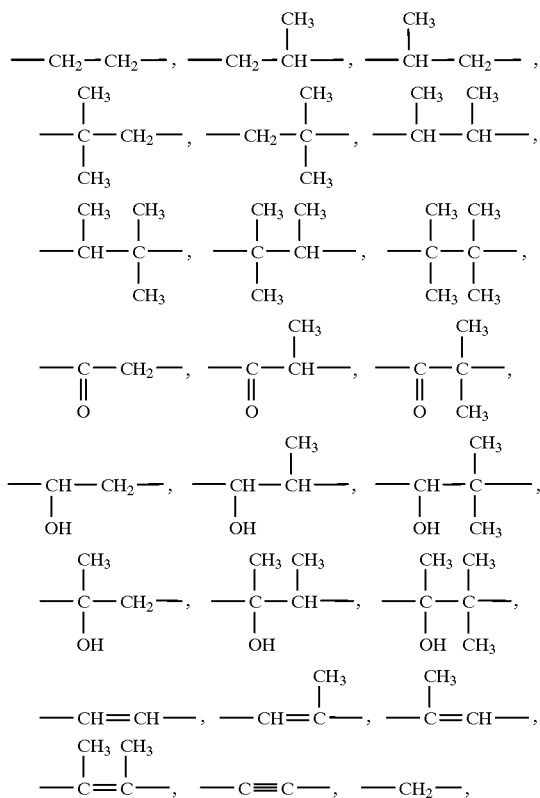

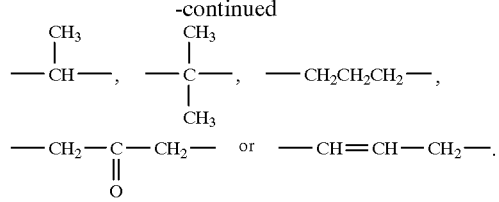

11. The pyridine type compound of the formula (I) or its salt according to claim 1, wherein:

A is

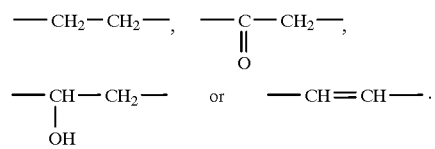

12. A hypoglycemic agent containing the pyridine type compound or its salt according to claim 1 as an active agent.

13. An anti-glycation agent containing the pyridine type compound or its salt according to claim 1 as an active agent.

14. A pharmaceutical agent for treating diabetes mellitus and diabetic complications, which contains the pyridine type compound or its salt according to claim 1 as an active agent.

15. The compound or the pharmaceutically acceptable salt thereof according to claim 1, which is 5-((5-(2-oxo-2-(2-(4-fluorophenyl)-5-methyl-4-oxazolyl)ethoxy)-2-pyridyl) methyl)thiazolidin-2,4-dione.

16. The compound or the pharmaceutically acceptable salt thereof according to claim 1, which is 5-((5-(2-oxo-2-(2-(4-methylphenyl)-5-methyl-4-oxazolyl)ethoxy)-2-pyridyl) methyl)thiazolidin-2,4-dione.

17. The compound or the pharmaceutically acceptable salt thereof according to claim 1, which is 5-((5-(2-oxo-2-(2-(4-phenylphenyl)-5-methyl-4-oxazolyl)ethoxy)-2 -pyridyl) methyl)thiazolidin-2,4-dione.

18. The compound or the pharmaceutically acceptable salt thereof according to claim 1, which is 5-((5-(2-oxo-2-(2-(4-phenylphenyl)-5-methyl-4-oxazolyl)ethoxy)-2-pyridyl) methyliden)thiazolidin-2,4-dione.

19. The compound or the pharmaceutically acceptable salt thereof according to claim 1, which is 5-((5-(2-oxo-2-(2-phenyl-5-methyl-4-oxazolyl)ethoxy)-2-pyridyl)methyliden) thiazolidin-2,4-dione.

* * * * *

UNITED STATES PATENT AND TRADEMARK OFFICE
CERTIFICATE OF CORRECTION

PATENT NO. : 5,955,481

DATED : September 21, 1999

INVENTOR(S): Yoshio OHARA, et al.

It is certified that an error appears in the above-identified patent and that said Letters Patent is hereby corrected as shown below:

On the title page, item [63] is incorrect. It should be:

--Related U.S. Application Data
[63] Continuation-in-part of application No 08/704,774,
Sep. 23, 1996, abandoned.--

Signed and Sealed this

Third Day of April, 2001

Attest:

NICHOLAS P. GODICI

*Attesting Officer*  *Acting Director of the United States Patent and Trademark Office*